(12) United States Patent
Suh et al.

(10) Patent No.: US 10,995,098 B2
(45) Date of Patent: May 4, 2021

(54) HETEROCYCLIC COMPOUND AND ORGANIC LIGHT EMITTING DEVICE COMPRISING THE SAME

(71) Applicant: LG CHEM, LTD., Seoul (KR)

(72) Inventors: Sang Duk Suh, Daejeon (KR); Sung Kil Hong, Daejeon (KR); Kyung Seok Jeong, Daejeon (KR)

(73) Assignee: LG CHEM, LTD., Seoul (KR)

( * ) Notice: Subject to any disclaimer, the term of this patent is extended or adjusted under 35 U.S.C. 154(b) by 160 days.

(21) Appl. No.: 16/313,810

(22) PCT Filed: Dec. 14, 2017

(86) PCT No.: PCT/KR2017/014686
§ 371 (c)(1),
(2) Date: Dec. 27, 2018

(87) PCT Pub. No.: WO2018/110989
PCT Pub. Date: Jun. 21, 2018

(65) Prior Publication Data
US 2019/0152985 A1 May 23, 2019

(30) Foreign Application Priority Data
Dec. 14, 2016 (KR) .......................... 10-2016-0170675

(51) Int. Cl.
*H01L 51/50* (2006.01)
*C07D 493/14* (2006.01)
(Continued)

(52) U.S. Cl.
CPC ......... *C07D 493/14* (2013.01); *C07D 493/04* (2013.01); *C07D 519/00* (2013.01); *C09K 11/06* (2013.01); *H01L 51/00* (2013.01); *H01L 51/006* (2013.01); *H01L 51/0052* (2013.01); *H01L 51/0061* (2013.01); *H01L 51/0067* (2013.01); *H01L 51/0072* (2013.01); *H01L 51/0073* (2013.01); *H01L 51/0094* (2013.01);
(Continued)

(58) Field of Classification Search
None
See application file for complete search history.

(56) References Cited

U.S. PATENT DOCUMENTS

2015/0034914 A1 2/2015 Lee et al.
2016/0351816 A1 12/2016 Kim et al.
(Continued)

FOREIGN PATENT DOCUMENTS

CN 106206999 A 12/2016
CN 107033128 A 8/2017
(Continued)

OTHER PUBLICATIONS

Berg et al., Quinone oligonnerization. An x-ray study; Tetrahedron Letters (1977), (21), 1831-4 (Year: 1977).*

*Primary Examiner* — Gregory D Clark
(74) *Attorney, Agent, or Firm* — Dentons US LLP

(57) ABSTRACT

The present invention relates to a cyclic compound having a novel structure and an organic light emitting device comprising the same. The cyclic compound of Chemical Formula 1 used in an organic material layer of the organic light emitting device provides improved driving voltage, light efficiency, and lifetime characteristics.

10 Claims, 1 Drawing Sheet

(51) Int. Cl.
  *C07D 493/04*   (2006.01)
  *C07D 519/00*   (2006.01)
  *H01L 51/00*    (2006.01)
  *C09K 11/06*    (2006.01)

(52) U.S. Cl.
  CPC .......... *H01L 51/50* (2013.01); *H01L 51/5012* (2013.01); *H01L 51/5056* (2013.01); *H01L 51/5072* (2013.01); *H01L 51/5096* (2013.01)

(56) References Cited

U.S. PATENT DOCUMENTS

| | | |
|---|---|---|
| 2016/0380206 A1 | 12/2016 | Kim et al. |
| 2017/0222160 A1 | 8/2017 | Lee et al. |
| 2018/0375035 A1 | 12/2018 | Ji et al. |
| 2020/0028097 A1 | 1/2020 | Lee et al. |
| 2020/0227644 A1 | 7/2020 | Lee et al. |

FOREIGN PATENT DOCUMENTS

| | | | |
|---|---|---|---|
| CN | 109111488 A | 1/2019 | |
| CN | 110088110 A | 8/2019 | |
| CN | 110248945 A | 9/2019 | |
| CN | 110325537 A | 10/2019 | |
| CN | 110892539 A | 3/2020 | |
| EP | 2301926 A1 | 3/2011 | |
| JP | 2012-028548 A | 2/2012 | |
| KR | 10-2000-0051826 A | 8/2000 | |
| KR | 10-2011-0018340 A | 2/2011 | |
| KR | 10-2013-0050237 A | 5/2013 | |
| KR | 10-2014-0128890 A | 11/2014 | |
| KR | 10-2015-0016845 A | 2/2015 | |
| KR | 10-2015-0085766 A | 7/2015 | |
| KR | 10-2016-0028737 A | 3/2016 | |
| KR | 10-2017-0056425 A | 5/2017 | |
| KR | 10-2017-0086211 A | 7/2017 | |
| KR | 10-2017-0086243 A | 7/2017 | |
| KR | 2017-082459 | * 7/2017 | ............. H01L 51/50 |
| WO | 2015/108325 A1 | 7/2015 | |

* cited by examiner

[FIG. 1]
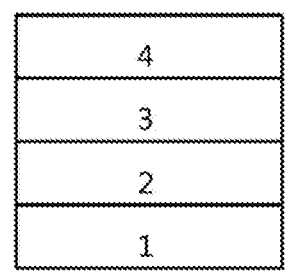
[FIG. 2]
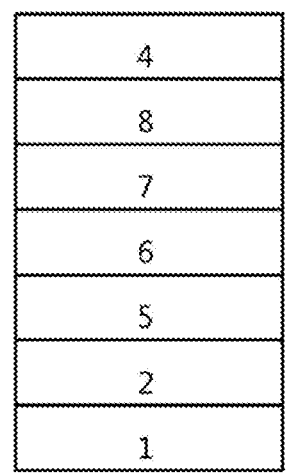

HETEROCYCLIC COMPOUND AND ORGANIC LIGHT EMITTING DEVICE COMPRISING THE SAME

CROSS-REFERENCE TO RELATED APPLICATION(S)

This application is a National Stage Entry of International Application No. PCT/KR2017/014686, filed on Dec. 14, 2017, and claims the benefit of and priority to Korean Application No. 10-2016-0170675, filed on Dec. 14, 2016, all of which are hereby incorporated by reference in their entirety for all purposes as if fully set forth herein.

TECHNICAL FIELD

The present invention relates to a novel heterocyclic compound having a novel structure and to an organic light emitting device comprising the same.

BACKGROUND ART

In general, an organic light emitting phenomenon refers to a phenomenon where electric energy is converted into light energy by using an organic material. The organic light emitting device using the organic light emitting phenomenon has characteristics such as a wide viewing angle, an excellent contrast, a fast response time, an excellent luminance, driving voltage and response speed, and thus many studies have proceeded.

The organic light emitting device generally has a structure which comprises an anode, a cathode, and an organic material layer interposed between the anode and the cathode. The organic material layer frequently have a multilayered structure that comprises different materials in order to enhance efficiency and stability of the organic light emitting device, and for example, the organic material layer may be formed of a hole injection layer, a hole transport layer, a light emitting layer, an electron transport layer, an electron injection layer and the like. In the structure of the organic light emitting device, if a voltage is applied between two electrodes, the holes are injected from an anode into the organic material layer and the electrons are injected from the cathode into the organic material layer, and when the injected holes and the electrons meet each other, an exciton is formed, and light is emitted when the exciton falls to a ground state again.

There is a continuing need for the development of new materials for the organic materials used in such organic light emitting devices.

PRIOR ART LITERATURE

Patent Literature (Patent Literature 1) Korean Patent Laid-open Publication No. 10-2000-0051826

DETAILED DESCRIPTION OF THE INVENTION

Technical Problem

It is an object of the present invention to provide a heterocyclic compound having a novel structure and an organic light emitting device comprising the same.

Technical Solution

The present invention provides a compound represented by the following Chemical Formula 1:

[Chemical Formula 1]

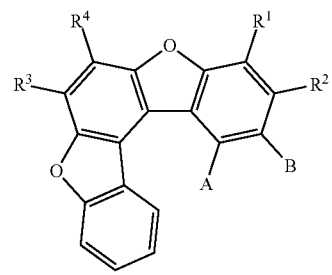

in Chemical Formula 1,
A and B are hydrogen, or are linked to

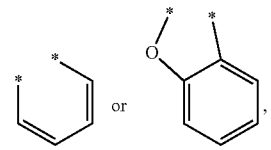 [SMILES: */C=C\C=C/* ; *Oc1ccccc1*]

at least one of $R^1$ to $R^4$ is the following Chemical Formula 2 or Chemical Formula 3, and the rest are hydrogen, $$*\text{—}L^1\text{—}Ar^1$$ [Chemical Formula 2]

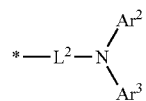 [Chemical Formula 3]

in Chemical Formulae 2 and 3,
$L^1$ and $L^2$ are each independently a single bond; or a substituted or unsubstituted $C_{6\text{-}60}$ arylene;
$Ar^1$ is a substituted or unsubstituted $C_{6\text{-}60}$ aryl; a substituted or unsubstituted $C_{2\text{-}60}$ heteroaryl containing at least one of C), N, Si and S; or —$PO(Ar^4)(Ar^5)$, and
$Ar^2$ to $Ar^5$ are each independently a substituted or unsubstituted $C_{6\text{-}60}$ aryl; or a substituted or unsubstituted $C_{2\text{-}60}$ heteroaryl containing at least one of O, N, Si and S.

The present invention also provides an organic light emitting device comprising a first electrode; a second electrode provided at a side opposite to the first electrode; and at least one layer of the organic material layers provided between the first electrode and the second electrode, wherein the at least one layer of the organic material layers includes the compound represented by Chemical Formula 1.

Advantageous Effects

The compound represented by Chemical Formula 1 can be used as a material of an organic material layer of an organic light emitting device, and can achieve an improvement of the efficiency, a low driving voltage and/or an improvement of the lifetime characteristic when applied to the organic light emitting device. The compound represented by Chemical Formula 1 can be used as hole injection, hole transport, hole injection and transport, light emitting, electron transport, or electron injection materials.

BRIEF DESCRIPTION OF DRAWINGS

FIG. 1 shows an example of an organic light emitting device comprising a substrate 1, an anode 2, a light emitting layer 3, and a cathode 4.

FIG. 2 shows an example of an organic light emitting device comprising a substrate 1, an anode 2, a hole injection layer 5, a hole transport layer 6, a light emitting layer 7, an electron transport layer 8, and a cathode 4.

DETAILED DESCRIPTION OF THE EMBODIMENTS

Hereinafter, the present invention will be described in more detail to help understanding of the present invention.

The present invention provides a compound represented by Chemical Formula 1.

As used herein, "single bond" means the case in which no separate atom is present at a part represented by $L^1$ or $L^2$. For example, if $R^2$ in Chemical Formula 1 is Chemical Formula 2 and $L^1$ in Chemical Formula 2 is a single bond, $Ar^1$ in Chemical Formula 2 can be directly linked to the central structure of Chemical Formula 1.

As used herein, the term "substituted or unsubstituted" means being unsubstituted or substituted by $R^a$, wherein $R^a$ may be deuterium, halogen, a cyano group, a nitro group, an amino group, an alkyl group having 1 to 40 carbon atoms, a haloalkyl group having 1 to 40 carbon atoms, a substituted or unsubstituted heteroalkyl group having 1 to 40 carbon atoms, containing at least one of O, N, Si and S, a substituted or unsubstituted heterohaloalkyl group having 1 to 40 carbon atoms, containing at least one of O, N, Si and S, or an alkenyl group having 2 to 40 carbon atoms.

As used herein, "halogen" may be fluorine, chlorine, bromine, or iodine.

As used herein, "alkyl group having 1 to 40 carbon atoms" may be a straight-chain, branched or cyclic alkyl group. Specifically, the alkyl group having 1 to 40 carbon atoms may be a straight-chain alkyl group having 1 to 40 carbon atoms; a straight-chain alkyl group having 1 to 20 carbon atoms; a straight-chain alkyl group having 1 to 10 carbon atoms; a branched or cyclic alkyl group having 3 to 40 carbon atoms; a branched or cyclic alkyl group having 3 to 20 carbon atoms; or a branched or cyclic alkyl group having 3 to 10 carbon atoms. More specifically, the alkyl group having 1 to 40 carbon atoms may be a methyl group, an ethyl group, an n-propyl group, an iso-propyl group, an n-butyl group, an iso-butyl group, a t-butyl group, an n-pentyl group, an iso-pentyl group, a neo-pentyl group, a cyclohexyl group, or the like, but are not limited thereto.

As used herein, "heteroalkyl group having 1 to 40 carbon atoms" may be one in which at least one carbon of the alkyl group is each independently substituted with O, N, Si, or S. As an example of the straight-chain alkyl group, the heteroalkyl group in which the $1^{st}$ carbon of n-butyl group is substituted with O is an n-propoxy group, the heteroalkyl group substituted with N is an n-propylamino group, the heteroalkyl group substituted with Si is an n-propylsilyl group, and the heteroalkyl group substituted with S is an n-propylthio group. In addition, as an example of the branched alkyl group, the heteroalkyl group in which the $1^{st}$ carbon of neopentyl group is substituted with O is a t-butoxy group, the heteroalkyl group substituted with N is a t-butylamino group, the heteroalkyl group substituted with Si is a t-butylsilyl group, and the heteroalkyl group substituted with S is a t-butylthio group. Further, as an example of the cyclic alkyl group, the heteroalkyl group in which the $2^{nd}$ carbon of cyclohexyl group is substituted with O is a 2-tetrahydropyranyl group, the heteroalkyl group substituted with N is a 2-piperidinyl group, the heteroalkyl group substituted with Si is a 1-sila-cyclohexyl group, and the heteroalkyl group substituted with S is a 2-tetrahydrothiopyranyl group. Specifically, the heteroalkyl group having 1 to 40 carbon atoms may include a straight-chain, branched or cyclic hydroxyalkyl group having 1 to 40 carbon atoms; a straight-chain, branched or cyclic alkoxy group having 1 to 40 carbon atoms; a straight-chain, branched or cyclic alkoxyalkyl group having 2 to 40 carbon atoms; a straight-chain, branched chain or cyclic aminoalkyl group having 1 to 40 carbon atoms; a straight-chain, branched or cyclic alkylamino group having 1 to 40 carbon atoms; a straight-chain, branched or cyclic alkylaminoalkyl group having 1 to 40 carbon atoms; a straight-chain, branched or cyclic silylalkyl (oxy) group having 1 to 40 carbon atoms; a straight-chain, branched or cyclic alkyl(oxy)silyl group having 1 to 40 carbon atoms; a straight-chain, branched or cyclic alkyl (oxy)silylalkyl(oxy) group having 1 to 40 carbon atoms; a straight-chain, branched or cyclic mercaptoalkyl group having 1 to 40 carbon atoms; a straight-chain, branched or cyclic alkylthio group having 1 to 40 carbon atoms; or a straight-chain, branched or cyclic alkylthioalkyl group having 2 to 40 carbon atoms. More specifically, the heteroalkyl group having 1 to 40 carbon atoms may include a hydroxymethyl group, a methoxy group, an ethoxy group, an n-propoxy group, an iso-propoxy group, a t-butoxy group, a cycloheptoxy group, a methoxymethyl group, an iso-propoxymethyl group, a cyclohexylmethyl group, a 2-tetrahydropyranyl group, an aminomethyl group, a methylamino group, an n-propylamino group, a t-butylamino group, a methylaminopropyl group, a 2-piperidinyl group, an n-propylsilyl group, a trimethylsilyl group, a dimethylmethoxysilyl group, a t-butylsilyl group, a 1-sila-cyclohexyl group, an n-propylthio group, a t-butylthio group, a 2-tetrahydrothiopyranyl group, or the like. However, the present invention is not limited thereto.

As used herein, "alkenyl group having 2 to 40 carbon atoms" may be a straight-chain, branched or cyclic alkenyl group. Specifically, the alkenyl group having 2 to 40 carbon atoms may include a straight-chain alkenyl group having 2 to 40 carbon atoms; a straight-chain alkenyl group having 2 to 20 carbon atoms; a straight-chain alkenyl group having 2 to 10 carbon atoms; a branched alkenyl group having 3 to 40 carbon atoms; a branched alkenyl group having 3 to 20 carbon atoms; a branched alkenyl group having 3 to 10 carbon atoms; a cyclic alkenyl group having 5 to 40 carbon atoms; a cyclic alkenyl group having 5 to 20 carbon atoms; or a cyclic alkenyl group having 5 to 10 carbon atoms. More specifically, the alkenyl group having 2 to 40 carbon atoms may include an ethenyl group, a propenyl group, a butenyl group, a pentenyl group, a cyclohexenyl group, or the like. However, the present invention is not limited thereto.

As used herein, "aryl group having 6 to 60 carbon atoms" may be a monocyclic aryl group or a polycyclic aryl group. Specifically, the aryl group having 6 to 60 carbon atoms may be a monocyclic or polycyclic aryl group having 6 to 30 carbon atoms; or a monocyclic or polycyclic aryl group having 6 to 20 carbon atoms. More specifically, the aryl group having 6 to 60 carbon atoms may be a phenyl group, a biphenyl group, a terphenyl group or the like as the monocyclic aryl group, and the polycyclic aryl group may include a naphthyl group, an anthracenyl group, a phenanthryl group, a triphenylenyl group, a pyrenyl group, a perylenyl group, a chrycenyl group, a fluorenyl group or the like. However, the present invention is not limited thereto.

As used herein, "fluorenyl group" may be substituted, and two substituent groups may be linked with each other to form a spiro structure. In the case where the fluorenyl group is substituted,

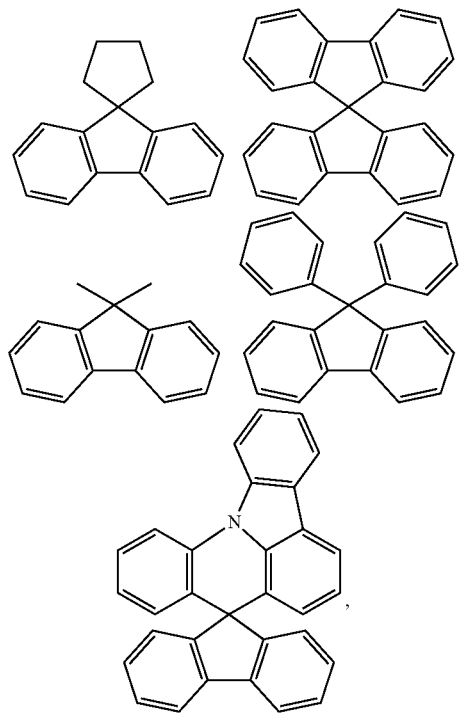

and the like can be formed. However, the structure is not limited thereto.

As used herein, "heteroaryl group having 2 to 60 carbon atoms" may be one in which at least one carbon of aryl group is each independently substituted with O, N, Si or S. For example, the heteroaryl group in which the 9th carbon of fluorenyl group is substituted with O is a dibenzofuranyl group, the heteroaryl group substituted with N is a carbazolyl group, the heteroaryl group substituted with Si is a 9-sila-fluorenyl group, and the heteroaryl group substituted with S is a dibenzothiophenyl group. Specifically, the heteroaryl group having 2 to 60 carbon atoms may be a heteroaryl group having 2 to 30 carbon atoms; or a heteroaryl group having 2 to 20 carbon atoms. More specifically, the heteroaryl group having 2 to 60 carbon atoms may include a thiophene group, a furan group, a pyrrole group, an imidazole group, a thiazole group, an oxazole group, an oxadiazole group, a triazole group, a pyridyl group, a bipyridyl group, a pyrimidyl group, a triazine group, a triazole group, an acridyl group, a pyridazine group, a pyrazinyl group, a quinolinyl group, a quinazoline group, a quinoxalinyl group, a phthalazinyl group, a pyridopyrimidinyl group, a pyridopyrazinyl group, a pyrazinopyrazinyl group, an isoquinoline group, an indole group, a carbazole group, a benzoxazole group, a benzimidazole group, a benzothiazole group, a benzocarbazole group, a benzothiophene group, a dibenzothiophene group, a benzofuranyl group, a phenanthroline group, a thiazolyl group, an isoxazolyl group, an oxadiazolyl group, a thiadiazolyl group, a benzothiazolyl group, a phenothiazinyl group, a dibenzofuranyl group, and the like, but are not limited thereto.

As used herein, "arylene group" means a divalent organic group in which any one hydrogen radical of the above-mentioned aryl group is removed.

In Chemical Formula 1, when A and B are linked to

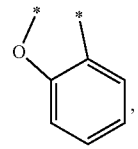

it may be represented by the following Chemical Formula 1-A. When A and B are hydrogen, it may be represented by the following Chemical Formula 1-B. When A and B are linked to

it may be represented by the following Chemical Formula 1-C.

[Chemical Formula 1-A]

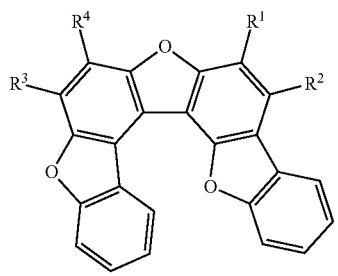

[Chemical Formula 1-B]

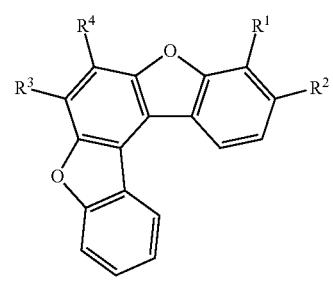

[Chemical Formula 1-C]

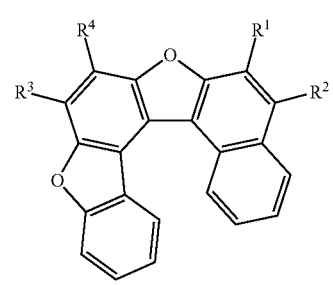

in Chemical Formulae 1-A, 1-B and 1-C, $R^1$ to $R^4$ are as defined in Chemical Formula 1.

In Chemical Formulae 1, $R^1$ and $R^4$ may be hydrogen, and $R^2$ and/or $R^3$ may be Chemical Formula 2 or Chemical Formula 3. That is, $R^1$ and $R^4$ may be hydrogen, and $R^2$ and $R^3$ may be Chemical Formula 2. Further, $R^1$ and $R^4$ may be hydrogen, and $R^2$ and $R^3$ may be Chemical Formula 3. Further, $R^1$, $R^3$ and $R^4$ may be hydrogen, and $R^2$ may be Chemical Formula 2. Further, $R^1$, $R^2$ and $R^4$ may be hydrogen, and $R^3$ may be Chemical Formula 2. Further, $R^1$, $R^3$ and $R^4$ may be hydrogen, and $R^2$ may be Chemical Formula 3. Further, $R^1$, $R^2$ and $R^4$ may be hydrogen, and $R^3$ may be Chemical Formula 3.

The Chemical Formula 1 may be represented by the following Chemical Formula 1-1 or 1-2:

[Chemical Formula 1-1]

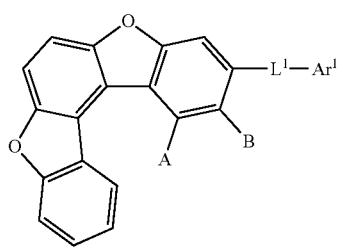

[Chemical Formula 1-2]

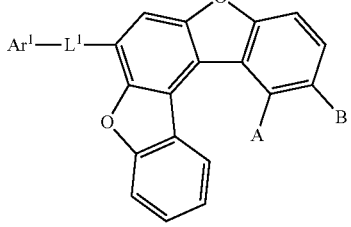

in Chemical Formulae 1-1 and 1-2,

A and B are hydrogen, or are linked to

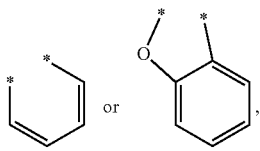

$L^1$ is a single bond; or a substituted or unsubstituted $C_{6-60}$ arylene;

$Ar^1$ is a substituted or unsubstituted $C_{6-60}$ aryl; a substituted or unsubstituted $C_{2-60}$ heteroaryl containing at least one of O, N, Si and S; or —PO($Ar^4$)($Ar^5$), and $Ar^4$ and $Ar^5$ are each independently a substituted or unsubstituted $C_{6-60}$ aryl; or a substituted or unsubstituted $C_{2-60}$ heteroaryl containing at least one of O, N, Si and S.

In addition, the Chemical Formula 1 may be represented by the following Chemical Formula 1-3, 1-4 or 1-5:

[Chemical Formula 1-3]

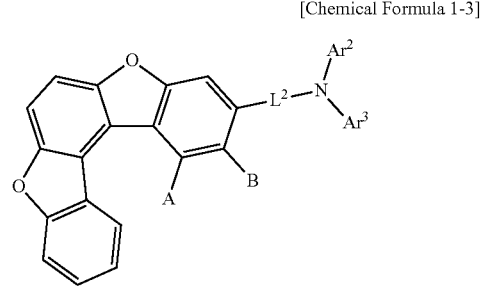

[Chemical Formula 1-4]

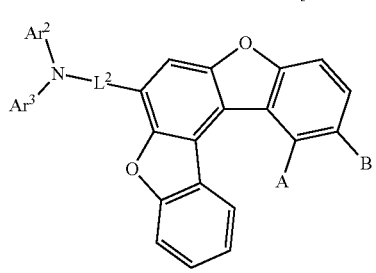

[Chemical Formula 1-5]

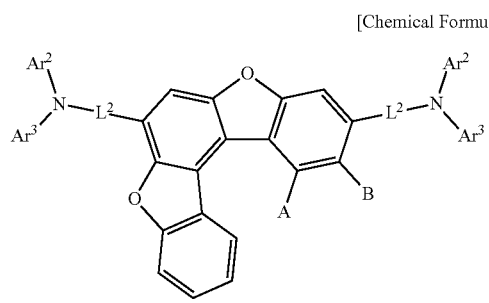

in Chemical Formulae 1-3 to 1-5,

A and B are hydrogen, or are linked to

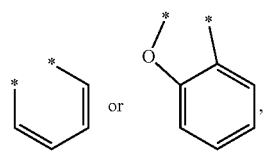 [SMILES: */C=C\C=C/* ; *Oc1ccccc1*]

$L^2$ is a single bond; or a substituted or unsubstituted $C_{6-60}$ arylene;

$Ar^2$ and $Ar^3$ are each independently a substituted or unsubstituted $C_{6-60}$ aryl; a substituted or unsubstituted $C_{2-60}$ heteroaryl containing at least one of O, N, Si and S.

In Chemical Formula 2, $L^1$ is a single bond or $C_{6-20}$ arylene, and $Ar^1$ may be $C_{2-30}$ heteroaryl containing N, or —PO($Ar^4$)($Ar^5$). Herein, in the —PO($Ar^4$)($Ar^5$), $Ar^4$ and $Ar^5$ may be each independently $C_{6-20}$ aryl.

Specifically, in Chemical Formula 2, $L^1$ is a single bond or phenylene, and $Ar^1$ may be selected from the group consisting of the following structures.

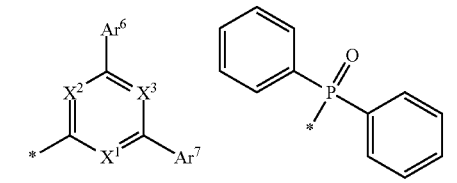
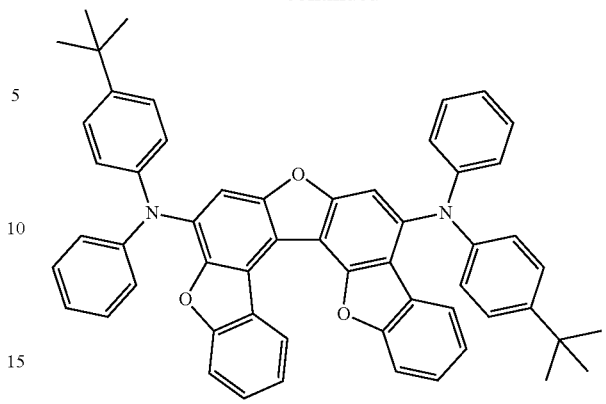

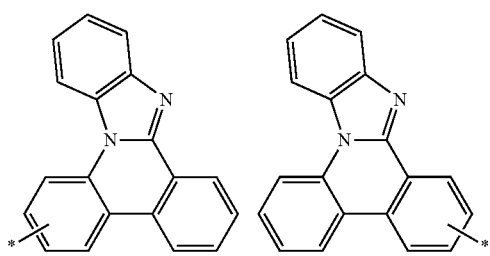

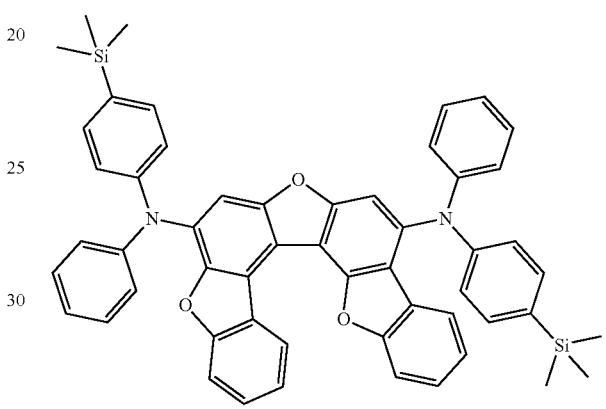

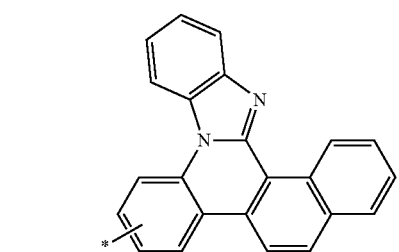

wherein, at least one of X¹ to X³ is N, the rest are C—H, and Ar⁶ and Ar⁷ are each independently hydrogen, phenyl, biphenyl or terphenyl.

In Chemical Formula 3, $L^2$ is a single bond or $C_{6-20}$ arylene, $Ar^2$ and $Ar^3$ are each independently a substituted or unsubstituted $C_{6-20}$ aryl; or a $C_{2-20}$ heteroaryl containing O.

Specifically, in Chemical Formula 3, $L^2$ is a single bond, or phenylene, $Ar^2$ and $Ar^3$ may be each independently a monovalent residue derived from arene selected from the group consisting of benzene, methylbenzene, t-butylbenzene, trimethylsilylbenzene, naphthalene, biphenyl, methyl biphenyl, terphenyl, methyltriphenyl, 9,9-dimethylfluorene and dibenzofuran.

The compound represented by Chemical Formula 1 may be selected from the group consisting of the following compounds.

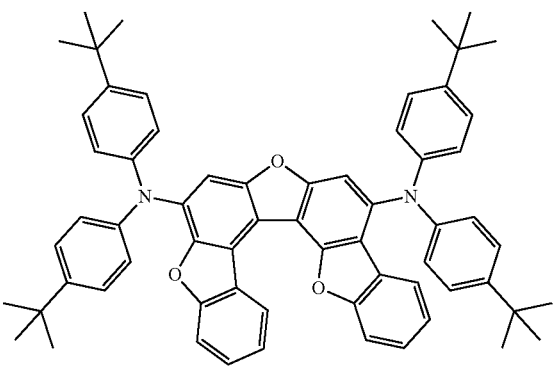

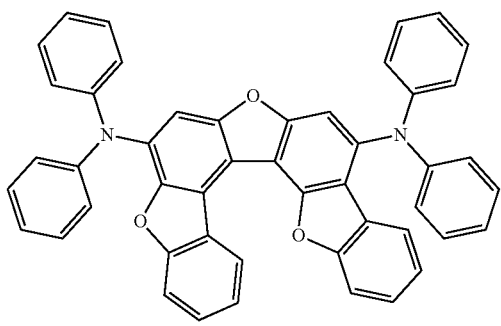
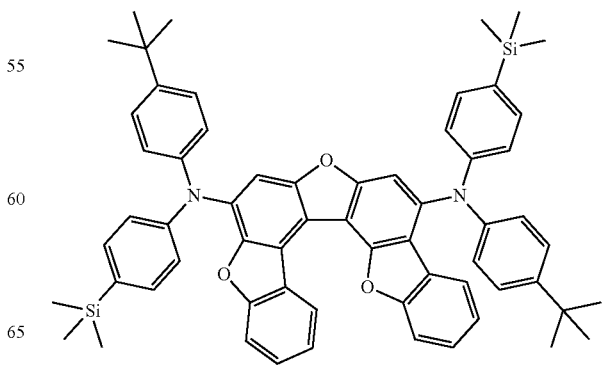

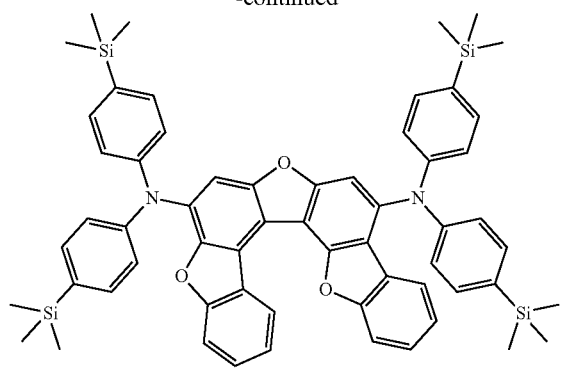
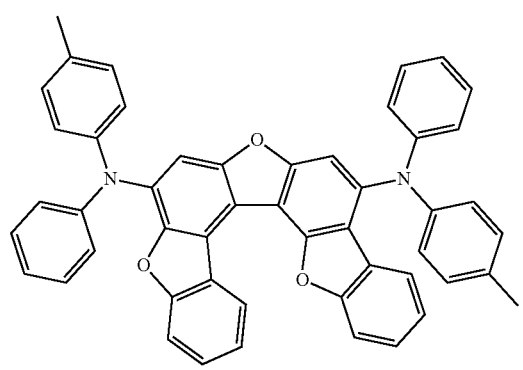
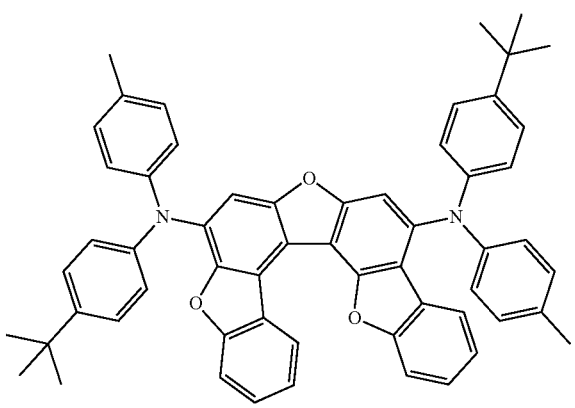
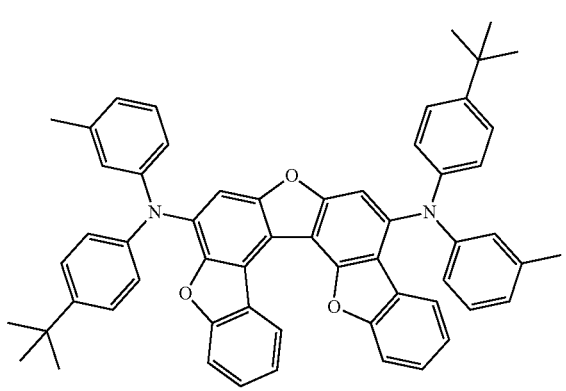
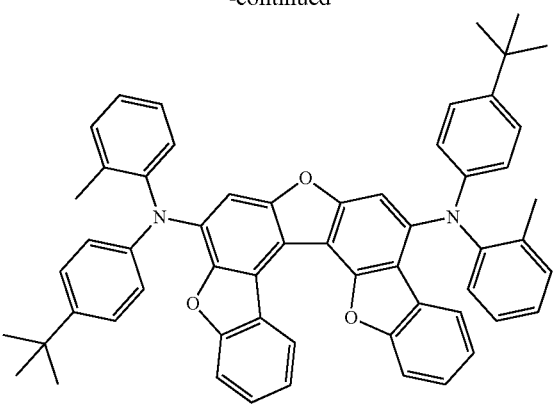
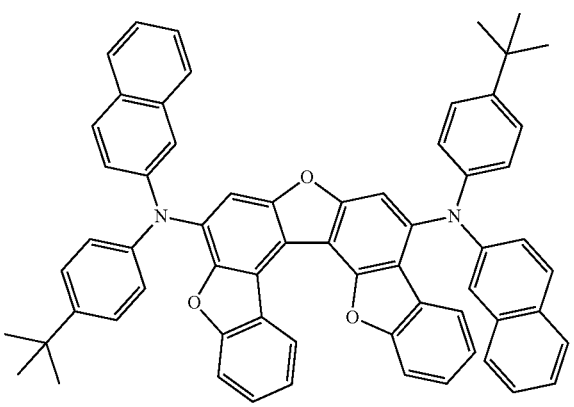

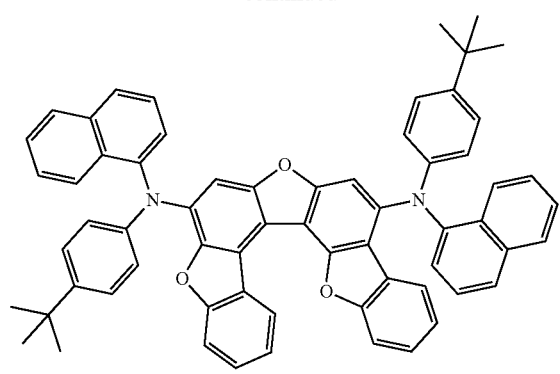
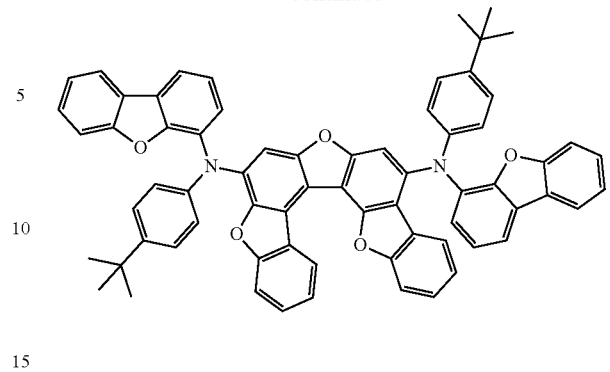
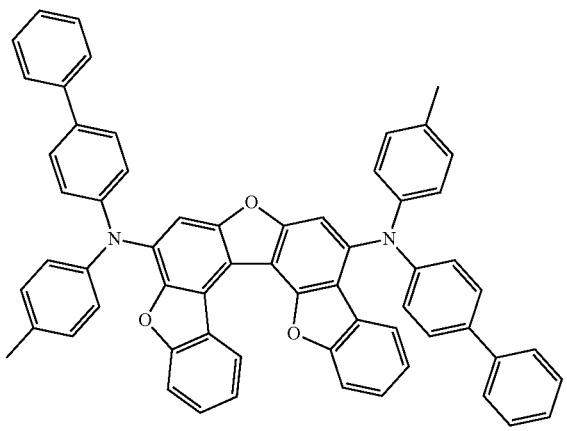
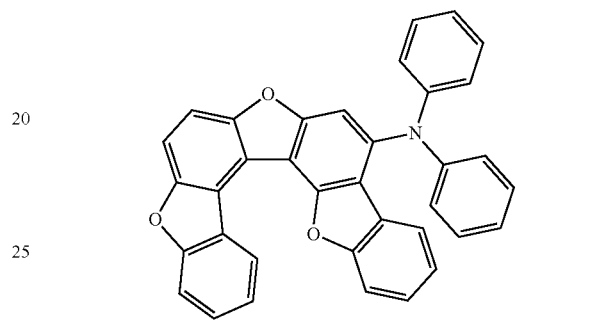
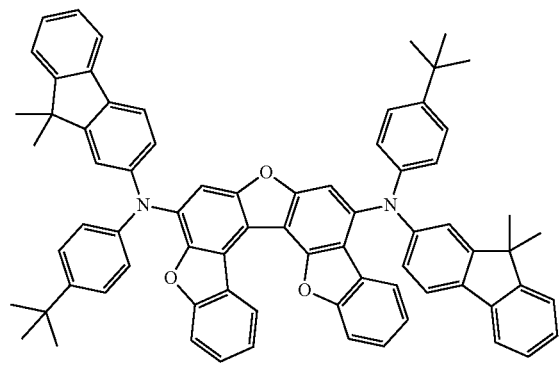
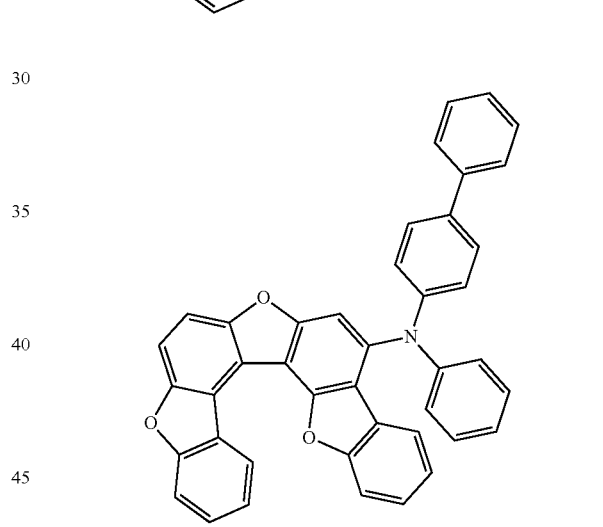
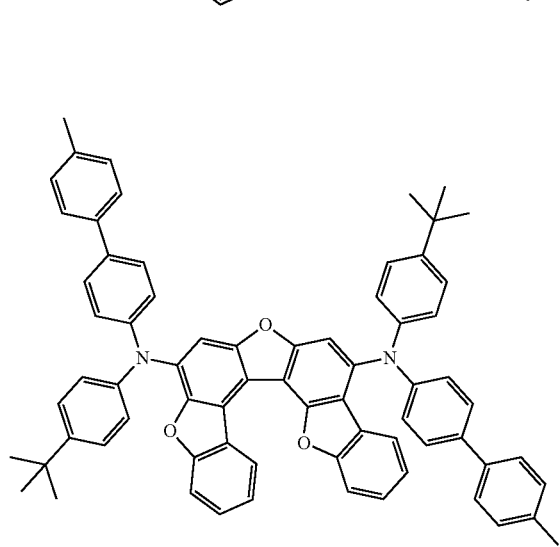
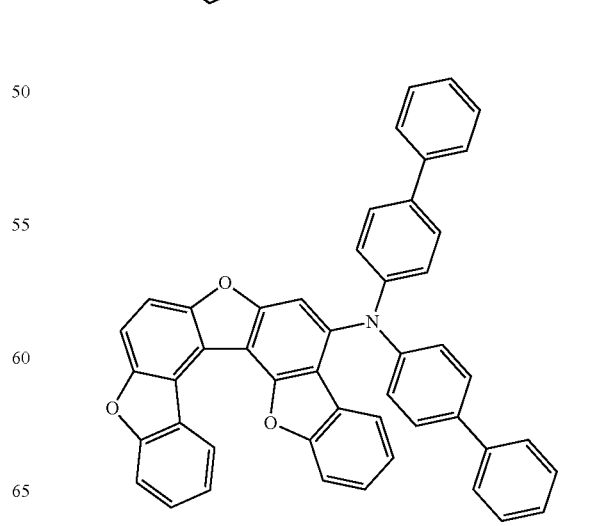

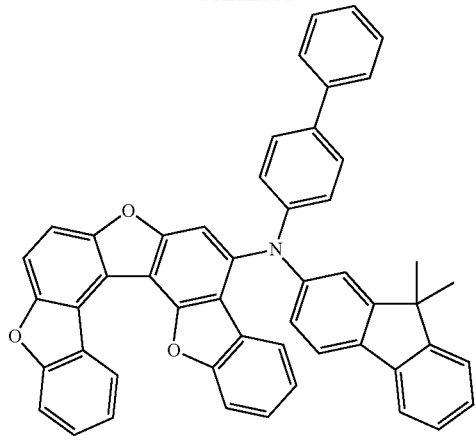
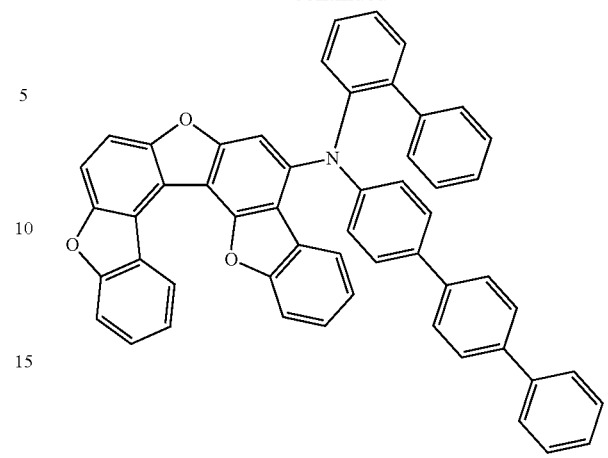
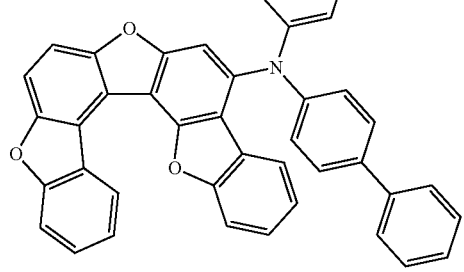
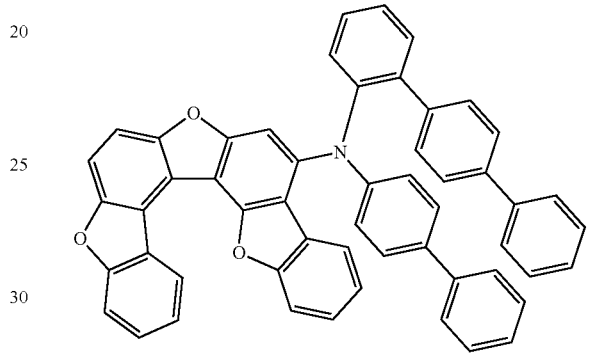
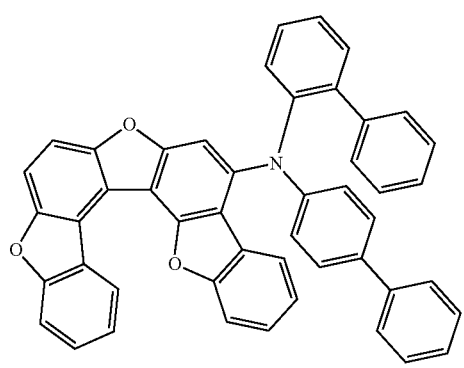
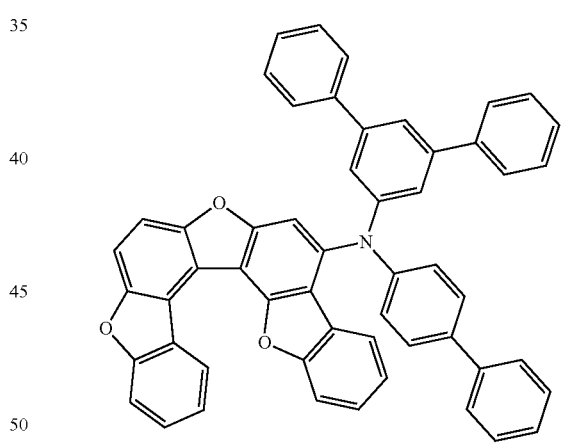
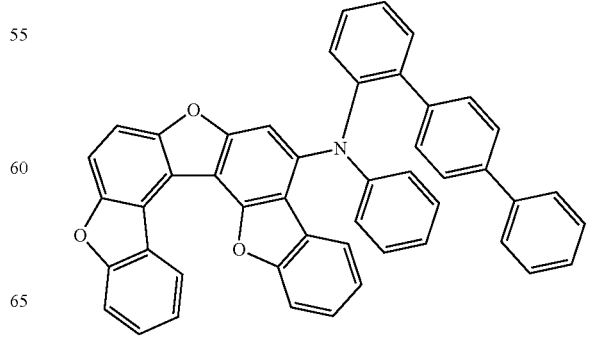

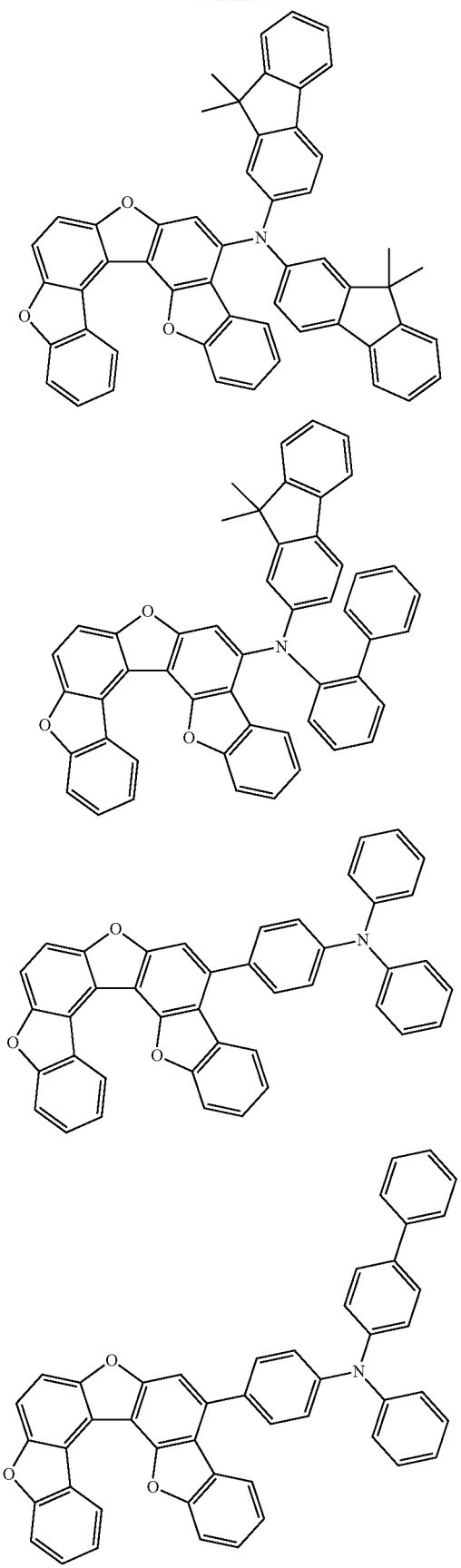

19
-continued
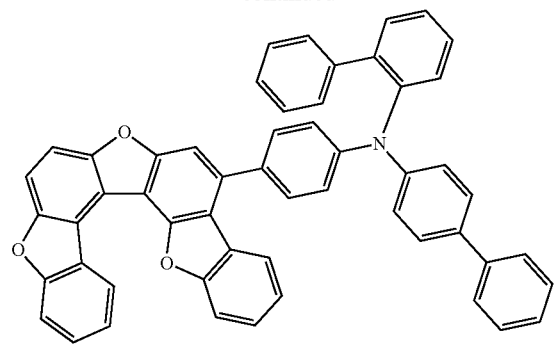
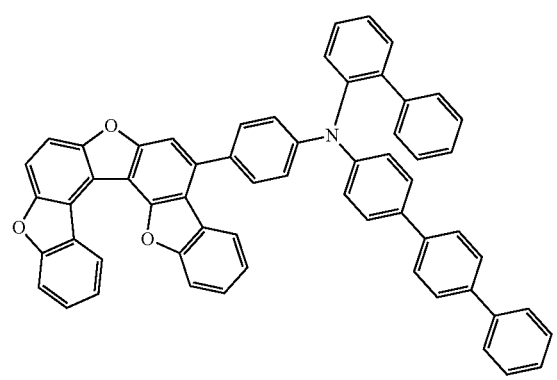
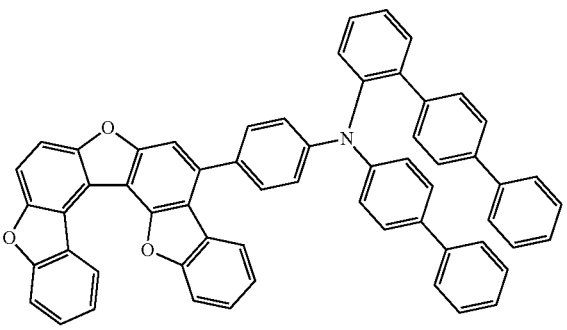
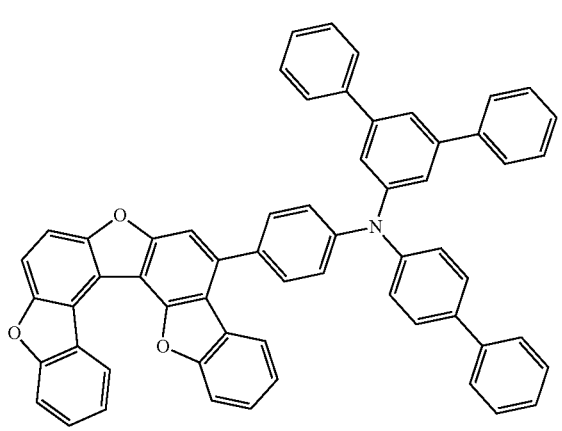
20
-continued
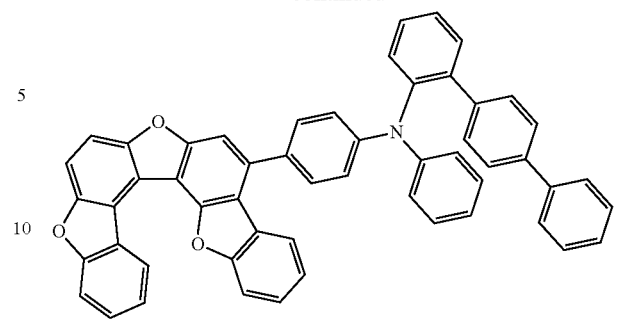
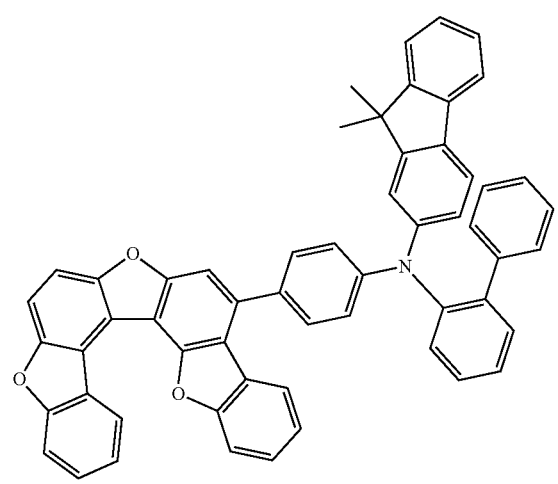
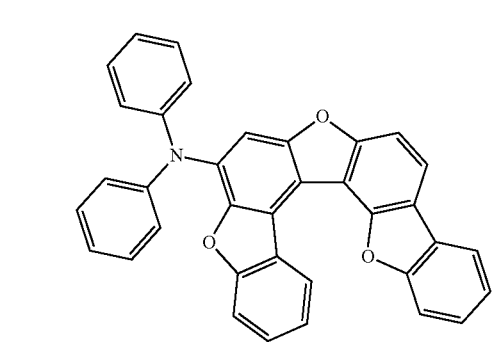

21
-continued
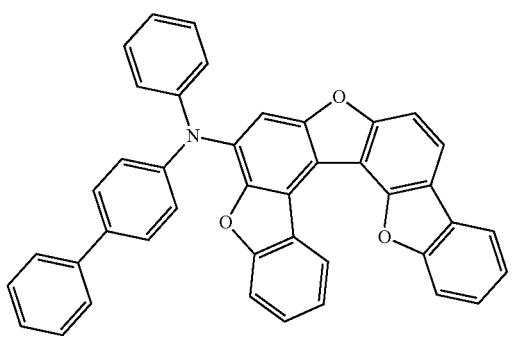
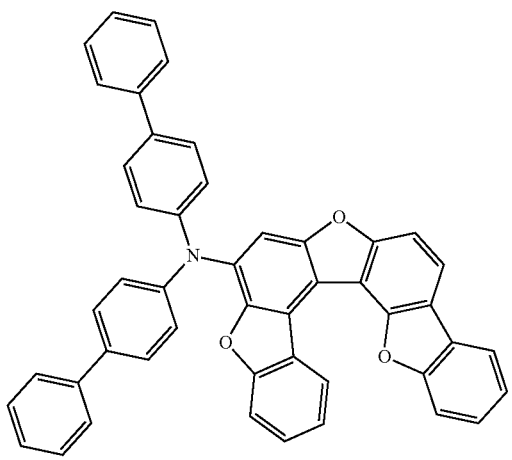
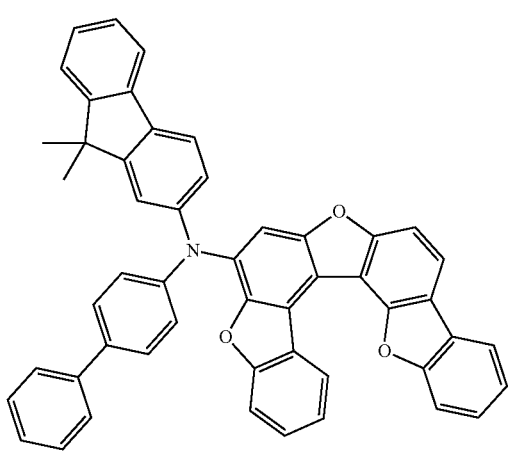
22
-continued
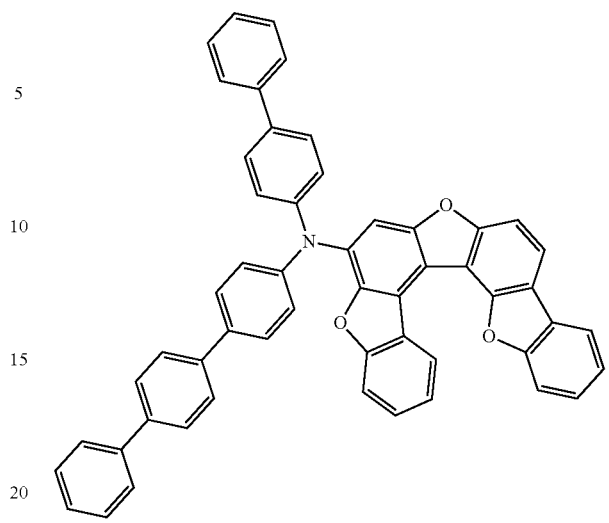
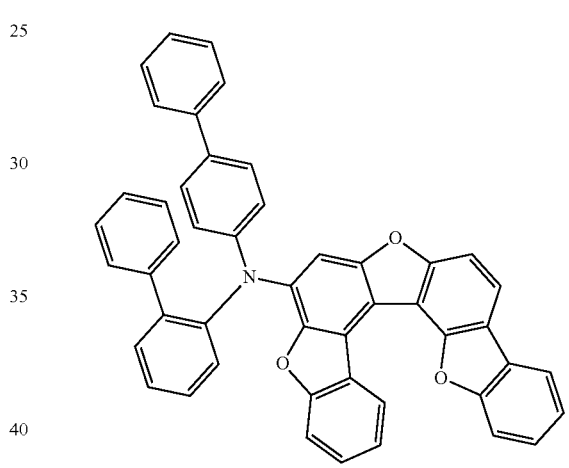
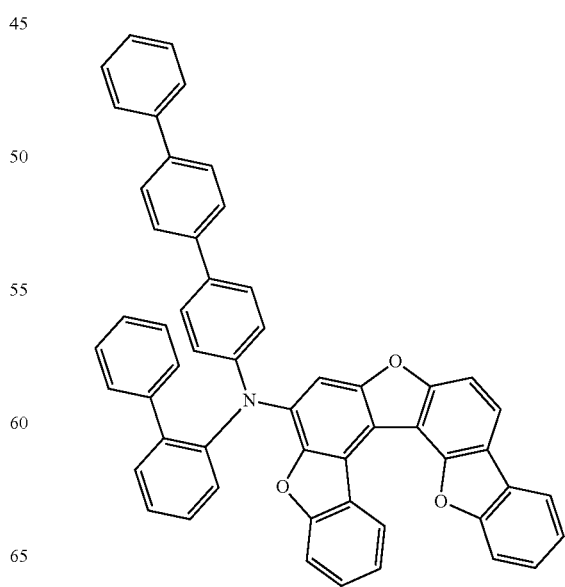

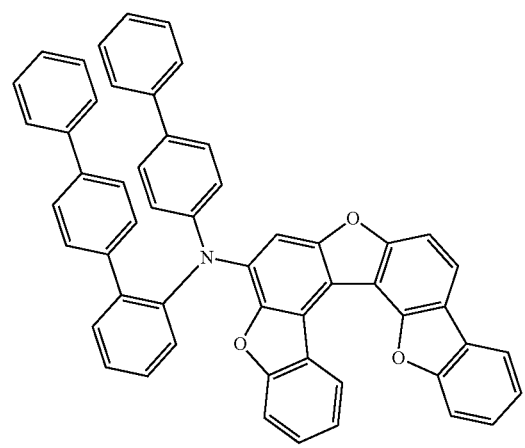
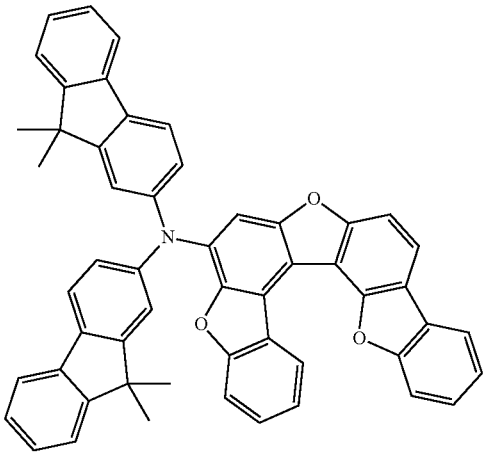
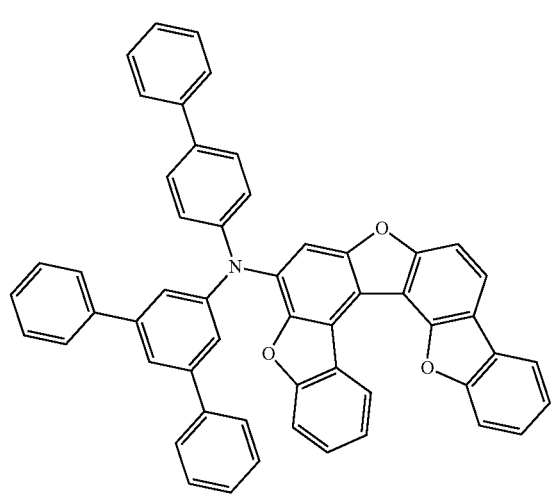
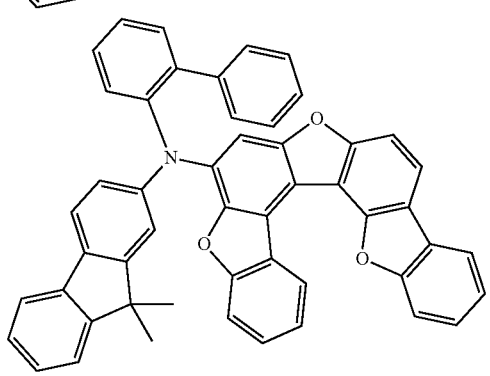
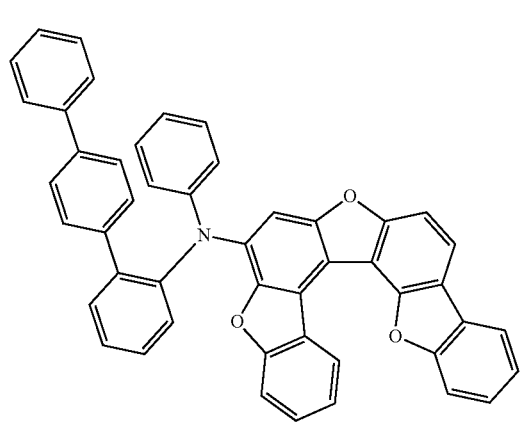
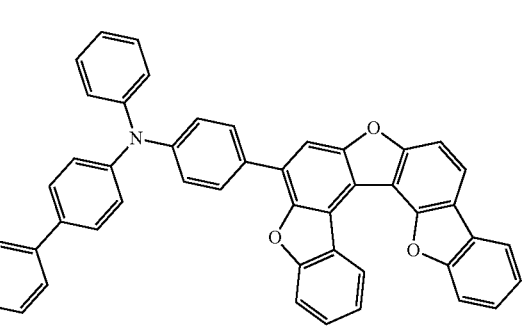

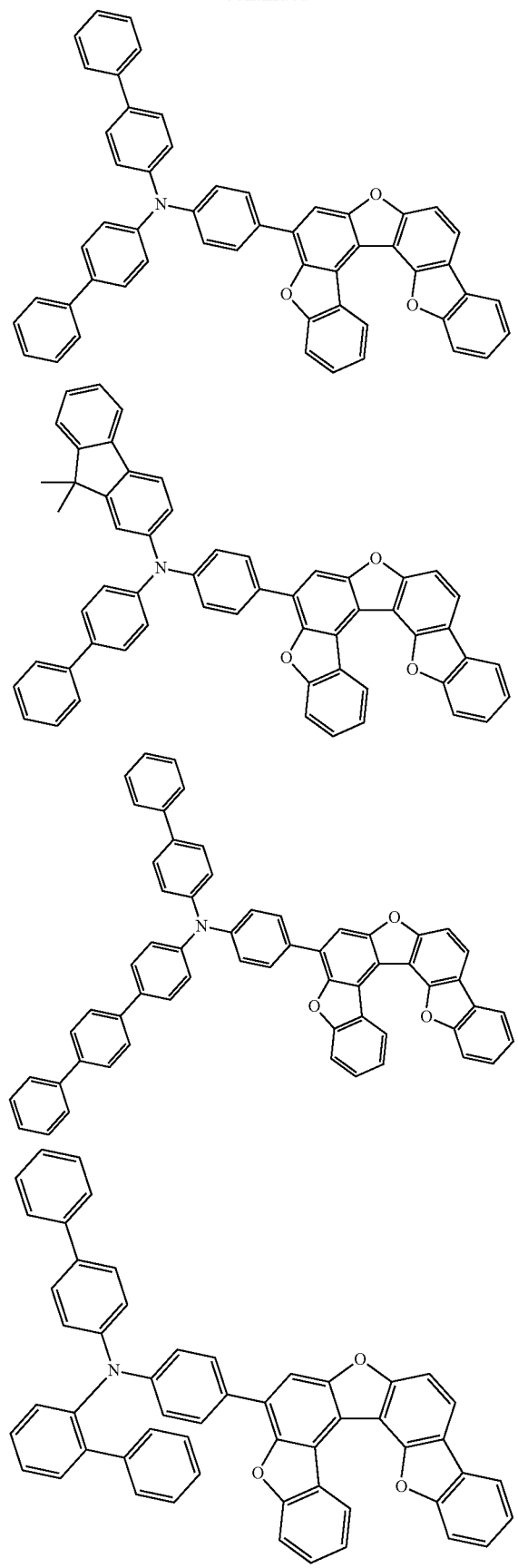
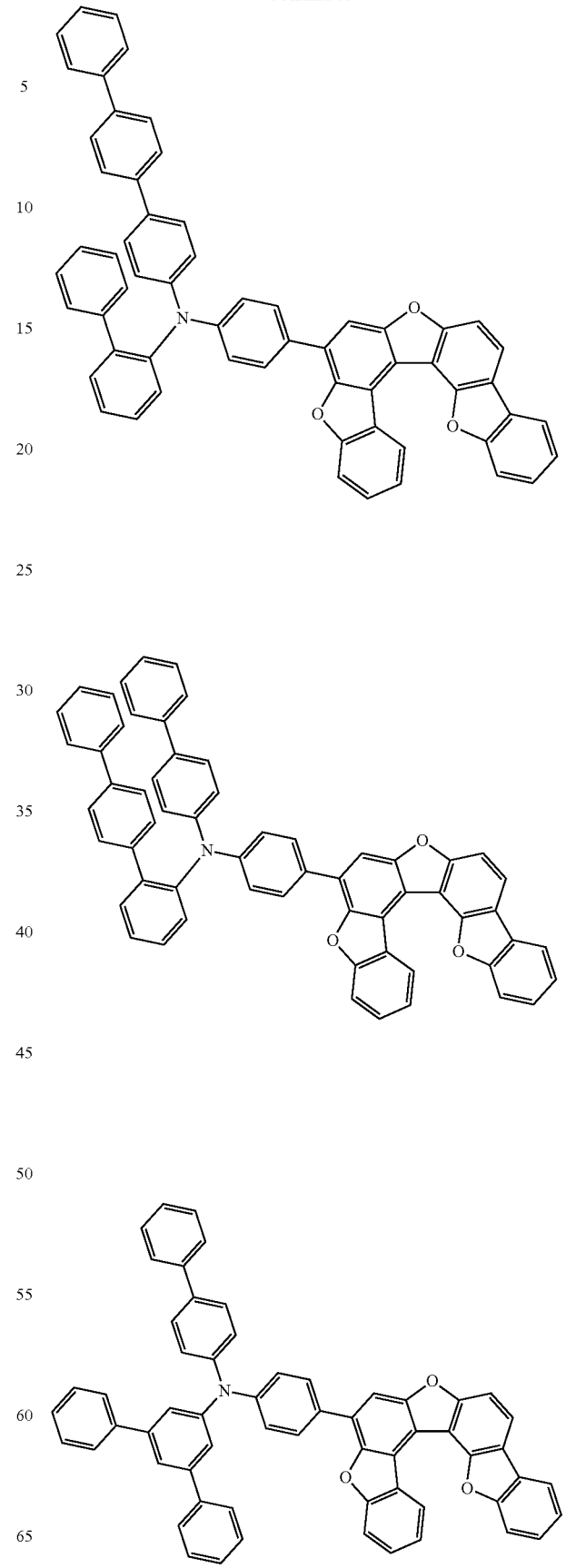

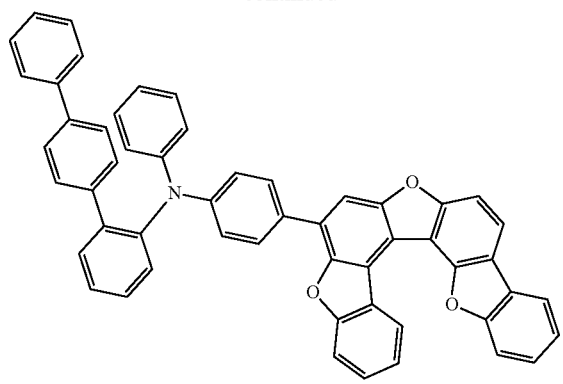
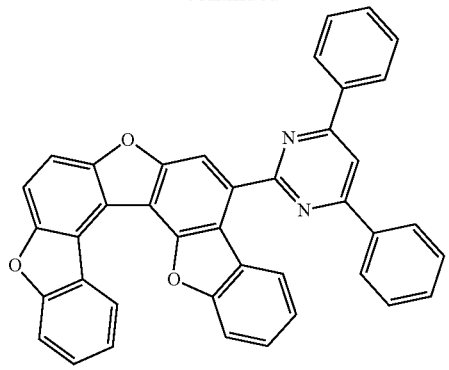
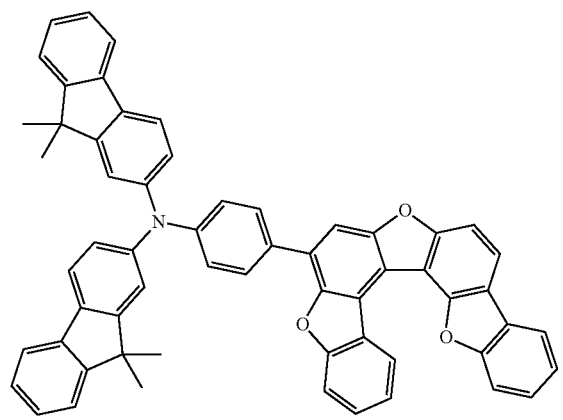
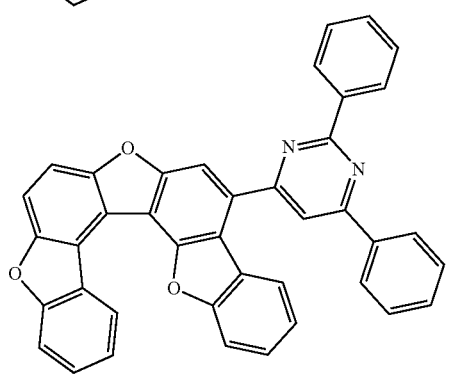
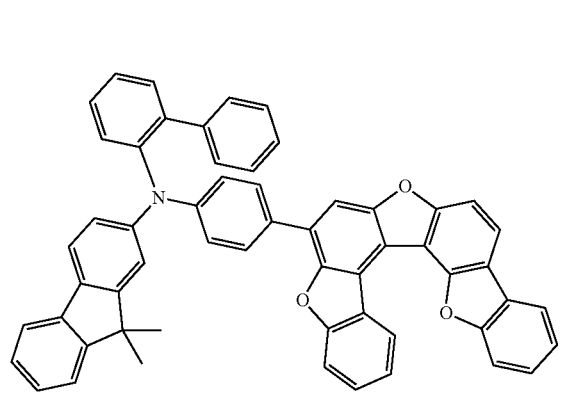
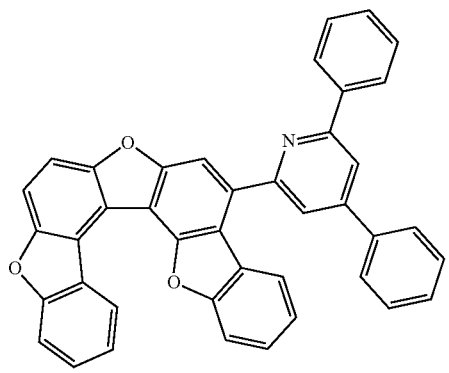
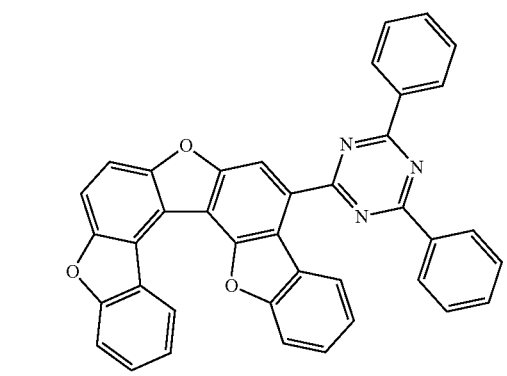
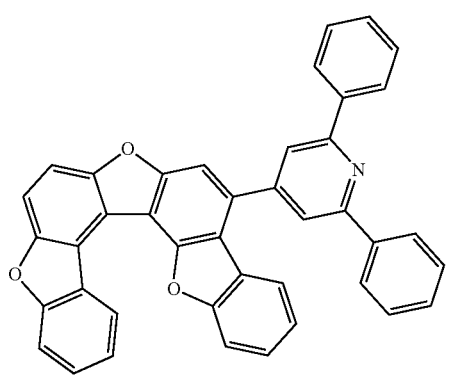

-continued
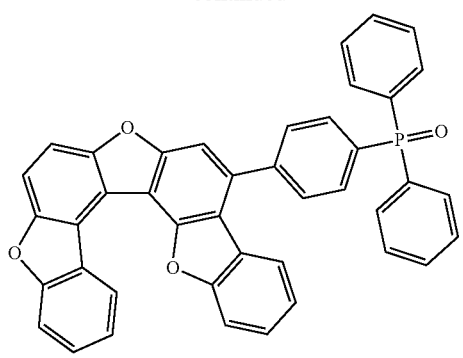
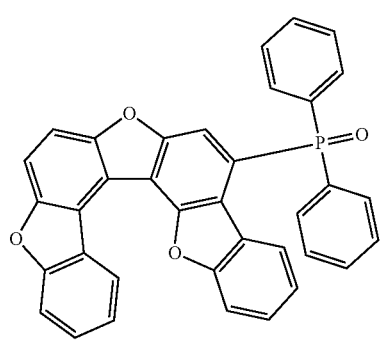
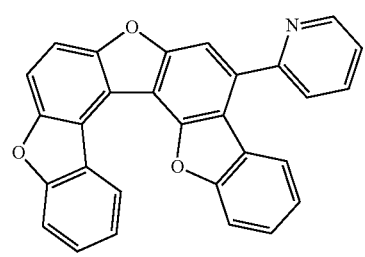
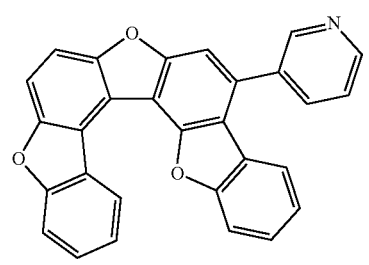
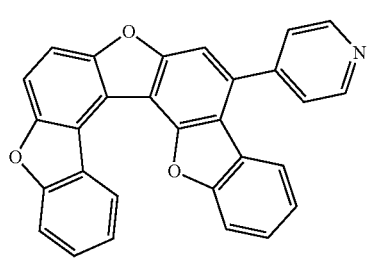
-continued
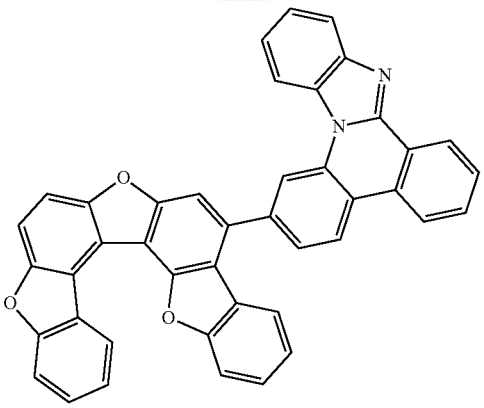
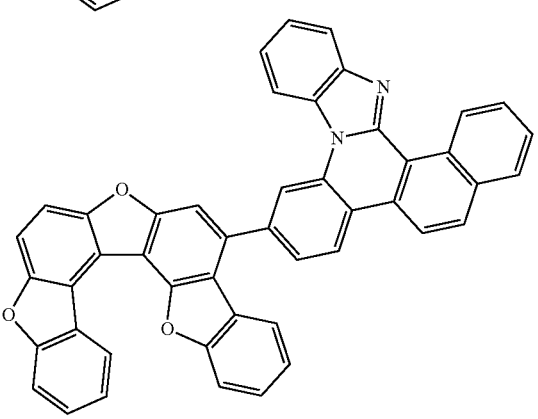
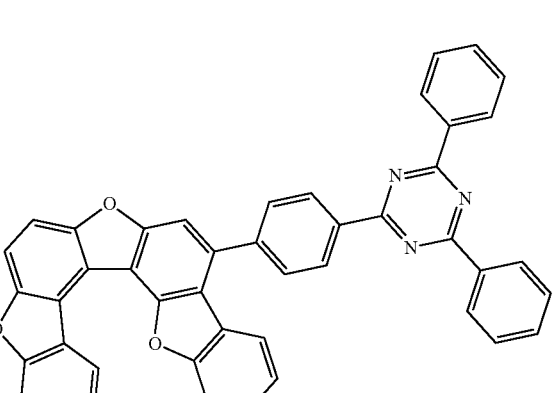
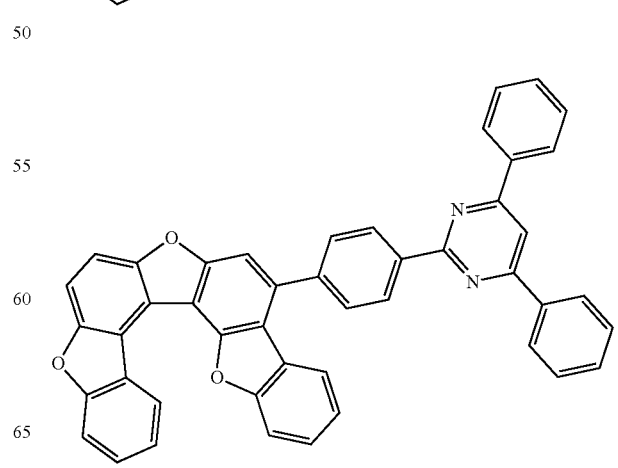

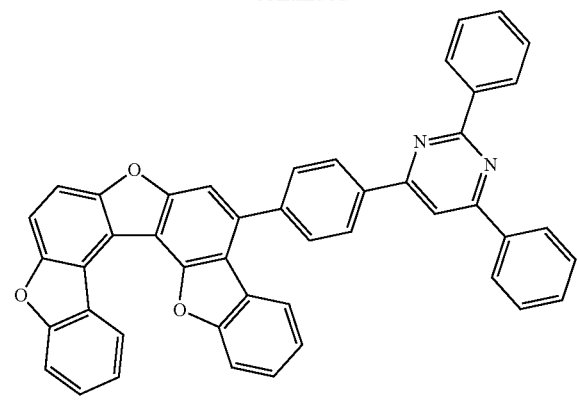
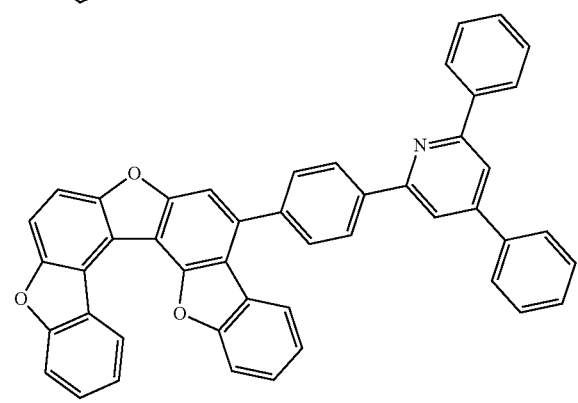
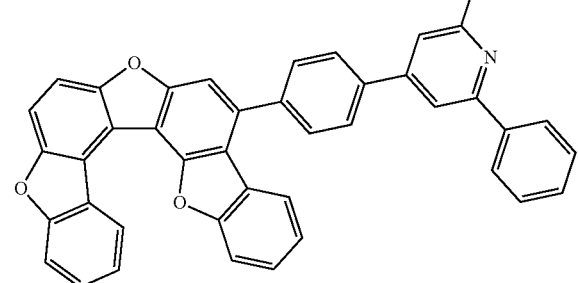
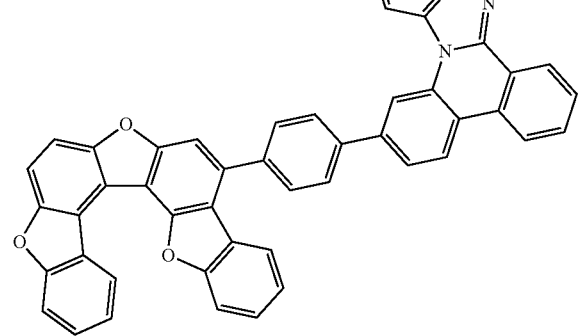
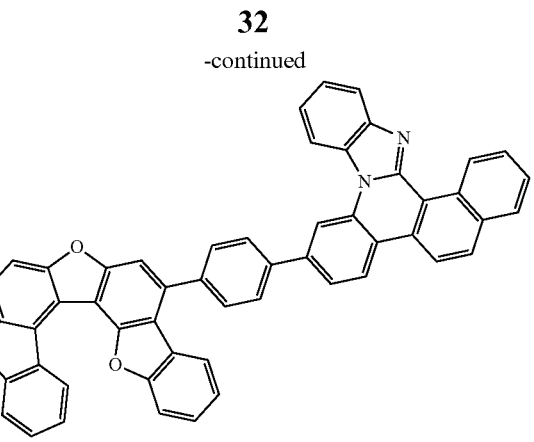
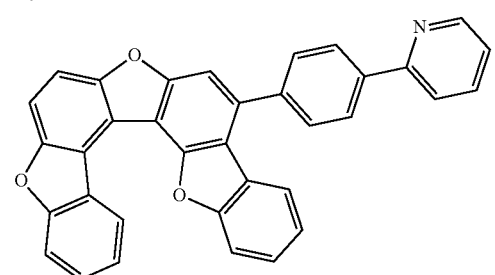
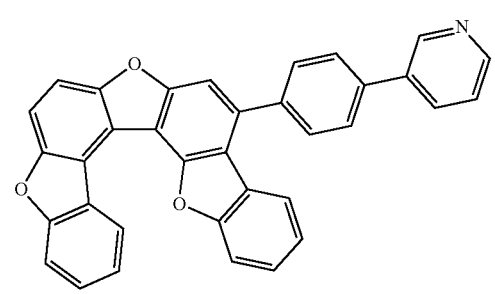
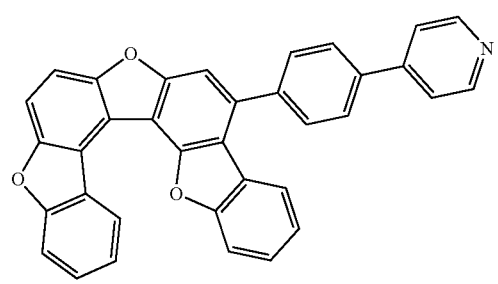
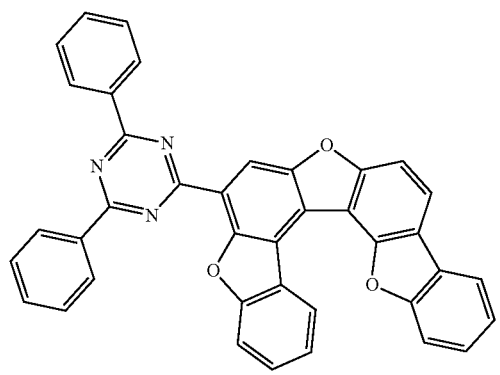

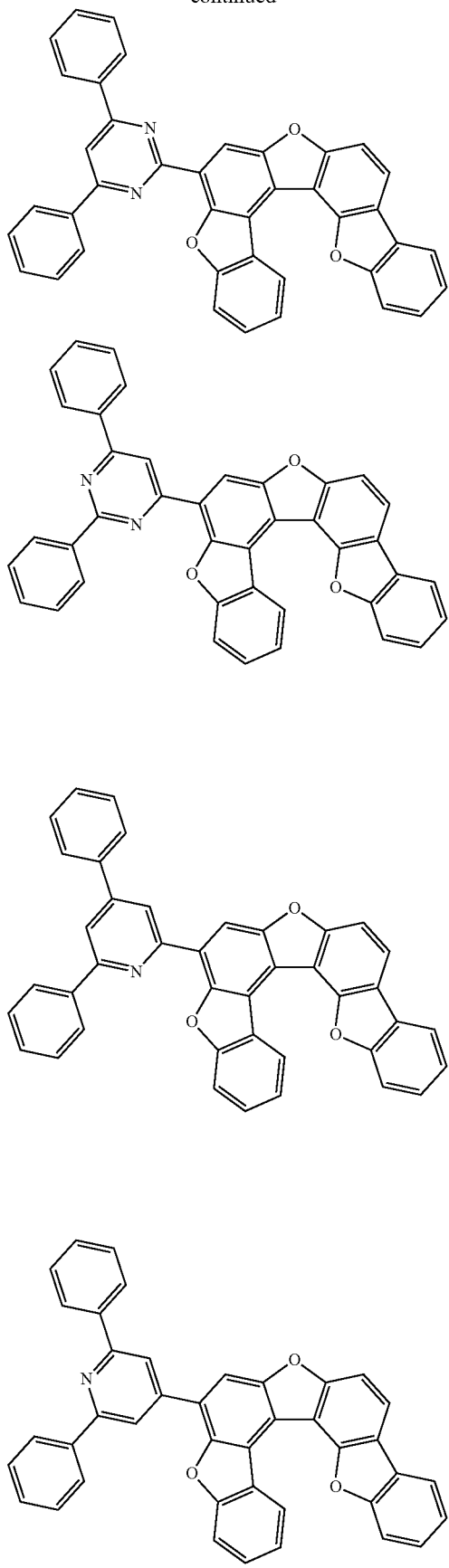
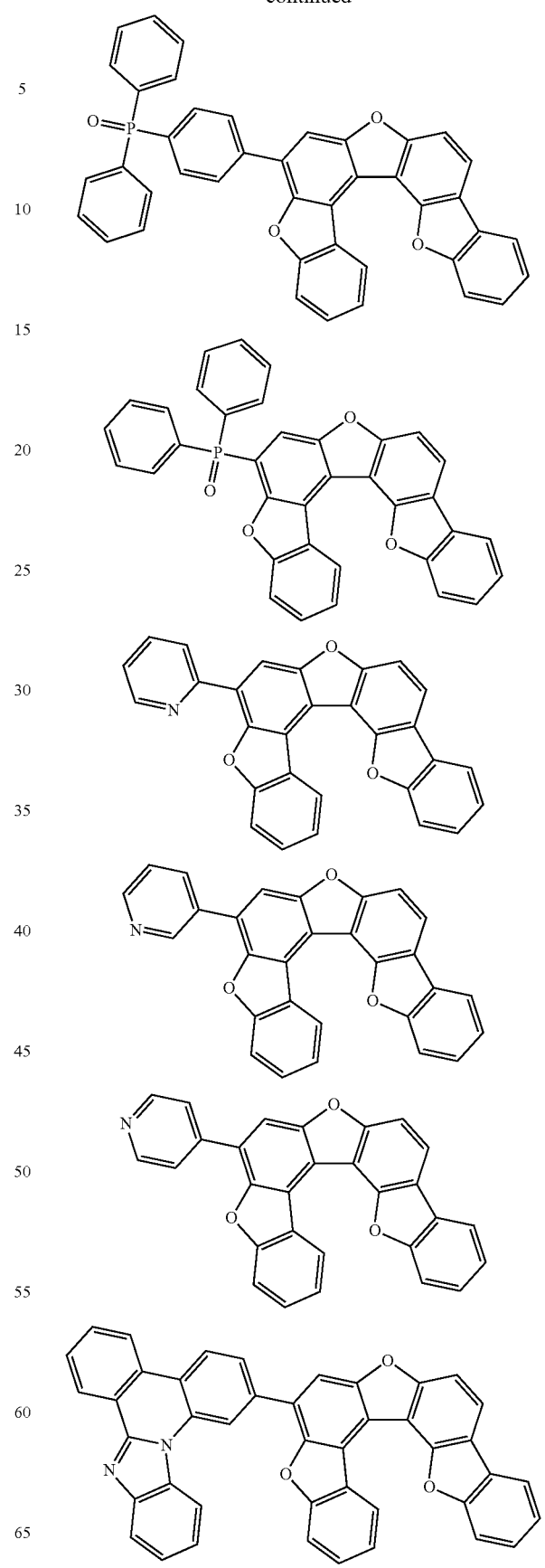

35
-continued
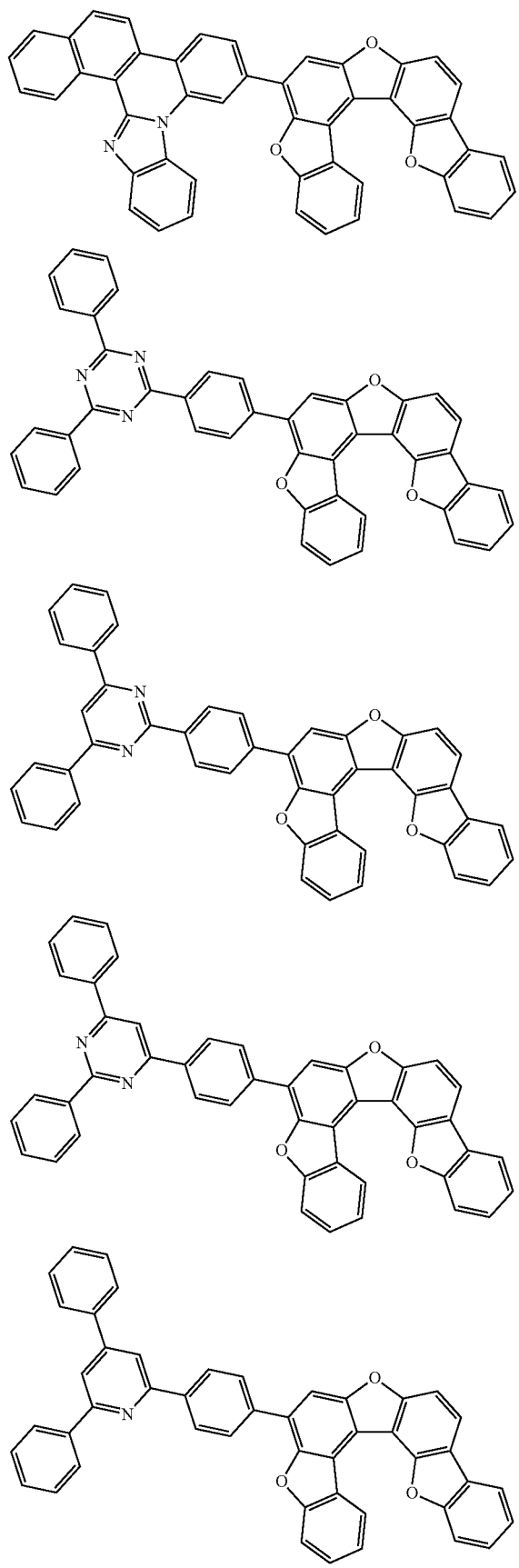
36
-continued
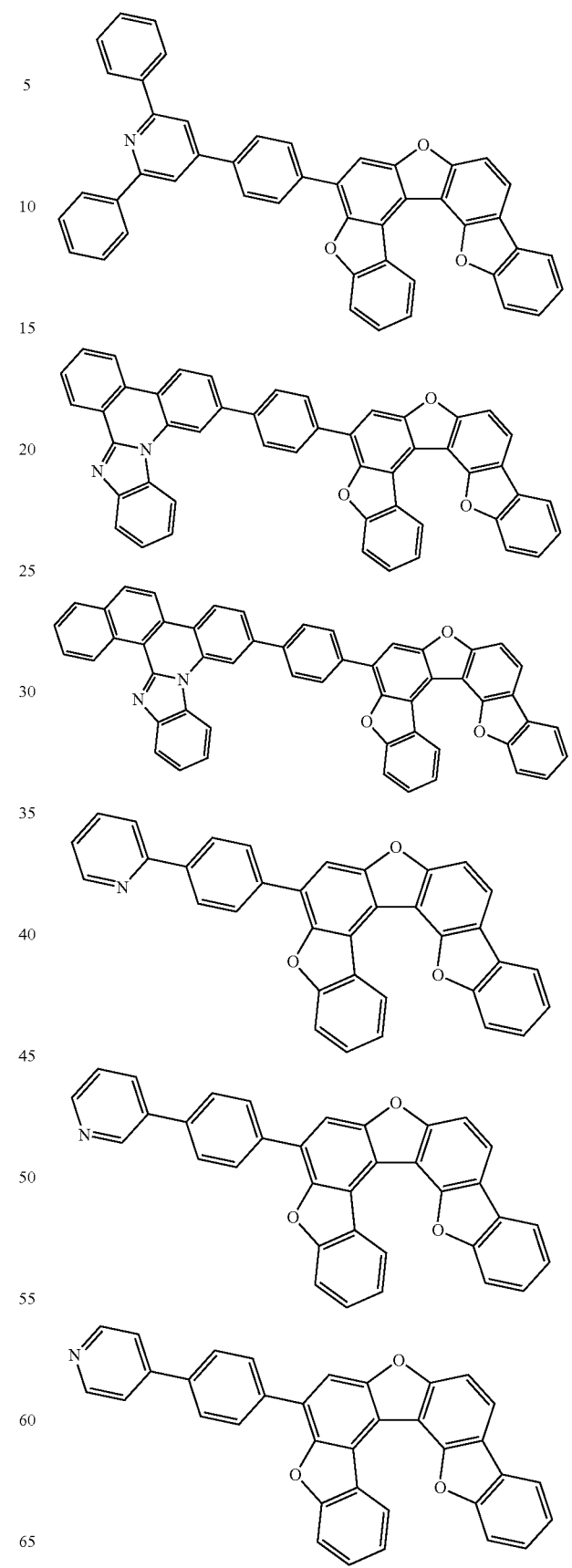

37
-continued
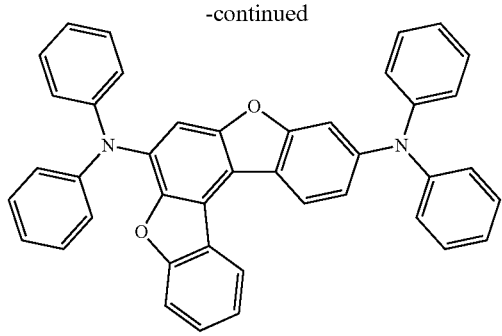
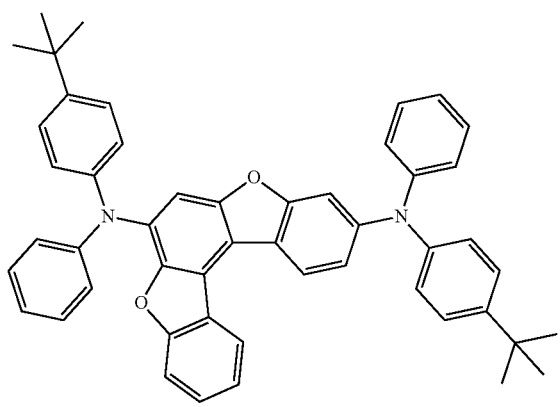
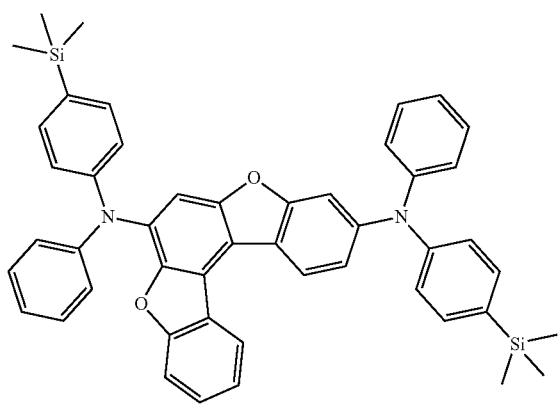
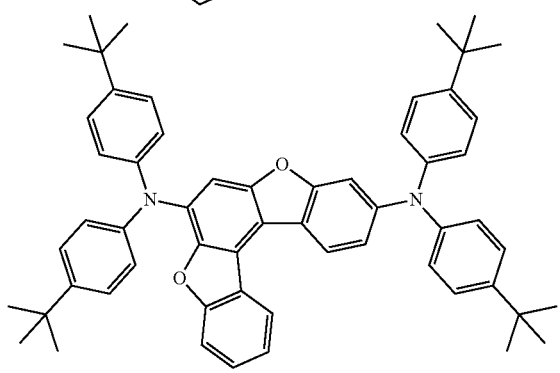
38
-continued
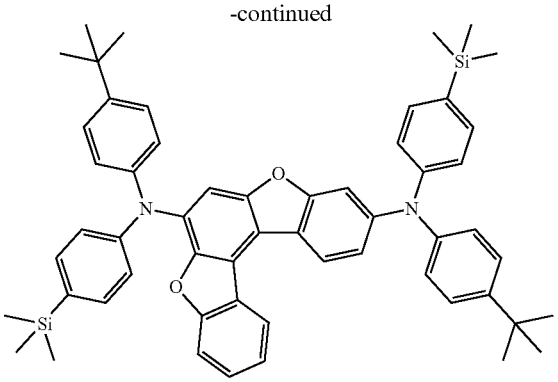
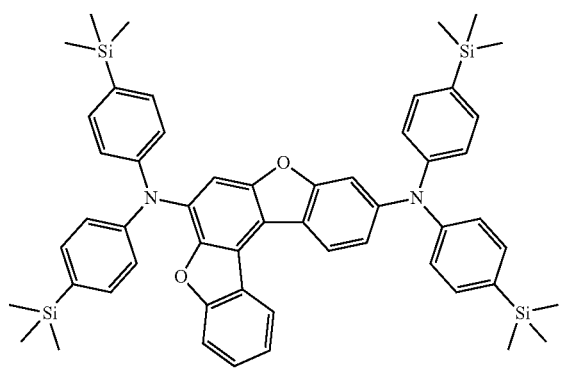
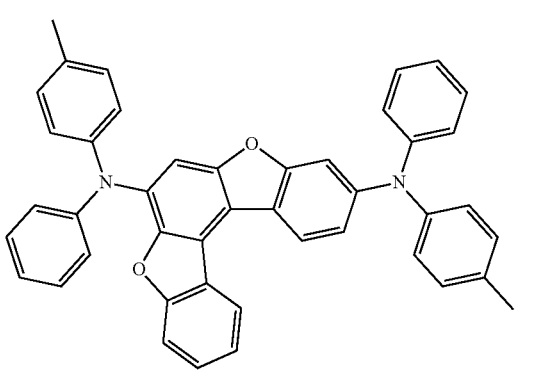

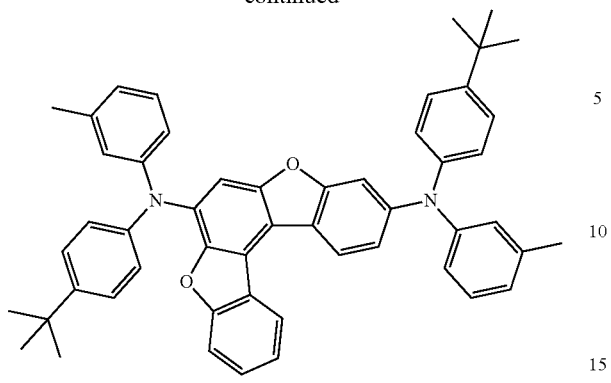
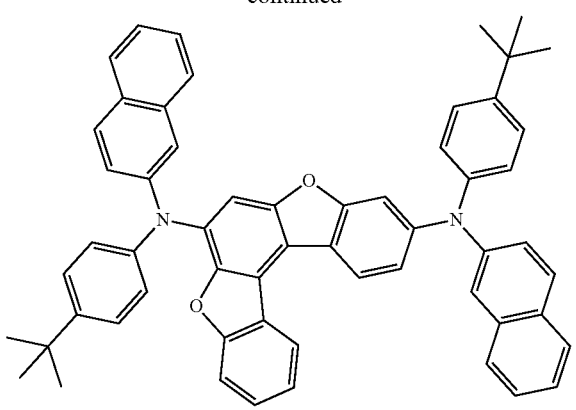
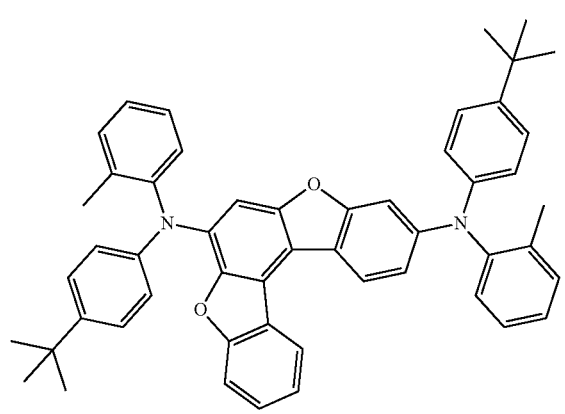
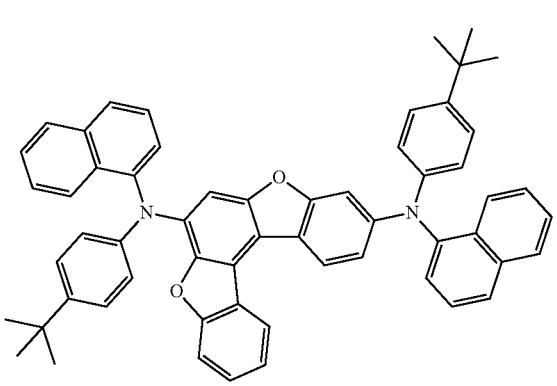
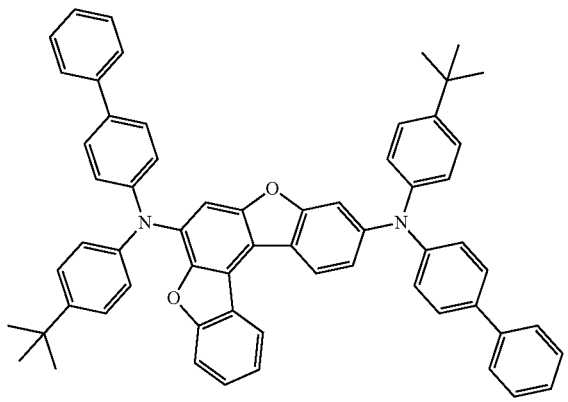
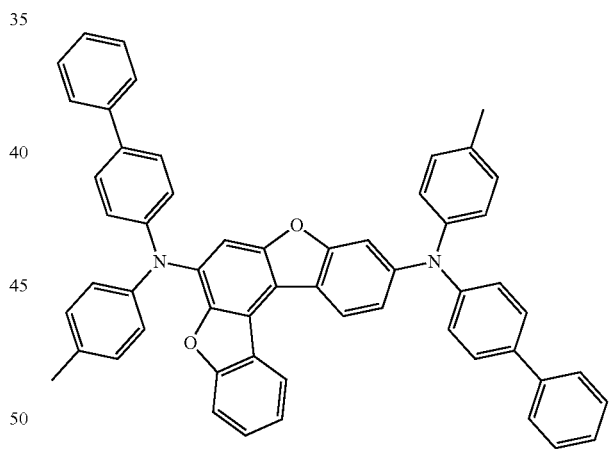
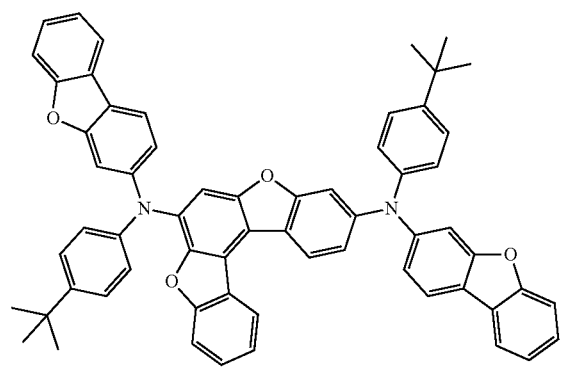
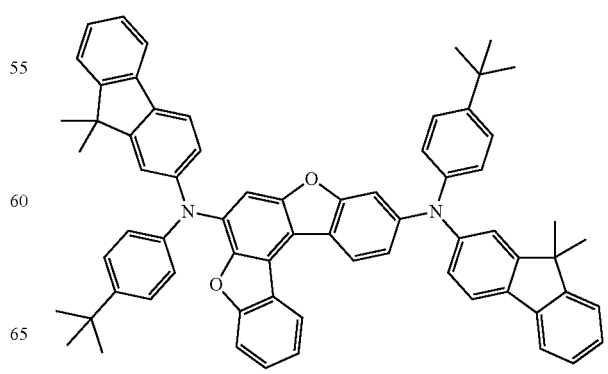

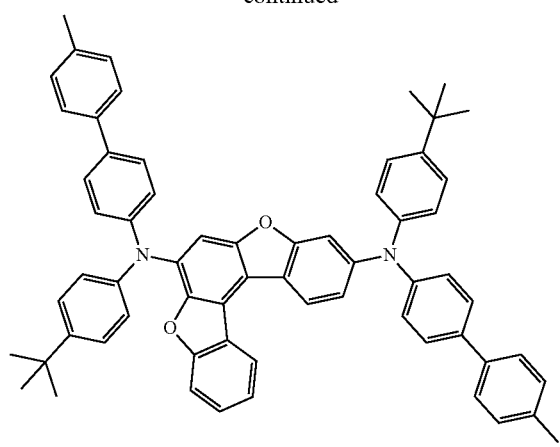
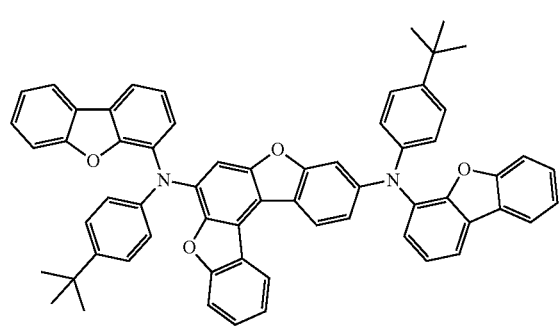
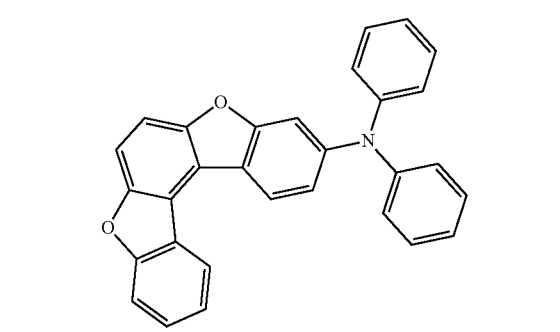
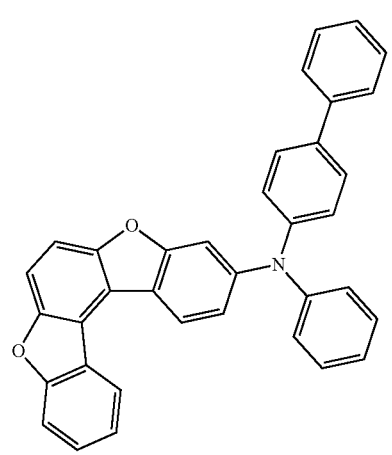
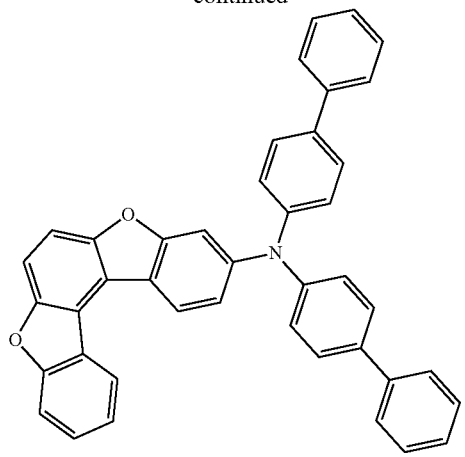
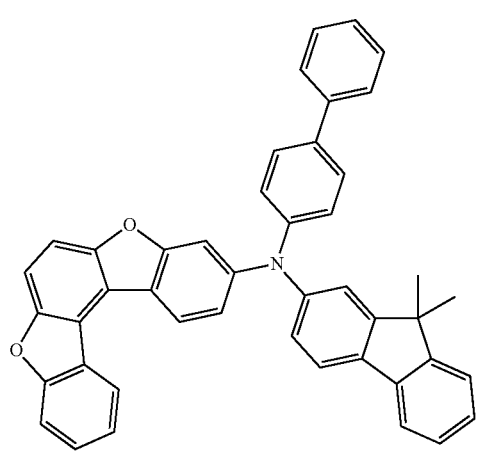
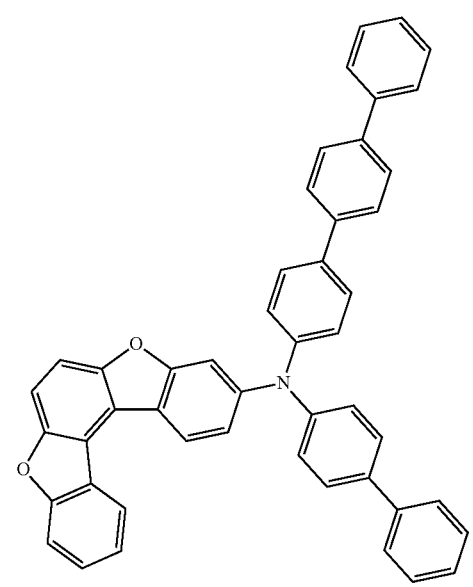

43
-continued
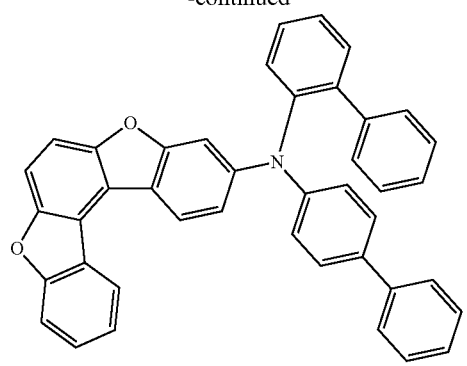
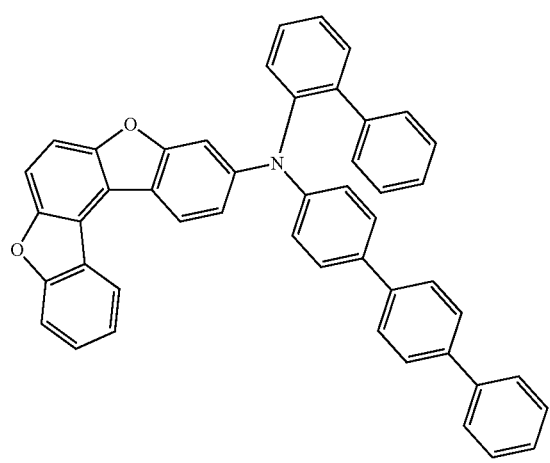
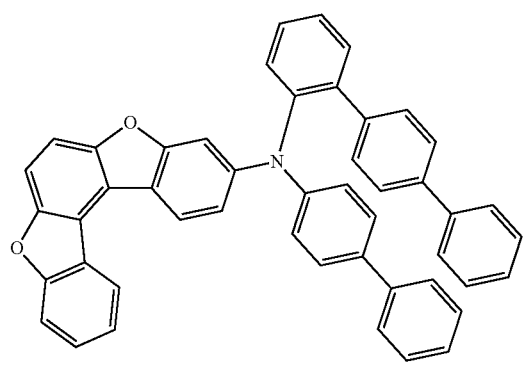
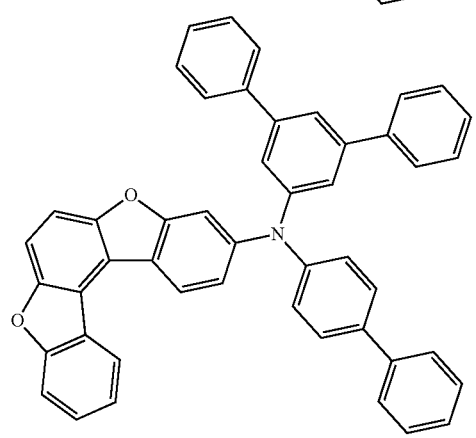
44
-continued
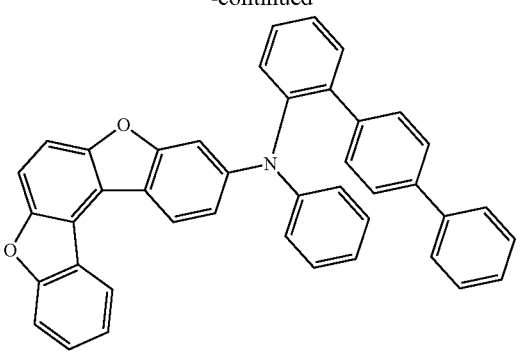
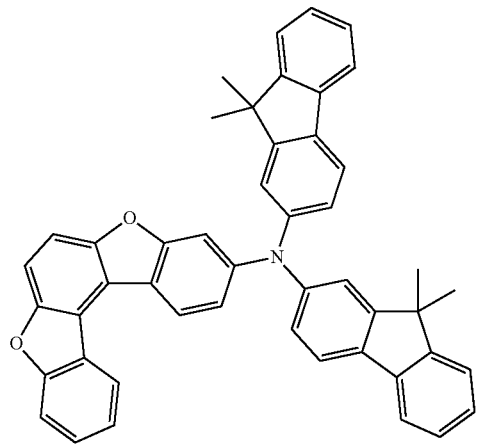
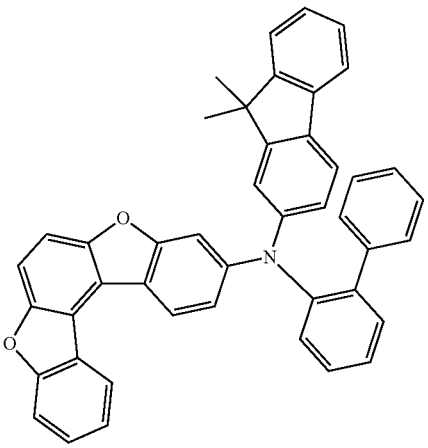
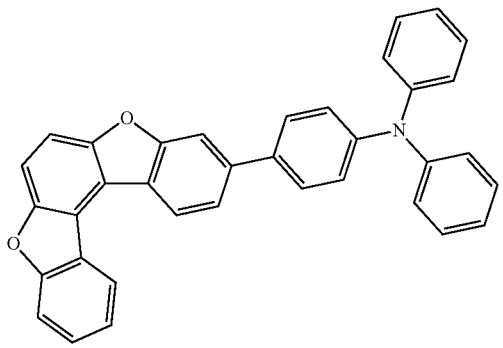

45
-continued
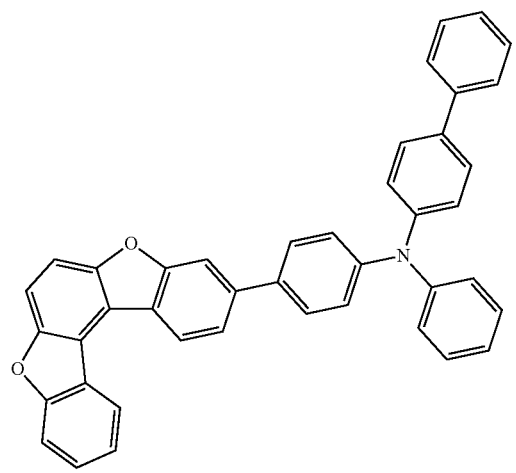
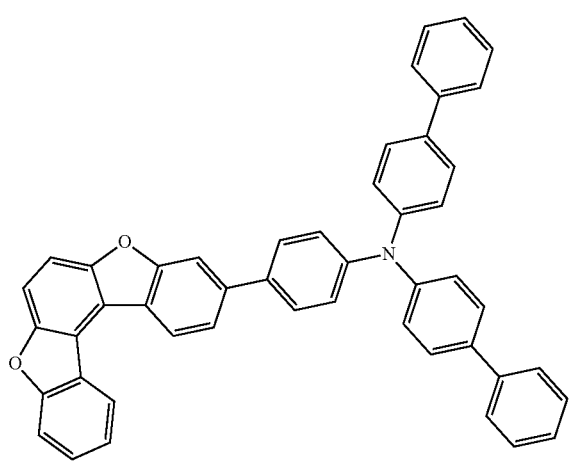
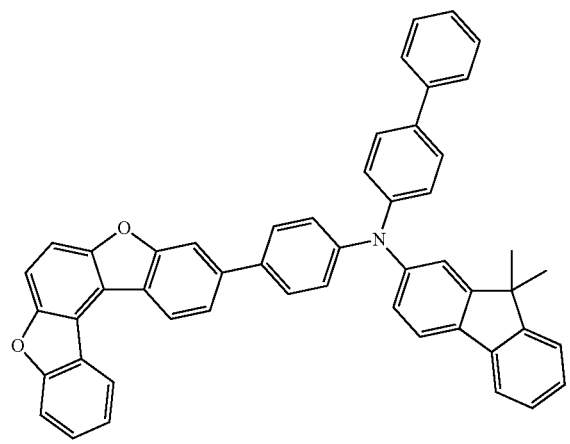
46
-continued
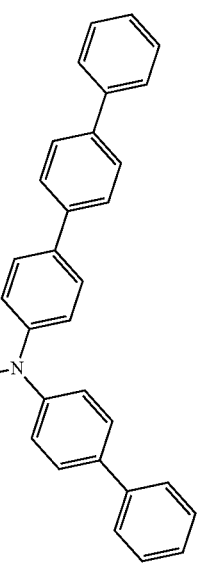
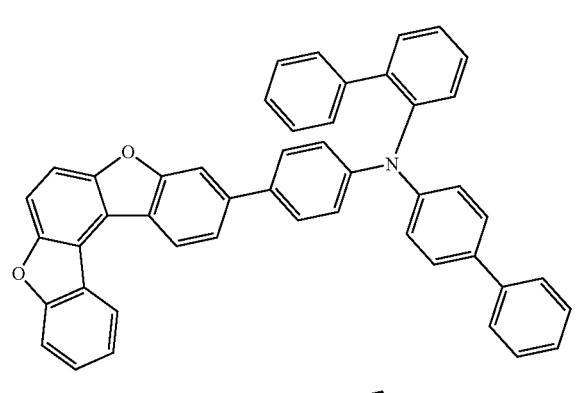
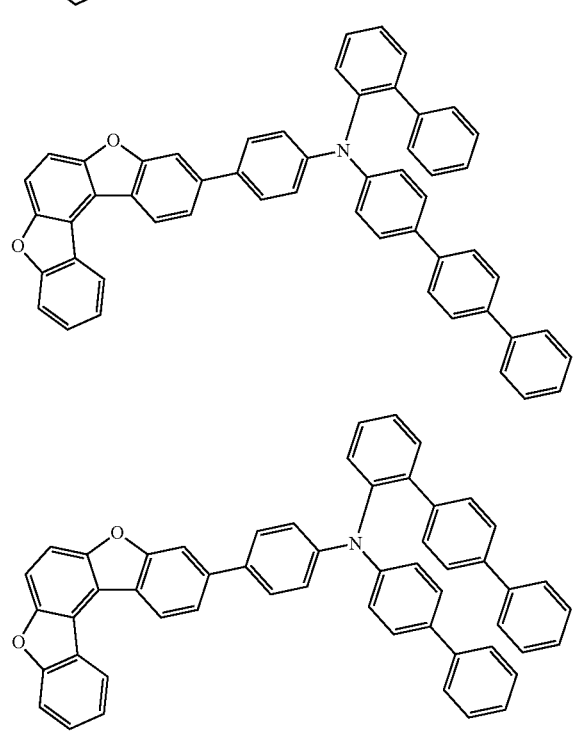

-continued
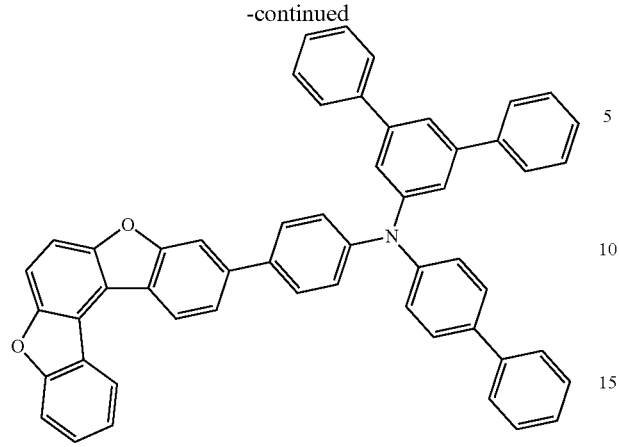
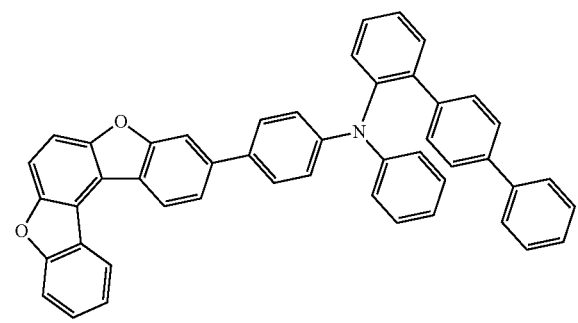
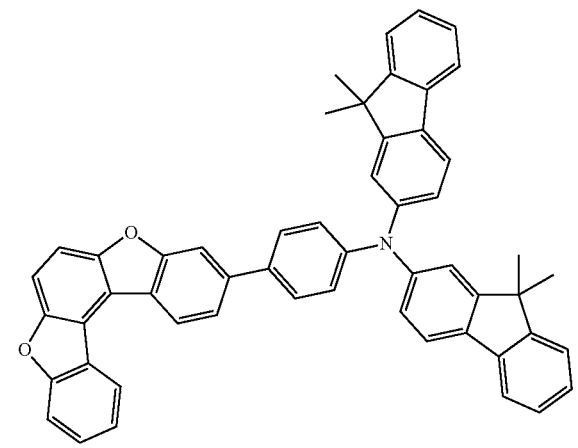
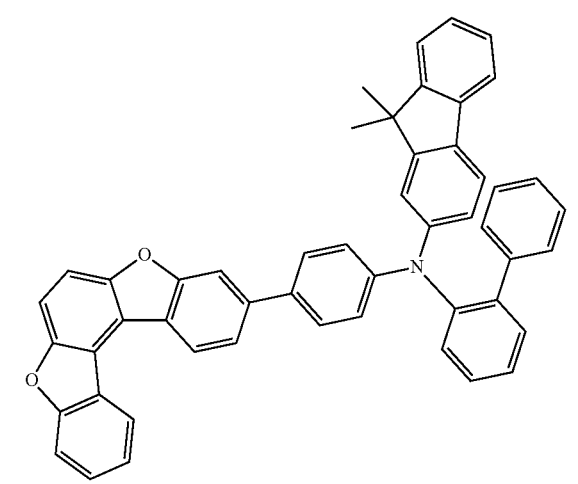
-continued
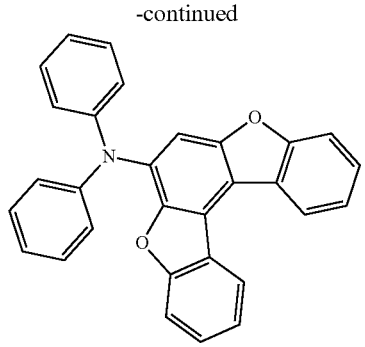
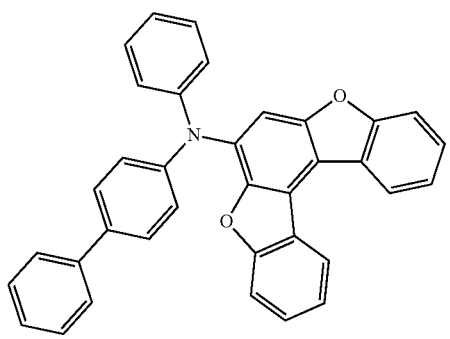
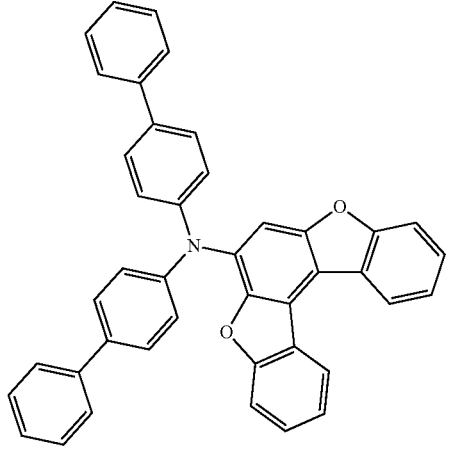
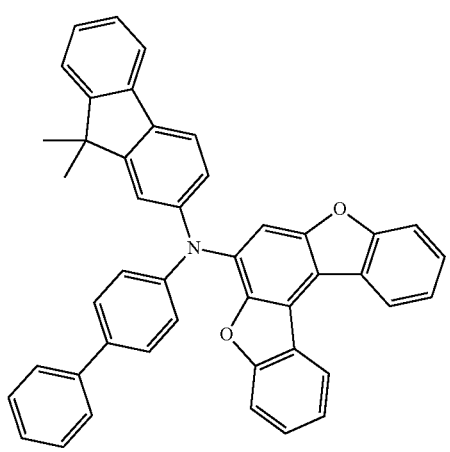

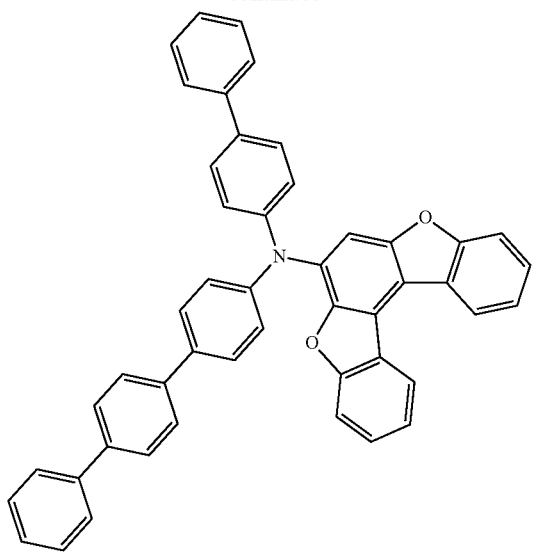
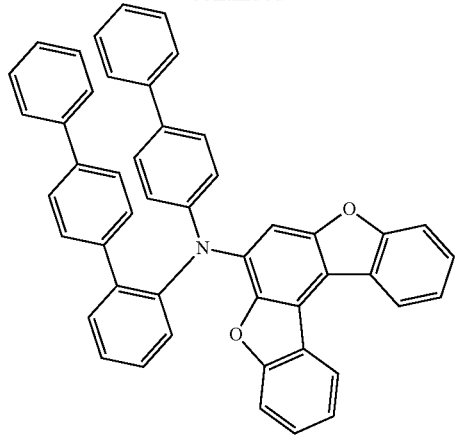
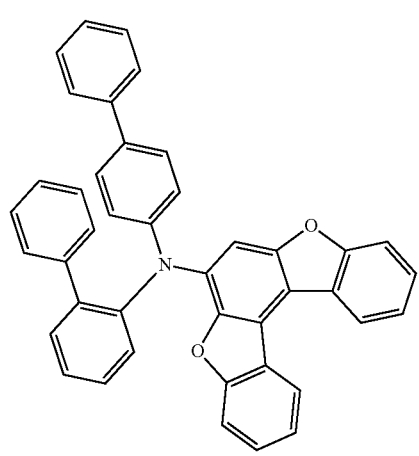
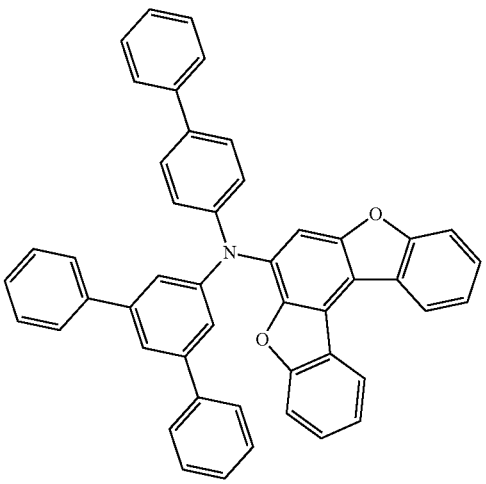
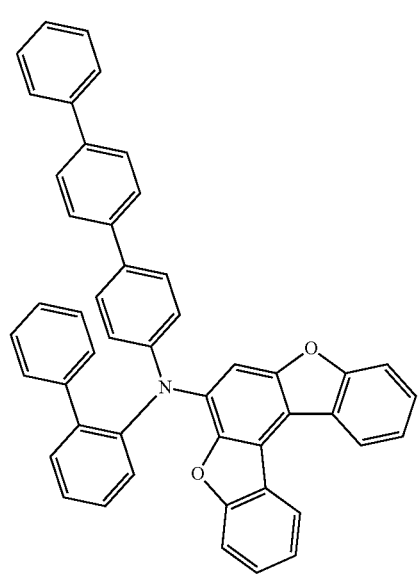
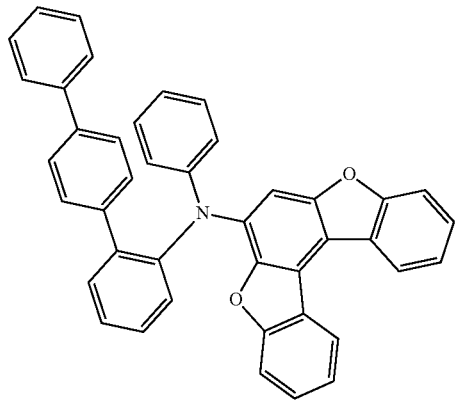

51
-continued
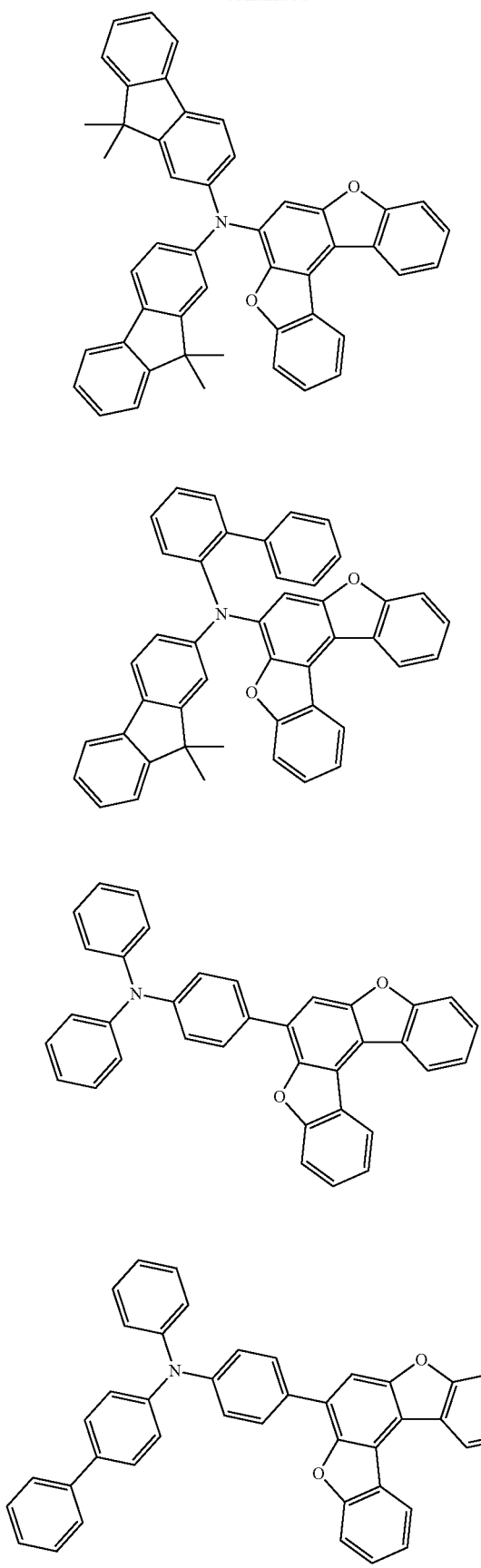
52
-continued
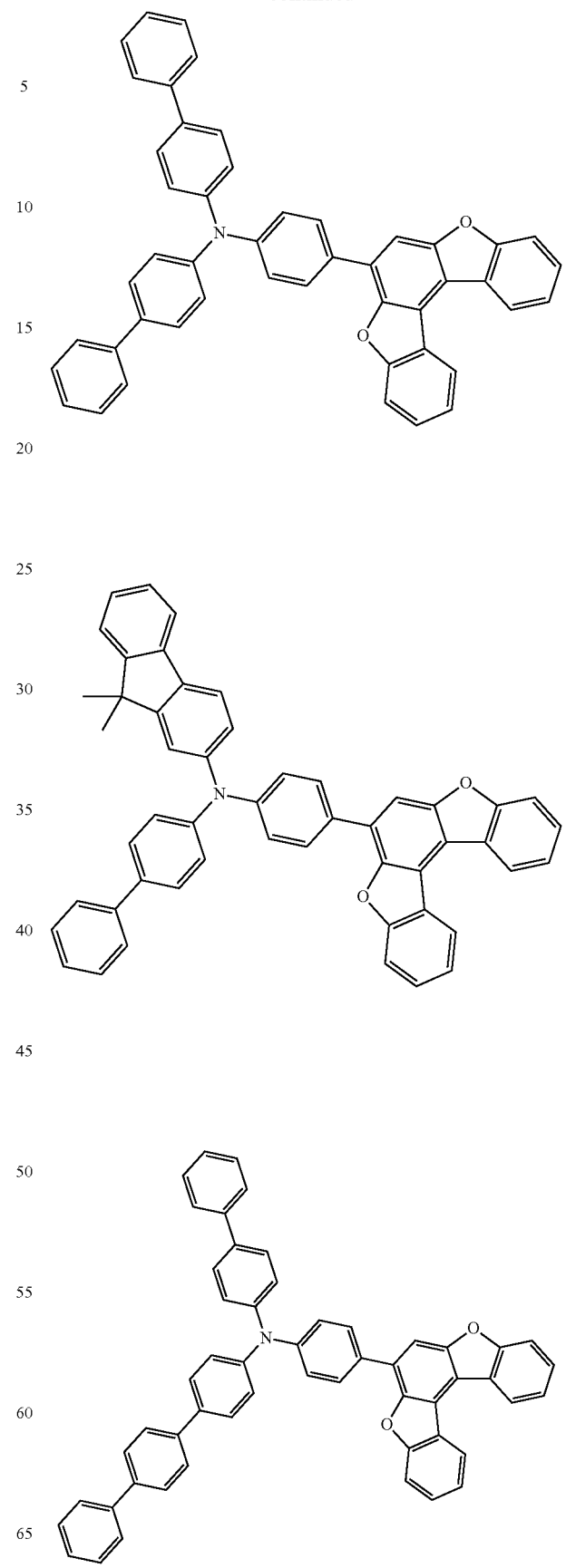

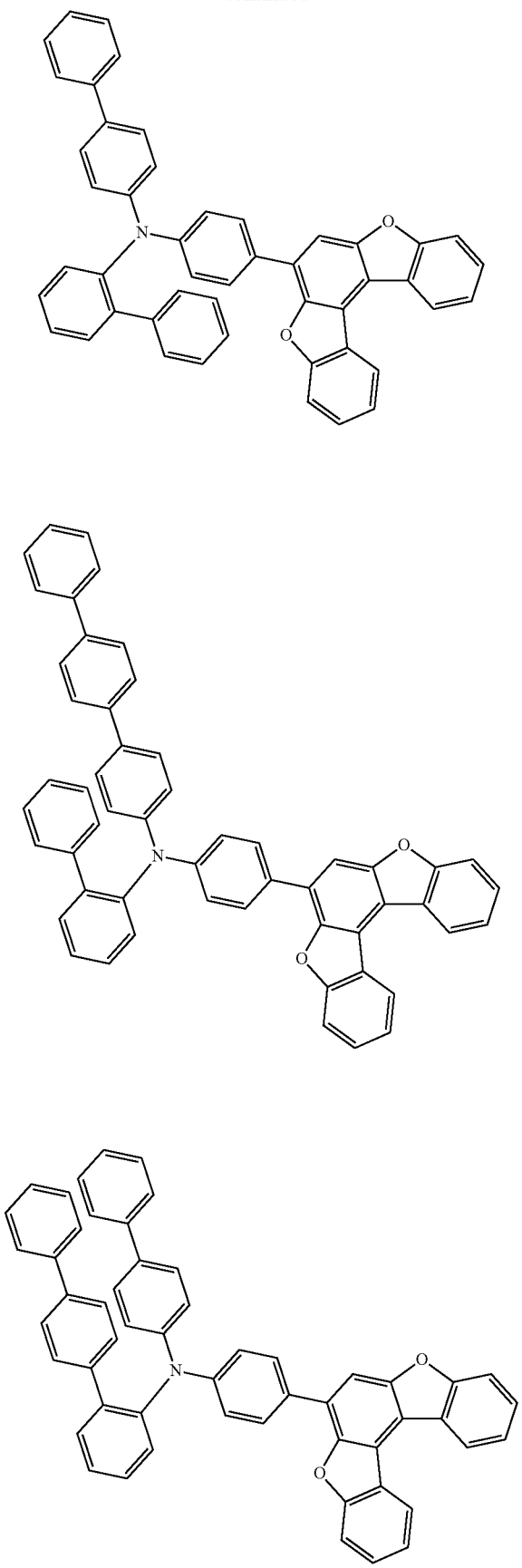
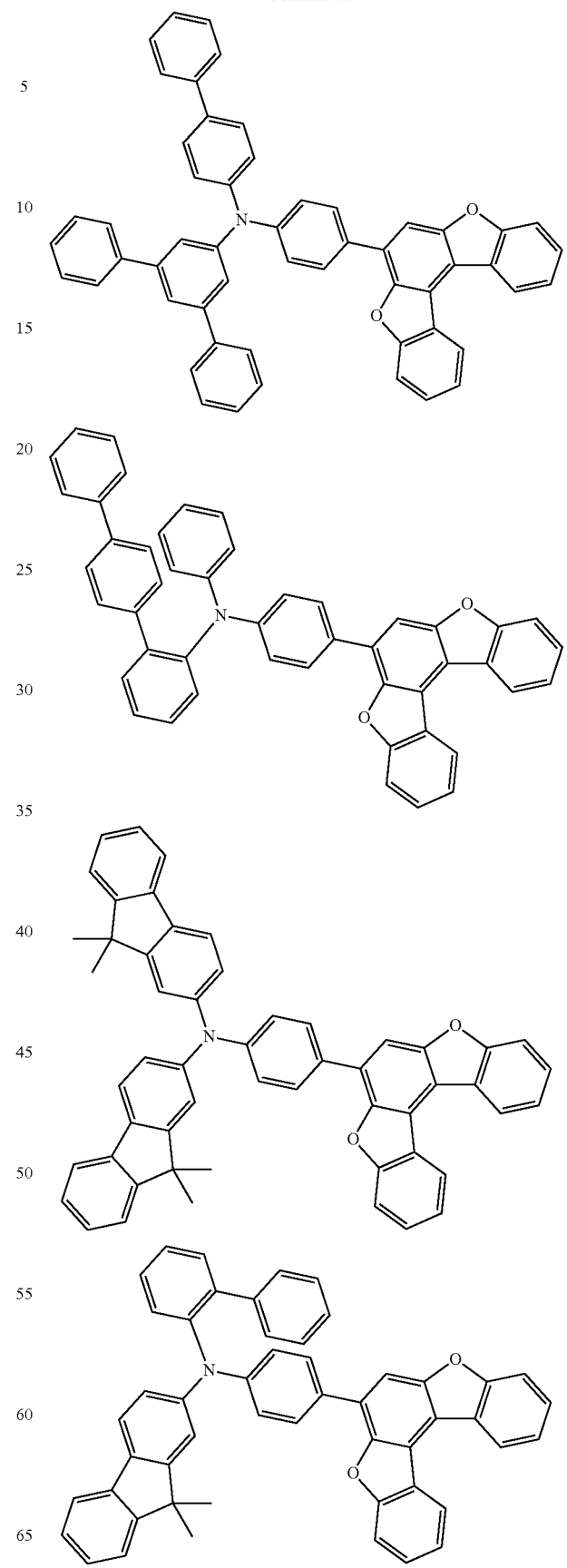

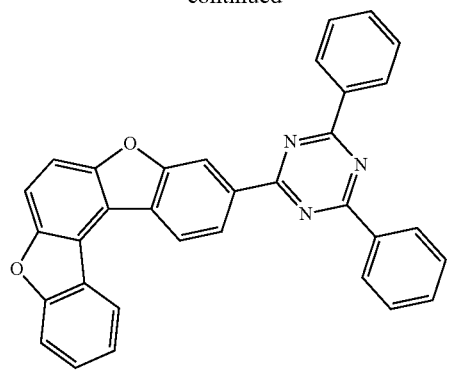
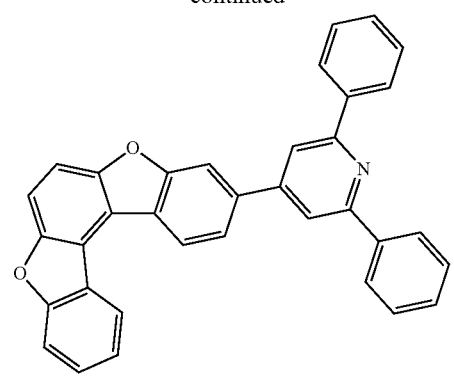
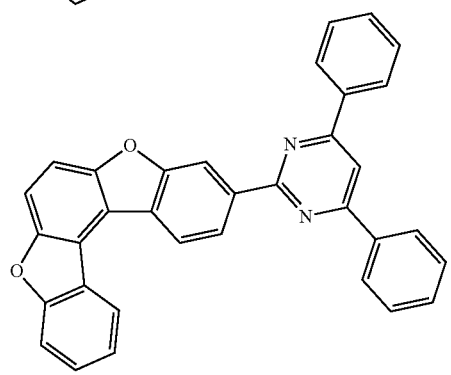
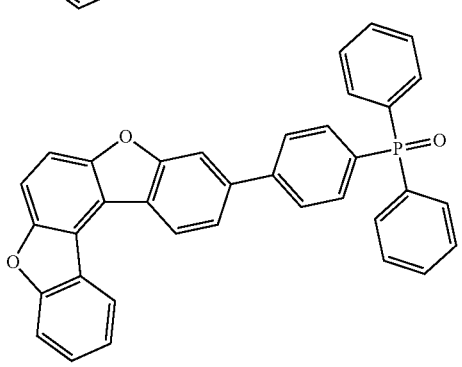
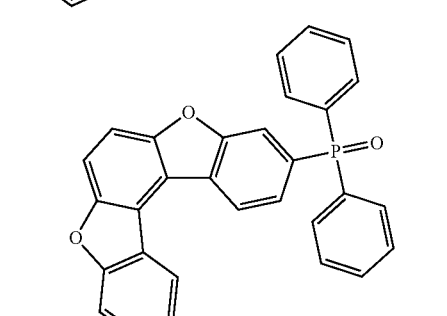
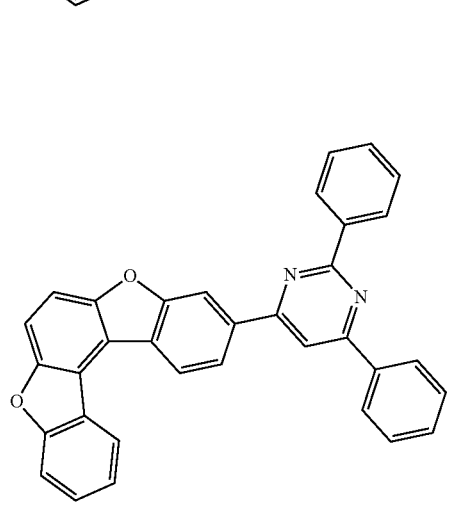
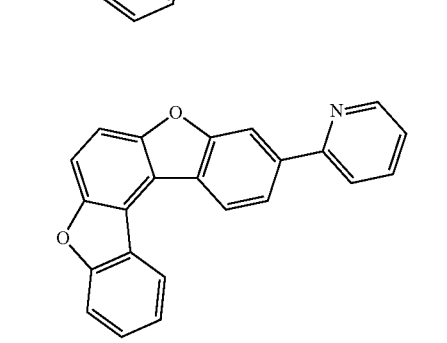
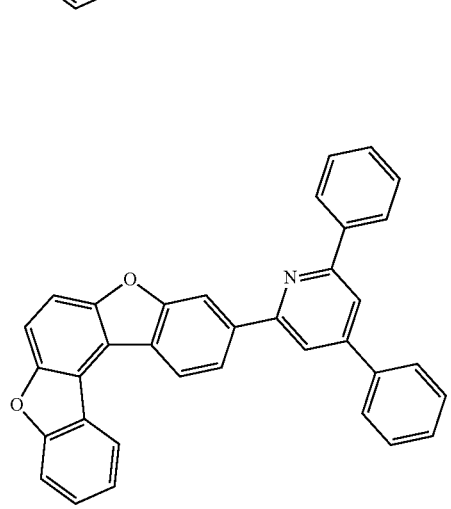
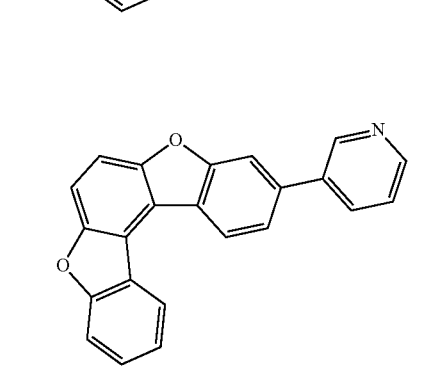

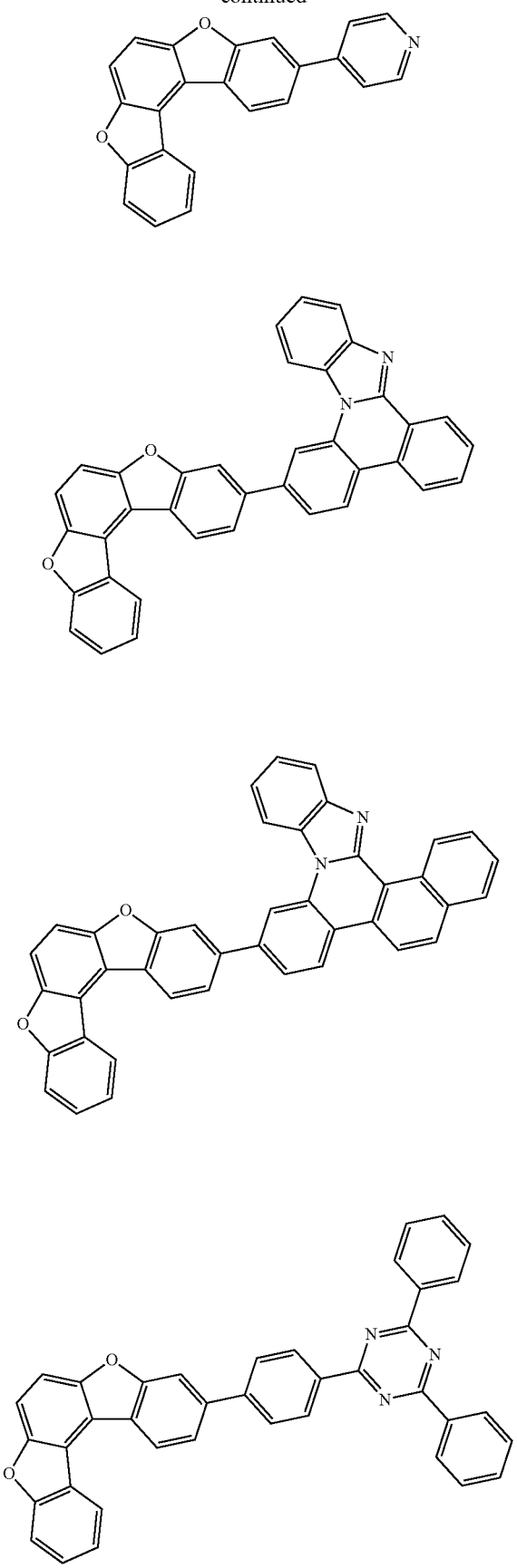

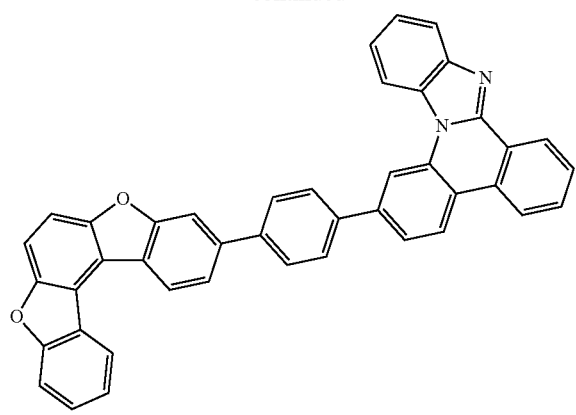
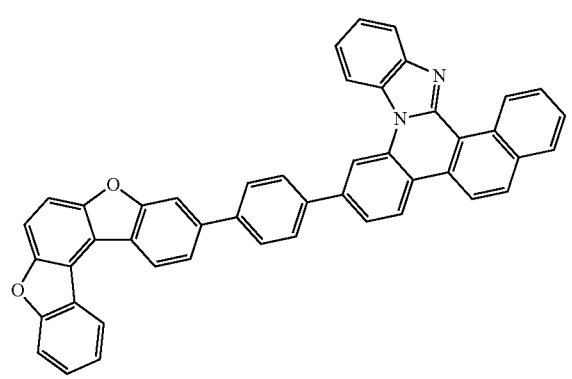
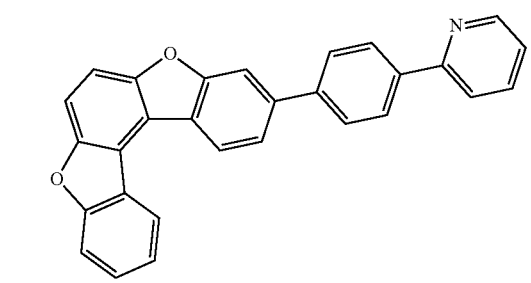
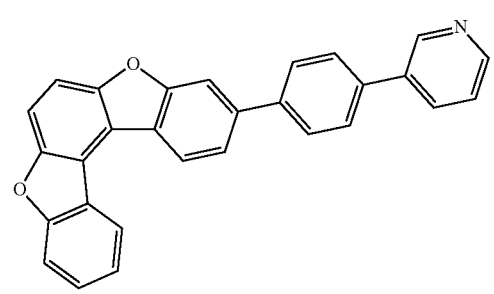
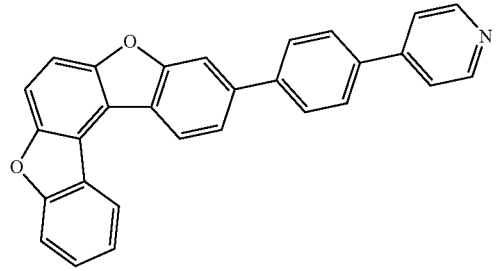
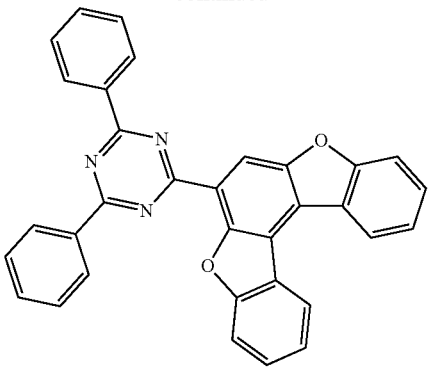
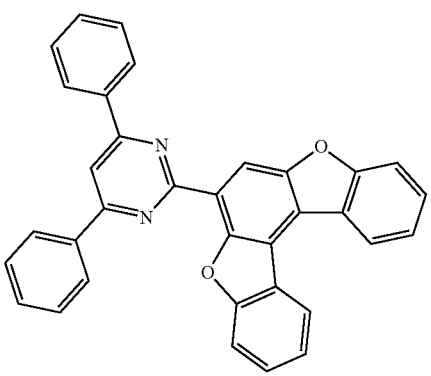
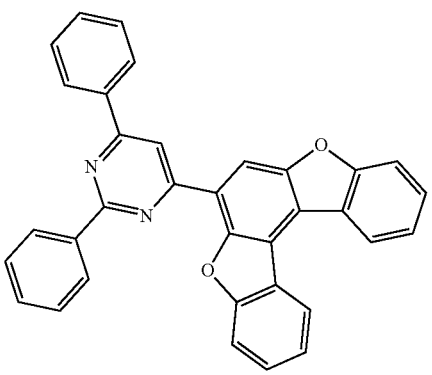
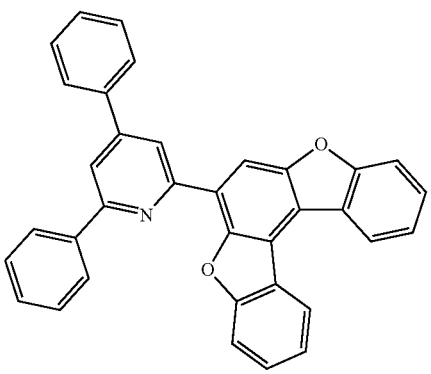

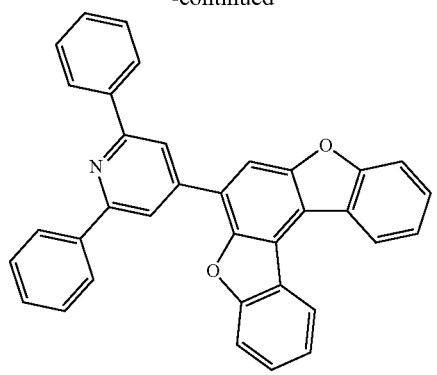
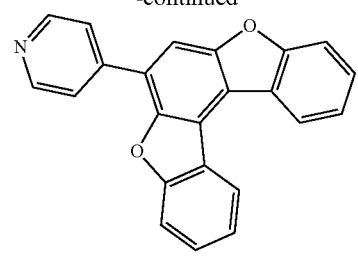
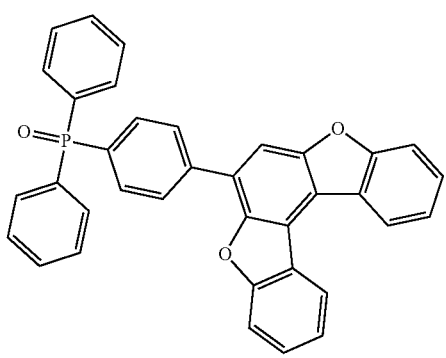
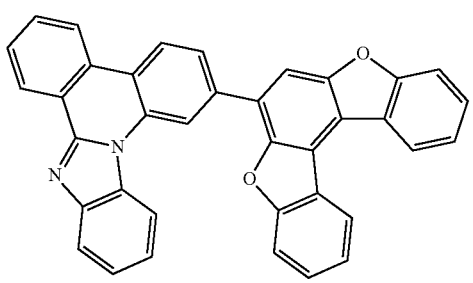
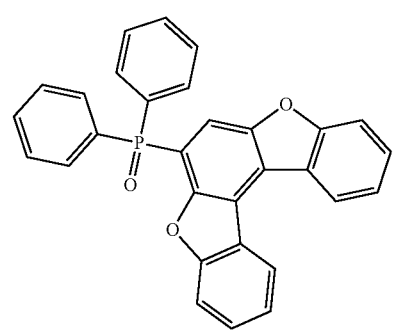
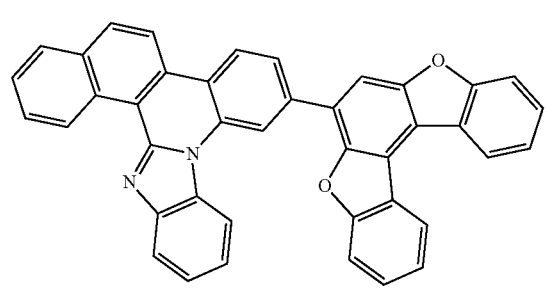
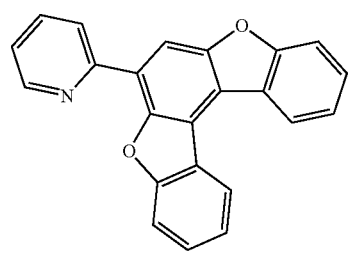
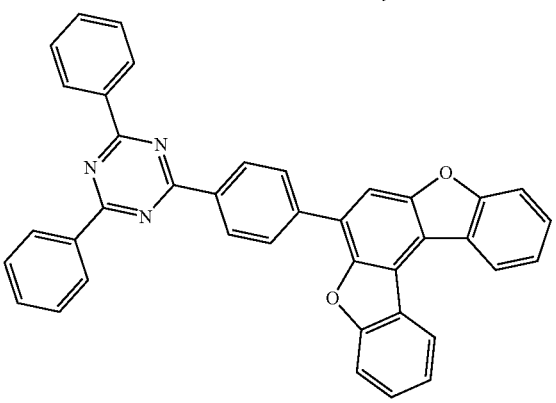
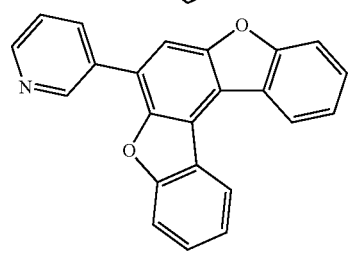
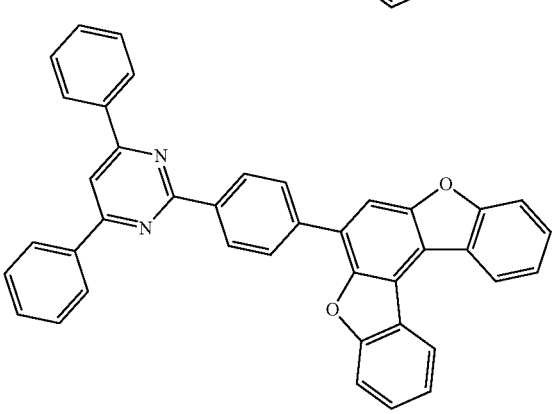

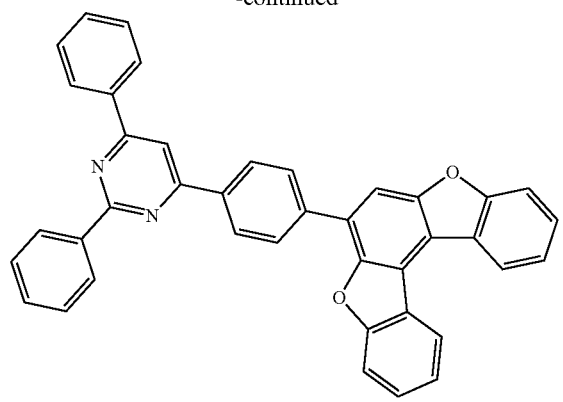
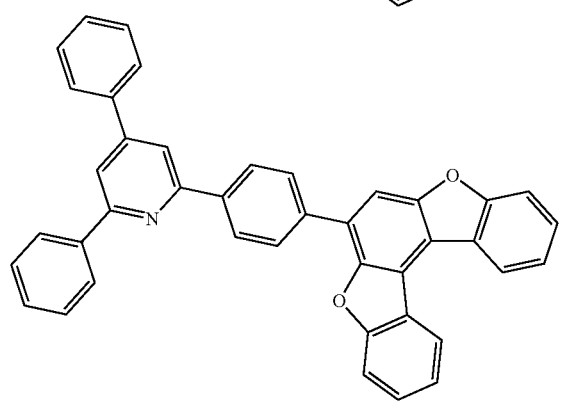
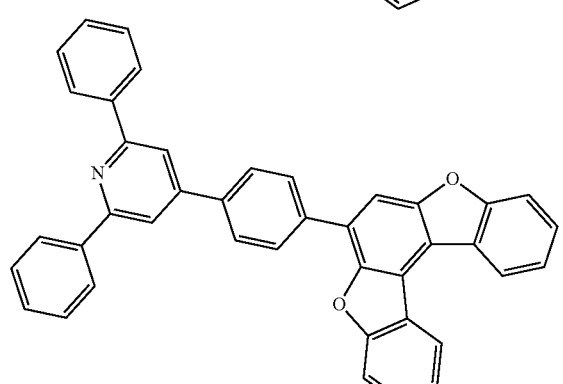
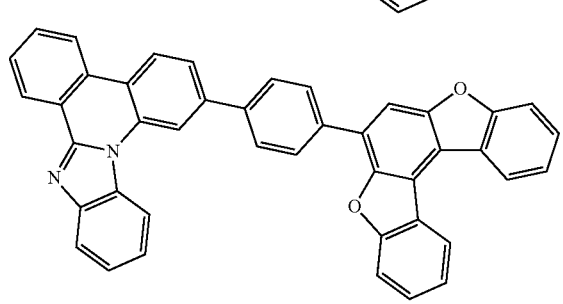
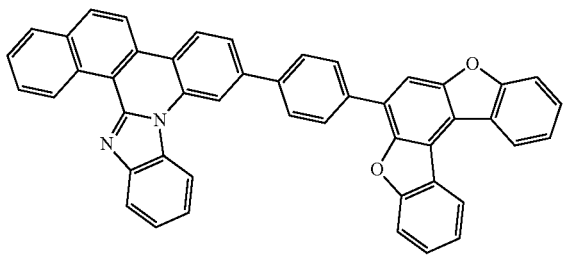
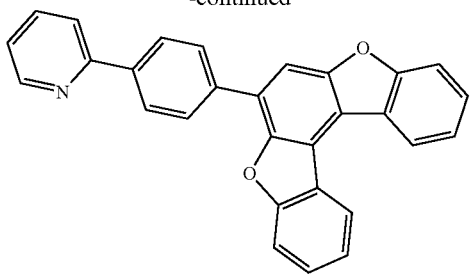
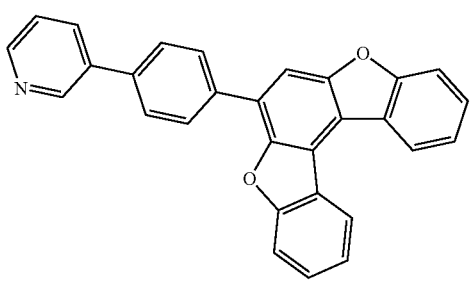
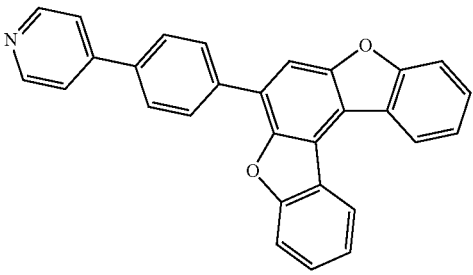
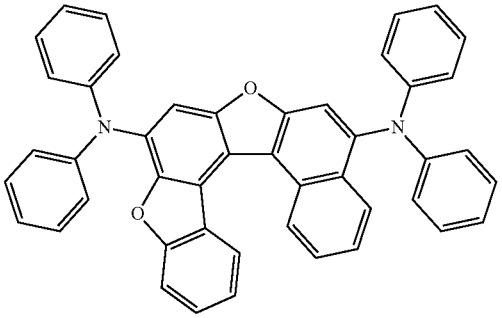
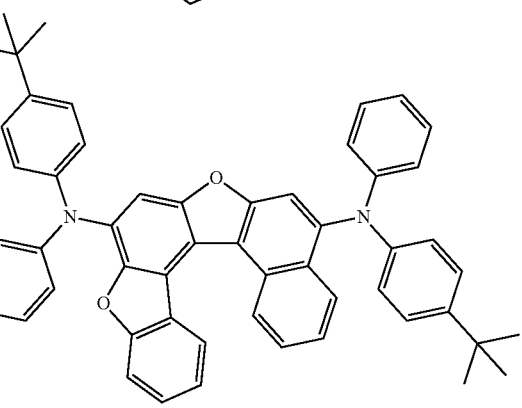

65
-continued
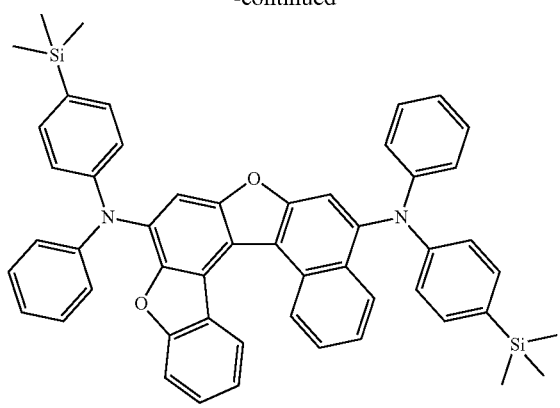
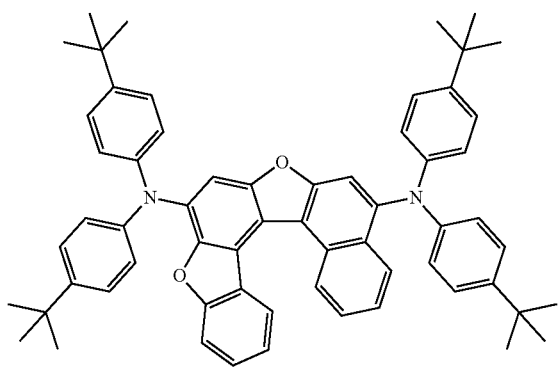
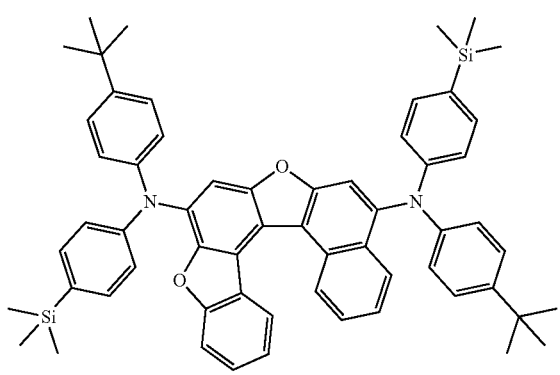
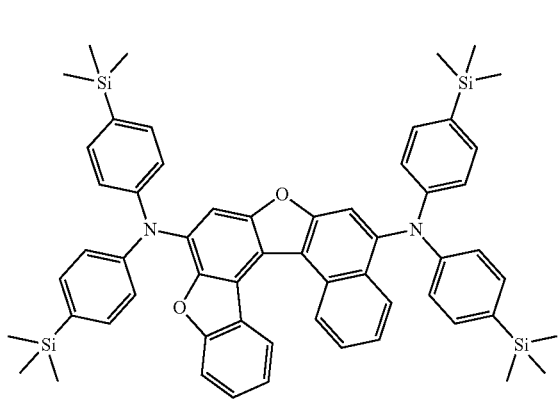
66
-continued
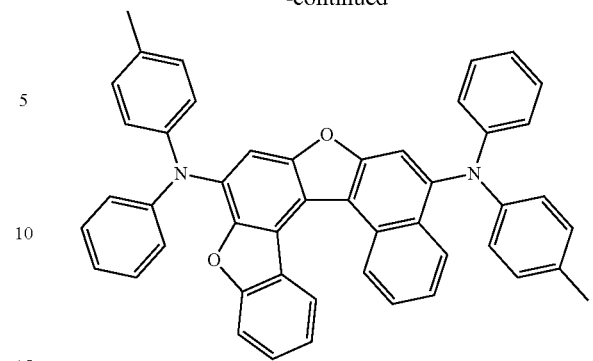
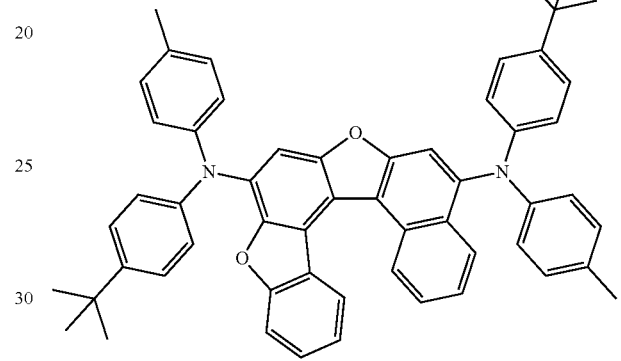
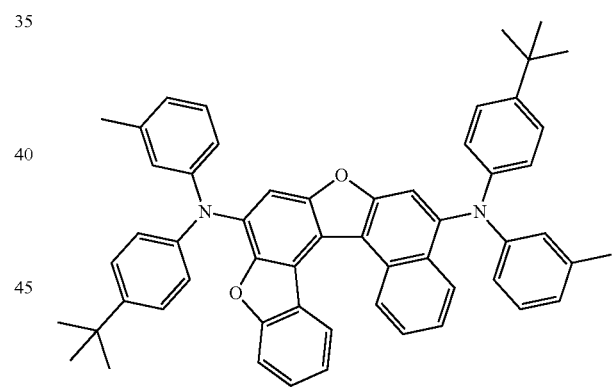
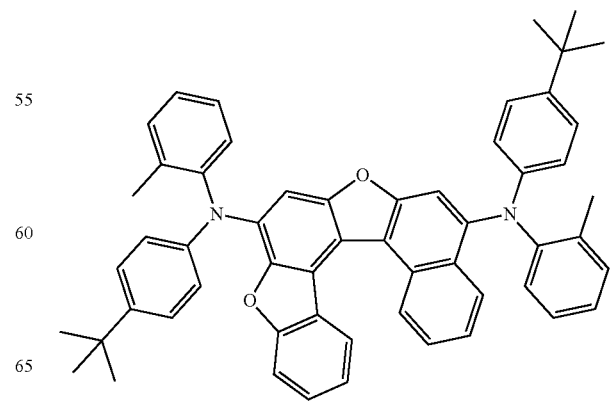

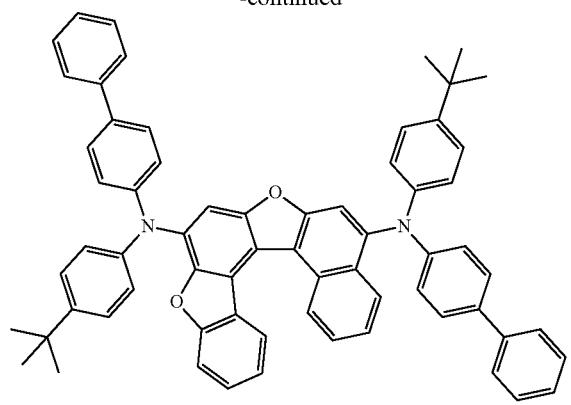
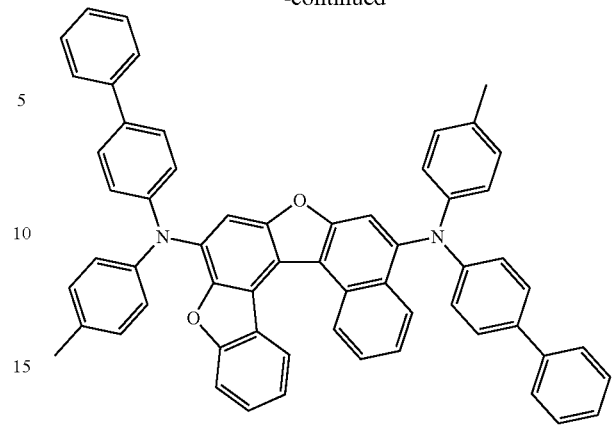
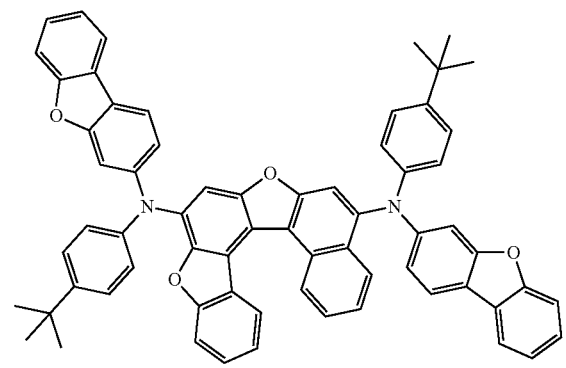
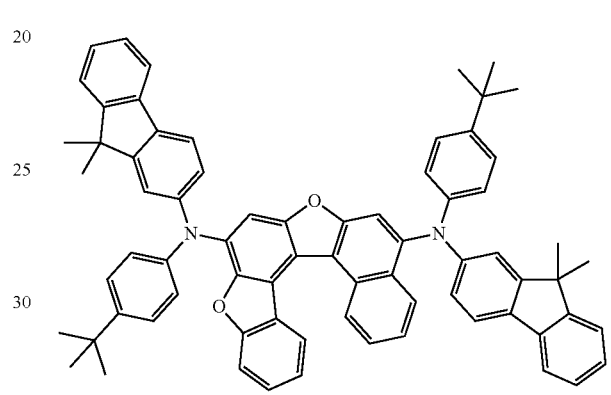
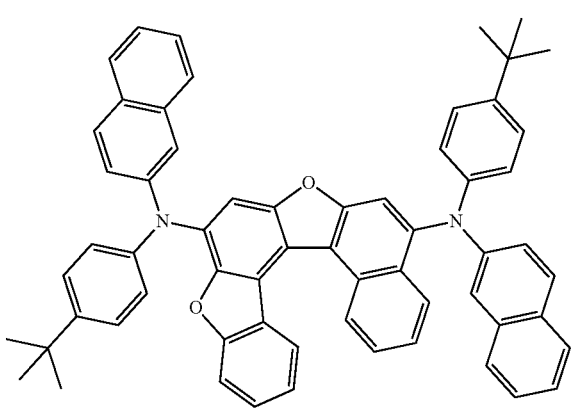
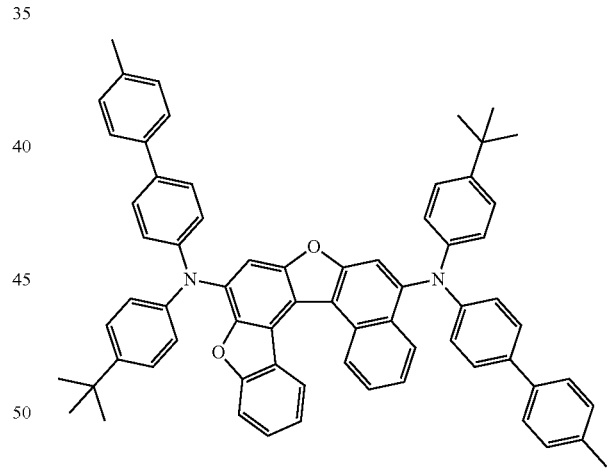
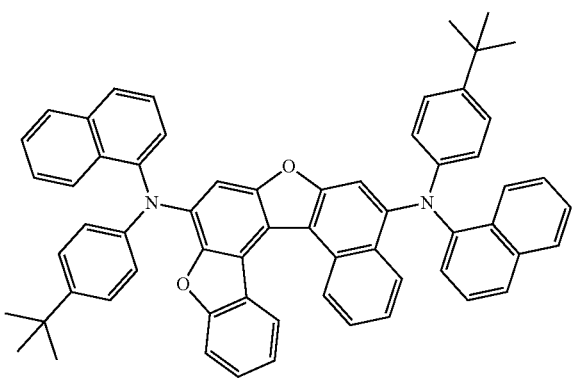
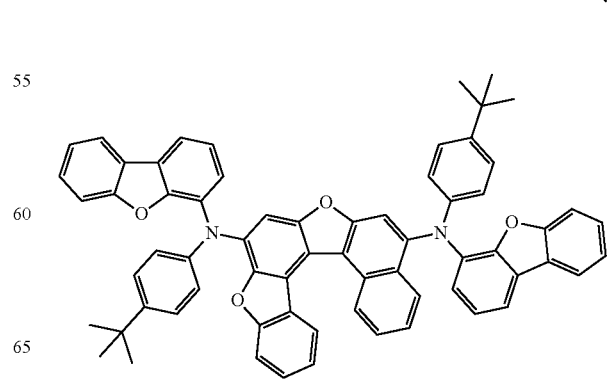

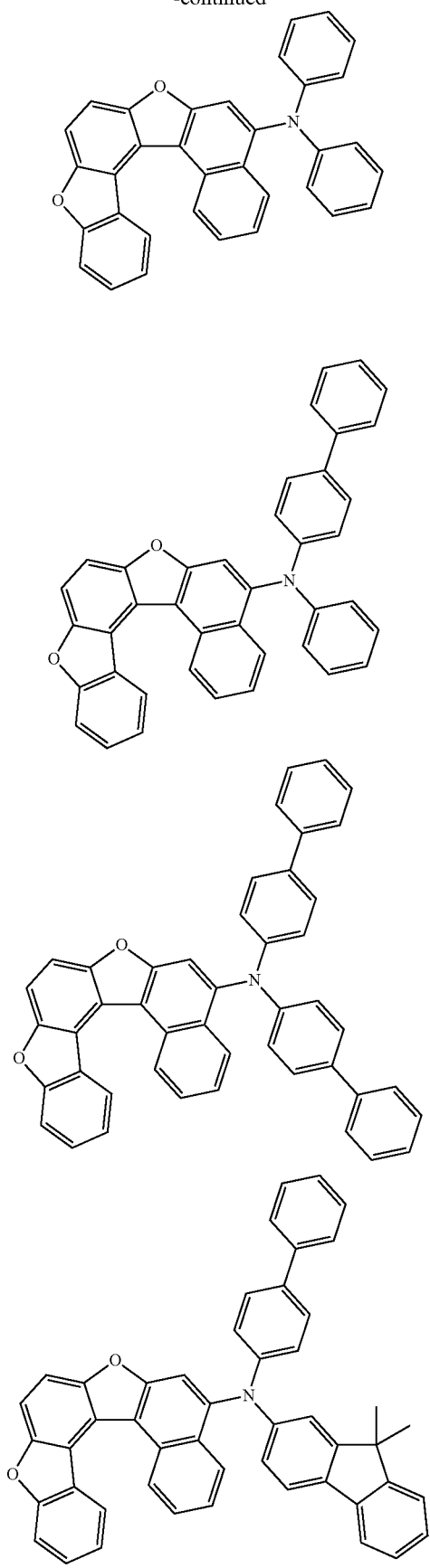

71
-continued
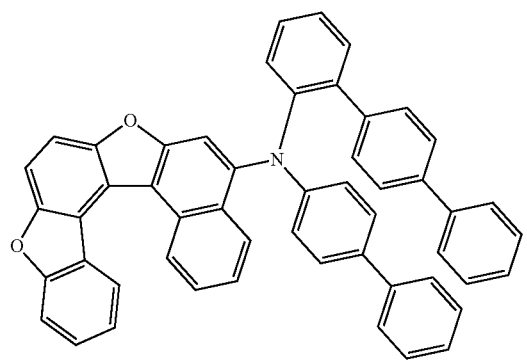
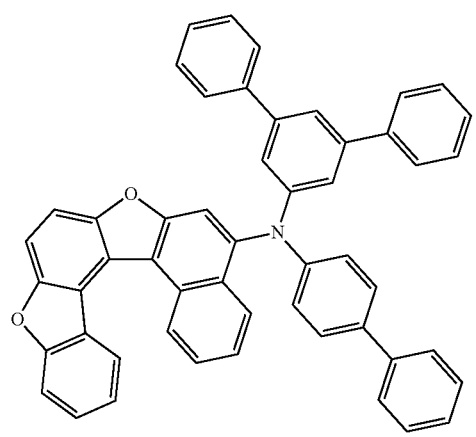
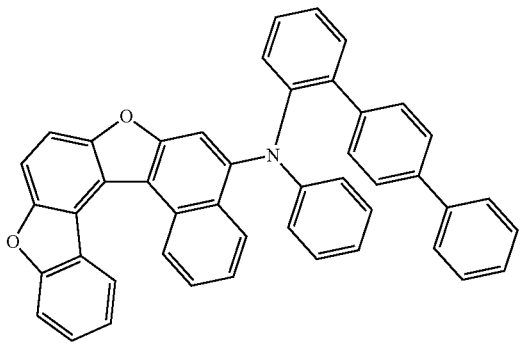
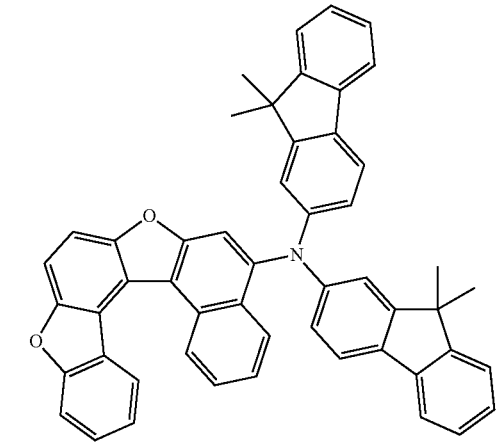
72
-continued
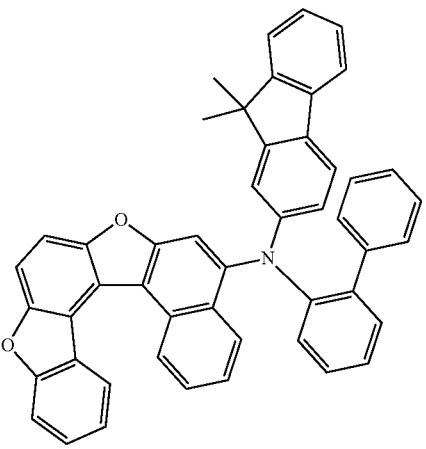
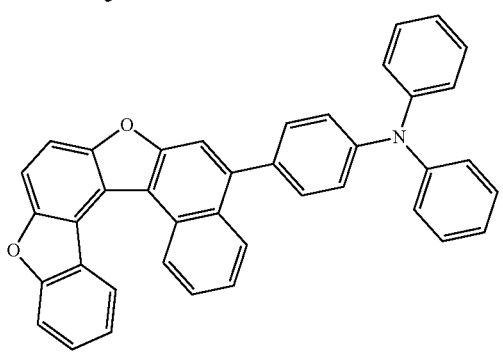
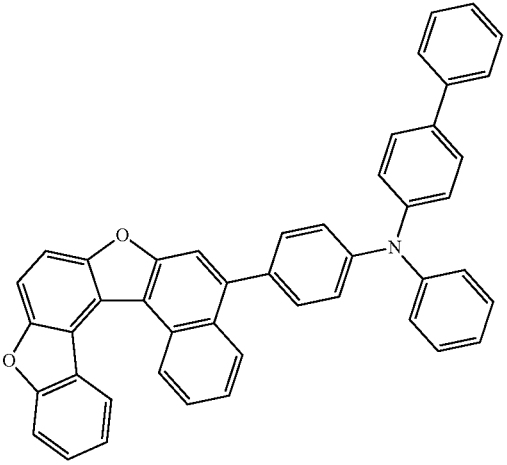
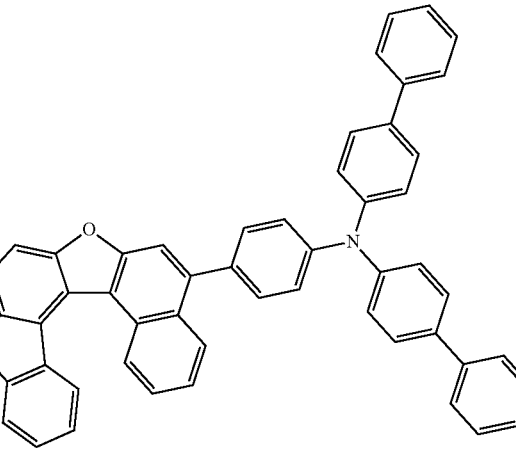

73
-continued
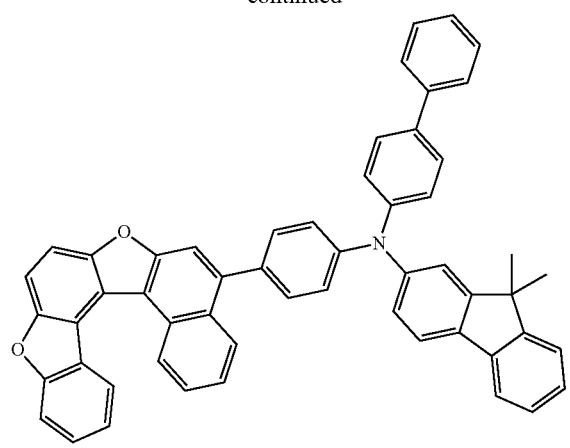
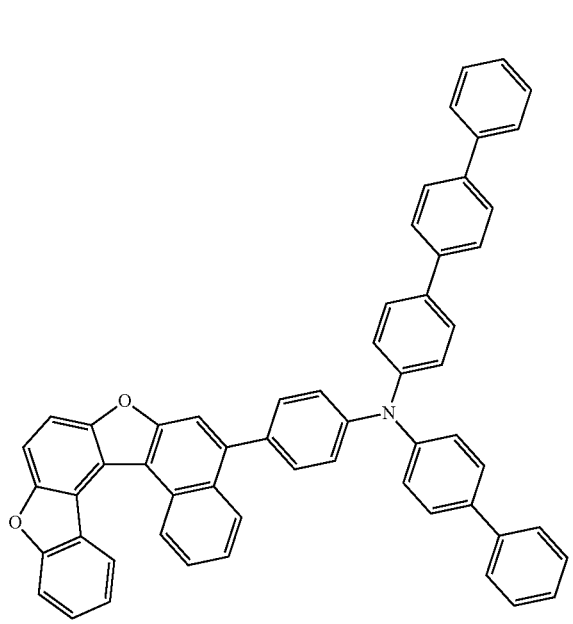
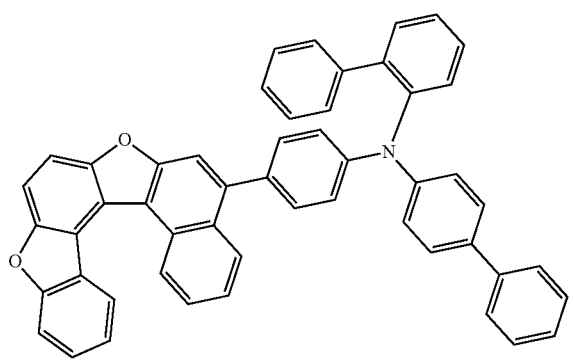
74
-continued
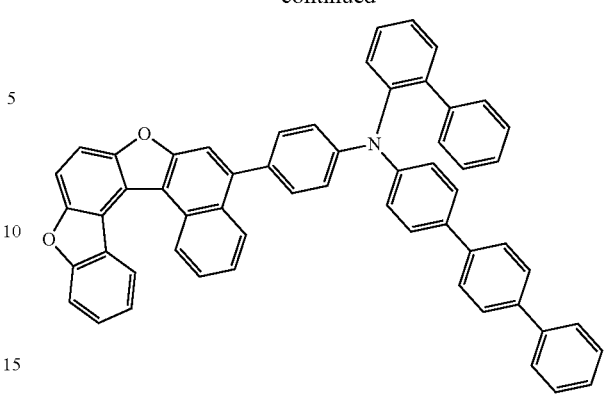
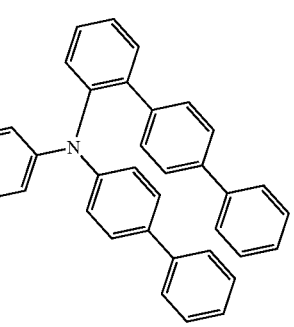
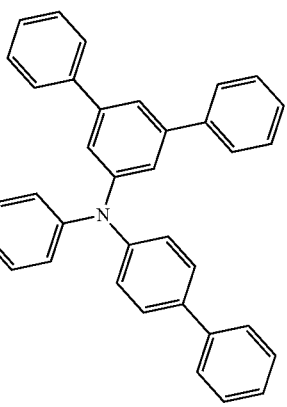
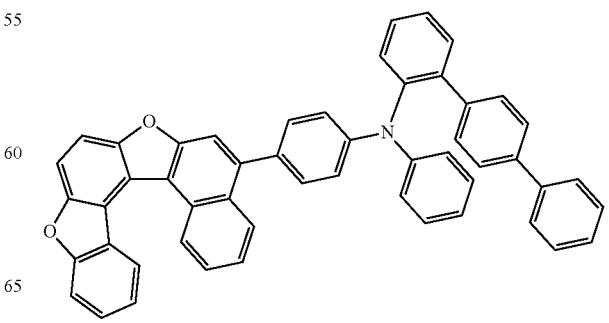

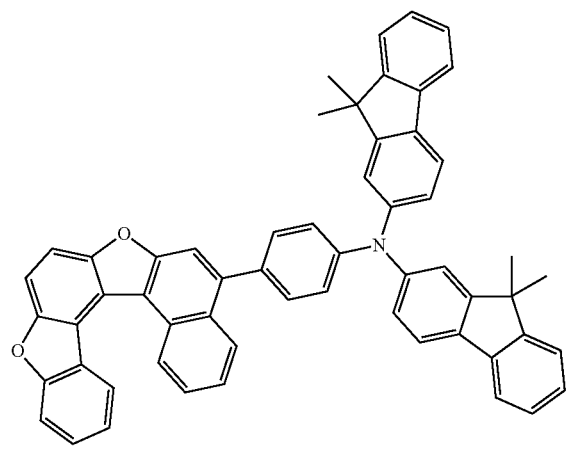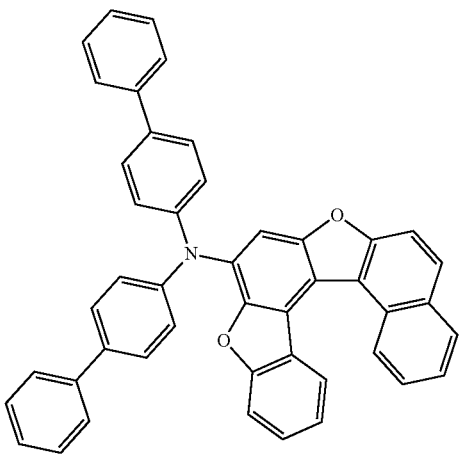

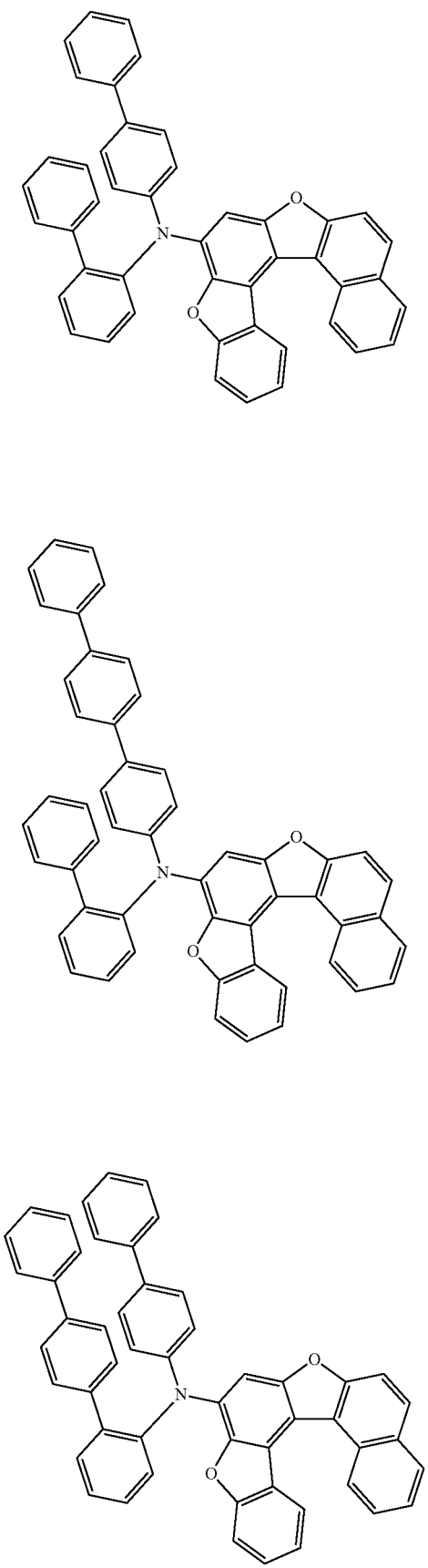
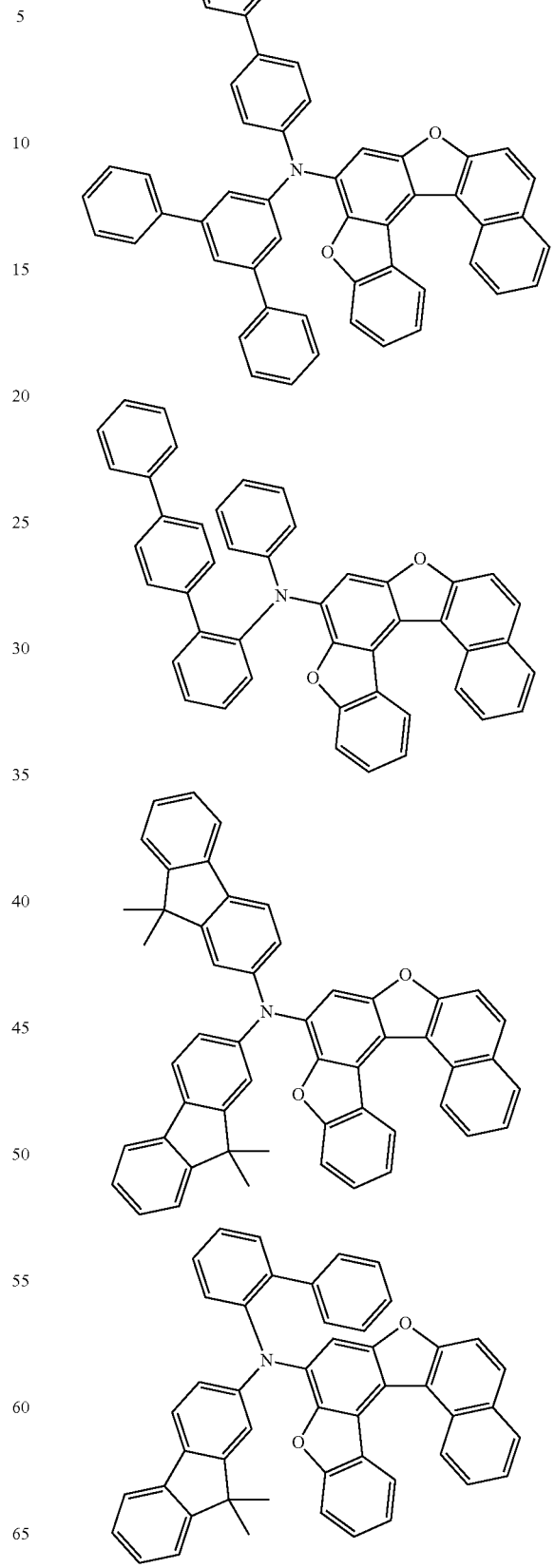

79
-continued
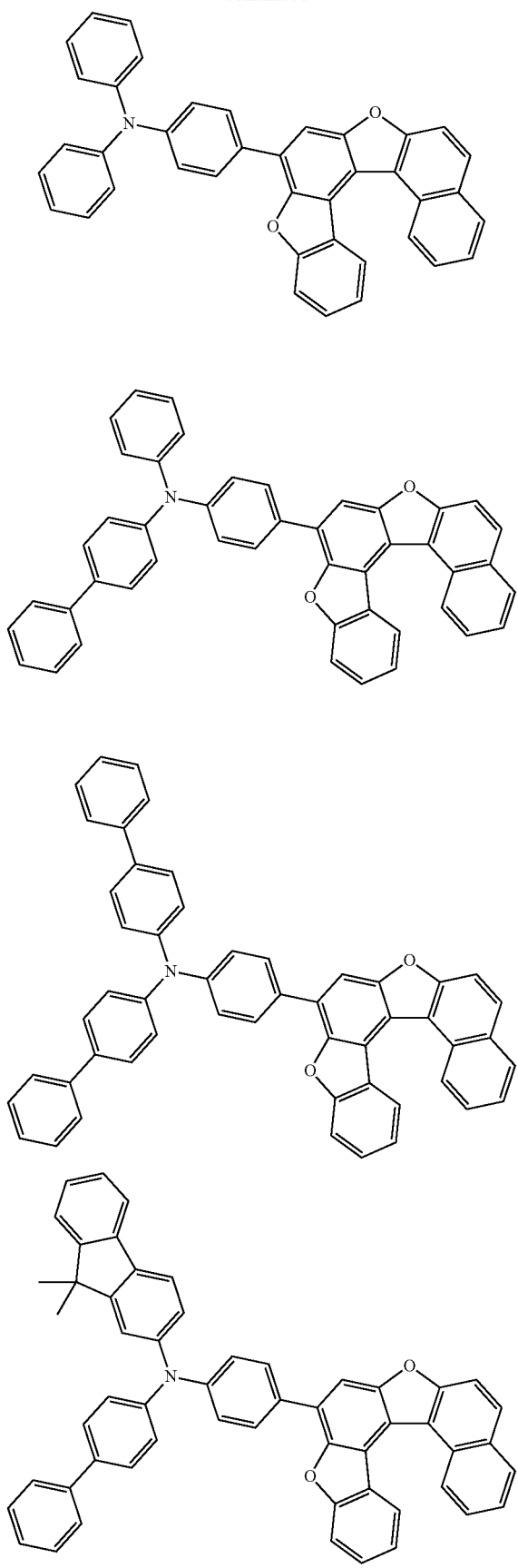
80
-continued
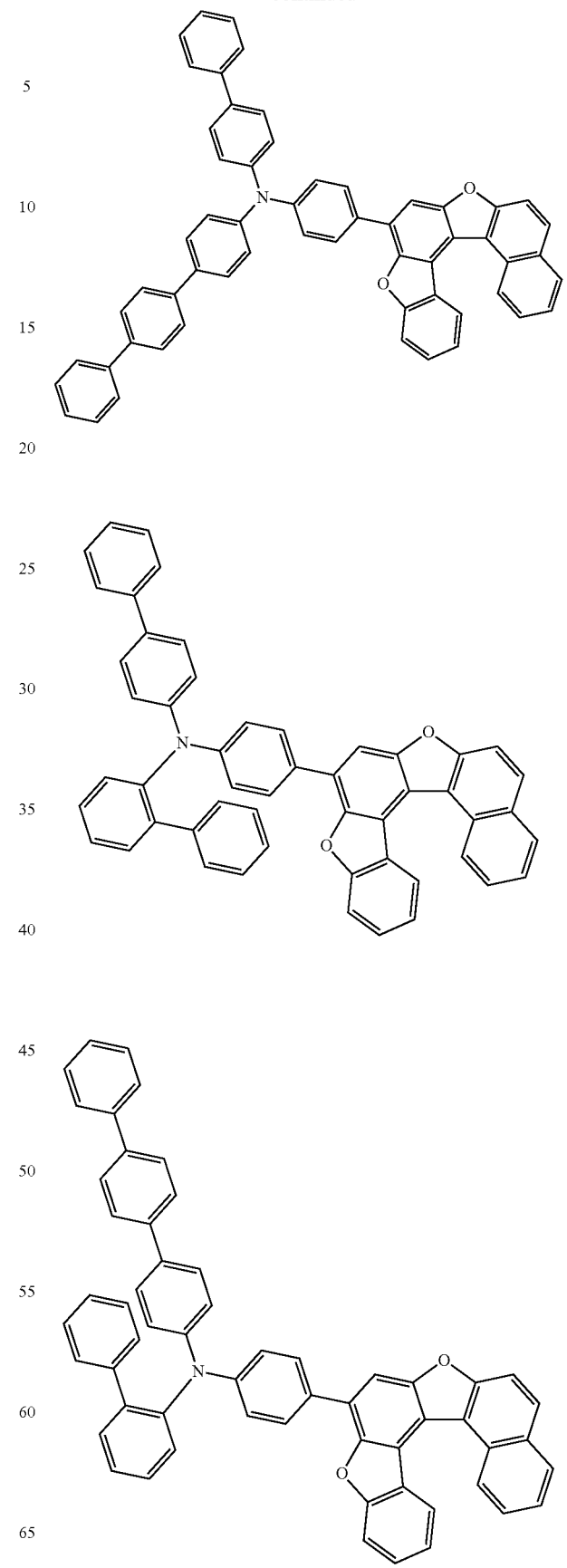

81
-continued
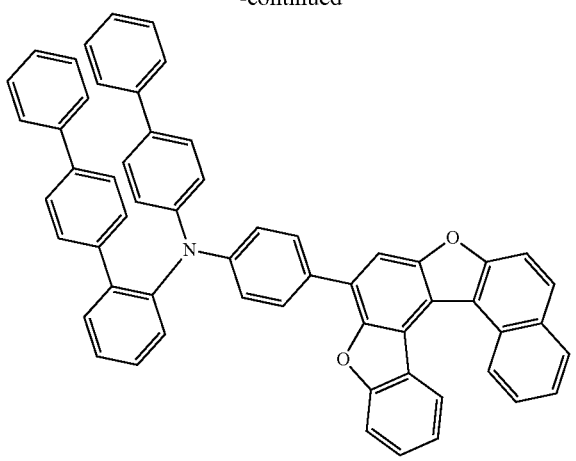
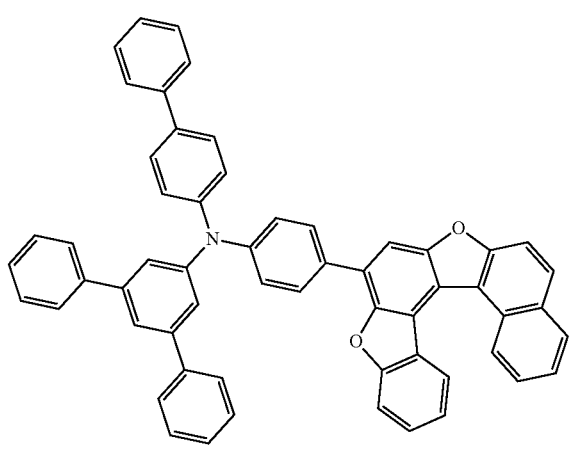
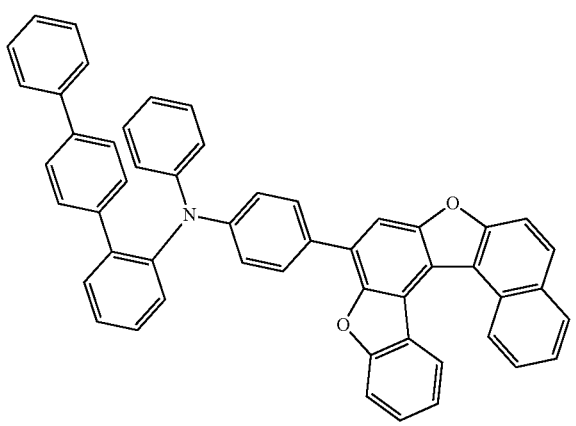
82
-continued
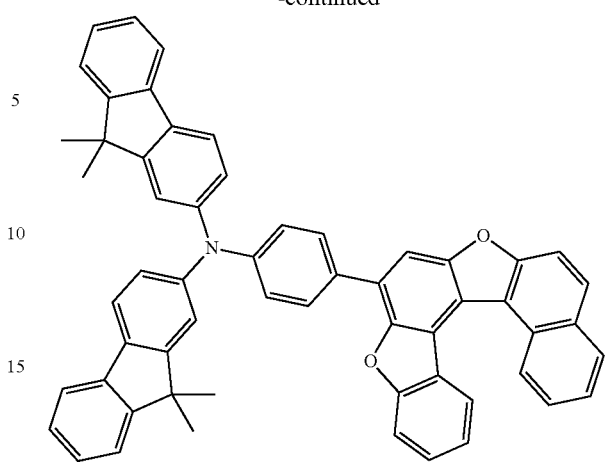
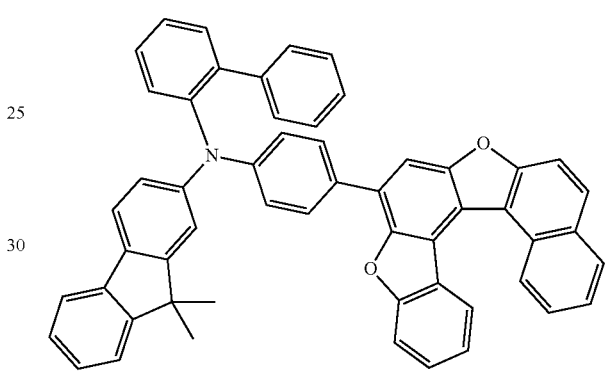
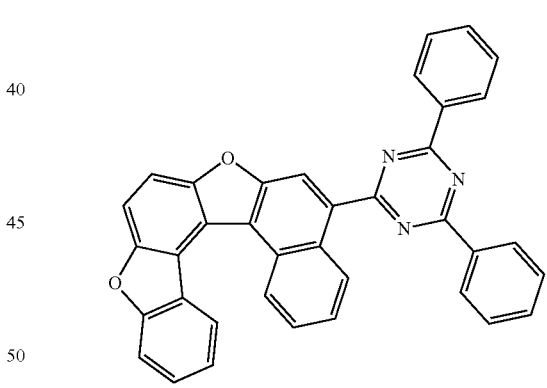
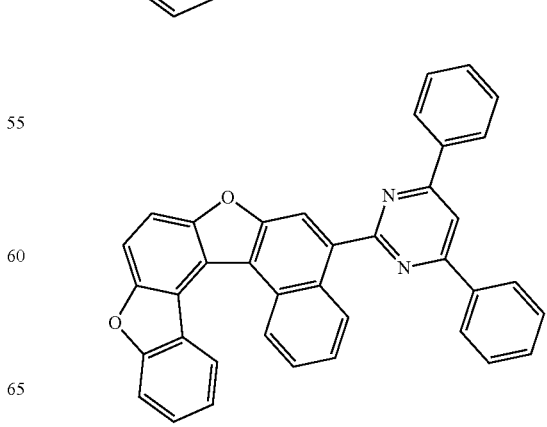

83
-continued
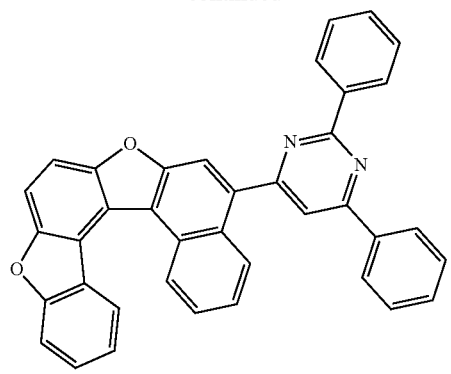
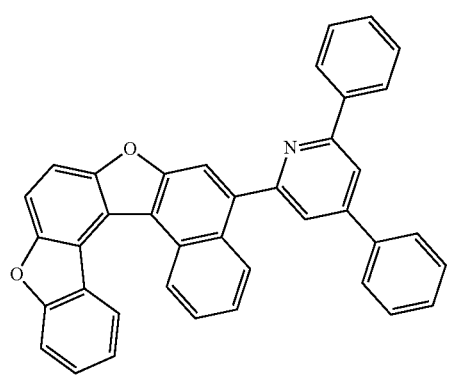
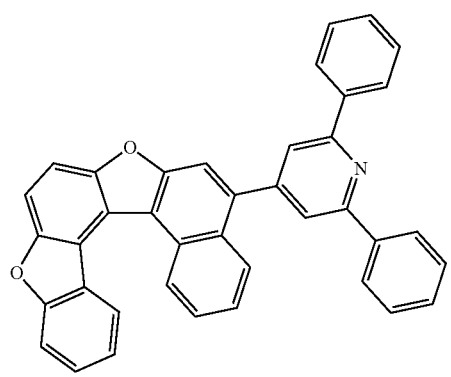
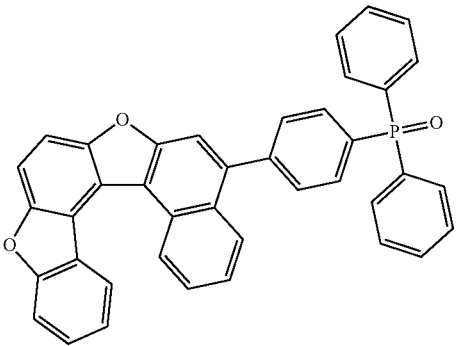
84
-continued
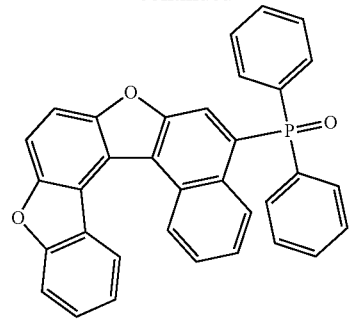
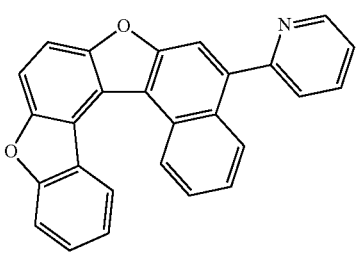
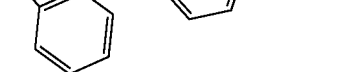
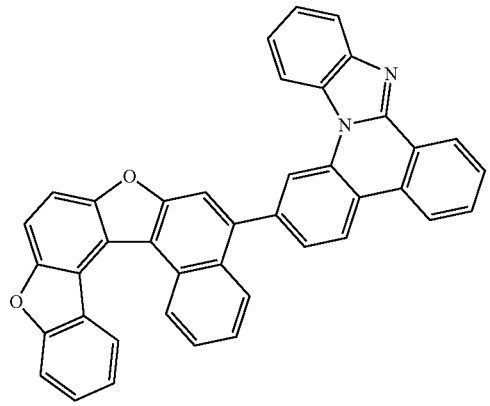

-continued
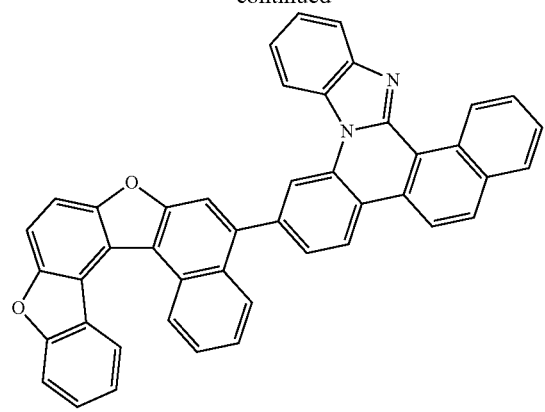
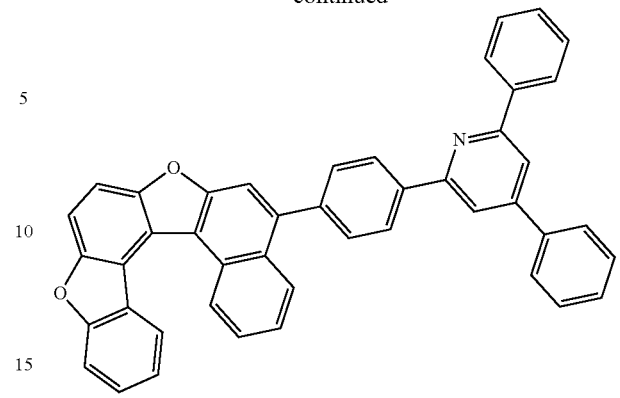
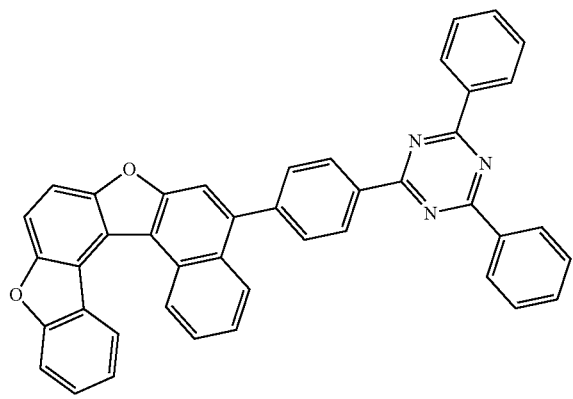
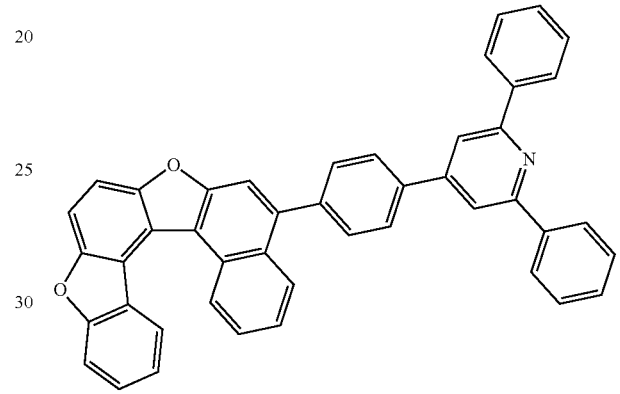
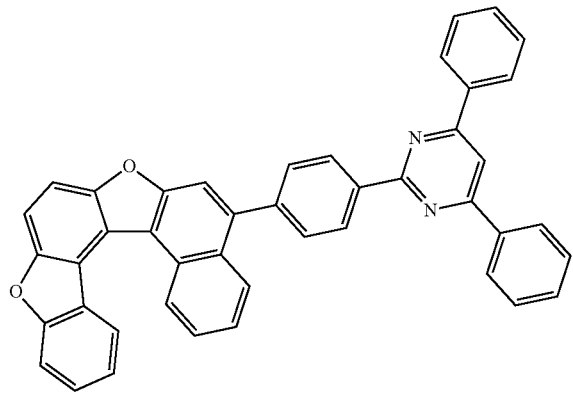
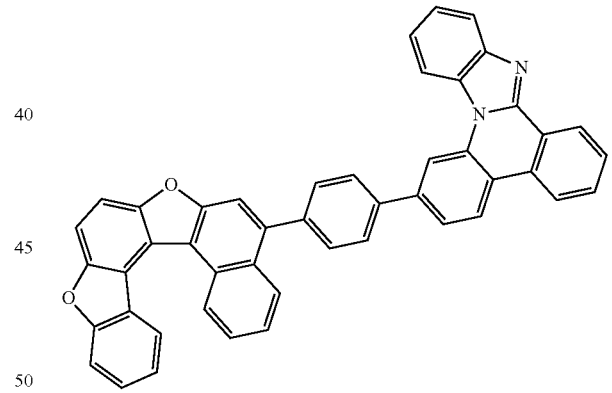
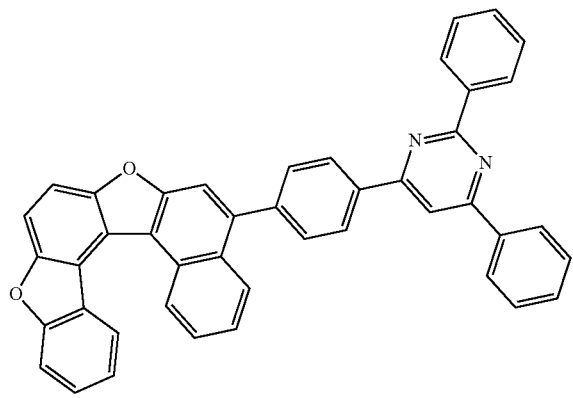
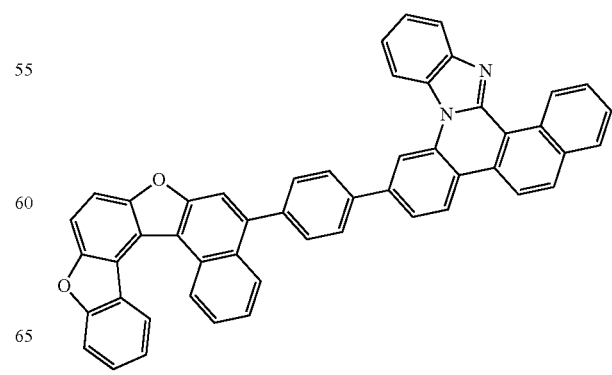

-continued
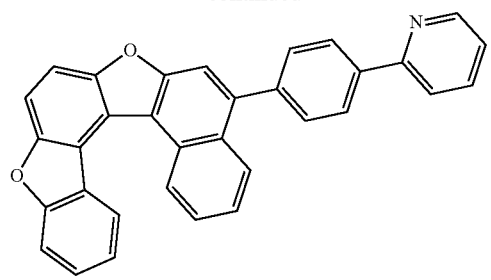
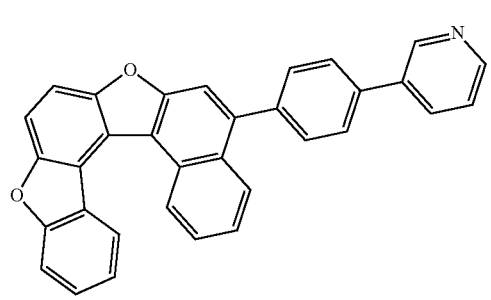
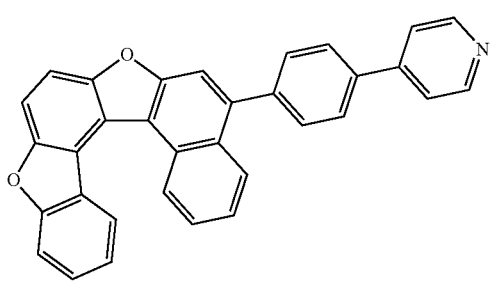
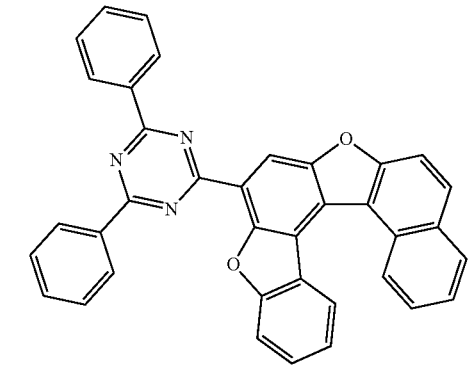
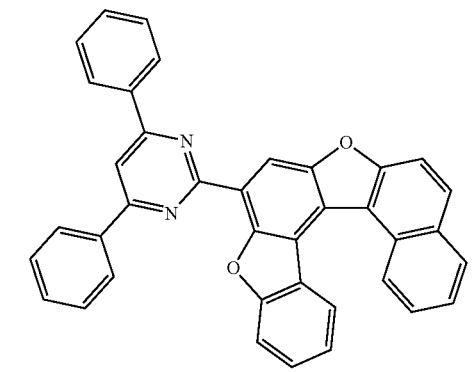
-continued
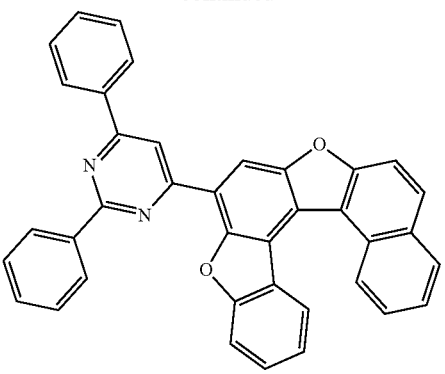
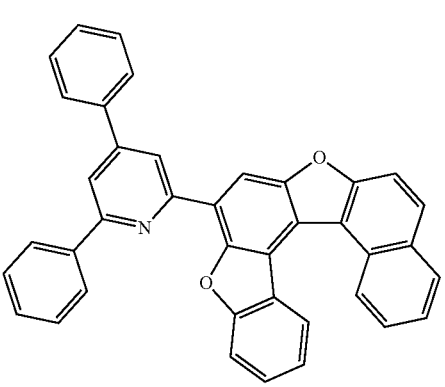
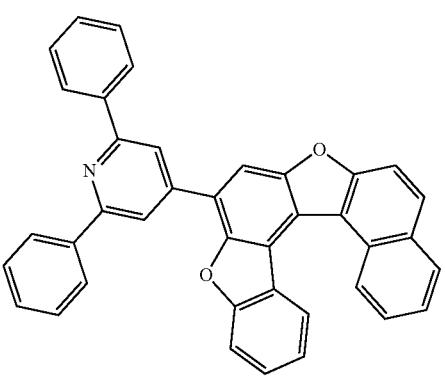
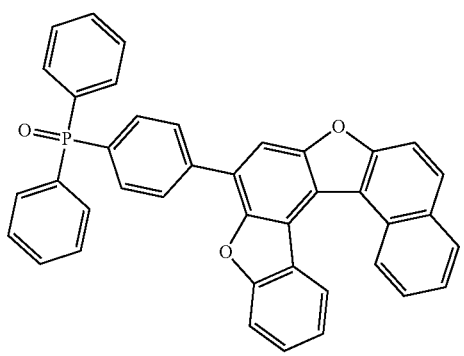

-continued
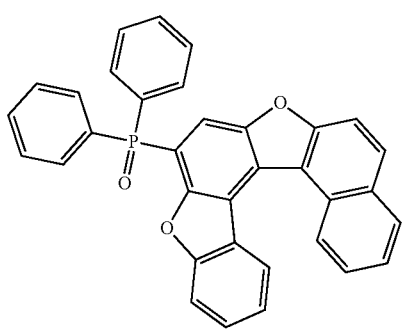
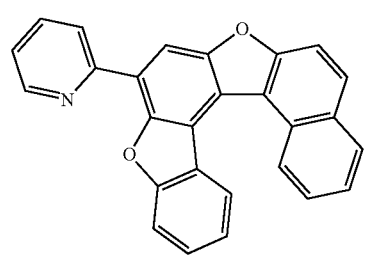
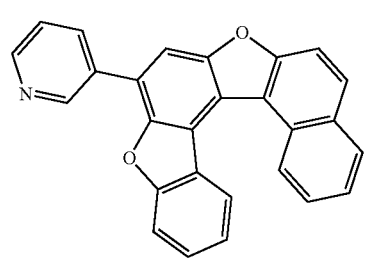
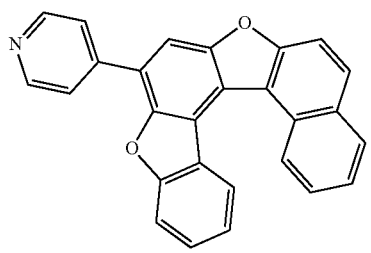
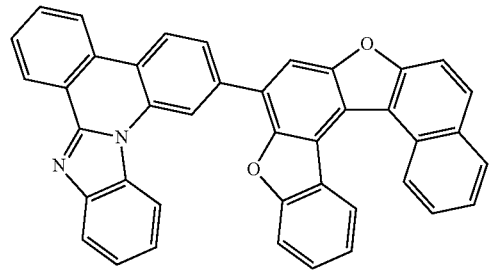
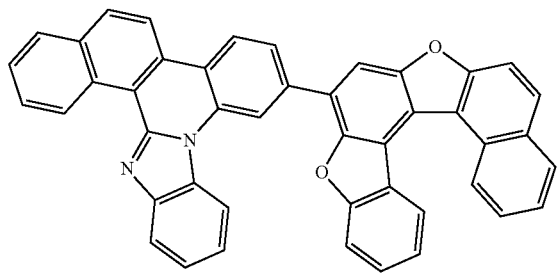
-continued
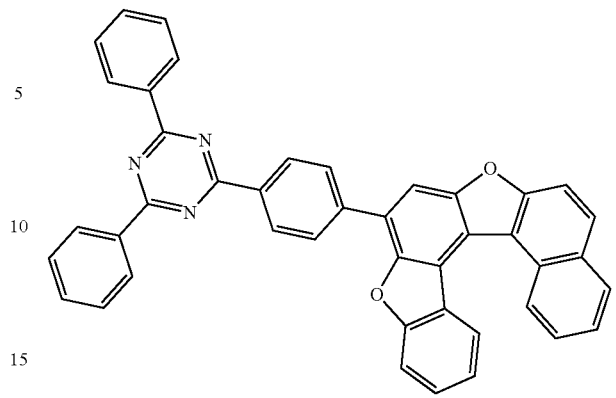
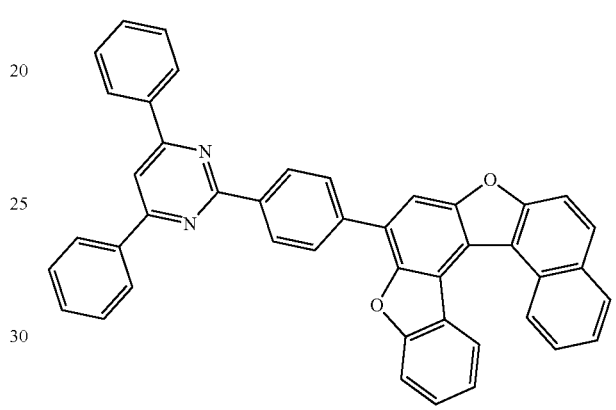
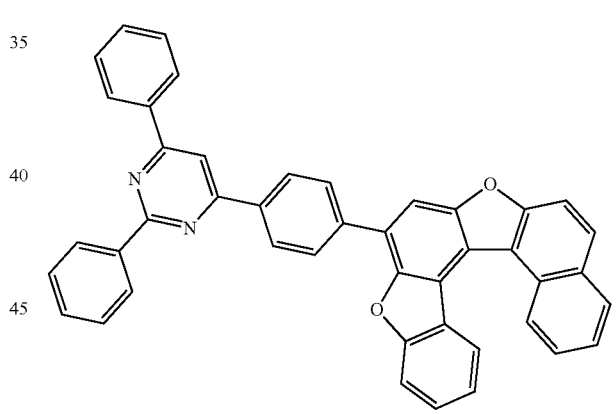
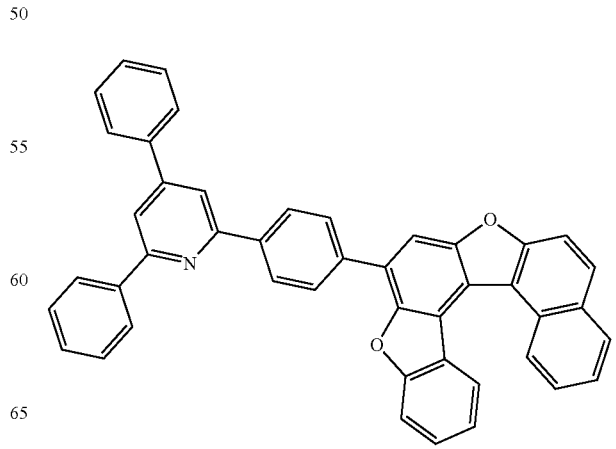

91
-continued
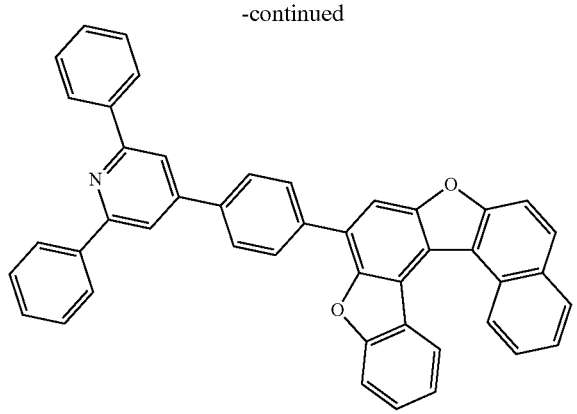
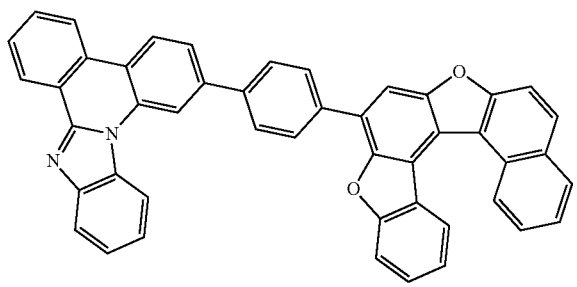
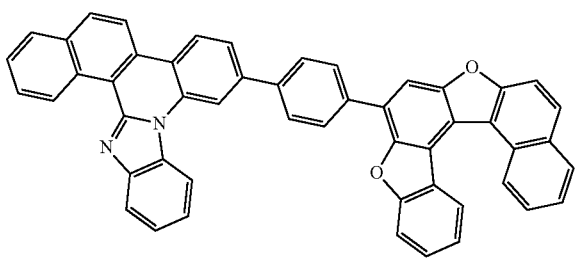
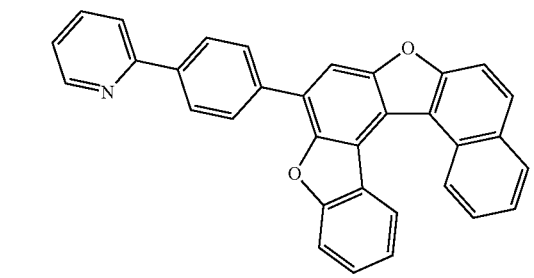
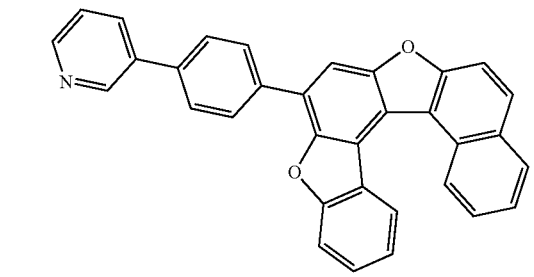
92
-continued
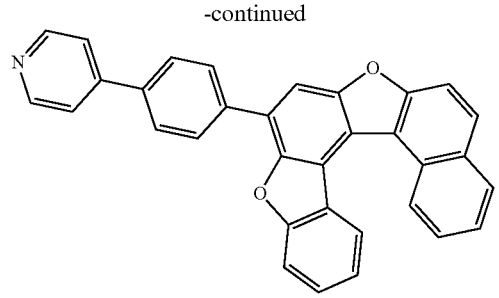
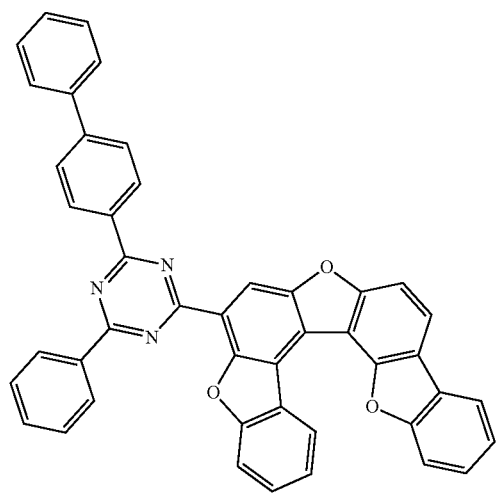
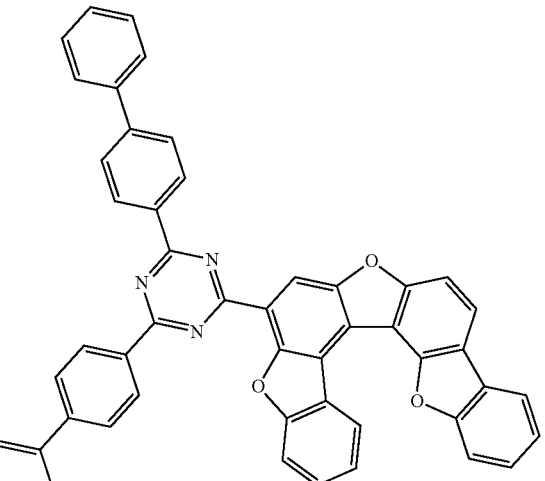
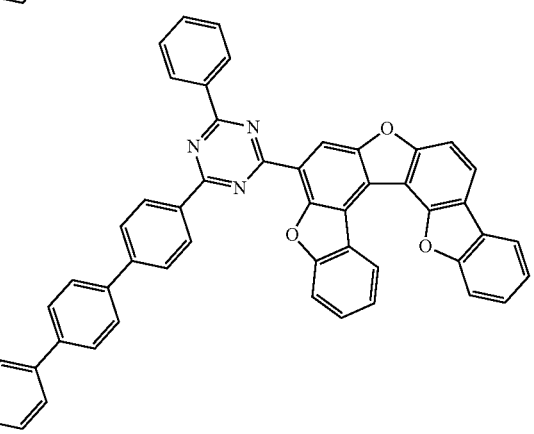

93
-continued
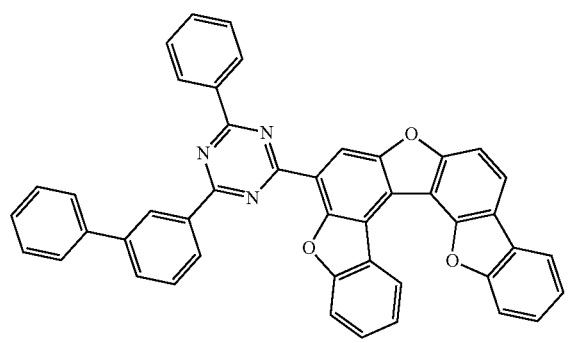
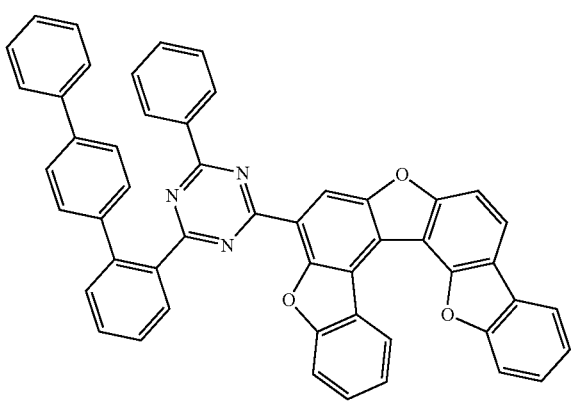
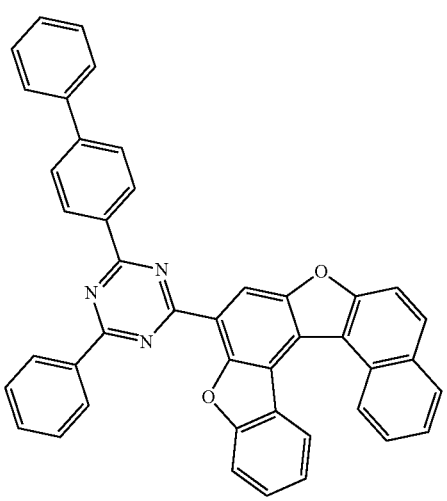
94
-continued
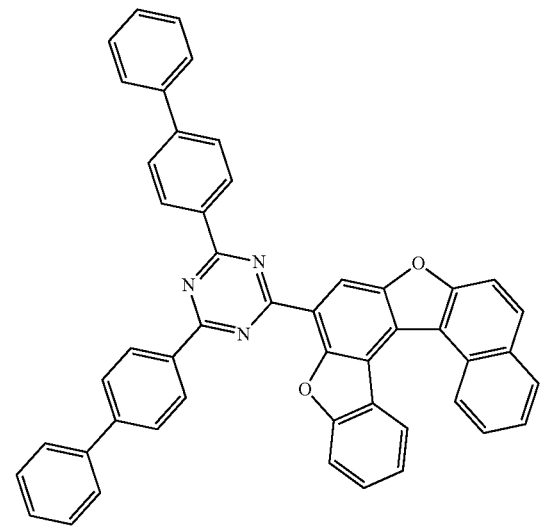
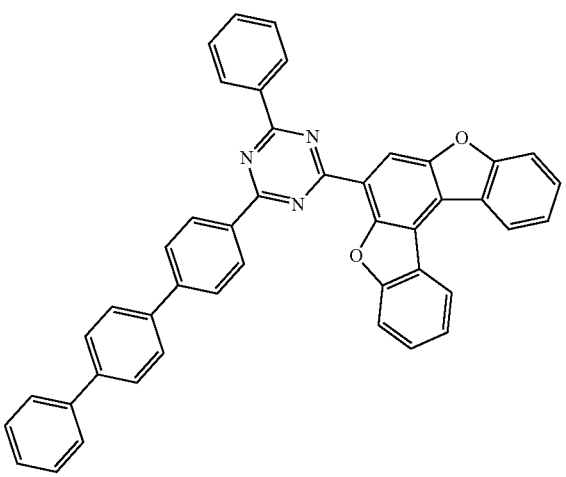
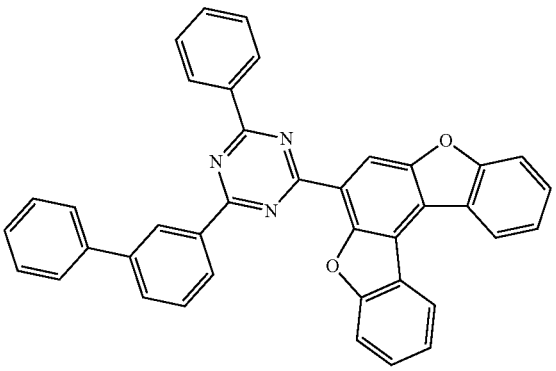

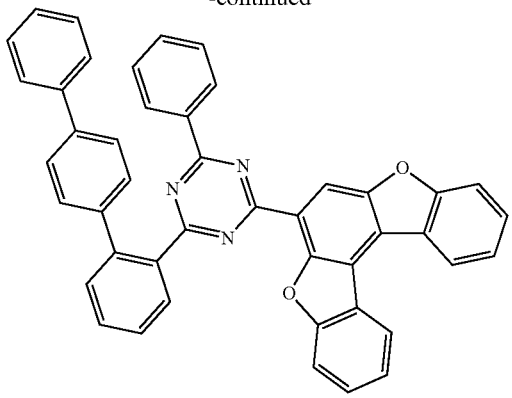
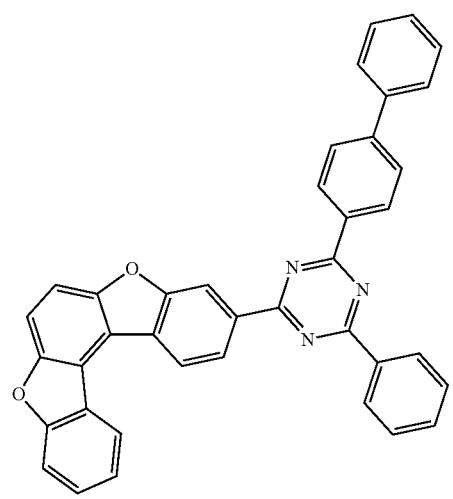
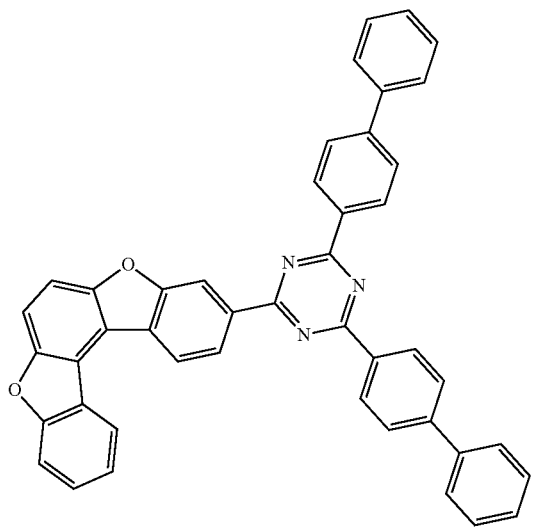
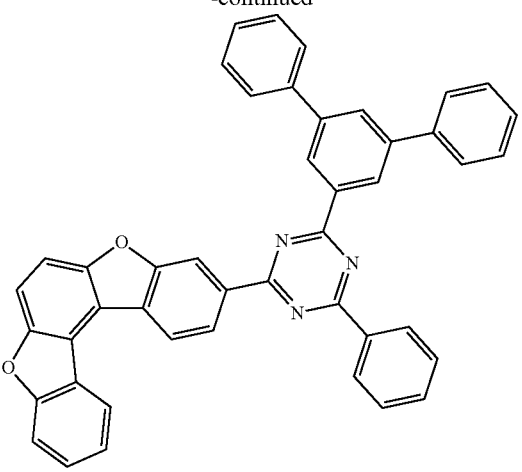
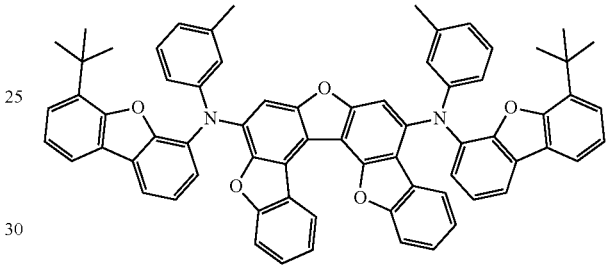
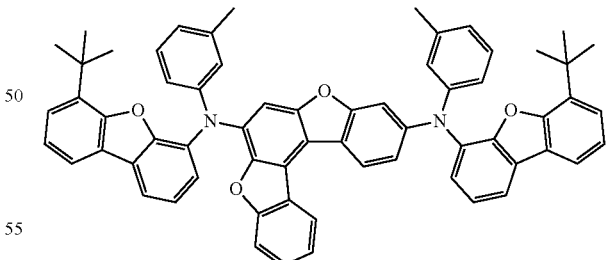
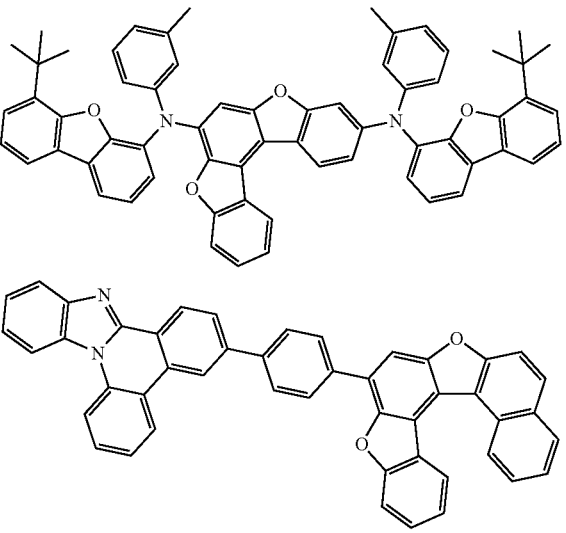

97
-continued
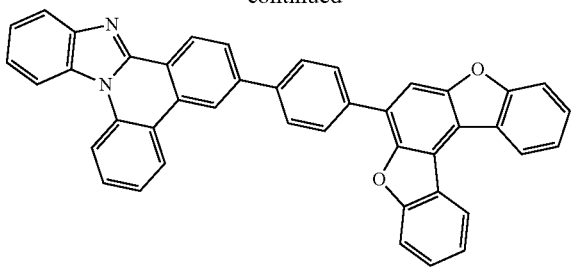
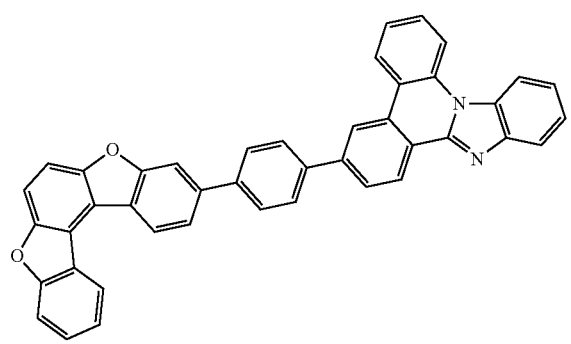
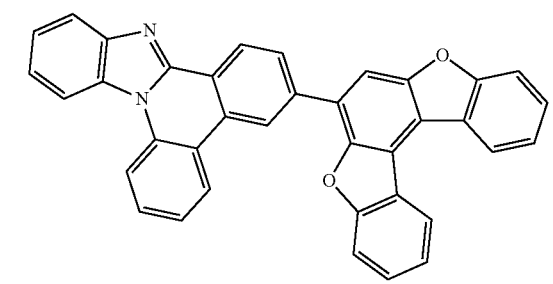
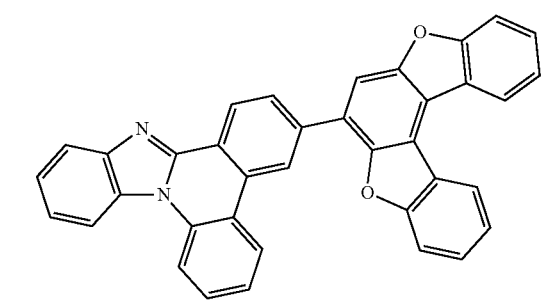
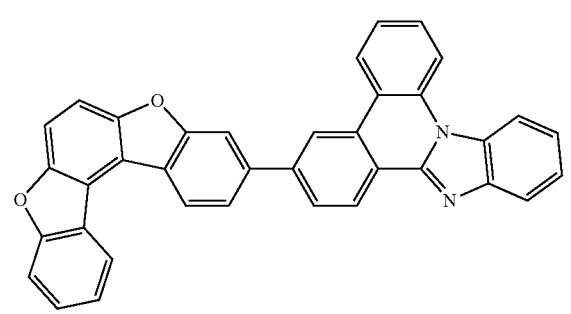
98
-continued
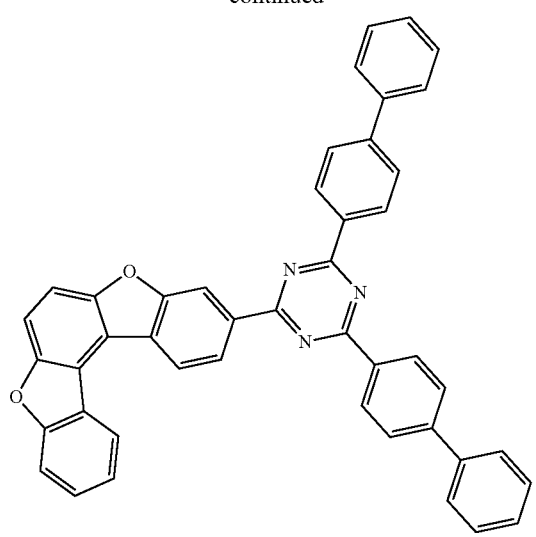
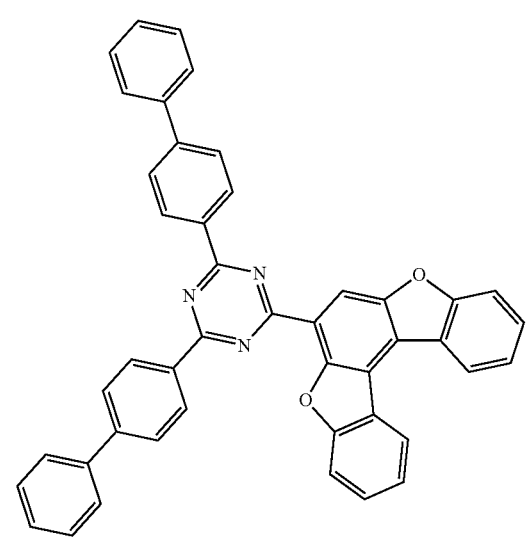
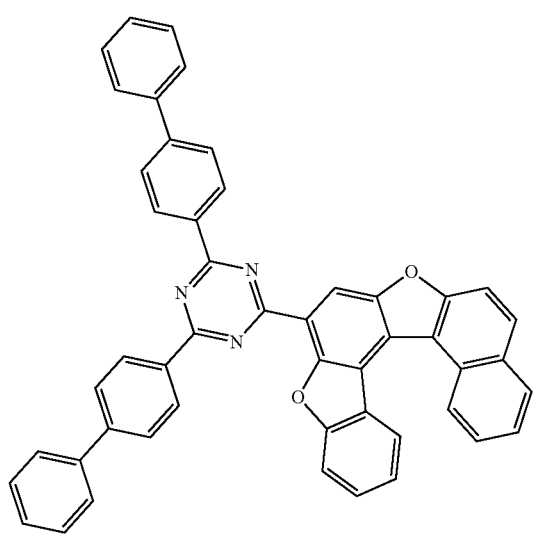

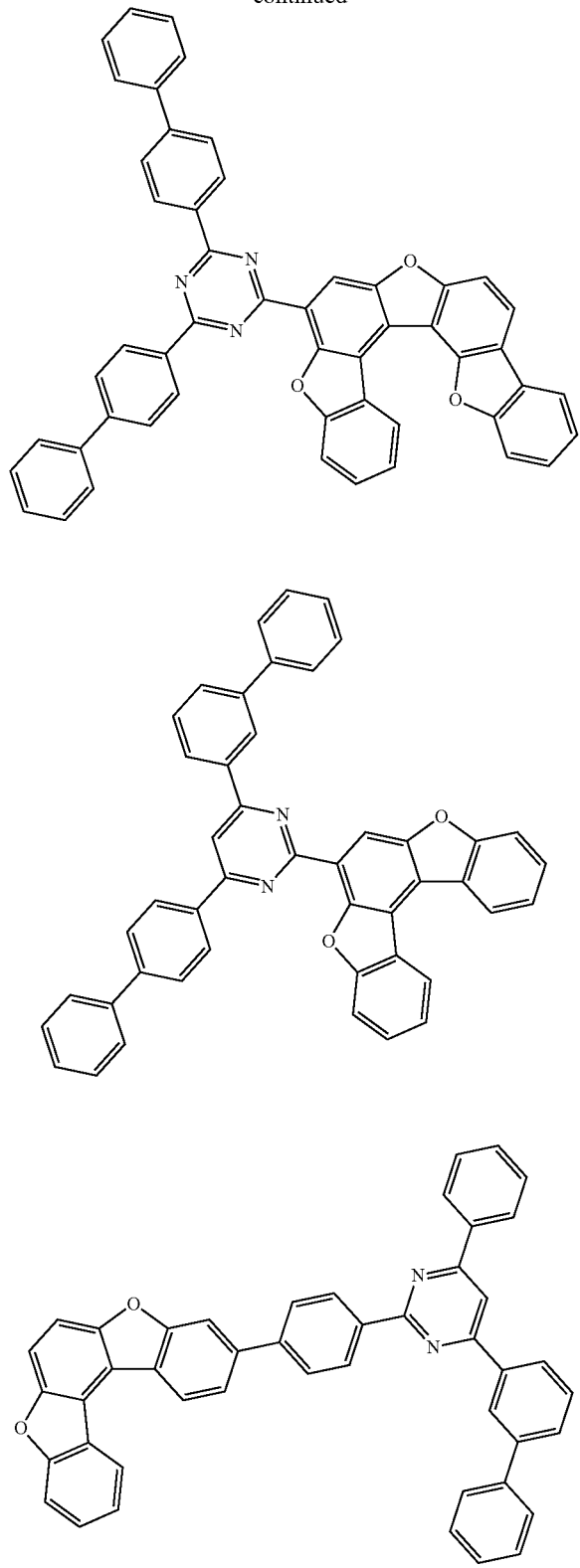

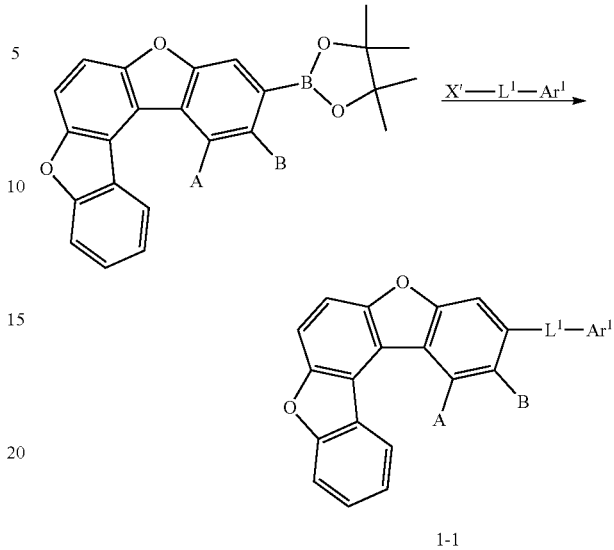

1-1

Among the compounds represented by Chemical Formula 1, the compound represented by Chemical Formula 1-1 can be prepared by the preparation method as shown in the following Reaction Scheme 1, which can also be applied to the remaining compounds.

in Reaction Scheme 1, the remaining definition except X' are as defined above, and X' is halogen, more preferably bromo, or chloro.

Reaction Scheme 1 is a Suzuki coupling reaction, which is preferably carried out in the presence of a palladium catalyst and base, and the reactive group for the Suzuki coupling reaction can be changed as known in the art. The above preparation method can be further specified in Preparation Examples described hereinafter.

In addition, the present invention provides an organic light emitting device comprising the compound represented by Chemical Formula 1. In one example, the present invention provides an organic light emitting device comprising a first electrode; a second electrode provided at a side opposite to the first electrode; and at least one layer of organic material layers provided between the first electrode and the second electrode, wherein the at least one layer of the organic material layers includes a compound represented by Chemical Formula 1.

The organic material layer of the organic light emitting device of the present invention may have a single layer structure, but it may have a multilayered structure in which two or more organic material layers are stacked. For example, the organic light emitting device of the present invention may have a structure comprising a hole injection layer, a hole transport layer, a light emitting layer, an electron transport layer, an electron injection layer and the like as the organic material layer. However, the structure of the organic light emitting device is not limited thereto, and it may include a smaller number of organic layers.

Further, the organic material layer may include a hole injection layer, a hole transport layer, and a layer simultaneously performing hole injection and transport, wherein the hole injection layer, the hole transport layer, and the layer simultaneously performing a hole injection and a hole transport include a compound represented by Chemical Formula 1.

Further, the organic material layer may include a light emitting layer, wherein the light emitting layer may include a compound represented by Chemical Formula 1.

Further, the organic material layer may include an electron transport layer, an electron injection layer, and a layer simultaneously performing electron transport and injection, wherein the electron transport layer, the electron injection layer, and the layer simultaneously performing electron transport and injection may include a compound represented by Chemical Formula 1.

Further, the organic light emitting device according to the present invention may be a normal type organic light emitting device in which an anode, at least one organic material layer, and a cathode are sequentially stacked on a substrate. Further, the organic light emitting device according to the present invention may be an inverted type organic light emitting device in which a cathode, at least one organic material layer and an anode are sequentially stacked on a substrate. For example, the structure of an organic light emitting device according to an embodiment of the present invention is illustrated in FIGS. 1 and 2.

FIG. 1 shows an example of an organic light emitting device comprising a substrate 1, an anode 2, a light emitting layer 3, and a cathode 4. In such a structure, the compound represented by Chemical Formula 1 may be included in the light emitting layer.

FIG. 2 shows an example of an organic light emitting device comprising a substrate 1, an anode 2, a hole injection layer 5, a hole transport layer 6, a light emitting layer 7, an electron transport layer 8, and a cathode 4. In such a structure, the compound represented by Chemical Formula 1 may be included in at least one layer of the hole injection layer, the hole transport layer, the light emitting layer and the electron transport layer.

The organic light emitting device according to the present invention may be manufactured by materials and methods known in the art, except that at least one layer of the organic material layers includes the compound represented by Chemical Formula 1. In addition, when the organic light emitting device includes a plurality of organic material layers, the organic material layers may be formed of the same material or different materials.

For example, the organic light emitting device according to the present invention can be manufactured by sequentially stacking a first electrode, an organic material layer and a second electrode on a substrate. In this case, the organic light emitting device may be manufactured by depositing a metal, metal oxides having conductivity, or an alloy thereof on the substrate using a PVD (physical vapor deposition) method such as a sputtering method or an e-beam evaporation method to form an anode, forming an organic material layer including the hole injection layer, the hole transport layer, the light emitting layer, and the electron transport layer thereon, and then depositing a material that can be used as the cathode thereon. In addition to such a method, the organic light emitting device may be manufactured by sequentially depositing a cathode material, an organic material layer and an anode material on a substrate.

In addition, the compound represented by Chemical Formula 1 may be formed into an organic layer by a solution coating method as well as a vacuum deposition method at the time of manufacturing an organic light emitting element. Herein, the solution coating method means a spin coating, a dip coating, a doctor blading, an inkjet printing, a screen printing, a spray method, a roll coating, or the like, but is not limited thereto.

In addition to such a method, the organic light emitting device may be manufactured by sequentially depositing a cathode material, an organic material layer, and an anode material on a substrate (International Publication WO 2003/012890). However, the manufacturing method is not limited thereto.

For example, the first electrode is an anode and the second electrode is a cathode, or the first electrode is a cathode and the second electrode is an anode.

As the anode material, generally, a material having a large work function is preferably used so that holes can be smoothly injected into the organic material layer. Specific examples of the anode material include metals such as vanadium, chrome, copper, zinc, and gold, or an alloy thereof; metal oxides such as zinc oxides, indium oxides, indium tin oxides (ITO), and indium zinc oxides (IZO); a combination of metals and oxides, such as ZnO:Al or $SNO_2$:Sb; conductive polymers such as poly(3-methylthiophene), poly[3,4-(ethylene-1,2-dioxy)thiophene](PEDOT), polypyrrole, and polyaniline, and the like, but are not limited thereto.

As the cathode material, generally, a material having a small work function is preferably used so that electrons can be easily injected into the organic material layer. Specific examples of the cathode material include metals such as magnesium, calcium, sodium, potassium, titanium, indium, yttrium, lithium, gadolinium, aluminum, silver, tin, and lead, or an alloy thereof; a multilayered structure material such as LiF/Al or $LiO_2$/Al, and the like, but are not limited thereto.

The hole injection layer is a layer for injecting holes from the electrode, and the hole injection material is preferably a compound which has an ability of transporting the holes, thus a hole injecting effect in the anode and an excellent hole injecting effect to the light emitting layer or the light emitting material, prevents movement of an exciton generated in the light emitting layer to the electron injection layer or the electron injection material, and has an excellent thin film forming ability. It is preferable that a HOMO (highest occupied molecular orbital) of the hole injection material is between the work function of the anode material and a HOMO of a peripheral organic material layer. Specific examples of the hole injection material include metal porphyrine, oligothiophene, an arylamine-based organic material, a hexanitrilehexaazatriphenylene-based organic material, a quinacridone-based organic material, a perylene-based organic material, anthraquinone, polyaniline and polythiophene-based conductive polymer, and the like, but are not limited thereto.

The hole transport layer is a layer that receives holes from a hole injection layer and transports the holes to the light emitting layer. The hole transport material is suitably a material having large mobility to the holes, which may receive holes from the anode or the hole injection layer and transfer the holes to the light emitting layer. Specific examples thereof include an arylamine-based organic material, a conductive polymer, a block copolymer in which a conjugate portion and a non-conjugate portion are present together, and the like, but are not limited thereto.

The light emitting material is a material capable of emitting light in the visible light region by combining holes and electrons respectively transported from the hole transport layer and the electron transport layer, and having good quantum efficiency for fluorescence or phosphorescence. Specific examples include 8-hydroxy-quinoline aluminum complex ($Alq_3$); carbazole-based compounds; dimerized styryl compounds; BAlq; 10-hydroxybenzoquinoline-metal compounds; benzoxazole, benzothiazole and benzimidazole-based compunds; Poly(p-phenylenevinylene)(PPV)-based polymers; spiro compounds; polyfluorene, rubrene, and the like, but are not limited thereto.

The light emitting layer may include a host material and a dopant material. The host material may be a fused aromatic ring derivative, a heterocycle-containing compound or the like. Specific examples of the fused aromatic ring derivatives include anthracene derivatives, pyrene derivatives, naphthalene derivatives, pentacene derivatives, phenanthrene compounds, and fluoranthene compounds. Examples of heterocyclic compounds include carbazole derivatives, dibenzofuran derivatives, ladder-type furan compounds, pyrimidine derivatives, and the like, but are not limited thereto.

Examples of the dopant material include an aromatic amine derivative, a styrylamine compound, a boron complex, a fluoranthene compound, a metal complex, and the like. Specific examples of the aromatic amine derivatives include substituted or unsubstituted fused aromatic ring derivatives having an arylamino group, examples thereof include pyrene, anthracene, chrysene, and periflanthene having the arylamino group, and the like, the styrylamine compound is a compound where at least one arylvinyl group is substituted in substituted or unsubstituted arylamine, in which one or two or more substituent groups selected from the group consisting of an aryl group, a silyl group, an alkyl group, a cycloalkyl group, and an arylamino group are substituted or unsubstituted. Specific examples thereof include styrylamine, styryldiamine, styryltriamine, styryltetramine, and the like, but are not limited thereto. Further, examples of the metal complex include an iridium complex, a platinum complex, and the like, but are not limited thereto.

The electron transport layer is a layer receiving the electrons from the electron injection layer and transporting the electrons to the light emitting layer, the electron transport material is a material that can receive the electrons well from the cathode and transport the electrons to the light emitting layer, and a material having large mobility to the electrons is suitable. Specific examples thereof include an 8-hydroxyquinoline Al complex; a complex including Alq$_3$; an organic radical compound; a hydroxyflavone-metal complex, and the like, but are not limited thereto. The electron transport layer may be used together with a predetermined desired cathode material as used according to the prior art. Particularly, an example of an appropriate cathode material is a general material having the low work function and followed by an aluminum layer or a silver layer. Specific examples thereof include cesium, barium, calcium, ytterbium, and samarium, and each case is followed by the aluminum layer or the silver layer.

The electron injection layer is a layer injecting the electrons from the electrode, and a compound which has an ability of transporting the electrons, an electron injecting effect from the cathode, and an excellent electron injecting effect to the light emitting layer or the light emitting material, prevents movement of an exciton generated in the light emitting layer to the hole injection layer, and has an excellent thin film forming ability is preferable. Specific examples thereof include fluorenone, anthraquinodimethane, diphenoquinone, thiopyran dioxide, oxazole, oxadiazole, triazole, imidazole, perylene tetracarboxylic acid, fluorenylidene methane, anthrone, and the like, and its derivative, a metal complex compound, a nitrogen-containing 5-membered cycle derivative, and the like, but are not limited thereto.

Examples of the metal complex compound include 8-hydroxyquinolinato lithium, bis(8-hydroxyquinolinato)zinc, bis(8-hydroxyquinolinato)copper, bis(8-hydroxyquinolinato)manganese, tris(8-hydroxyquinolinato)aluminum, tris(2-methyl-8-hydroxyquinolinato)aluminum, tris(8-hydroxyquinolinato)gallium, bis(10-hydroxybenzo[h]quinolinato) beryllium, bis(10-hydroxybenzo[h]quinolinato)zinc, bis(2-methyl-8-quinolinato)chlorogallium, bis(2-methyl-8-quinolinato)(o-cresolato)gallium, bis(2-methyl-8-quinolinato)(1-naphtholato)aluminum, bis(2-methyl-8-quinolinato)(2-naphtholato)gallium, and the like, but are not limited thereto.

The organic light emitting device according to the present invention may be a front side emission type, a back side emission type, or a double side emission type according to the used material.

In addition, the compound represented by Chemical Formula 1 may be included in an organic solar cell or an organic transistor in addition to an organic light emitting device.

The preparation of the compound represented by Chemical Formula 1 and the organic light emitting device comprising the same will be described in detail in the following examples. However, these examples are presented for illustrative purposes only, and the scope of the present invention is not limited thereto.

PREPARATION EXAMPLE

Preparation Example 1

Preparation of Intermediate A

Step 1) Preparation of Intermediate A-1

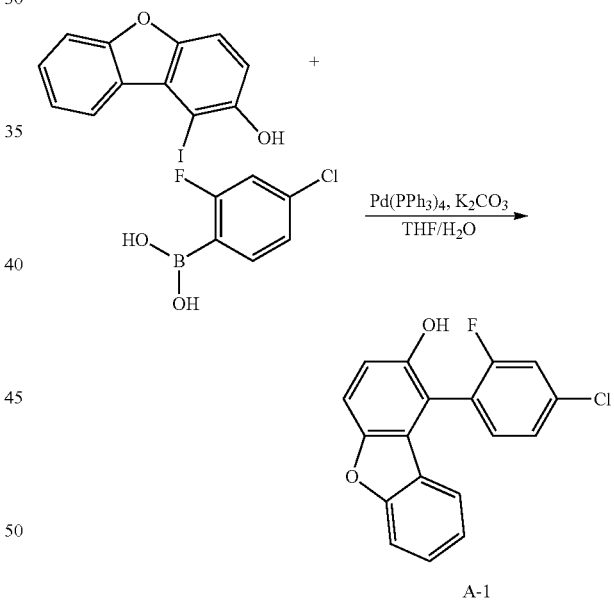

To a three-necked flask, 1-iododibenzo[b,d]furan-2-ol (30.0 g, 96.7 mmol), and (4-chloro-2-fluorophenyl)boronic acid (18.6 g, 106.4 mmol) were dissolved in THF (450 mL) and K$_2$CO$_3$ (53.5 g, 387.0 mmol) was dissolved in water (225 mL) and added. Pd(PPh$_3$)$_4$ (4.5 g, 3.9 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography to obtain Intermediate A-1 (25.1 g, yield 83%, MS: [M+H]$^+$=313).

Step 2) Preparation of Intermediate A

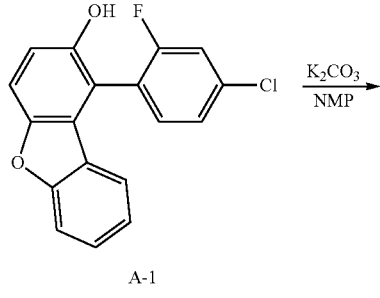

A-1

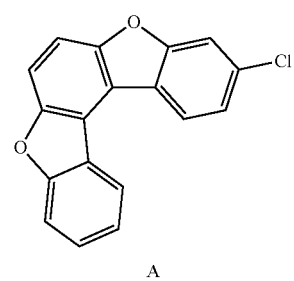

A

To a three-necked flask, Intermediate A-1 (25.0 g, 79.9 mmol), K$_2$CO$_3$ (22.1 g, 159.9 mmol) and NMP (325 mL) were added and stirred overnight at 120° C. After completion of the reaction, the reaction solution was cooled to room temperature, and water (200 mL) was added dropwise little by little thereto. The reaction solution was then transferred to a separatory funnel, and the organic layer was extracted with water and ethyl acetate. The extract was dried over MgSO$_4$, filtered and concentrated. The sample was then purified by silica gel column chromatography to obtain Intermediate A (20.1 g, yield 86%, MS: [M+H]$^+$=293).

Preparation Example 2

Preparation of Intermediate B

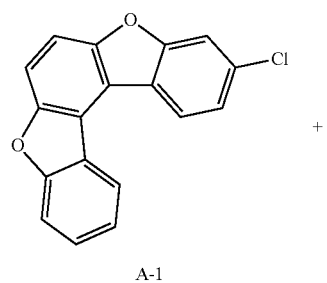

A-1

+

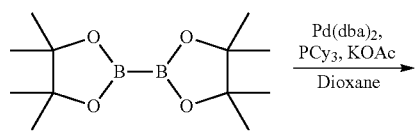

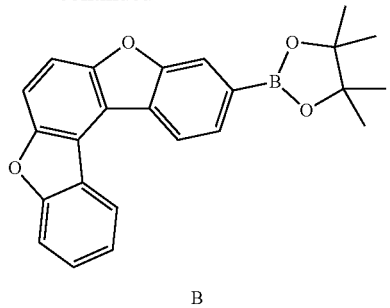

B

To a three-necked flask, Intermediate A (20.0 g, 68.3 mmol), bis(pinacolato)diboron (20.8 g, 82.0 mmol), Pd(dba)$_2$ (0.8 g, 1.4 mmol), tricyclohexylphosphine (0.8 g, 2.7 mmol), KOAc (13.4 g, 136.6 mmol) and 1,4-dioxane (300 mL) were added, and the mixture was stirred under the argon atmosphere and reflux conditions for 12 hours. After completion of the reaction, the reaction solution was cooled to room temperature and then transferred to a separatory funnel, to which water (200 mL) was added and extracted with ethyl acetate. The extract was dried over MgSO$_4$, filtered and concentrated. The sample was purified by silica gel column chromatography to obtain Intermediate B (20.5 g, yield 78%, MS: [M+H]$^+$=384).

Preparation Example 3

Preparation of Intermediate C

Step 1) Preparation of Intermediate C-1

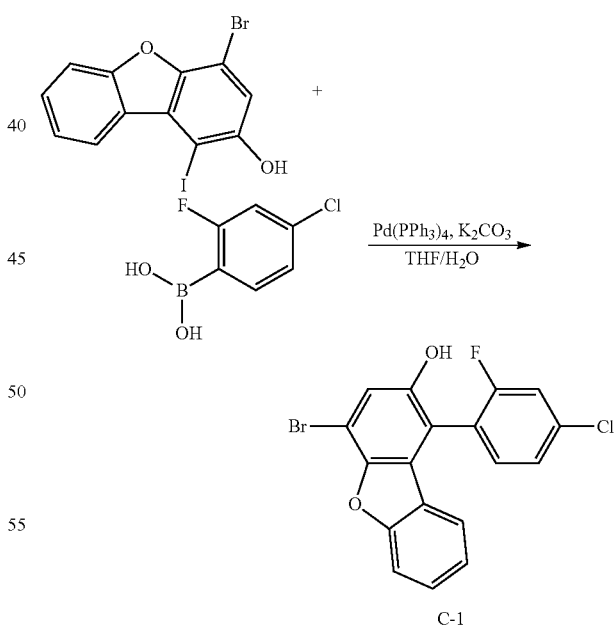

C-1

To a three-necked flask, 4-bromo-1-iododibenzo[b,d]furan-2-ol (30.0 g, 77.1 mmol) and (4-chloro-2-fluorophenyl)boronic acid (14.8 g, 84.8 mmol) were dissolved in THF (450 mL) and K$_2$CO$_3$ (42.6 g, 308.5 mmol) was dissolved in water (225 mL) and added. Pd(PPh$_3$)$_4$ (3.6 g, 3.1 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography to obtain Intermediate C-1 (23.3 g, yield 77%, MS: [M+H]$^+$=392).

Step 2) Preparation of Intermediate C

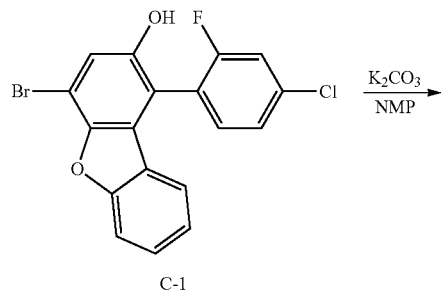

C-1

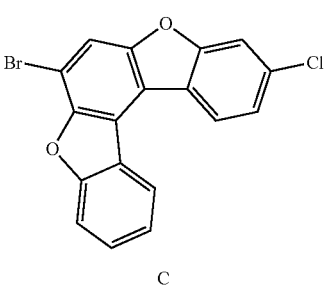

C

To a three-necked flask, Intermediate C-1 (20.0 g, 51.1 mmol), K$_2$CO$_3$ (14.1 g, 102.1 mmol) and NMP (250 mL) were added and stirred overnight at 120° C. After completion of the reaction, the reaction solution was cooled to room temperature, and water (200 mL) was added dropwise little by little thereto. The reaction solution was then transferred to a separatory funnel, and the organic layer was extracted with water and ethyl acetate. The extract was dried over MgSO$_4$, filtered and concentrated. The sample was then purified by silica gel column chromatography to obtain Intermediate C (15.8 g, yield 83%, MS: [M+H]$^+$=372).

Preparation Example 4

Preparation of Intermediate D

Step 1) Preparation of Intermediate D-1

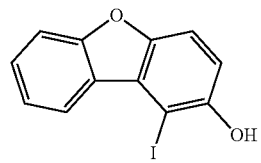

I

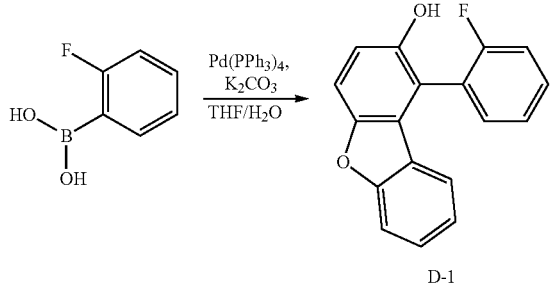

D-1

To a three-necked flask, 1-iododibenzo[b,d]furan-2-ol (30.0 g, 96.7 mmol) and (2-fluorophenyl)boronic acid (14.9 g, 106.4 mmol) were dissolved in THF (450 mL) and K$_2$CO$_3$ (53.5 g, 387.0 mmol) was dissolved in water (225 mL) and added. Pd(PPh$_3$)$_4$ (4.5 g, 3.9 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography to obtain Intermediate D-1 (22.6 g, yield 84%, MS: [M+H]$^+$=278).

Step 2) Preparation of Intermediate D-2

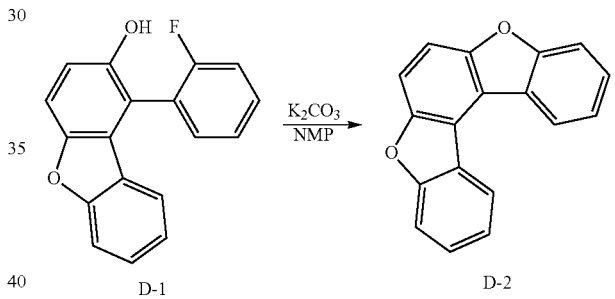

D-1                    D-2

To a three-necked flask, Intermediate D-1 (22.0 g, 79.1 mmol), K$_2$CO$_3$ (21.9 g, 158.1 mmol) and NMP (280 mL) were added and stirred overnight at 120° C. After completion of the reaction, the reaction solution was cooled to room temperature, and water (200 mL) was added dropwise little by little thereto. The reaction solution was then transferred to a separatory funnel, and the organic layer was extracted with water and ethyl acetate. The extract was dried over MgSO$_4$, filtered and concentrated. The sample was then purified by silica gel column chromatography to obtain Intermediate D-2 (15.1 g, yield 74%, MS: [M+H]$^+$=258).

Step 3) Preparation of Intermediate D

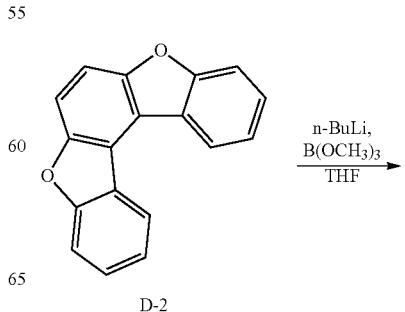

D-2

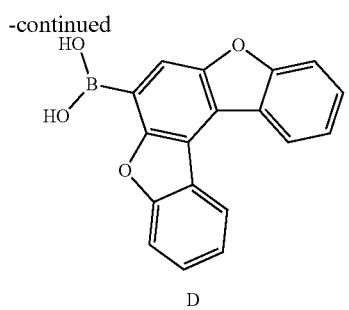

D

To a three-necked flask, Intermediate D-2 (15.0 g, 258.28 mmol) was dissolved in THF (150 mL) under nitrogen atmosphere, and then 1.6 M n-butyllithium (38 mL, 61.0 mmol) was slowly added dropwise while stirring at −78° C. After completion of the dropwise addition, the reaction mixture was further stirred for 1 hour while maintaining the temperature at −78° C. Then, trimethylborate (7.2 g, 69.7 mmol) was slowly added dropwise, and the mixture was warmed to room temperature and stirred for 1 hour. After completion of the reaction, 2N HCl aqueous solution (50 mL) was added dropwise at room temperature and then stirred for 30 minutes. The reaction solution was transferred to a separatory funnel, and the organic layer was extracted with water and ethyl acetate, concentrated under reduced pressure, and then recrystallized from $CH_2Cl_2$ and hexane to obtain Intermediate D (13.7 g, yield 78%, MS: $[M+H]^+$=302).

Preparation Example 5

Preparation of Intermediate E

Step 1) Preparation of Intermediate E-1

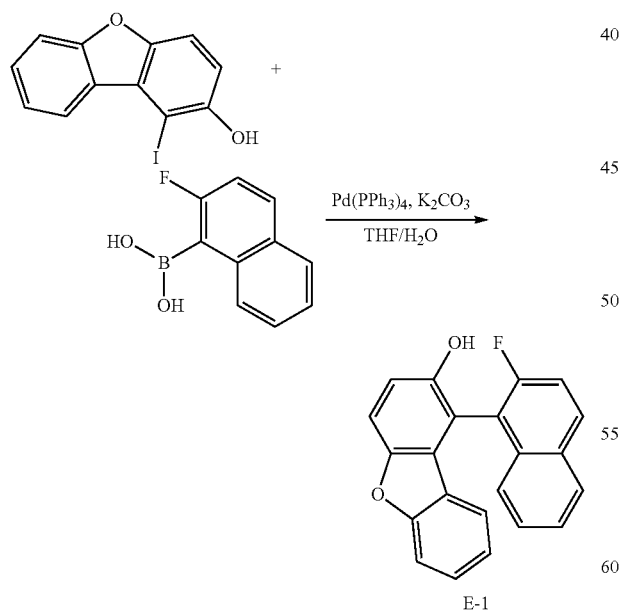

To a three-necked flask, 1-iododibenzo[b,d]furan-2-ol (30.0 g, 96.7 mmol) and (2-fluoronaphthalen-1-yl)boronic acid (20.2 g, 106.4 mmol) were dissolved in THF (450 mL) and $K_2CO_3$ (53.5 g, 387.0 mmol) was dissolved in water (225 mL) and added. $Pd(PPh_3)_4$ (4.5 g, 3.9 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over $MgSO_4$, filtered and concentrated. The sample was purified by silica gel column chromatography to obtain Intermediate E-1 (27.0 g, yield 85%, MS: $[M+H]^+$=328).

Step 2) Preparation of Intermediate E-2

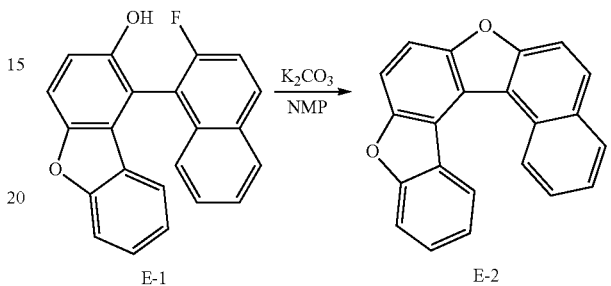

To a three-necked flask, Intermediate E-1 (27.0 g, 82.2 mmol), $K_2CO_3$ (22.7 g, 164.5 mmol) and NMP (350 mL) were added and stirred overnight at 120° C. After completion of the reaction, the reaction solution was cooled to room temperature, and water (200 mL) was added dropwise little by little thereto. The reaction solution was then transferred to a separatory funnel, and the organic layer was extracted with water and ethyl acetate. The extract was dried over $MgSO_4$, filtered and concentrated. The sample was then purified by silica gel column chromatography to obtain Intermediate E-2 (20.5 g, yield 81%, MS: $[M+H]^+$=308).

Step 3) Preparation of Intermediate E

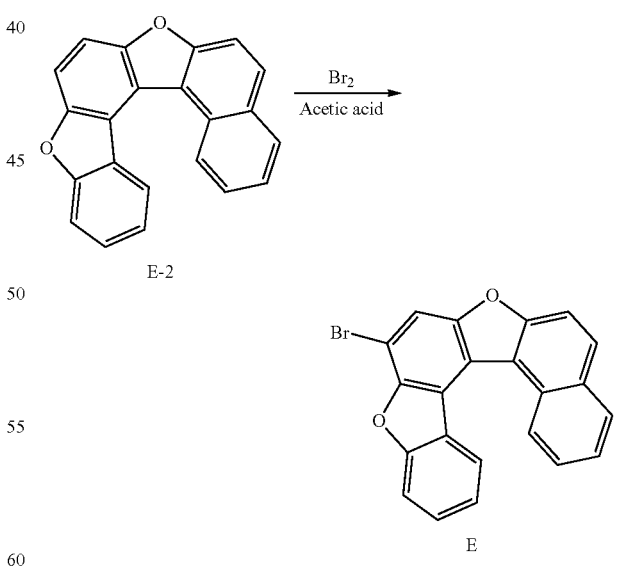

In a two-necked flask, Intermediate E-2 (20.0 g, 64.9 mmol) was dissolved in acetic acid (200 mL) by heating under argon atmosphere. Bromine (3 mL, 68.1 mmol) was slowly added dropwise thereto, and then stirred for 10 hours while cooling to room temperature. After completion of the reaction, the resulting solid was filtered, and washed with acetic acid and water. The sample was then purified by silica gel column chromatography to obtain Intermediate E (16.8 g, yield 67%, MS: [M+H]⁺=387).

Preparation Example 6

Preparation of Intermediate F

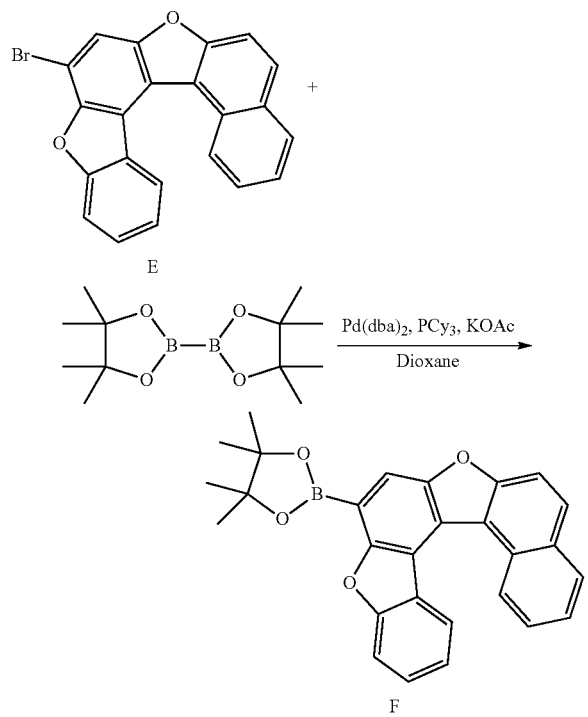

To a three-necked flask, Intermediate E (15.0 g, 38.7 mmol), bis(pinacolato)diboron (11.8 g, 46.5 mmol), Pd(dba)₂ (0.4 g, 0.8 mmol), tricyclohexylphosphine (0.4 g, 1.5 mmol), KOAc (7.6 g, 77.5 mmol) and 1,4-dioxane (225 mL) were added, and the mixture was stirred under the argon atmosphere and reflux conditions for 12 hours. After completion of the reaction, the reaction solution was cooled to room temperature and then transferred to a separatory funnel, to which water (150 ml) was added and extracted with ethyl acetate. The extract was dried over MgSO₄, filtered and concentrated. The sample was purified by silica gel column chromatography to obtain Intermediate F (13.1 g, yield 78%, MS: [M+H]⁺=434).

Preparation Example 7

Preparation of Intermediate G

Step 1) Preparation of Intermediate G-1

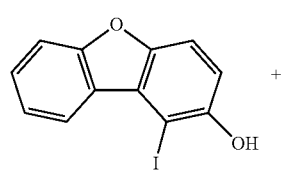

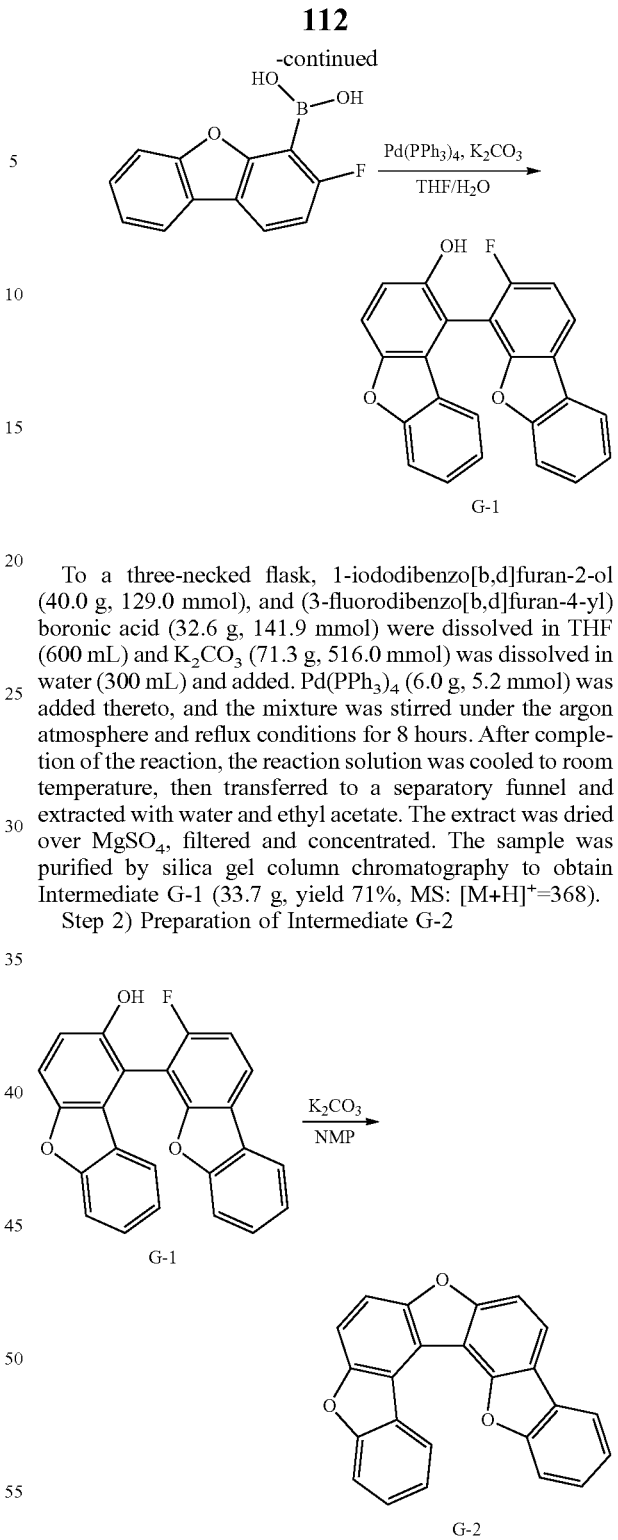

To a three-necked flask, 1-iododibenzo[b,d]furan-2-ol (40.0 g, 129.0 mmol), and (3-fluorodibenzo[b,d]furan-4-yl) boronic acid (32.6 g, 141.9 mmol) were dissolved in THF (600 mL) and K₂CO₃ (71.3 g, 516.0 mmol) was dissolved in water (300 mL) and added. Pd(PPh₃)₄ (6.0 g, 5.2 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO₄, filtered and concentrated. The sample was purified by silica gel column chromatography to obtain Intermediate G-1 (33.7 g, yield 71%, MS: [M+H]⁺=368).

Step 2) Preparation of Intermediate G-2

To a three-necked flask, Intermediate G-1 (30.0 g, 81.4 mmol), K₂CO₃ (22.5 g, 162.9 mmol) and NMP (390 mL) were added and stirred overnight at 120° C. After completion of the reaction, the reaction solution was cooled to room temperature, and water (200 mL) was added dropwise little by little thereto. The reaction solution was then transferred to a separatory funnel, and the organic layer was extracted with water and ethyl acetate. The extract was dried over MgSO₄, filtered and concentrated. The sample was then purified by silica gel column chromatography to obtain Intermediate G-2 (21.3 g, yield 75%, MS: [M+H]⁺=348).

Step 3) Preparation of Intermediate G

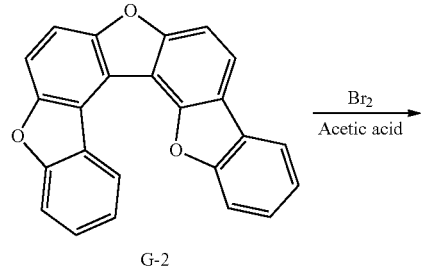

G-2

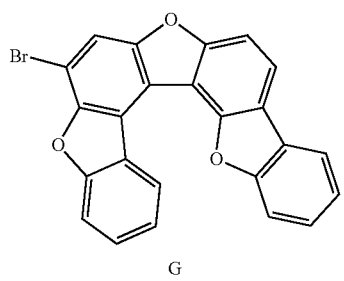

G

In a two-necked flask, Intermediate G-2 (21.0 g, 60.3 mmol) was dissolved in acetic acid (210 mL) by heating under argon atmosphere. Bromine (3 mL, 63.3 mmol) was slowly added dropwise thereto, and then stirred for 10 hours while cooling to room temperature. After completion of the reaction, the resulting solid was filtered, and washed with acetic acid and water. The sample was then purified by silica gel column chromatography to obtain Intermediate G (14.7 g, yield 57%, MS: [M+H]⁺=427).

Preparation Example 8

Preparation of Intermediate H

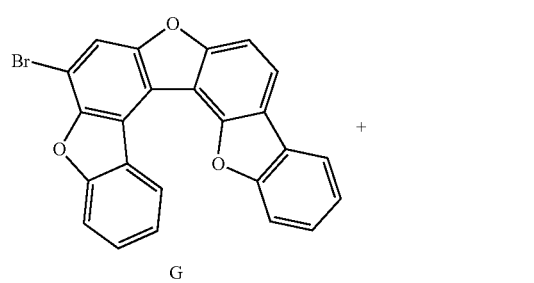

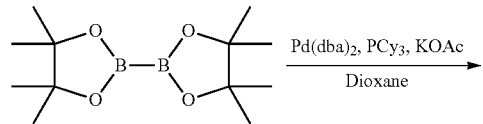

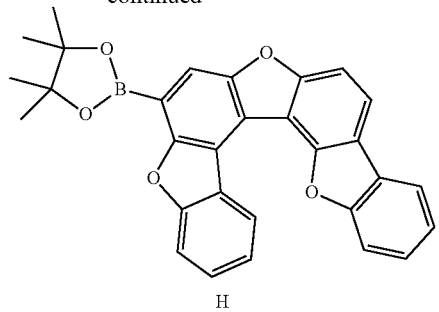

H

To a three-necked flask, Intermediate G (14.0 g, 32.8 mmol), bis(pinacolato)diboron (10.0 g, 39.3 mmol), Pd(dba)₂ (0.4 g, 0.7 mmol), tricyclohexylphosphine (0.4 g, 1.3 mmol), KOAc (6.4 g, 65.5 mmol), and 1,4-dioxane (210 mL) were added, and the mixture was stirred under the argon atmosphere and reflux conditions for 12 hours. After completion of the reaction, the reaction solution was cooled to room temperature, then transferred to a separatory funnel, to which water (150 ml) was added and extracted with ethyl acetate. The extract was dried over MgSO₄, filtered and concentrated. The sample was purified by silica gel column chromatography to obtain Intermediate H (12.6 g, yield 81%, MS: [M+H]⁺=474).

Preparation Example 9

Preparation of Intermediate I

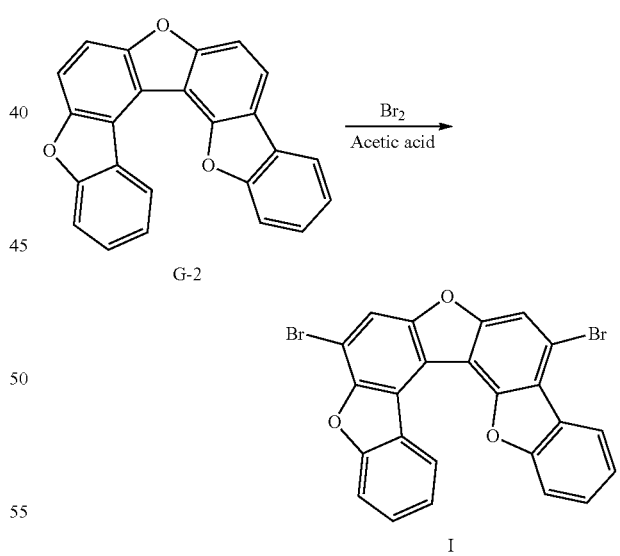

In a two-necked flask, Intermediate G-2 (15.0 g, 43.1 mmol) was dissolved in acetic acid (150 mL) by heating under argon atmosphere. Bromine (5 mL, 90.4 mmol) was slowly added dropwise thereto, and then stirred for 10 hours while cooling to room temperature. After completion of the reaction, the resulting solid was filtered, and washed with acetic acid and water. The sample was then purified by silica gel column chromatography to obtain Intermediate I (9.4 g, yield 43%, MS: [M+H]⁺=506).

EXAMPLE

Example 1-1

Preparation of Compound 1-1

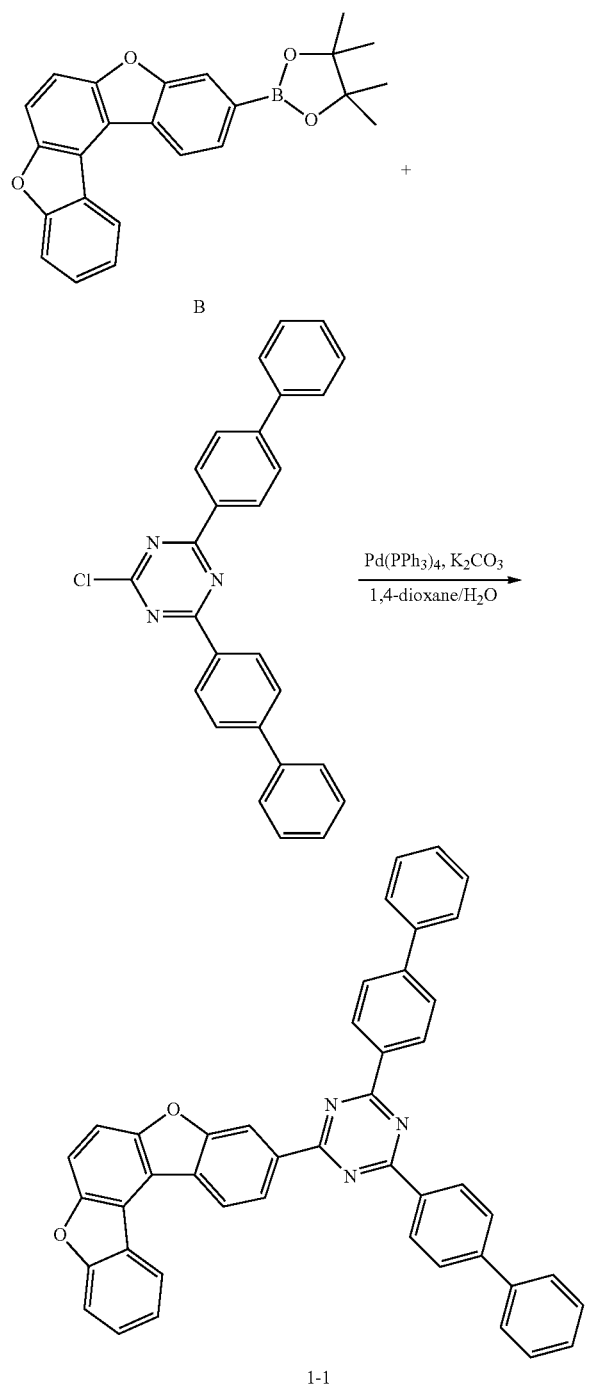

To a three-necked flask, Intermediate B (15.0 g, 39.0 mmol) and di([1,1-biphenyl]-4-yl)-6-chloro-1,3,5-triazine (18.0 g, 42.9 mmol) were dissolved in 1,4-dioxane (225 mL) and K$_2$CO$_3$ (21.6 g, 156.2 mmol) was dissolved in water (113 mL) and added. Pd(PPh$_3$)$_4$ (1.8 g, 1.6 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography, and then subjected to sublimation purification to obtain Compound 1-1 (7.0 g, yield 28%, MS: [M+H]$^+$=642).

Example 1-2

Preparation of Compound 1-2

Step 1) Preparation of Compound 1-2-A

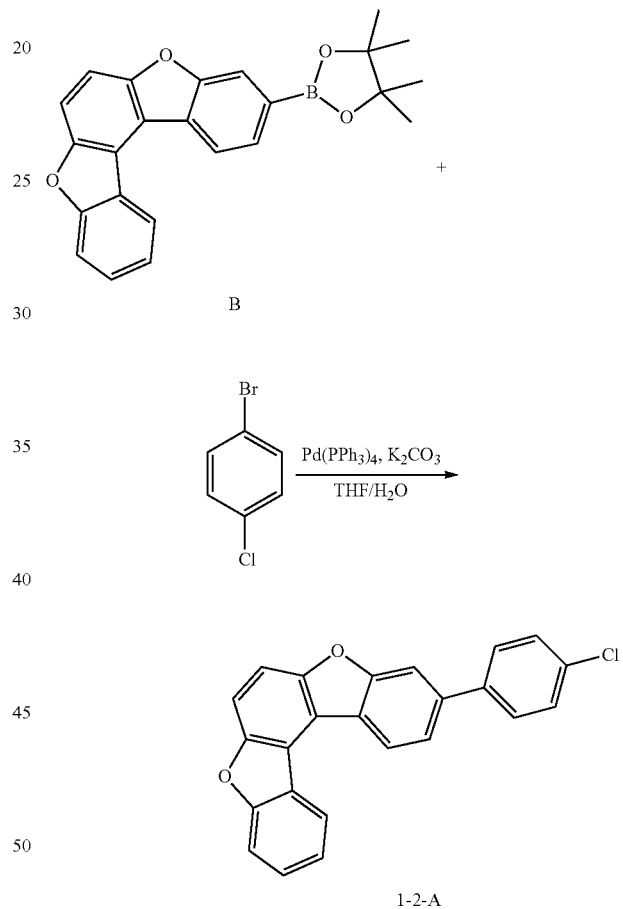

To a three-necked flask, Intermediate B (20.0 g, 52.1 mmol) and 1-bromo-4-chlorobenzene (11.0 g, 57.3 mmol) were dissolved in THF (300 mL) and K$_2$CO$_3$ (28.8 g, 208.2 mmol) was dissolved in water (150 mL) and added. Pd(PPh$_3$)$_4$ (2.4 g, 2.1 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography to obtain Compound 1-2-A (14.4 g, yield 75%, MS: [M+H]$^+$=369).

Step 2) Preparation of Compound 1-2-B

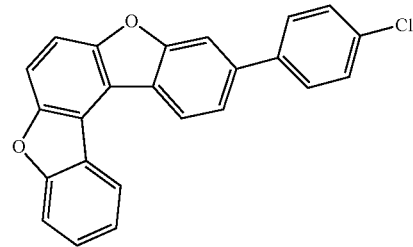

1-2-A

+

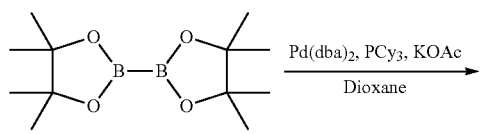

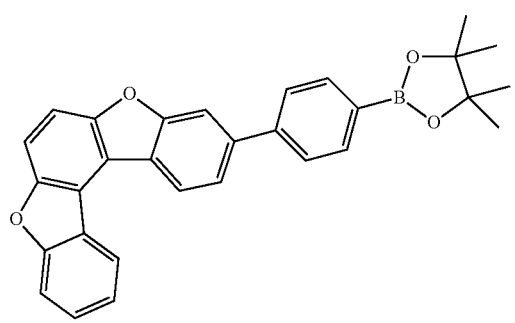

1-2-B

To a three-necked flask, Compound 1-2-A (14.0 g, 38.0 mmol), bis(pinacolato)diboron (11.6 g, 45.6 mmol), Pd(dba)$_2$ (0.4 g, 0.8 mmol), tricyclohexylphosphine (0.4 g, 1.5 mmol), KOAc (7.5 g, 75.9 mmol) and 1,4-dioxane (210 mL) were added, and the mixture was stirred under the argon atmosphere and reflux conditions for 12 hours. After completion of the reaction, the reaction solution was cooled to room temperature and then transferred to a separatory funnel, to which water (150 ml) was added and extracted with ethyl acetate. The extract was dried over MgSO$_4$, filtered and concentrated. The sample was purified by silica gel column chromatography to obtain Compound 1-2-B (11.9 g, yield 68%, MS: [M+H]$^+$=460).

Step 3) Preparation of Compound 1-2

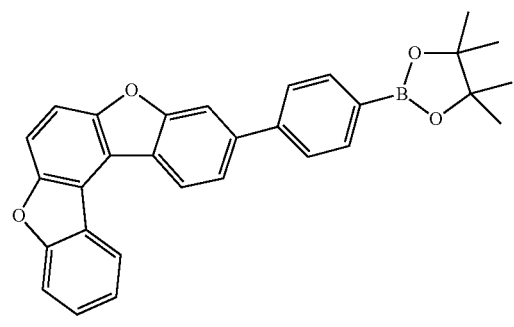

1-2-B

+

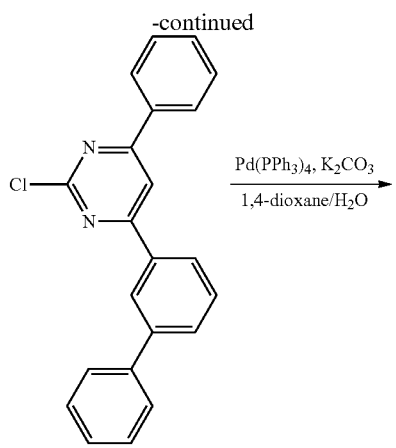

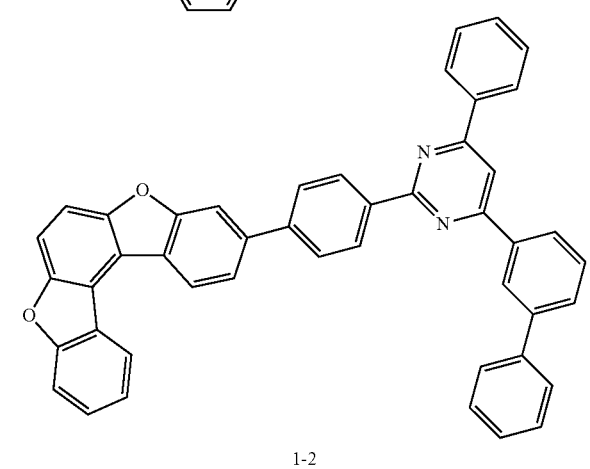

1-2

To a three-necked flask, Intermediate 1-2-B (10.0 g, 21.7 mmol) and 4-([1,1'-biphenyl]-3-yl)-2-chloro-6-phenylpyrimidine (8.2 g, 23.9 mmol) were dissolved in 1,4-dioxane (150 mL) and K$_2$CO$_3$ (12.0 g, 86.9 mmol) was dissolved in water (75 mL) and added. Pd(PPh$_3$)$_4$ (1.0 g, 0.9 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography, and then subjected to sublimation purification to obtain Compound 1-2 (4.9 g, yield 35%, MS: [M+H]$^+$=641).

Example 1-3

Preparation of Compound 1-3

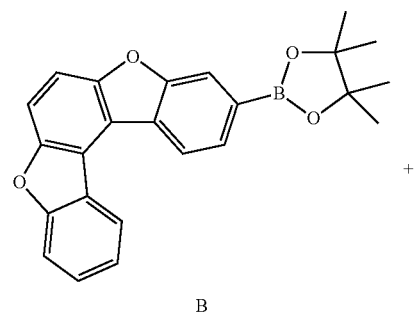

B

+

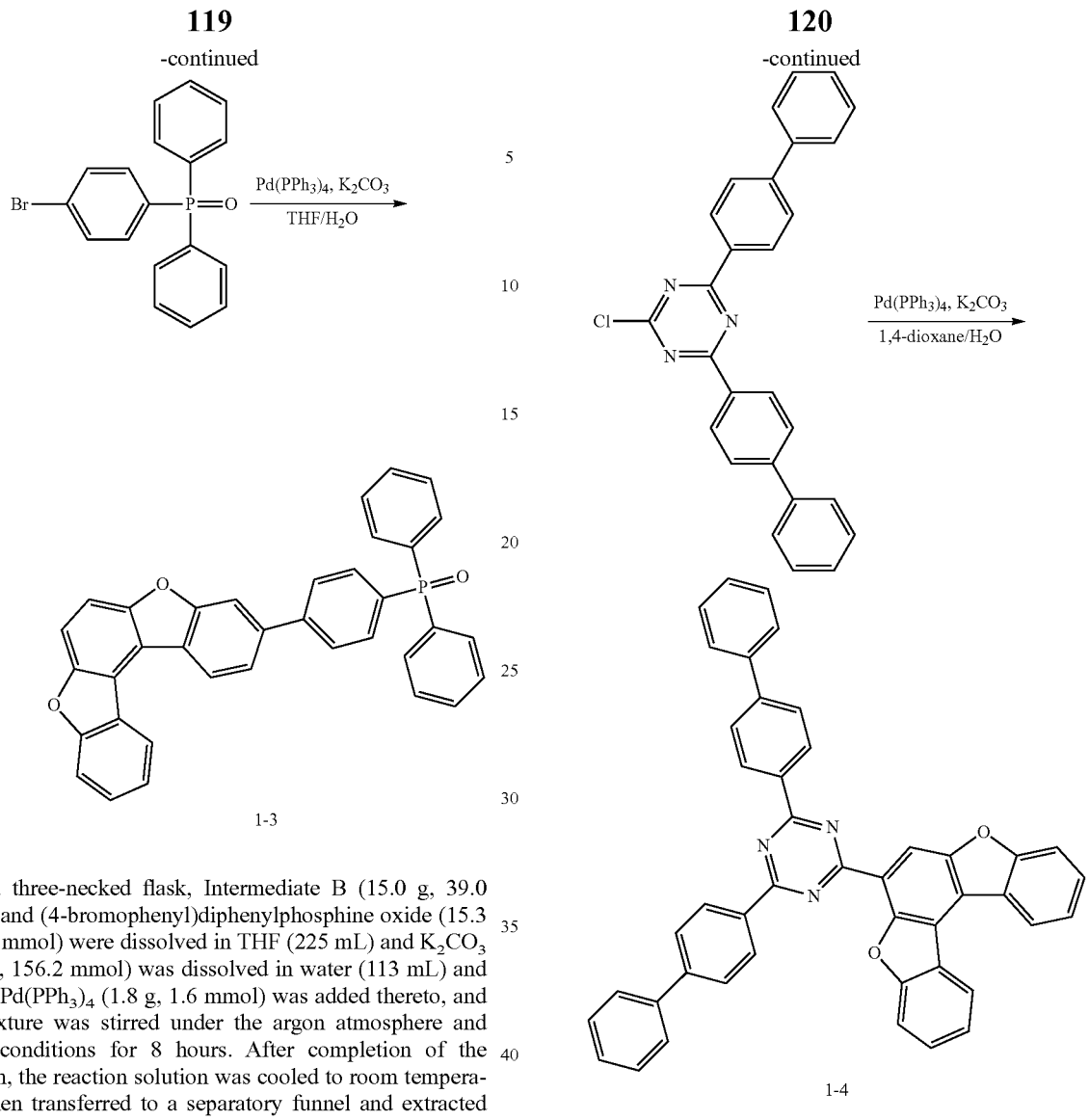

To a three-necked flask, Intermediate B (15.0 g, 39.0 mmol) and (4-bromophenyl)diphenylphosphine oxide (15.3 g, 42.9 mmol) were dissolved in THF (225 mL) and K$_2$CO$_3$ (21.6 g, 156.2 mmol) was dissolved in water (113 mL) and added. Pd(PPh$_3$)$_4$ (1.8 g, 1.6 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO$_4$, filtered and concentrated. The sample was purified by silica gel column chromatography, and then subjected to sublimation purification to obtain Compound 1-3 (6.5 g, yield 31%, MS: [M+H]$^+$=535).

Example 1-4

Preparation of Compound 1-4

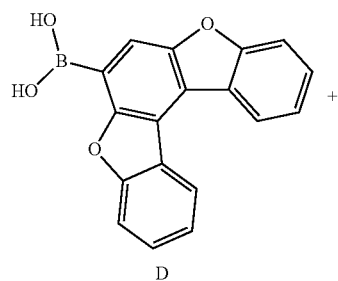

D

Compound 1-4 was prepared in the same manner as in Preparation of Compound 1-1, except that Intermediate D was used instead of Intermediate B (9.6 g, yield 30%, MS: [M+H]$^+$=642).

Example 1-5

Preparation of Compound 1-5

Step 1) Preparation of Compound 1-5-A

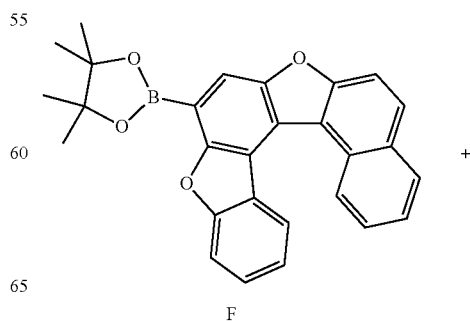

F

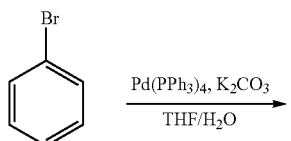

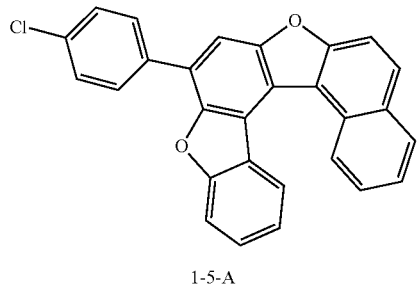

1-5-A

To a three-necked flask, Intermediate F (15.0 g, 34.5 mmol) and 1-bromo-4-chlorobenzene (7.3 g, 38.0 mmol) were dissolved in THF (225 mL) and K₂CO₃ (19.1 g, 138.2 mmol) was dissolved in water (113 mL) and added. Pd(PPh₃)₄ (1.6 g, 1.4 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO₄, filtered and concentrated. The sample was purified by silica gel column chromatography to obtain Compound 1-5-A (10.6 g, yield 73%, MS: [M+H]⁺=419).

Step 2) Preparation of Compound 1-5

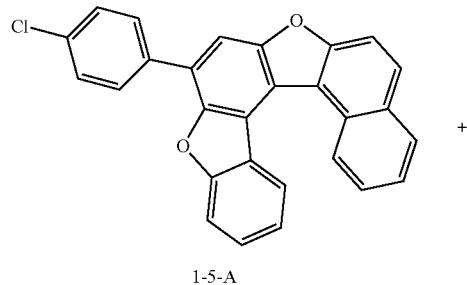

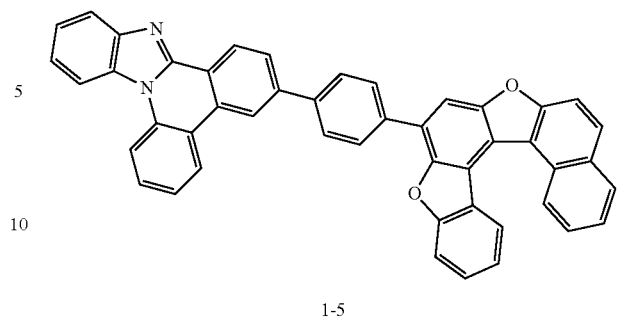

1-5

To a three-necked flask, Intermediate 1-5-A (10.0 g, 23.9 mmol) and 6-(4,4,5,5-tetramethyl-1,3,2-dioxaborolan-2-yl)benzo[4,5]imidazo[1,2-f]phenanthridine (10.4 g, 26.3 mmol) were dissolved in 1,4-dioxane (150 mL) and K₂CO₃ (13.2 g, 95.5 mmol) was dissolved in water (75 mL) and added. Pd(PPh₃)₄ (1.1 g, 1.0 mmol) was added thereto, and the mixture was stirred under the argon atmosphere and reflux conditions for 8 hours. After completion of the reaction, the reaction solution was cooled to room temperature, then transferred to a separatory funnel and extracted with water and ethyl acetate. The extract was dried over MgSO₄, filtered and concentrated. The sample was purified by silica gel column chromatography, and then subjected to sublimation purification to obtain Compound 1-5 (5.0 g, yield 32%, MS: [M+H]⁺=651).

Example 1-6

Preparation of Compound 1-6

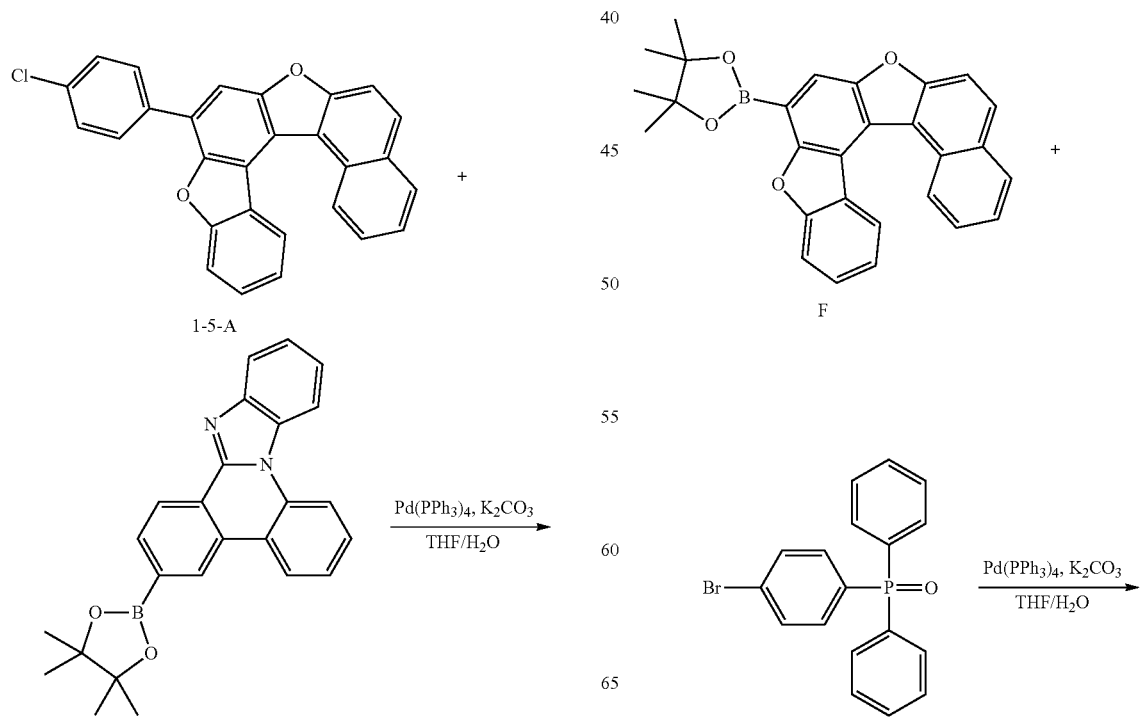

-continued

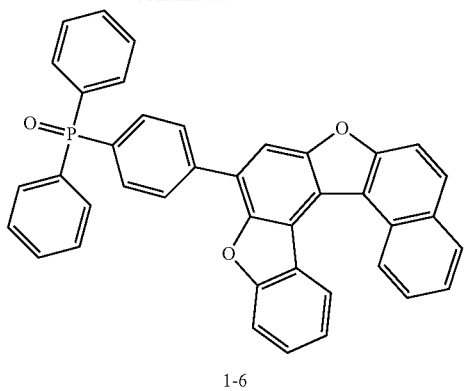

1-6

Compound 1-6 was prepared in the same manner as in Preparation of Compound 1-3, except that Intermediate F was used instead of Intermediate B (6.1 g, yield 30%, MS: [M+H]$^+$=585).

Example 1-7

Preparation of Compound 1-7

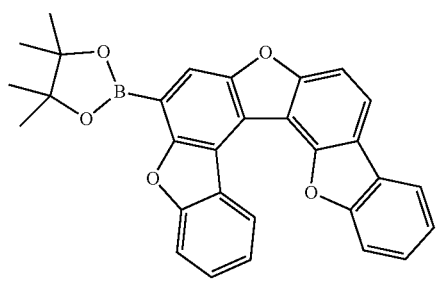

H

+

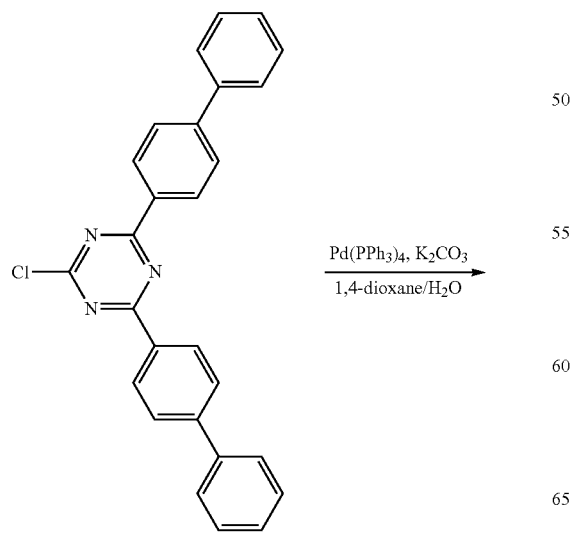

-continued

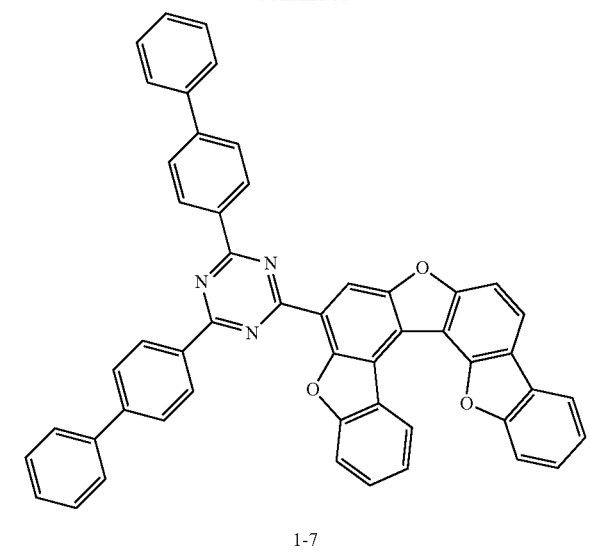

1-7

Compound 1-7 was prepared in the same manner as in Preparation of Compound 1-1, except that Intermediate H was used instead of Intermediate B (6.7 g, yield 31%, MS: [M+H]$^+$=732).

Example 2-1

Preparation of Compound 2-1

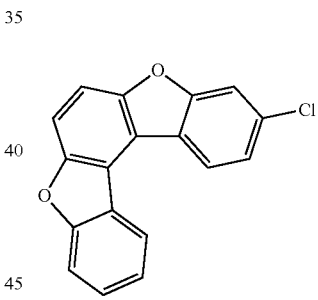

A

+

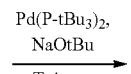

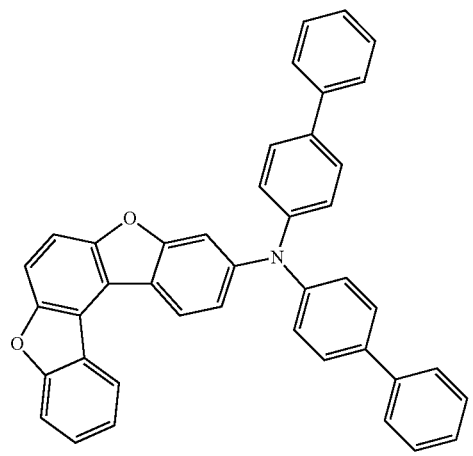

2-1

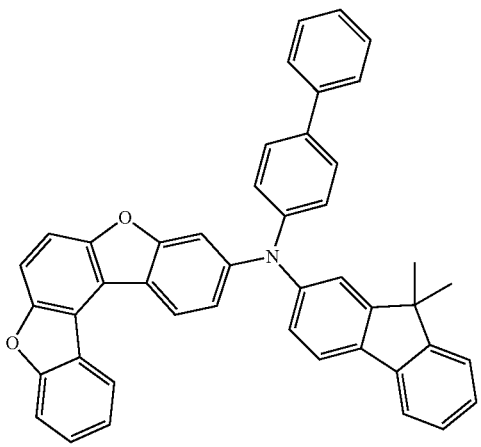

2-2

To a three-necked flask, Intermediate A (12.0 g, 41.0 mmol), di([1,1'-biphenyl]-4-yl)amine (14.5 g, 45.1 mmol) was dissolved in toluene (300 mL) and sodium tert-butoxide (11.8 g, 123.0 mmol) and bis(tri-tert-butylphosphine)palladium(0) (0.4 g, 0.8 mmol) were added, and then the mixture was stirred under the argon atmosphere and reflux conditions for 6 hours. After completion of the reaction, the reaction solution was cooled to room temperature, then transferred to a separatory funnel and extracted. The extract was dried over MgSO$_4$, filtered and concentrated. The sample was purified by silica gel column chromatography, and then subjected to sublimation purification to obtain Compound 2-1 (6.6 g, yield 28%, MS: [M+H]$^+$=578).

Example 2-2

Preparation of Compound 2-2

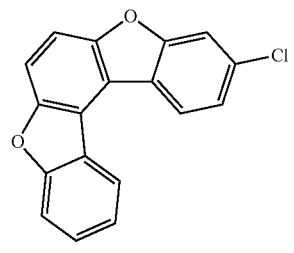

A

+

Compound 2-2 was prepared in the same manner as in Preparation of Compound 2-1, except that N-([1,1'-biphenyl]-4-yl)-9,9-dimethyl-9H-fluorene-2-amine was used instead of di([1,1'-biphenyl]-4-yl)amine (6.8 g, yield 27%, MS: [M+H]$^+$=618).

Example 2-3

Preparation of Compound 2-3

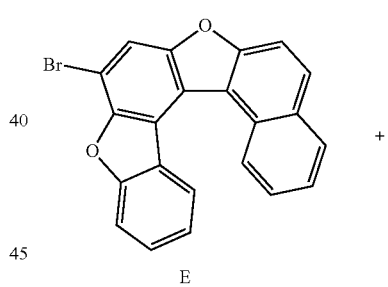

E

+

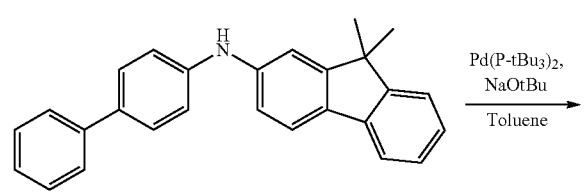

$\xrightarrow{\text{Pd(P-tBu}_3\text{)}_2,\ \text{NaOtBu}}_{\text{Toluene}}$

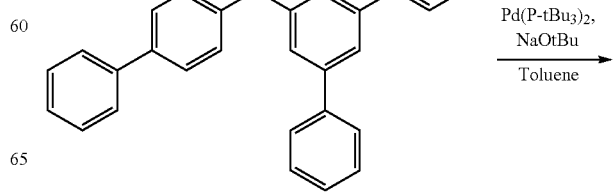

$\xrightarrow{\text{Pd(P-tBu}_3\text{)}_2,\ \text{NaOtBu}}_{\text{Toluene}}$

-continued

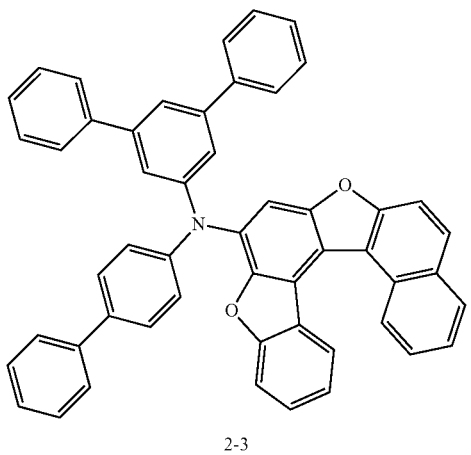

2-3

Compound 2-3 was prepared in the same manner as in Preparation of Compound 2-1, except that Intermediate E was used instead of Intermediate A and N-([1,1'-biphenyl]-4-yl)-[1,1':3',1''-terphenyl]-5'-amine was used instead of di([1,1'-biphenyl]-4-yl)amine (6.8 g, yield 31%, MS: [M+H]⁺=704).

Example 2-4

Preparation of Compound 2-4

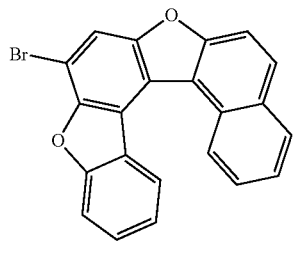

E

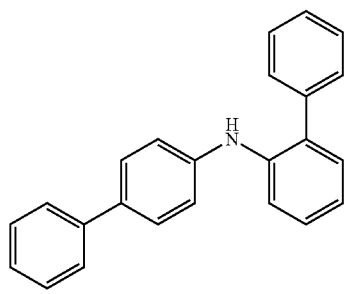

-continued

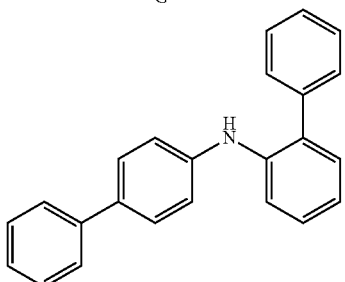

2-4

Compound 2-4 was prepared in the same manner as in Preparation of Compound 2-1, except that Intermediate E was used instead of Intermediate A and N-([1,1'-biphenyl]-4-yl)-[1,1'-biphenyl]-2-amine was used instead of di([1,1'-biphenyl]-4-yl)amine (6.4 g, yield 33%, MS: [M+H]⁺=628).

Example 2-5

Preparation of Compound 2-5

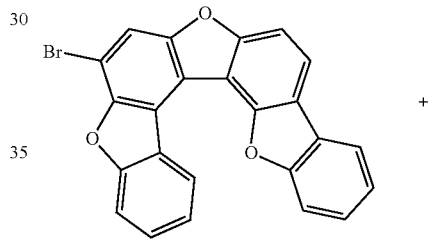

G

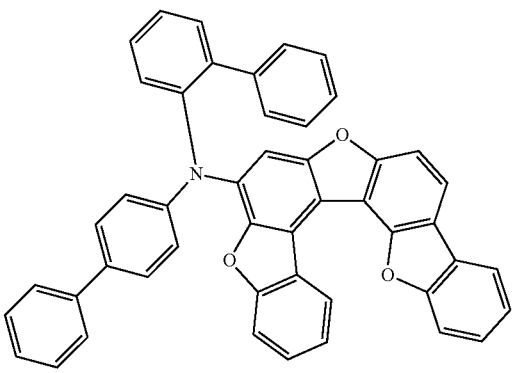

2-5

Compound 2-5 was prepared in the same manner as in Preparation of Compound 2-1, except that Intermediate G was used instead of Intermediate A and N-([1,1'-biphenyl]-4-yl)-[1,1'-biphenyl]-2-amine was used instead of di([1,1'-biphenyl]-4-yl)amine (5.6 g, yield 30%, MS: [M+H]$^+$=668).

Example 2-6

Preparation of Compound 2-6

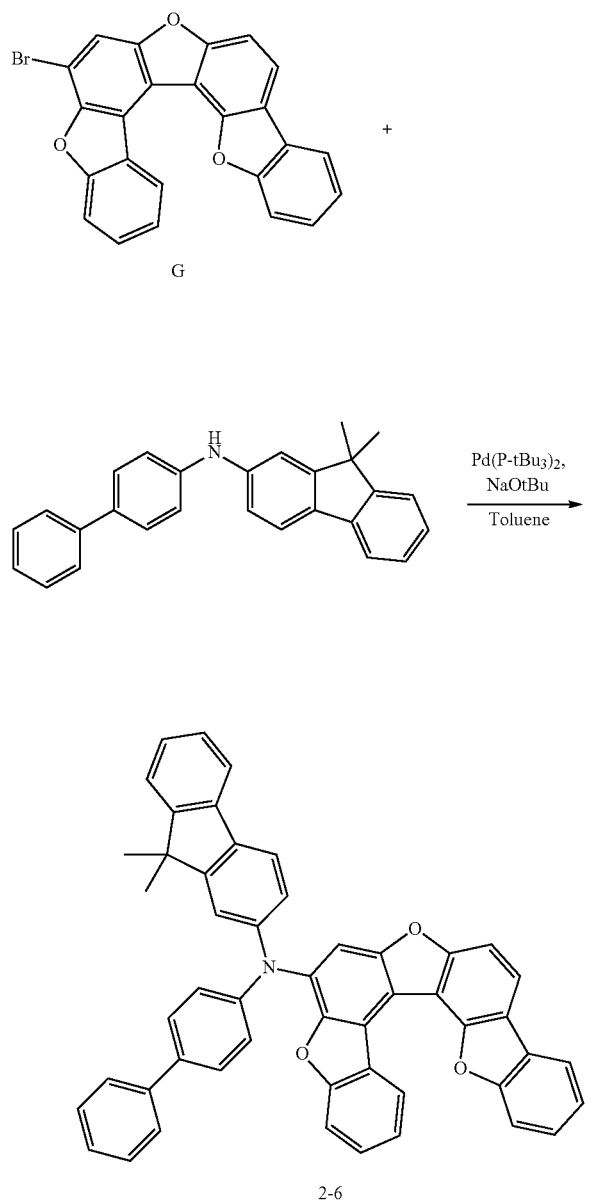

Compound 2-6 was prepared in the same manner as in Preparation of Compound 2-1, except that Intermediate G was used instead of Intermediate A and N-([1,1'-biphenyl]-4-yl)-9,9-dimethyl-9H-fluoren-2-amine was used instead of di([1,1'-biphenyl]-4-yl)amine (5.8 g, yield 29%, MS: [M+H]$^+$=708).

Example 3-1

Preparation of Compound 3-1

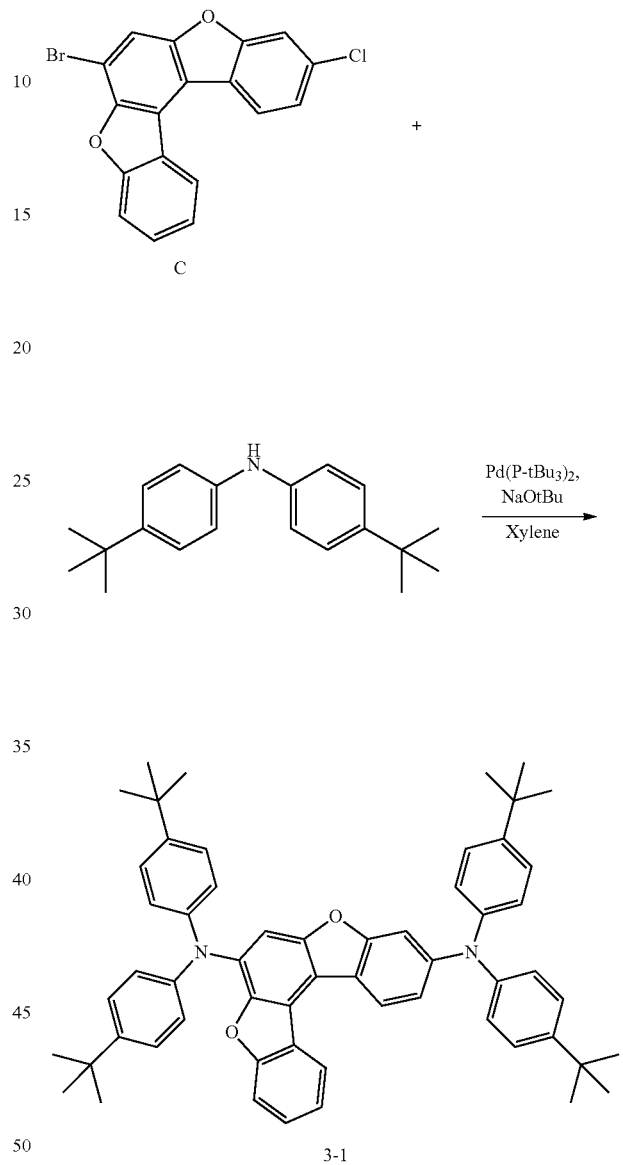

To a three-necked flask, Intermediate C (12.0 g, 32.3 mmol) and bis(4-(tert-butyl)phenyl)amine (20.0 g, 71.0 mmol) were dissolved in xylene (300 mL) and sodium tert-butoxide (9.3 g, 96.9 mmol) and bis(tri-tert-butylphosphine)palladium(0) (0.3 g, 0.6 mmol) were added, and then the mixture was stirred under the argon atmosphere and reflux conditions for 6 hours. After completion of the reaction, the reaction solution was cooled to room temperature, then transferred to a separatory funnel and extracted. The extract was dried over MgSO$_4$, filtered and concentrated. The sample was purified by silica gel column chromatography, and then subjected to sublimation purification to obtain Compound 3-1 (9.2 g, yield 35%, MS: [M+H]$^+$=817).

Example 3-2

Preparation of Compound 3-2

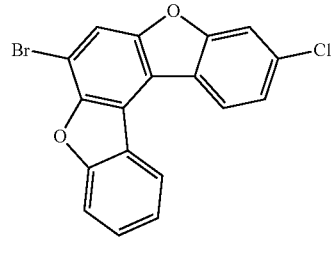

+

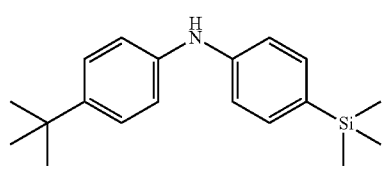

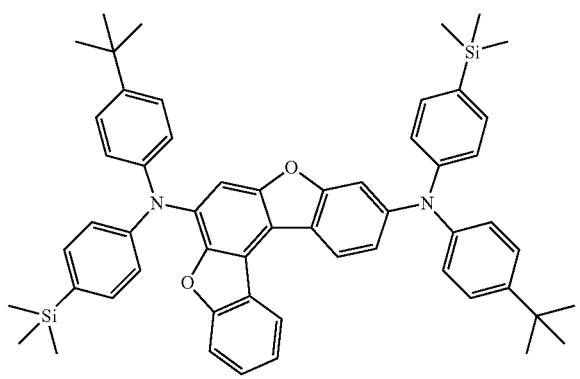

3-2

Compound 3-2 was prepared in the same manner as in Preparation of Compound 3-1, except that 4-(tert-butyl)-N-(4-(trimethylsilyl)phenyl)aniline was used instead of bis(4-(tert-butyl)phenyl)amine (9.3 g, yield 34%, MS: [M+H]$^+$= 849).

Example 3-3

Preparation of Compound 3-3

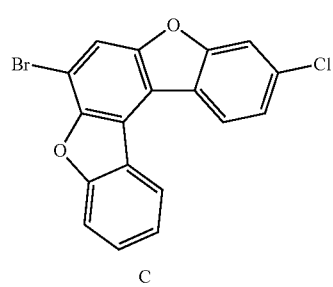

+

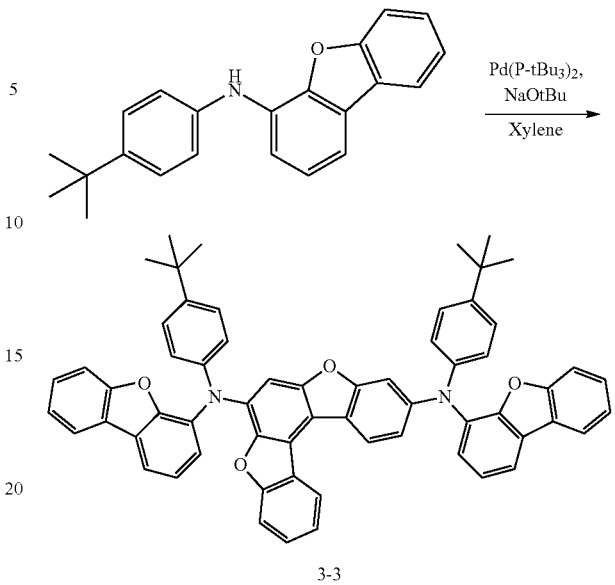

3-3

Compound 3-3 was prepared in the same manner as in Preparation of Compound 3-1, except that N-(4-(tert-butyl)phenyl)dibenzo[b,d]furan-4-amine was used instead of bis(4-(tert-butyl)phenyl)amine (8.3 g, yield 29%, MS: [M+H]$^+$= 885).

Example 3-4

Preparation of Compound 3-4

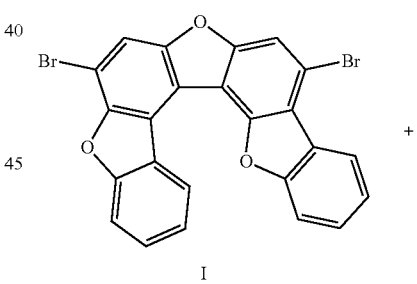

+

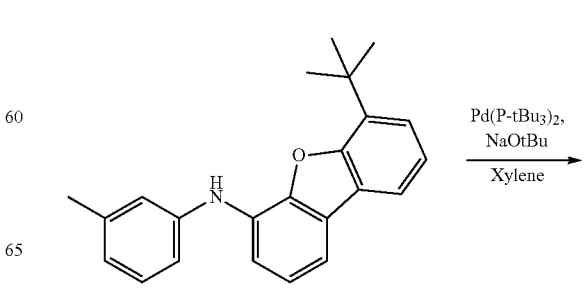

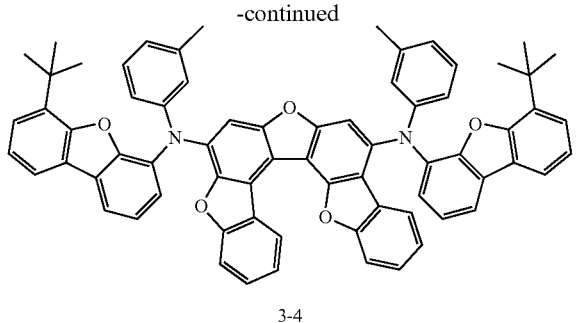

3-4

Compound 3-4 was prepared in the same manner as in Preparation of Compound 3-1, except that Intermediate I was used instead of Intermediate C and 6-(tert-butyl)-N-(m-tolyl)dibenzo[b,d]furan-4-amine was used instead of bis(4-(tert-butyl)phenyl)amine (7.1 g, yield 30%, MS: $[M+H]^+$= 1003).

Example 3-5

Preparation of Compound 3-5

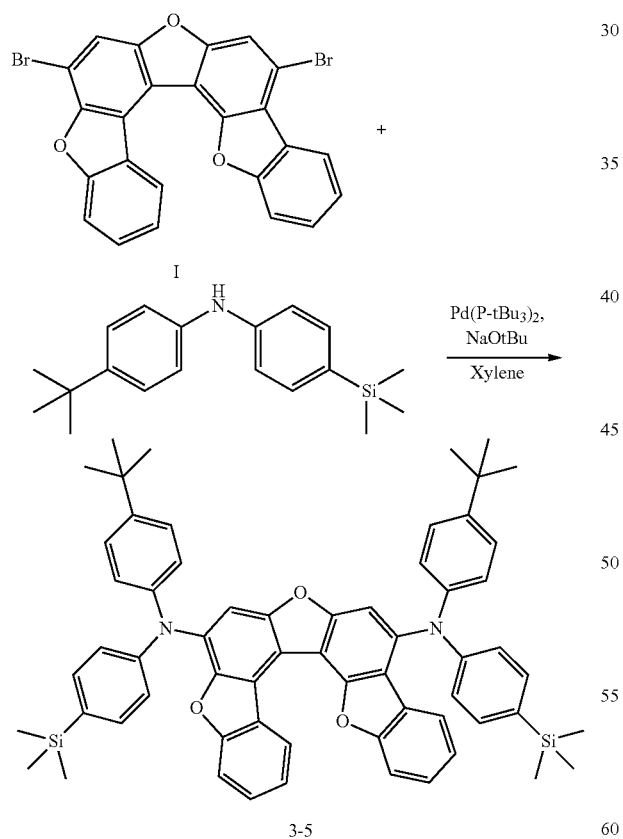

3-5

Compound 3-5 was prepared in the same manner as in Preparation of Compound 3-1, except that Intermediate I was used instead of Intermediate C and 4-(tert-butyl)-N-(m-trimethylsilyl)phenyl)aniline was used instead of bis(4-(tert-butyl)phenyl)arnine (6.0 g, yield 27%, MS: $[M+H]^+$=939).

TEST EXAMPLE

Comparative Test Example 1-1

A glass substrate on which ITO (indium tin oxide) was coated as a thin film to a thickness of 1,400 Å was put into distilled water in which a detergent was dissolved, and ultrasonically washed. In this case, a Decon™ CON705 product available at Fischer Co., was used as the detergent, and as the distilled water, distilled water twice filtered using a 0.22 um sterilizing filter manufactured by Millipore Co., was used. After the ITO was washed for 30 minutes, ultrasonic washing was conducted twice repeatedly using distilled water for 10 minutes. After the washing using distilled water was completed, ultrasonic washing was conducted using solvents of isopropyl alcohol, acetone, and methanol for 10 minutes, respectively, and then dried, after which it was transferred to a plasma cleaner. In addition, the substrate was cleaned for 5 minutes using oxygen plasma, and then transferred to a vacuum depositor.

On the ITO transparent electrode thus prepared, a compound HI-A below and a compound HAT-CN below were thermally vacuum-deposited sequentially in a thickness of 650 Å and in a thickness of 50 Å to form a hole injection layer. A compound HAT below was vacuum-deposited in a thickness of 600 Å on the hole injection layer to form a hole transport layer. Then, a compound HT-B below was thermally vacuum-deposited in a thickness of 50 Å on the hole transport layer to form an electron blocking layer. A compound BH below and a compound BD below were vacuum-deposited at a weight ratio of 96:4 to a thickness of 200 Å on the electron blocking layer to form a light emitting layer. A compound ET-A below was vacuum-deposited in a thickness of 50 Å on the light emitting layer to form a hole blocking layer. A compound ET-B below and a compound Liq below were vacuum-deposited at a weight ratio of 1:1 to a thickness of 310 ∈ on the hole blocking layer to form an electron transport layer. A compound Liq below was vacuum-deposited in a thickness of 5 Å on the electron transport layer to form an electron injection layer. Magnesium and silver were deposited sequentially at a weight ratio of 10:1 to a thickness of 120 Å on the electron injection layer, and aluminum was deposited in a thickness of 1000 Å to form a cathode, thereby completing the manufacture of an organic light emitting device.

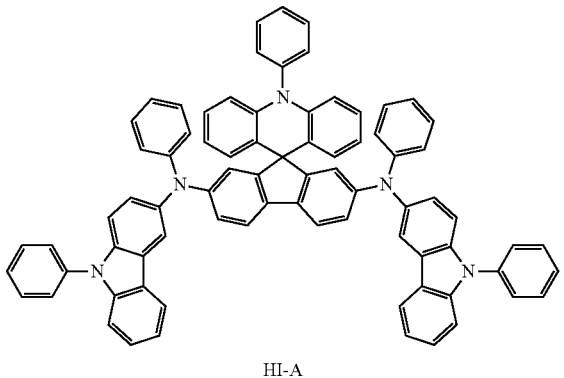

HI-A

135
-continued
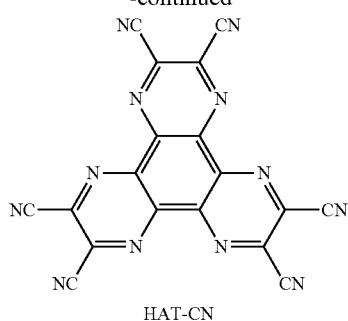
HAT-CN
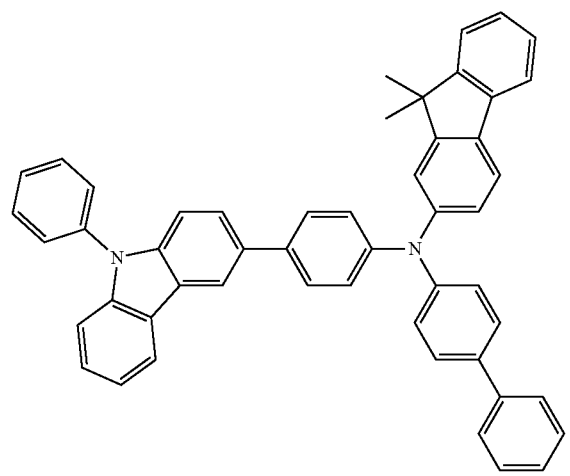
HT-A
HT-B
136
-continued
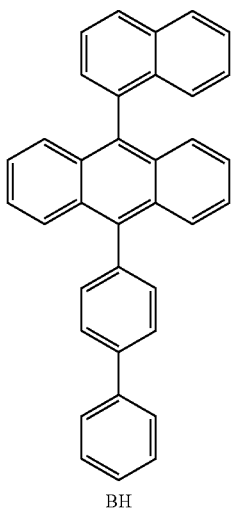
BH
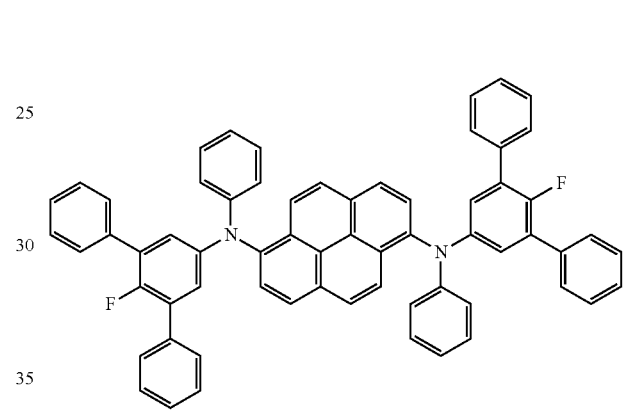
BD
ET-A
ET-B -continued

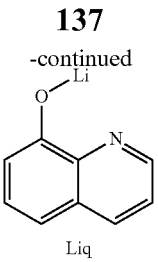

Liq

Test Examples 1-1 to 1-8

The organic light emitting devices were manufactured in the same manner as in Comparative Test Example 1-1, except that the compounds shown in Table 1 below were used instead of the compound ET-A in Comparative Test Example 1-1.

Comparative Test Examples 1-2 and 1-3

The organic light emitting devices were manufactured in the same manner as in Comparative Test Example 1-1, except that the compounds shown in Table 1 below were used instead of the compound ET-A in Comparative Test Example 1-1.

ET-D

A voltage, an efficiency and a lifetime (T95) were measured by applying a current to the organic light emitting devices manufactured in Test Examples and Comparative Test Examples. Here, the voltage and efficiency were measured by applying a current density of 10 mA/cm$^2$, and T95 refers to the elapsed time for the luminance to decrease to 95% of its initial value at a current density of 10 mA/cm$^2$.

TABLE 1

|  | Hole blocking layer | Voltage (V) (@10 mA/cm$^2$) | Efficiency (cd/A) (@10 mA/cm$^2$) | Lifetime (T95, hr) (@10 mA/cm$^2$) |
|---|---|---|---|---|
| Test Example 1-1 | Compound 1-1 | 3.32 | 6.08 | 65 |
| Test Example 1-2 | Compound 1-2 | 3.33 | 6.07 | 60 |
| Test Example 1-3 | Compound 1-3 | 3.36 | 6.01 | 66 |
| Test Example 1-4 | Compound 1-4 | 3.38 | 6.10 | 68 |
| Test Example 1-5 | Compound 1-5 | 3.41 | 6.07 | 67 |
| Test Example 1-6 | Compound 1-6 | 3.45 | 6.06 | 65 |
| Test Example 1-7 | Compound 1-7 | 3.43 | 6.13 | 63 |
| Test Example 1-8 | Compound 1-8 | 3.47 | 6.02 | 61 |
| Comparative Test Example 1-1 | ET-A | 4.21 | 5.11 | 40 |
| Comparative Test Example 1-2 | ET-C | 3.82 | 5.17 | 30 |
| Comparative Test Example 1-3 | ET-D | 3.73 | 5.29 | 20 |

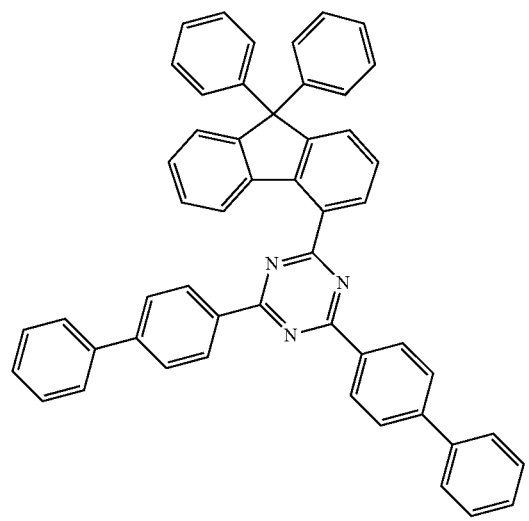

ET-C

Test Examples 2-1 and 2-6

The organic light emitting devices were manufactured in the same manner as in Comparative Test Example 1-1, except that the compounds shown in Table 2 below were used instead of the compound HT-B in Comparative Test Example 1-1.

Comparative Test Examples 2-1 and 2-2

The organic light emitting devices were manufactured in the same manner as in Comparative Test Example 1-1, except that the compounds shown in Table 2 below were used instead of the compound HT-B in Comparative Test Example 1-1. In Table 2, each of the compounds HT-C to HT-F are as follows.

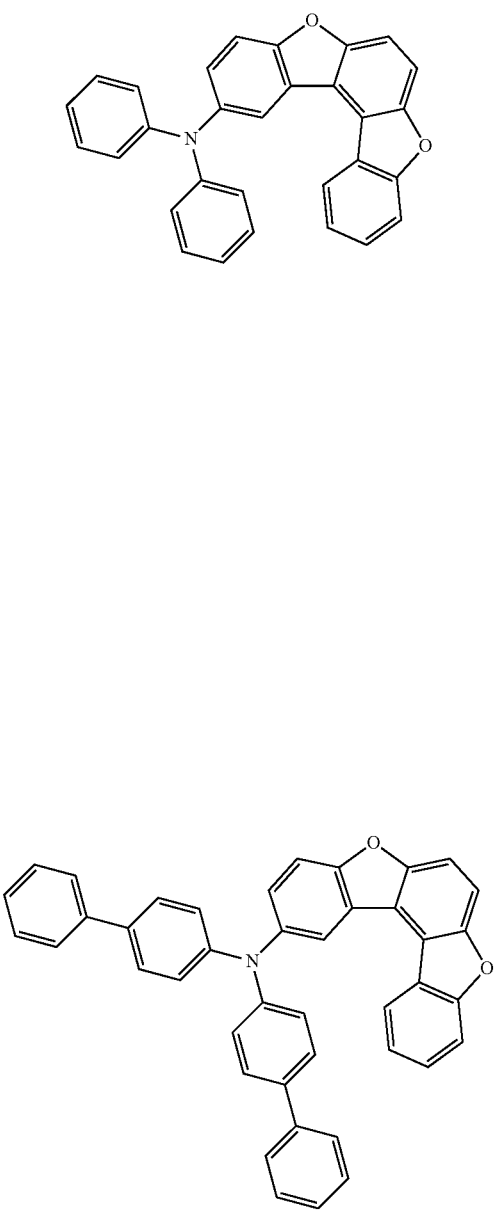

HT-C

HT-D

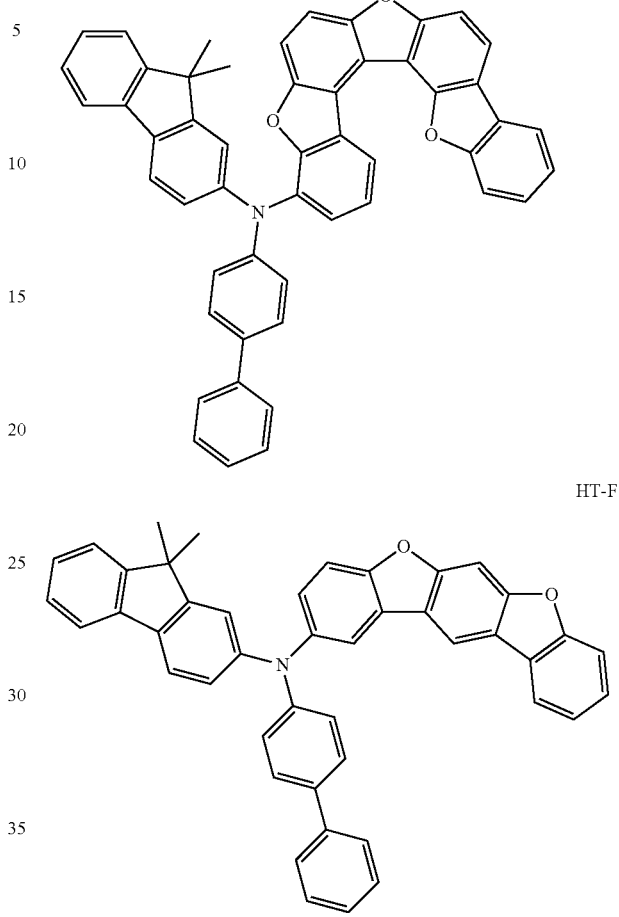

HT-E

HT-F

A voltage, an efficiency and a lifetime (T95) were measured by applying a current to the organic light emitting devices manufactured in Test Examples and Comparative Test Examples, and the results are shown in Table 2 below. Here, the voltage and efficiency were measured by applying a current density of 10 mA/cm$^2$, and T95 refers to the elapsed time for the luminance to decrease to 95% of its initial value at a current density of 10 mA/cm$^2$.

TABLE 2

|  | Electron blocking layer | Voltage (V) (@10 mA/cm$^2$) | Efficiency (cd/A) (@10 mA/cm$^2$) | Lifetime (T95, hr) (@10 mA/cm$^2$) |
|---|---|---|---|---|
| Test Example 2-1 | Compound 2-1 | 3.41 | 6.07 | 65 |
| Test Example 2-2 | Compound 2-2 | 3.38 | 6.03 | 60 |
| Test Example 2-3 | Compound 2-3 | 3.39 | 6.08 | 66 |
| Test Example 2-4 | Compound 2-4 | 3.30 | 6.11 | 68 |
| Test Example 2-5 | Compound 2-5 | 3.46 | 6.07 | 67 |
| Test Example 2-6 | Compound 2-6 | 3.33 | 6.09 | 65 |
| Comparative Test Example 1-1 | HT-B | 4.21 | 5.11 | 40 |
| Comparative Test Example 2-1 | HT-C | 6.13 | 3.82 | 15 |
| Comparative Test Example 2-2 | HT-D | 5.24 | 4.68 | 20 |

TABLE 2-continued

| | Electron blocking layer | Voltage (V) (@10 mA/cm²) | Efficiency (cd/A) (@10 mA/cm²) | Lifetime (T95, hr) (@10 mA/cm²) |
|---|---|---|---|---|
| Comparative Test Example 2-3 | HT-E | 4.82 | 5.21 | 42 |
| Comparative Test Example 2-4 | HT-F | 4.67 | 5.30 | 31 |

Test Examples 3-1 and 3-5

The organic light emitting devices were manufactured in the same manner as in Comparative Test Example 1-1, except that the compounds shown in Table 3 below were used instead of the compound BD in Comparative Test Example 1-1.

Comparative Test Examples 3-1 and 3-4

The organic light emitting devices were manufactured in the same manner as in Comparative Test Example 1-1, except that the compounds shown in Table 3 below were used instead of the compound BD in Comparative Test Example 1-1. In Table 3, each of the compounds BD-A to BD-D are as follows.

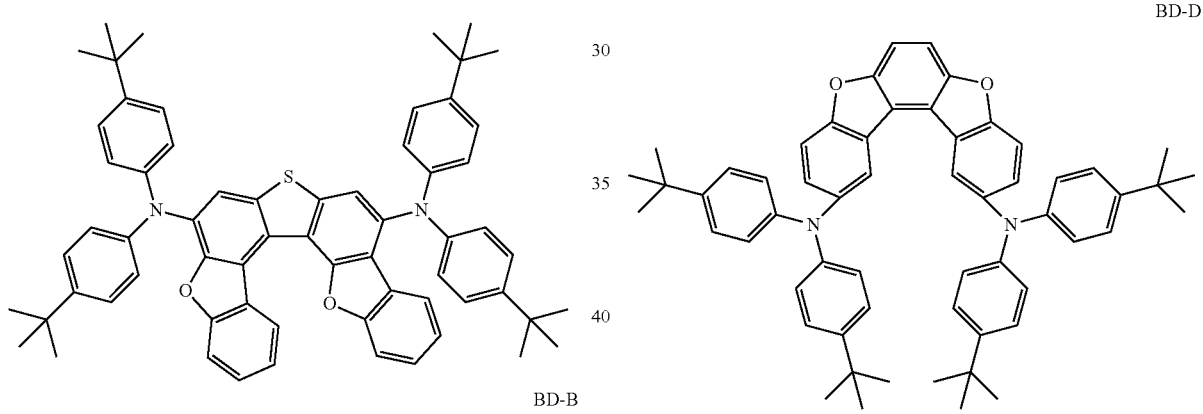

BD-A

BD-B

BD-C

BD-D

A voltage, an efficiency and a lifetime (T95) were measured by applying a current to the organic light emitting devices manufactured in Test Examples and Comparative Test Examples, and the results are shown in Table 3 below. Here, the voltage and efficiency were measured by applying a current density of 10 mA/cm², and T95 refers to the elapsed time for the luminance to decrease to 95% of its initial value at a current density of 10 mA/cm.

TABLE 3

| | Dopant | Voltage (V) (@10 mA/cm²) | Efficiency (cd/A) (@10 mA/cm²) | Lifetime (T95, hr) (@10 mA/cm²) |
|---|---|---|---|---|
| Test Example 3-1 | Compound 3-1 | 3.45 | 6.12 | 70 |
| Test Example 3-2 | Compound 3-2 | 3.38 | 6.10 | 65 |
| Test Example 3-3 | Compound 3-3 | 3.42 | 6.21 | 68 |
| Test Example 3-4 | Compound 3-4 | 3.31 | 6.15 | 69 |
| Test Example 3-5 | Compound 3-5 | 3.40 | 6.18 | 67 |
| Comparative Test Example 1-1 | BD | 4.21 | 5.11 | 40 |

TABLE 3-continued

|  | Dopant | Voltage (V) (@10 mA/cm$^2$) | Efficiency (cd/A) (@10 mA/cm$^2$) | Lifetime (T95, hr) (@10 mA/cm$^2$) |
|---|---|---|---|---|
| Comparative Test Example 3-1 | BD-A | 4.12 | 4.15 | 23 |
| Comparative Test Example 3-2 | BD-B | 6.81 | 2.21 | 12 |
| Comparative Test Example 3-3 | BD-C | 6.28 | 2.15 | 8 |
| Comparative Test Example 3-4 | BD-D | 6.31 | 2.38 | 10 |

Comparative Test Example 4-1

A glass substrate on which ITO (indium tin oxide) was coated as a thin film to a thickness of 1,400 Å was put into distilled water in which a detergent was dissolved, and ultrasonically washed. In this case, a Decon™ CON705 product available at Fischer Co., was used as the detergent, and as the distilled water, distilled water twice filtered using a 0.22 um sterilizing filter manufactured by Millipore Co., was used. After the ITO was washed for 30 minutes, ultrasonic washing was conducted twice repeatedly using distilled water for 10 minutes. After the washing using distilled water was completed, ultrasonic washing was conducted using solvents of isopropyl alcohol, acetone, and methanol for 10 minutes, respectively, and then dried, after which it was transferred to a plasma cleaner. In addition, the substrate was cleaned for 5 minutes using oxygen plasma, and then transferred to a vacuum depositor.

On the ITO transparent electrode thus prepared, a mixture of 95 wt % of a compound HI-A below and 5 wt % of a compound P-DOPANT below was thermally vacuum-deposited in a thickness of 100 Å and then only a compound HG-G below was deposited in a thickness of 1150 Å to form a hole transport layer. A compound HT-H below was thermally vacuum-deposited in a thickness of 450 Å on the hole transport layer to form an electron blocking layer. A mixture of 56.4 wt % of a compound GH-1 below as a first host, 37.6 wt % of the compound GH-2-A as a second host and 6 wt % of a compound GD below as a dopant was vacuum-deposited in a thickness of 400 Å on the electron blocking layer to form a light emitting layer. A compound ET-E below was vacuum-deposited in a thickness of 50 Å on the light emitting layer to form a hole blocking layer. A compound ET-F below and a compound Liq below were mixed at a weight ratio of 2:1 and thermally vacuum-deposited in a thickness of 250 Å on the hole blocking layer to form an electron transport layer. Then, LiF and magnesium were mixed at a weight ratio 1:1 and vacuum-deposited in a thickness of 30 Å to form an electron injection layer. Magnesium and silver were mixed at a weight ratio 1:4 and deposited in a thickness of 160 Å on the electron injection layer to a cathode, thereby completing the manufacture of an organic light emitting device.

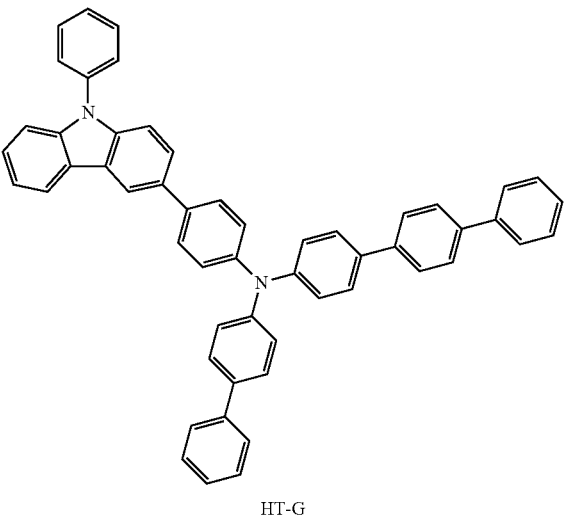

HT-G

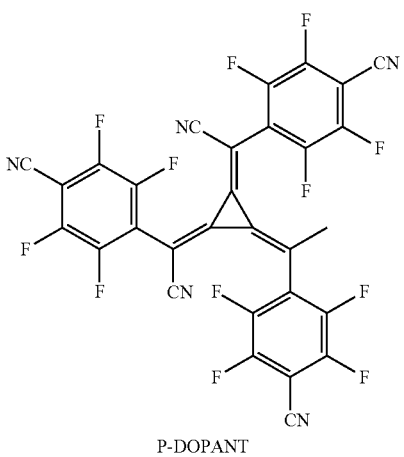

P-DOPANT

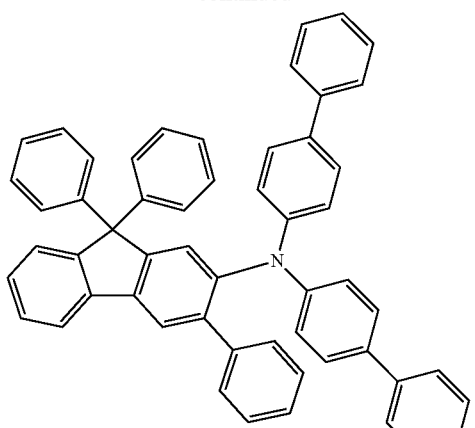

HT-H

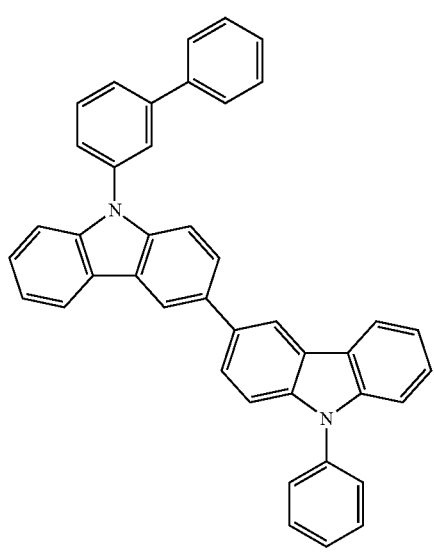

GH-1

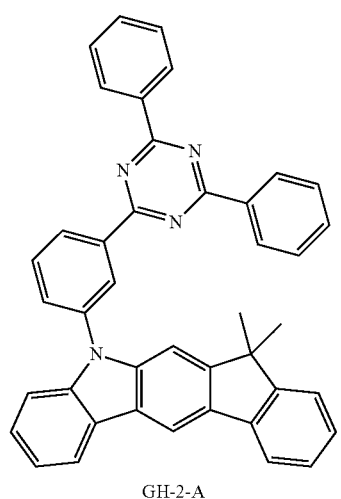

GH-2-A

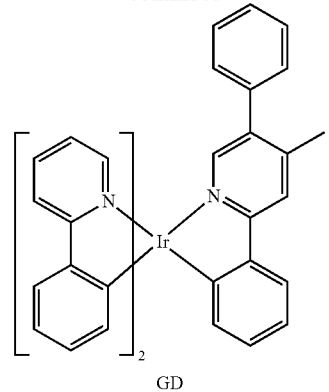

GD

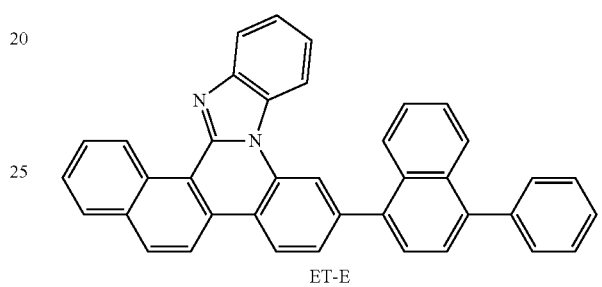

ET-E

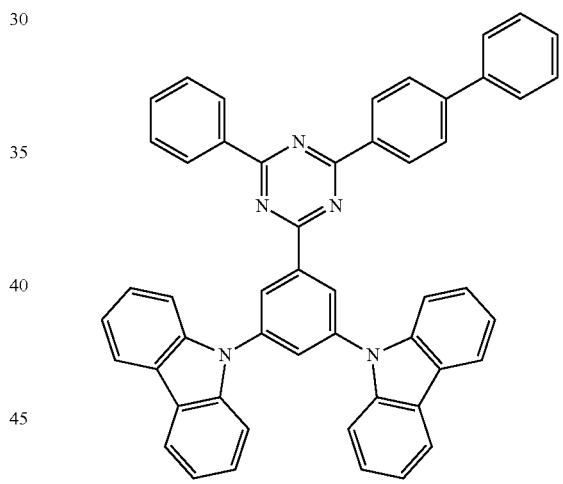

ET-F

Test Examples 4-1 and 4-5

The organic light emitting devices were manufactured in the same manner as in Comparative Test Example 4-1, except that the compounds shown in Table 4 below were used instead of the compound GH-2-A as a second host.

Comparative Test Examples 4-2 and 4-3

The organic light emitting devices were manufactured in the same manner as in Comparative Test Example 4-1, except that the compounds shown in Table 4 below were used instead of the compound GH-2-A as a second host. In Table 4, each of GH-2-B and GH-2-C are as follows.

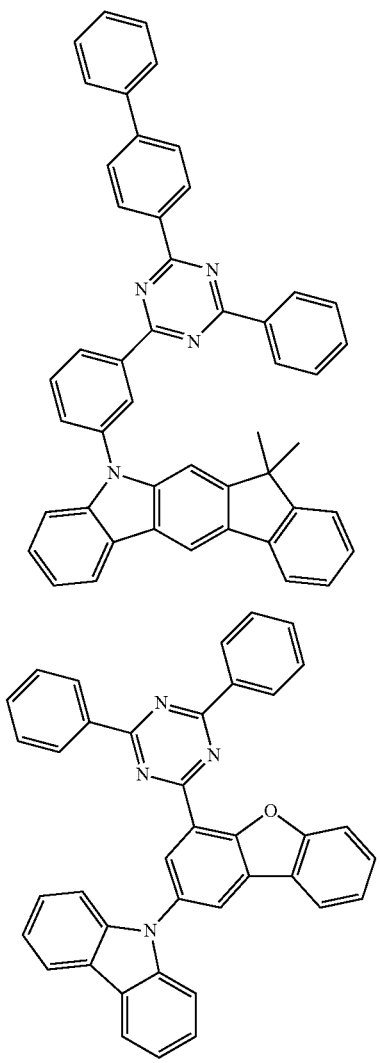

A voltage, an efficiency and a lifetime (T95) were measured by applying a current to the organic light emitting devices manufactured in Test Examples and Comparative Test Examples, and the results are shown in Table 4 below. Here, the voltage and efficiency were measured by applying a current density of 10 mA/cm$^2$, and T95 refers to the elapsed time for the luminance to decrease to 95% of its initial value at a current density of 20 mA/cm$^2$.

TABLE 4

|  | Second host | Voltage (V) (@10 mA/cm$^2$) | Efficiency(cd/A) (@10 mA/cm$^2$) | Lifetime (T95, hr) (@20 mA/cm$^2$) |
| --- | --- | --- | --- | --- |
| Test Example 4-1 | Compound 1-1 | 3.85 | 57.51 | 130 |
| Test Example 4-2 | Compound 1-2 | 3.90 | 54.16 | 120 |
| Test Example 4-3 | Compound 1-4 | 3.91 | 56.33 | 110 |
| Test Example 4-4 | Compound 1-5 | 3.87 | 55.18 | 130 |
| Test Example 4-5 | Compound 1-8 | 3.81 | 57.39 | 140 |
| Comparative Test Example 4-1 | GH-2-A | 4.56 | 32.11 | 80 |
| Comparative Test Example 4-2 | GH-2-B | 5.67 | 28.19 | 70 |
| Comparative Test Example 4-3 | GH-2-C | 6.65 | 36.55 | 60 |

The compound represented by Chemical Formula 1 according to the present invention has a high triplet energy, which can be confirmed from the fact that as shown in Table 1 and Table 2, when used for the hole blocking layer or the electron blocking layer in contact with the light emitting layer, the triplet exciton is confined in the light emitting layer and the organic electroluminescent device using the same is superior in properties.

In addition, as shown in Table 3, when a compound represented by Chemical Formula 1 is used as a dopant together with an anthracene-based host material having a low triplet energy, it is possible to amplify a phenomenon where singlet excitons are generated by triplet exciton collision and fusion (called triplet-triplet fusion (TTF)), thereby contributing to improvement in efficiency and lifetime of blue fluorescence. Furthermore, as shown in Table 4, the organic electroluminescent device using the phosphorescent dopant exhibits excellent characteristics when the compound represented by Chemical Formula 1 is used as a second host together with a P-type host material in the light emitting layer.

In conclusion, when the compound represented by Formula 1 according to the present invention is applied to an organic light-emitting device, an organic light emitting device having characteristics of low voltage, high efficiency, and long lifetime can be obtained.

| [Explanation of Sign] | |
| --- | --- |
| 1: substrate | 2: anode, |
| 3: light emitting layer | 4: cathode |
| 5: hole injection layer | 6: hole transport layer |
| 7: light emitting layer | 8: electron transport layer |

The invention claimed is:

1. A compound represented by the following Chemical Formula 1:

[Chemical Formula 1]

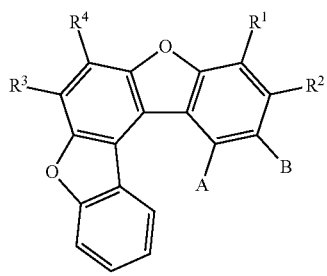

in Chemical Formula 1,

A and B are hydrogen, or are linked to

where * is a linking site, at least one of R¹ to R⁴ is the following Chemical Formula 2 or Chemical Formula 3, and the rest are hydrogen,

[Chemical Formula 2]

*—L¹—Ar¹

[Chemical Formula 3]

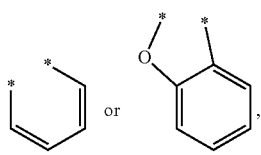

in Chemical Formulae 2 and 3,

L¹ and L² are each independently a single bond; or a substituted or unsubstituted $C_{6-60}$ arylene;

Ar¹ is a substituted or unsubstituted $C_{6-60}$ aryl; a substituted or unsubstituted $C_{2-60}$ heteroaryl containing at least one of O, N, Si and S; or —PO(Ar⁴)(Ar⁵), and Ar² to Ar⁵ are each independently a substituted or unsubstituted $C_{6-60}$ aryl; or a substituted or unsubstituted $C_{2-60}$ heteroaryl containing at least one of O, N, Si and S.

2. The compound of claim 1, wherein

R¹ and R⁴ is hydrogen, and at least one of R² and R³ is Chemical Formula 2 or Chemical Formula 3.

3. The compound of claim 1, wherein the Chemical Formula 1 is represented by the following Chemical Formula 1-1 or 1-2:

[Chemical Formula 1-1]

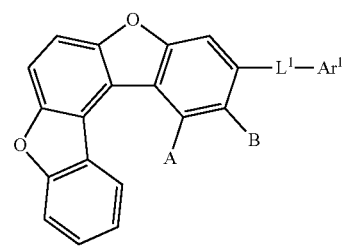

[Chemical Formula 1-2]

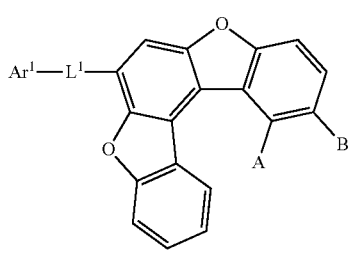

in Chemical Formulae 1-1 and 1-2,

A and B are hydrogen, or are linked to

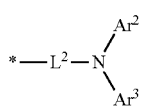

where * is a linking site,

L¹ is a single bond; or a substituted or unsubstituted $C_{6-60}$ arylene;

Ar¹ is a substituted or unsubstituted $C_{6-60}$ aryl; a substituted or unsubstituted $C_{2-60}$ heteroaryl containing at least one of O, N, Si and S; or —PO(Ar⁴)(Ar⁵), and Ar⁴ and Ar⁵ are each independently a substituted or unsubstituted $C_{6-60}$ aryl; or a substituted or unsubstituted $C_{2-60}$ heteroaryl containing at least one of O, N, Si and S.

4. The compound of claim 1, wherein the Chemical Formula 1 is represented by the following Chemical Formula 1-3, 1-4 or 1-5:

[Chemical Formula 1-3]

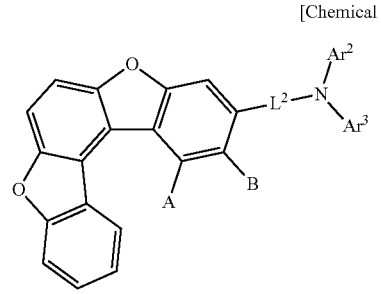

151
-continued

[Chemical Formula 1-4]

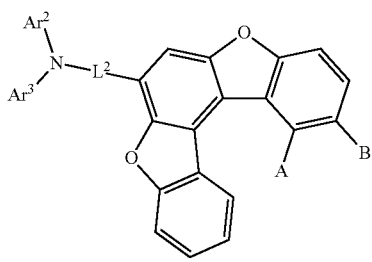

[Chemical Formula 1-5]

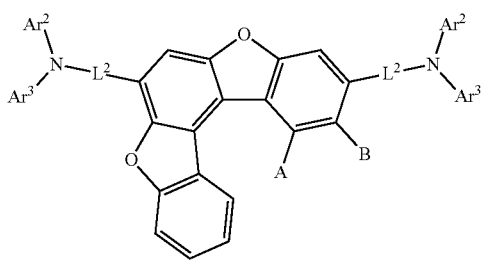

in Chemical Formulae 1-3 to 1-5,

A and B are hydrogen, or are linked to

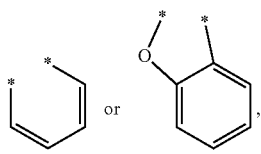

where * is a linking site, $L^2$ is a single bond; or a substituted or unsubstituted $C_{6-60}$ arylene;

$Ar^2$ and $Ar^3$ are each independently a substituted or unsubstituted $C_{6-60}$ aryl; a substituted or unsubstituted $C_{2-60}$ heteroaryl containing at least one of O, N, Si and S.

5. The compound of claim 1, wherein $L^1$ is a single bond or $C_{6-20}$ arylene, $Ar^1$ is $C_{2-30}$ heteroaryl containing N, or —PO($Ar^4$)($Ar^5$), and $Ar^4$ and $Ar^5$ are each independently $C_{6-20}$ aryl.

6. The compound of claim 1, wherein $L^1$ is a single bond or phenylene, and $Ar^1$ is selected from the group consisting of the following:

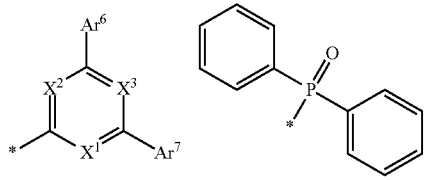

152
-continued

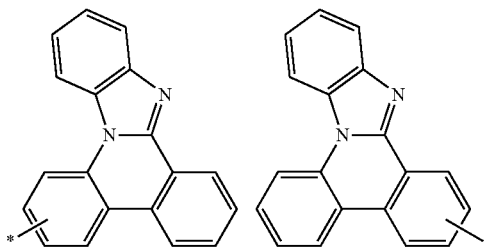

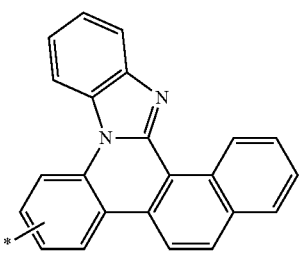

wherein, at least one of $X^1$ to $X^3$ is N, the rest is C—H,

* is a linking site, and $Ar^6$ and $Ar^7$ are each independently hydrogen, phenyl, biphenyl or terphenyl.

7. The compound of claim 1, wherein $L^2$ is a single bond or $C_{6-20}$ arylene, and $Ar^2$ and $Ar^3$ are each independently a substituted or unsubstituted $C_{6-20}$ aryl; or a $C_{2-20}$ heteroaryl containing O.

8. The compound of claim 1, wherein $L^2$ is a single bond, or phenylene, and $Ar^2$ and $Ar^3$ are each independently a monovalent residue derived from arene selected from the group consisting of benzene, methylbenzene, t-butylbenzene, trimethylsilylbenzene, naphthalene, biphenyl, methyl biphenyl, terphenyl, methyltriphenyl, 9,9-dimethylfluorene and dibenzofuran.

9. The compound of claim 1, wherein the compound is selected from the group consisting of the following compounds:

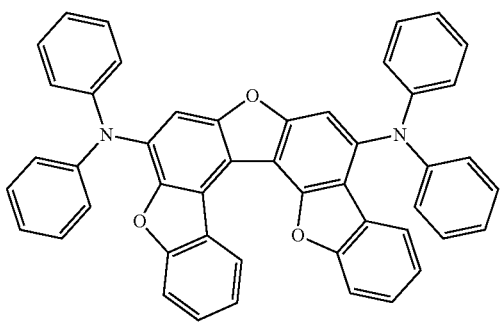

153
-continued
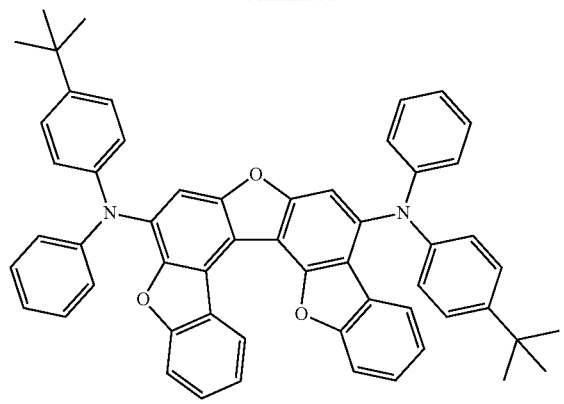
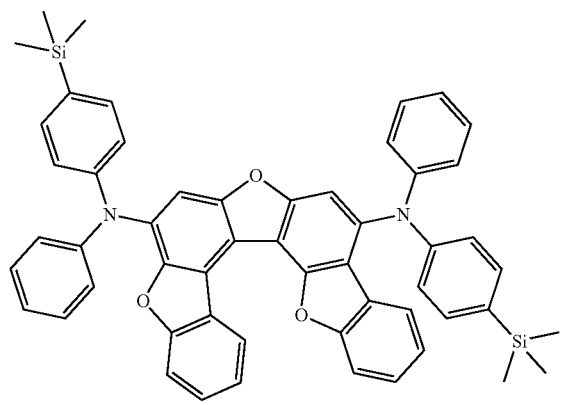
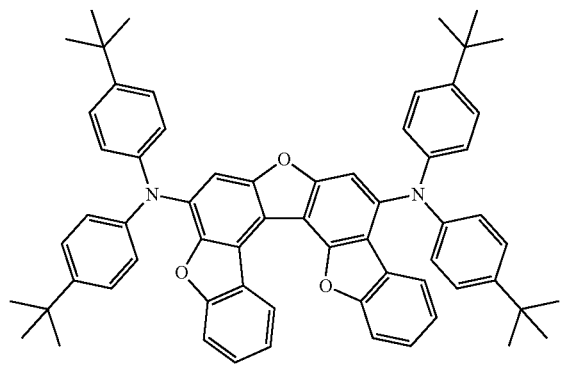
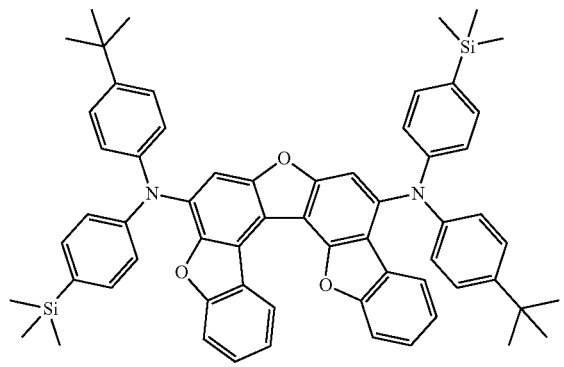
154
-continued
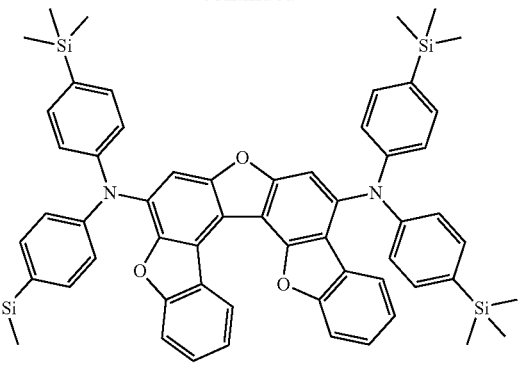
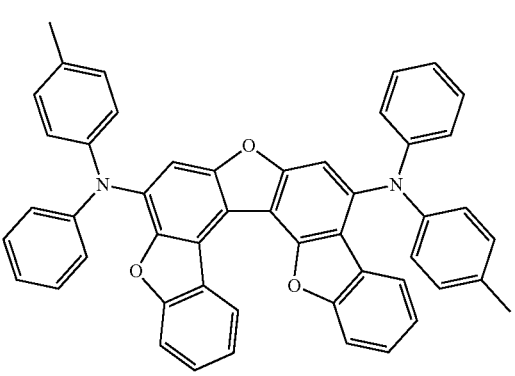
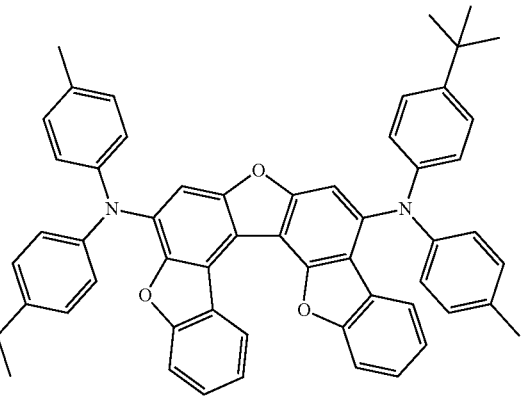
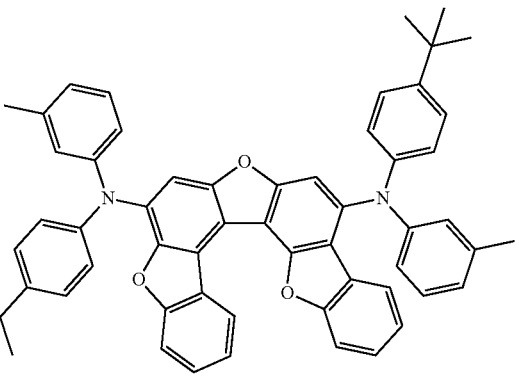

155
-continued
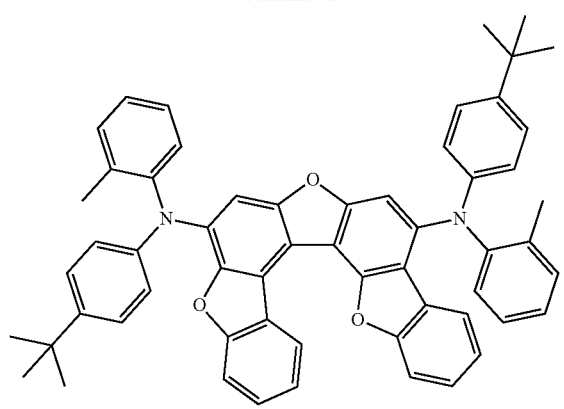
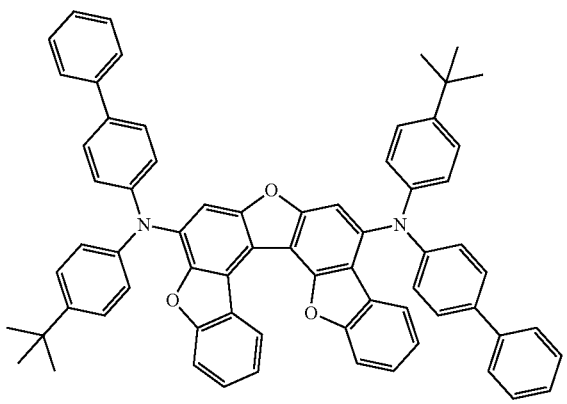
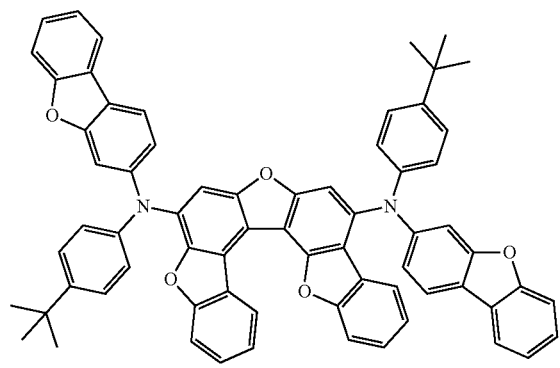
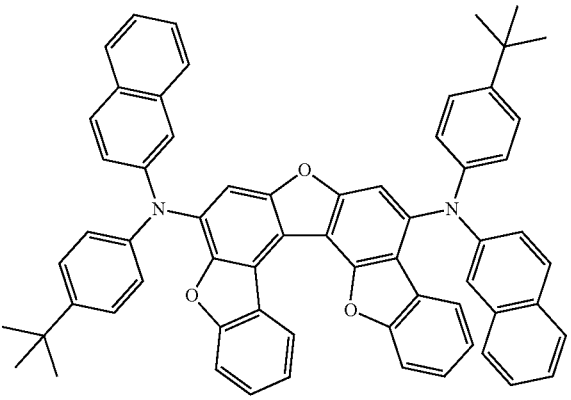
156
-continued
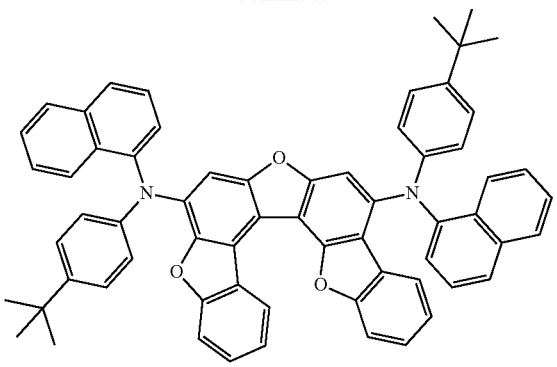
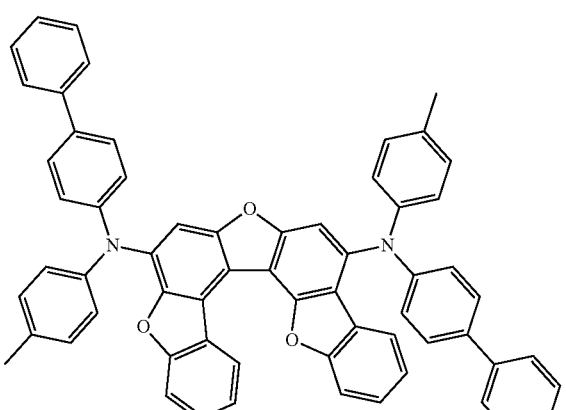
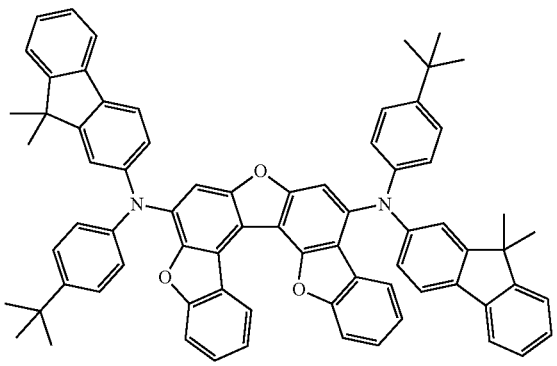
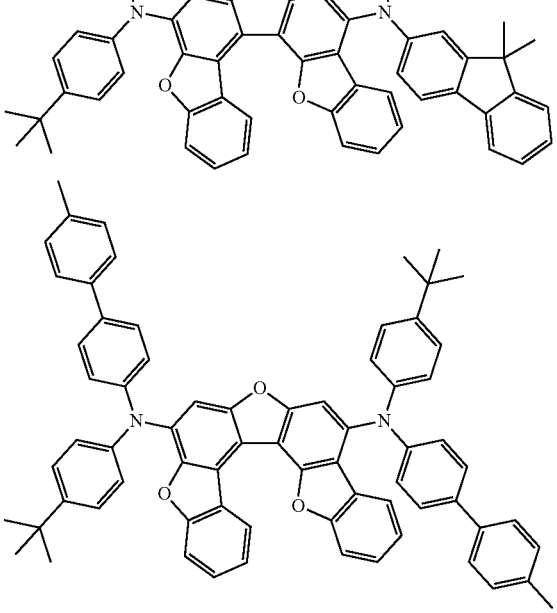

157
-continued
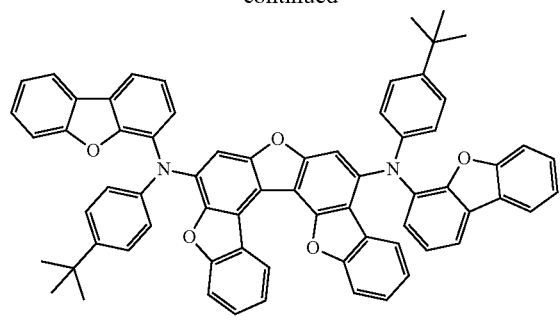
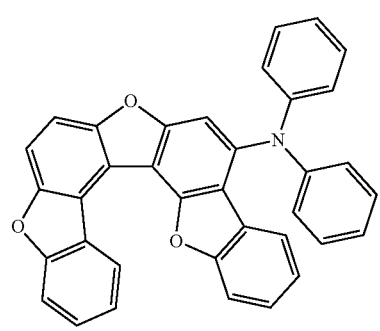
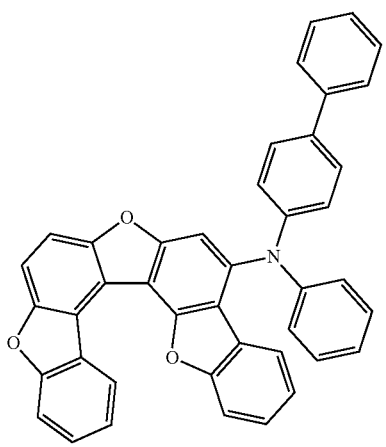
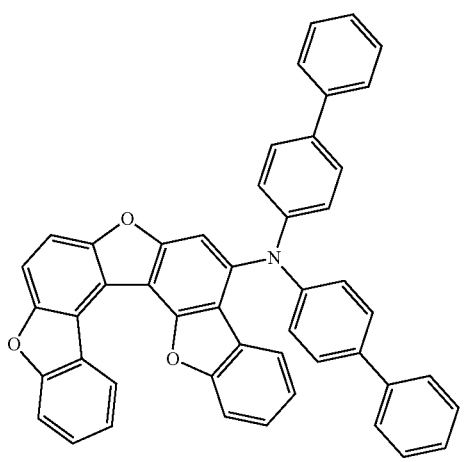
158
-continued
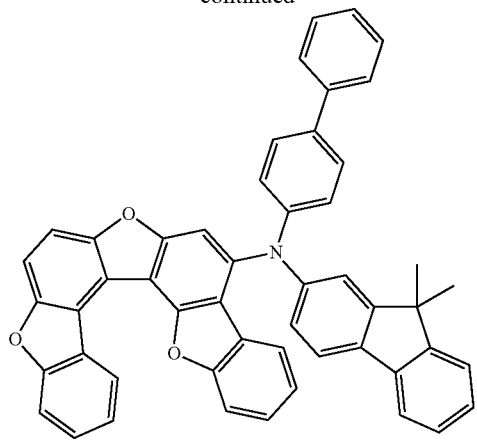
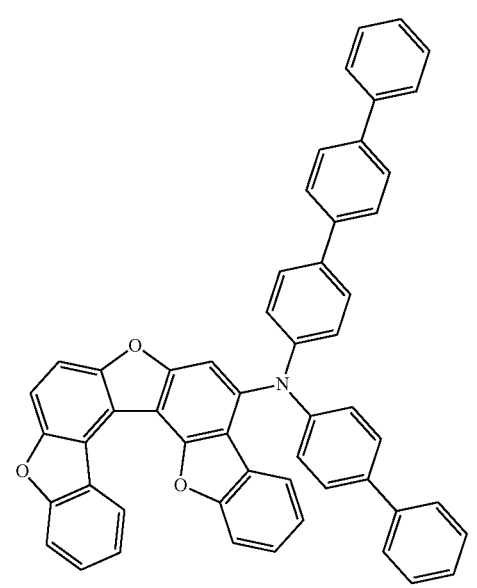
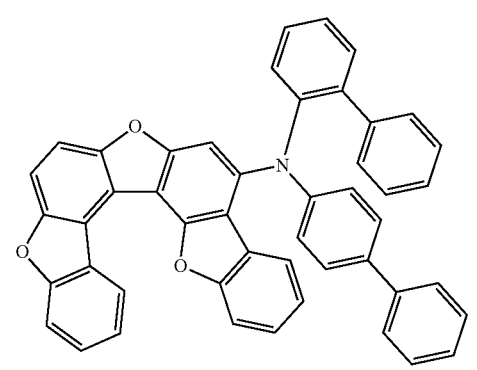

-continued
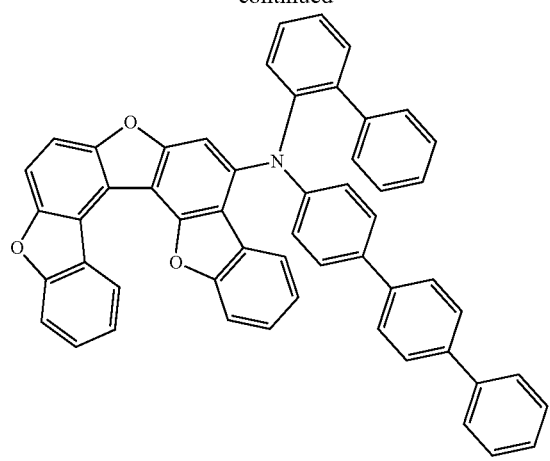
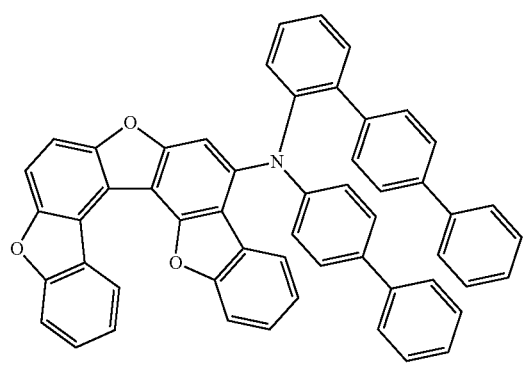
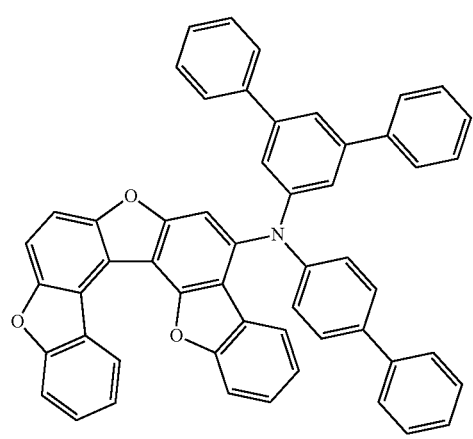
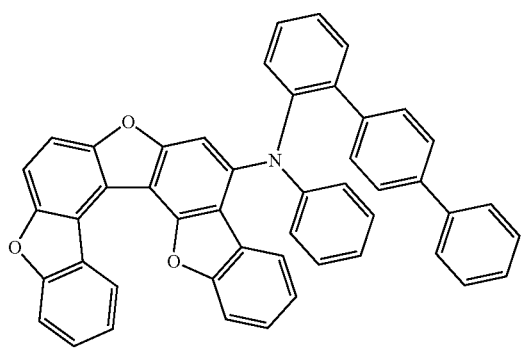
-continued
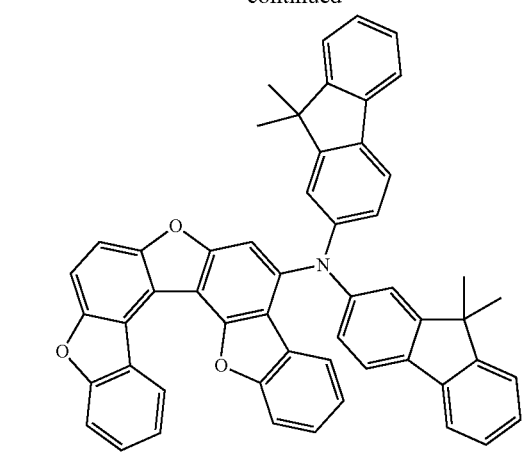
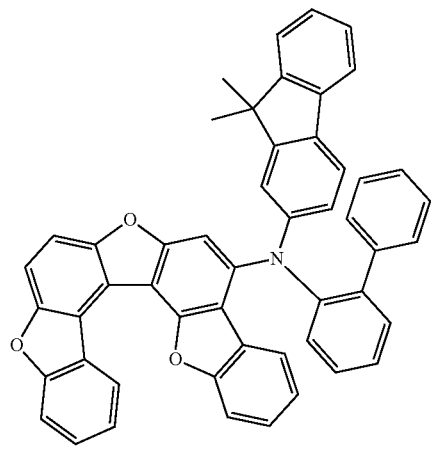
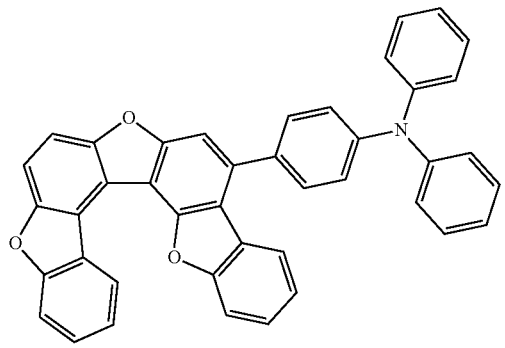
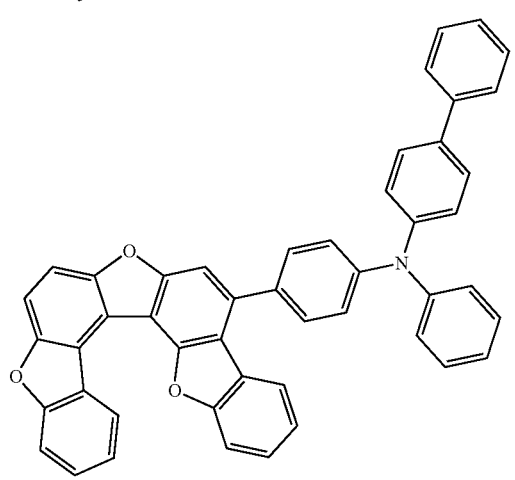

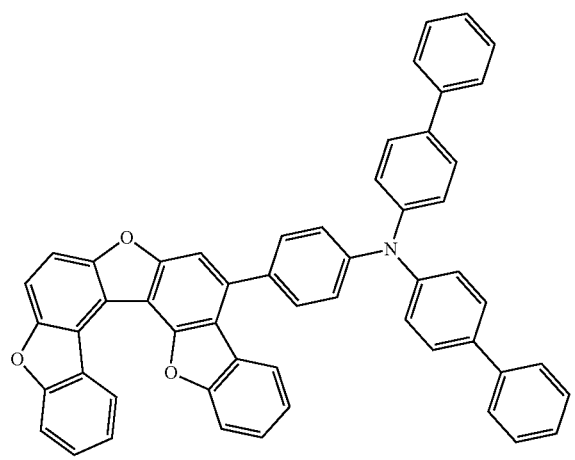
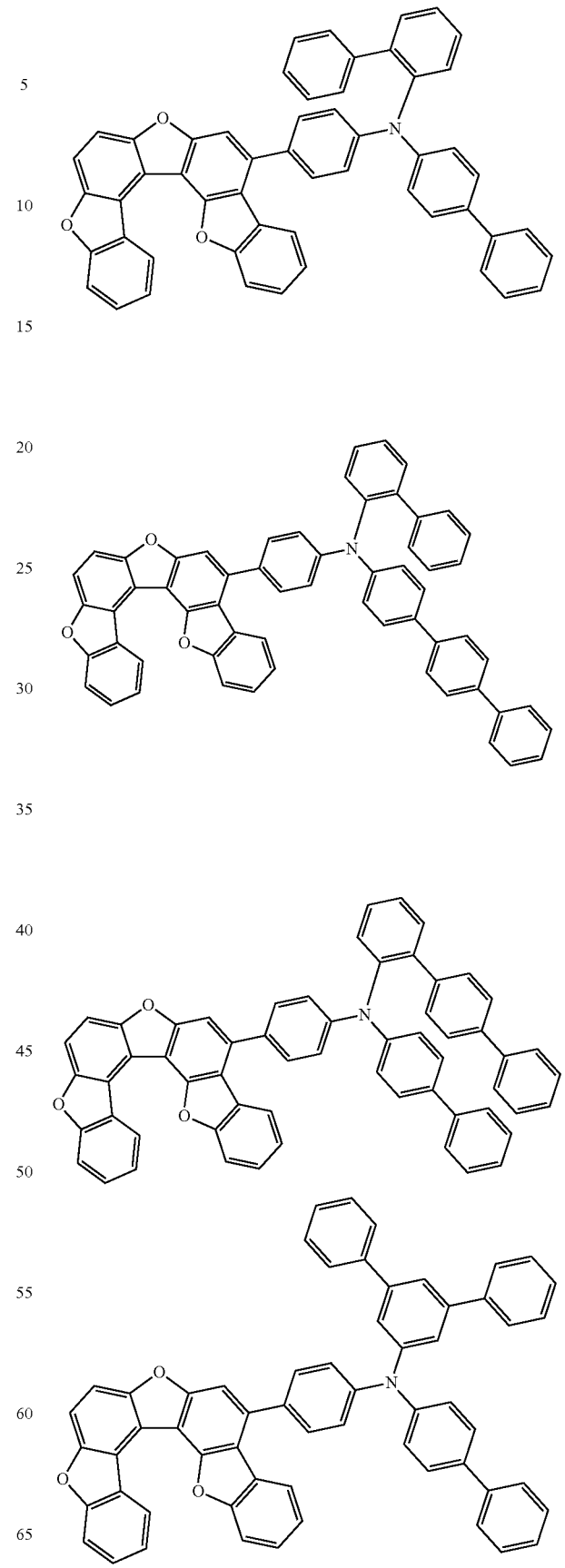

163
-continued
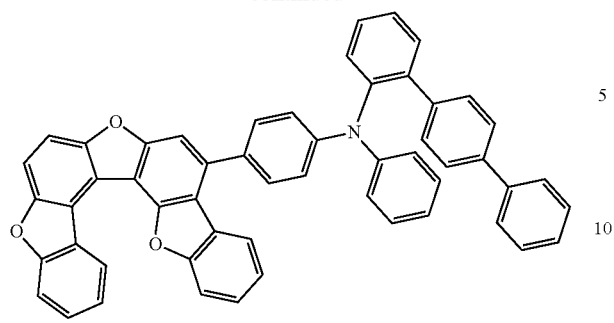
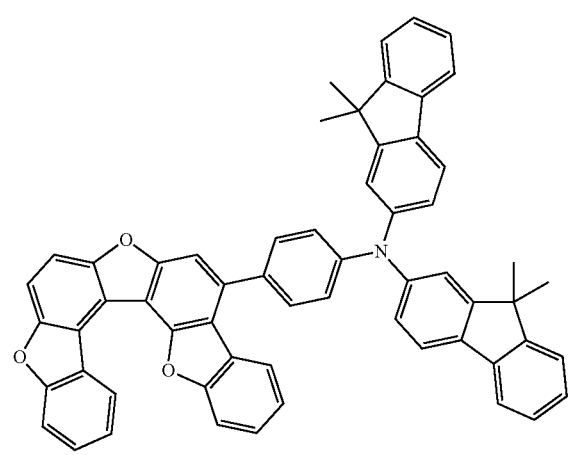
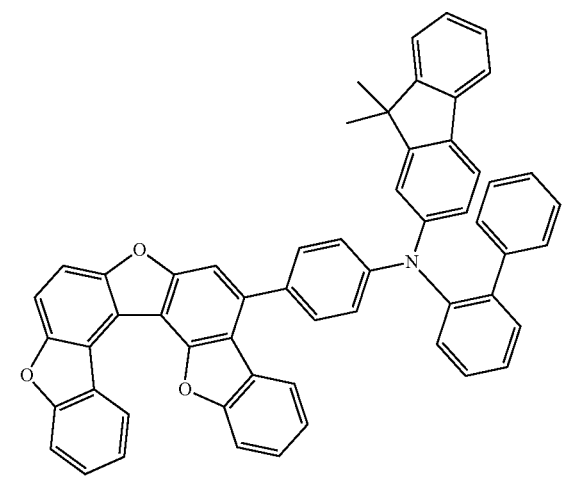
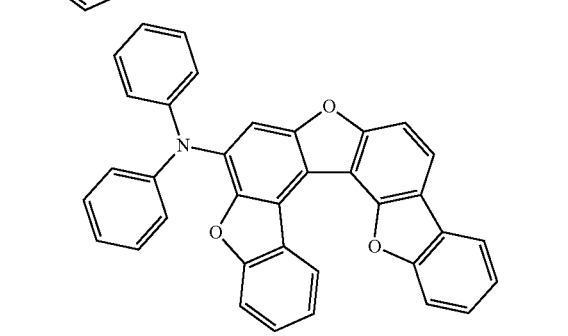
164
-continued
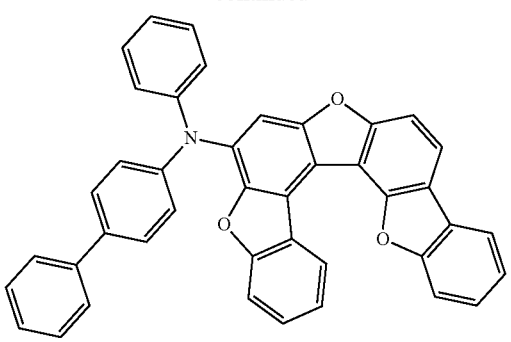
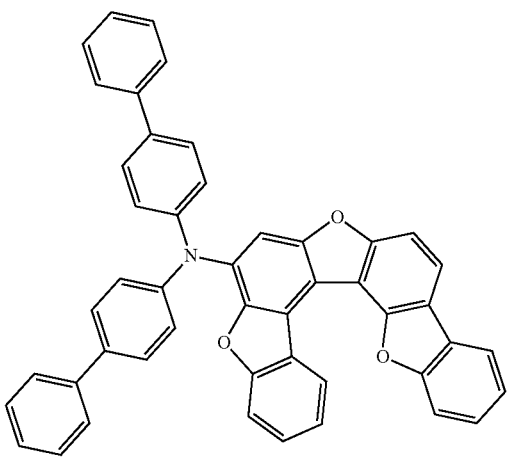
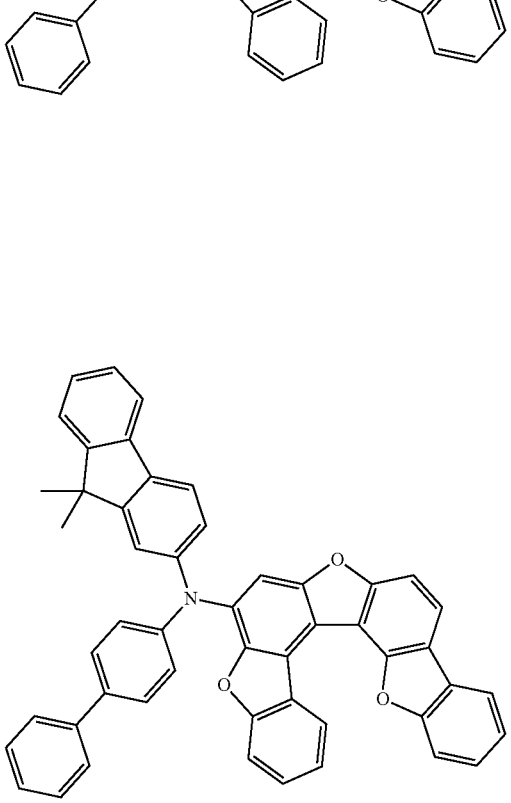

165
-continued
166
-continued
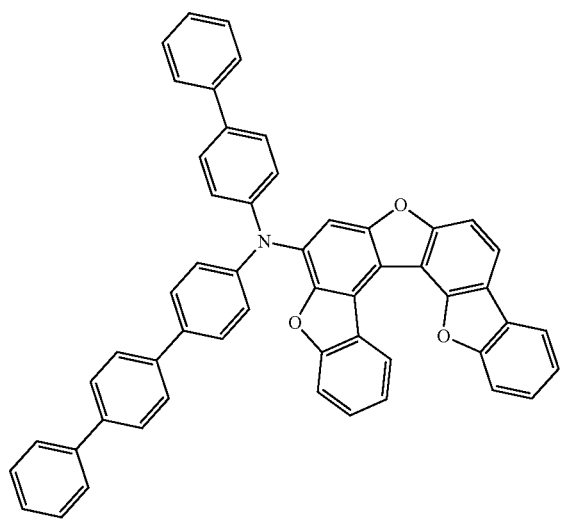
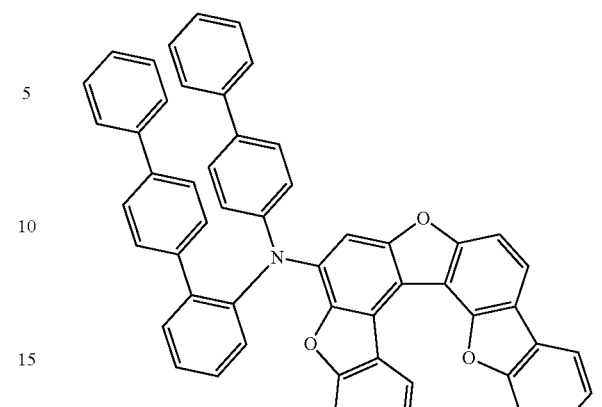
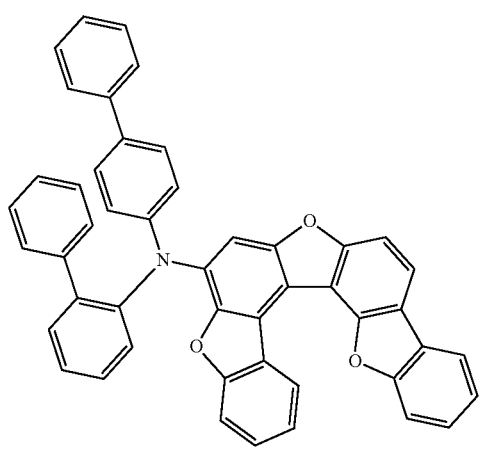
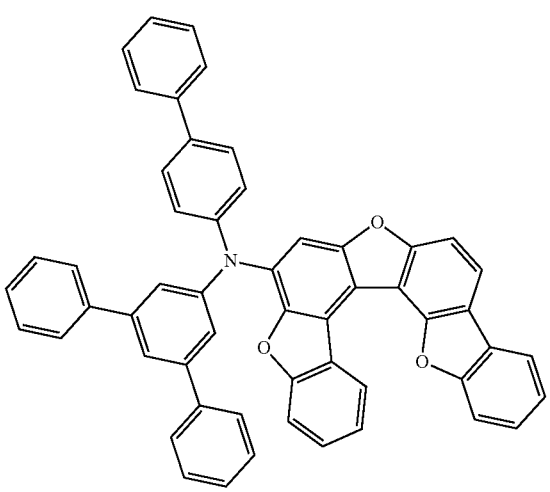
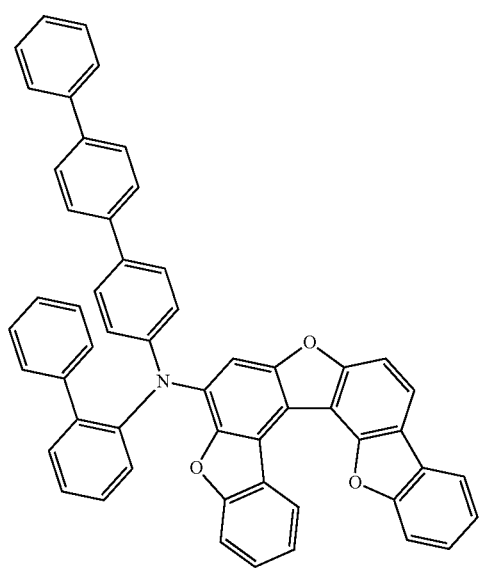
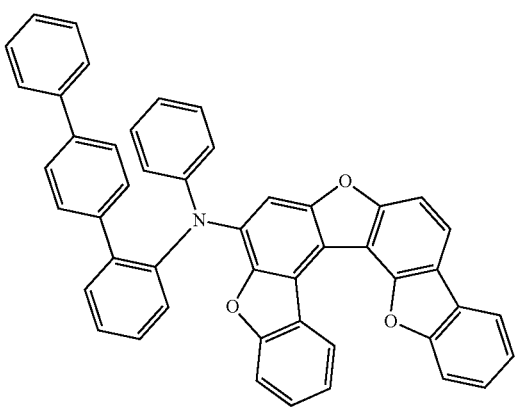

167
-continued
168
-continued
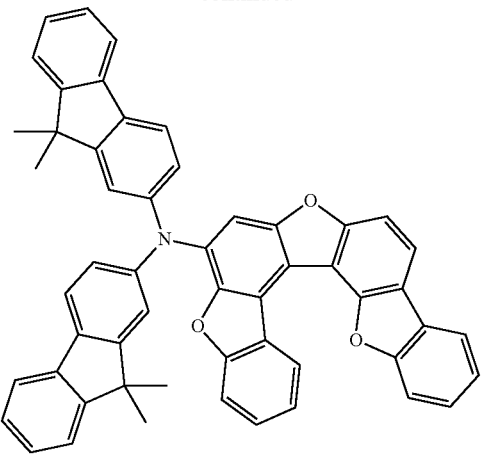
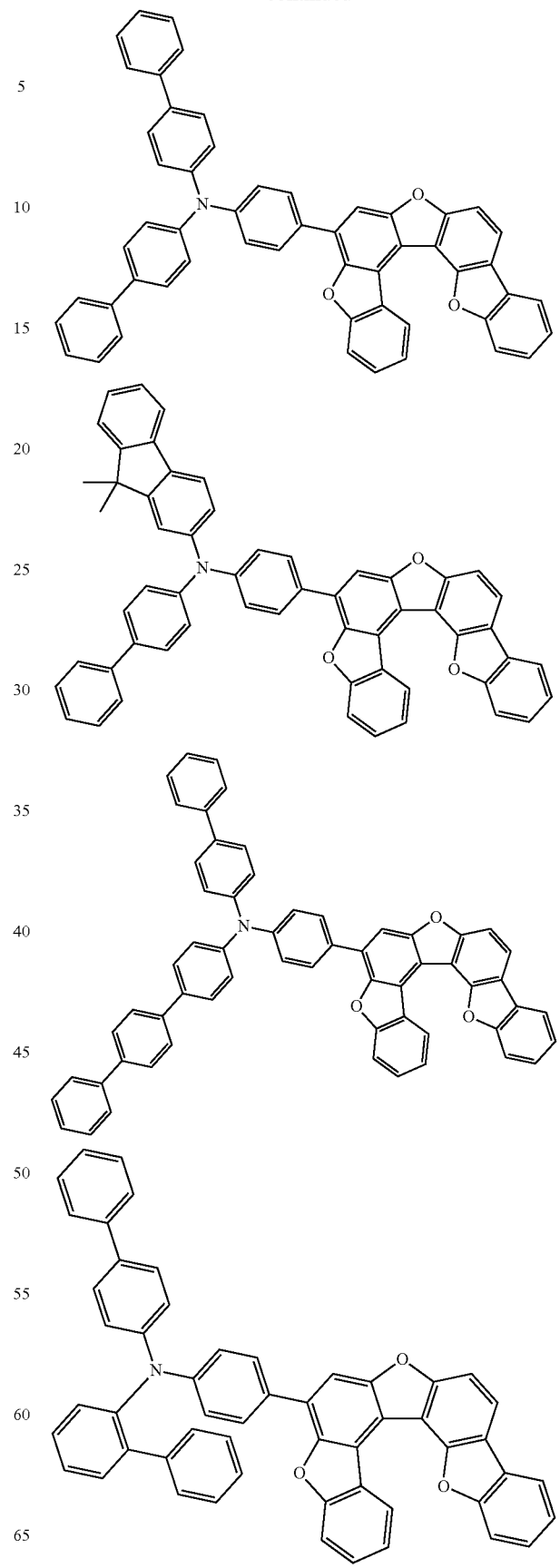

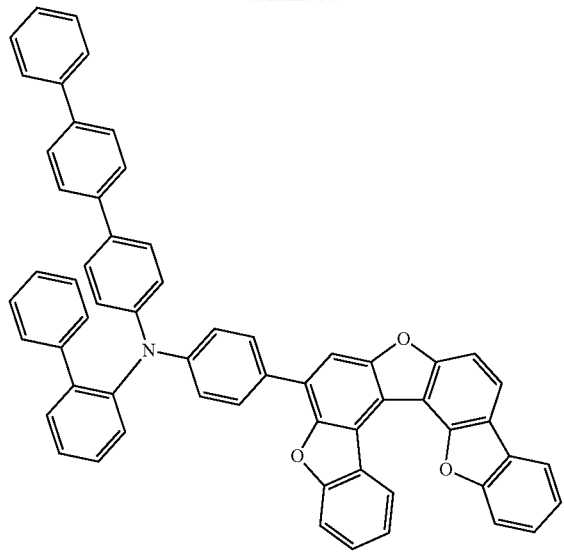
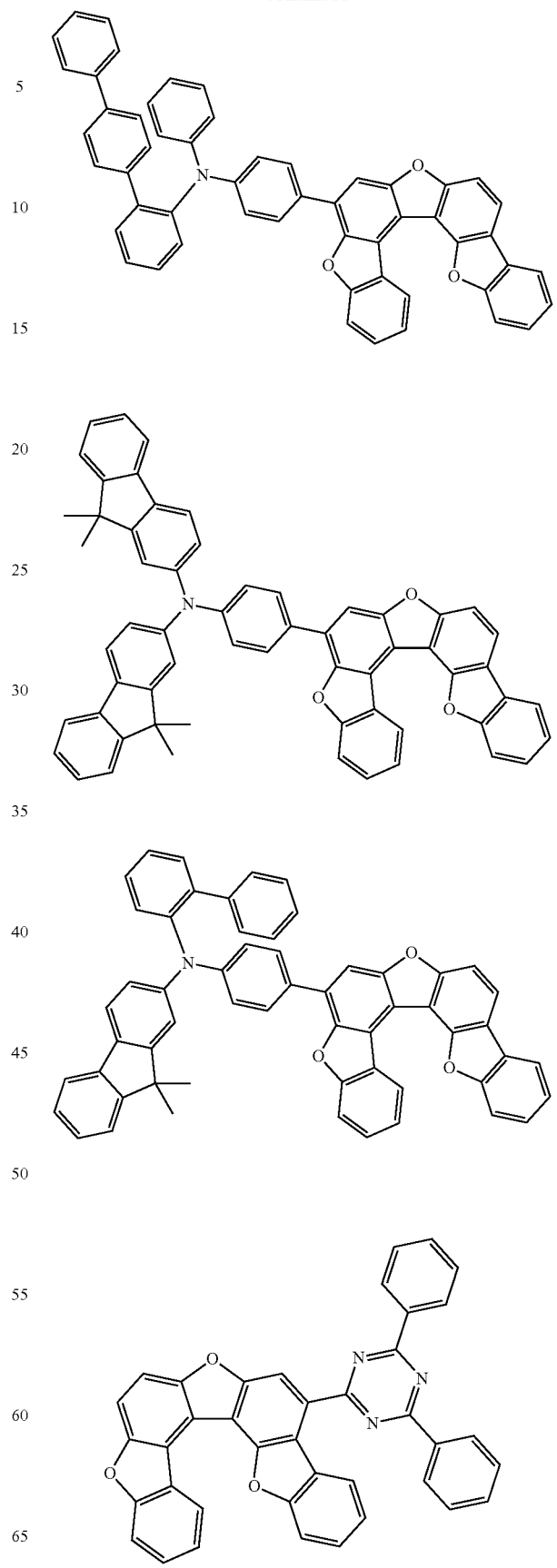

171
-continued
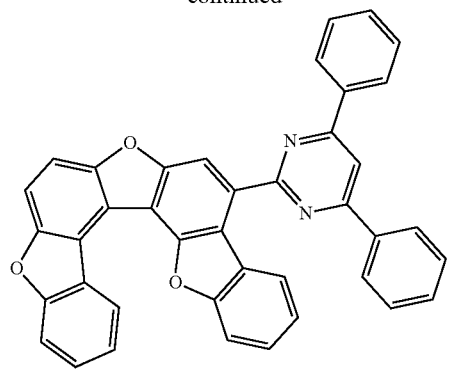
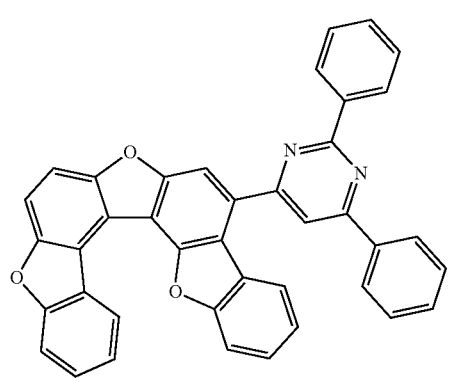
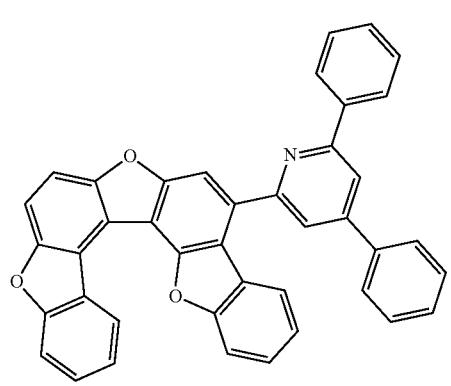
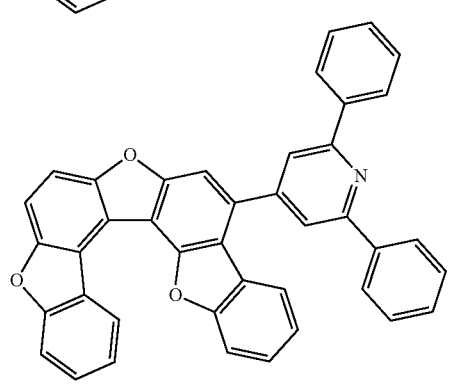
172
-continued
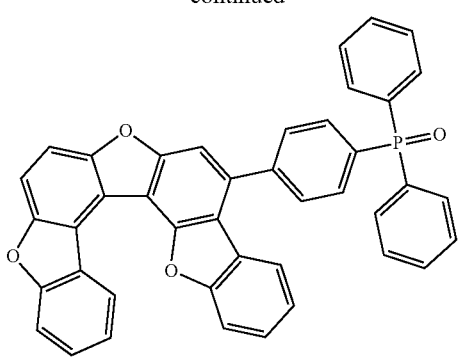
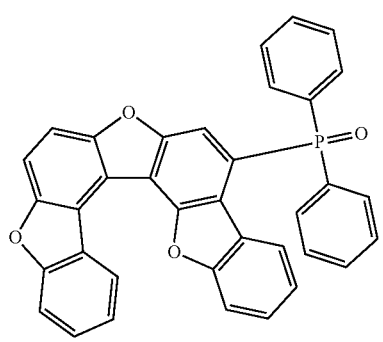
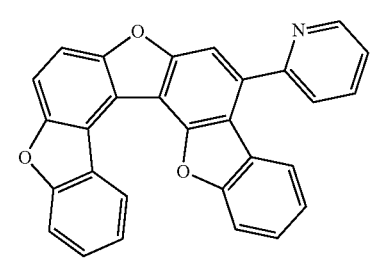
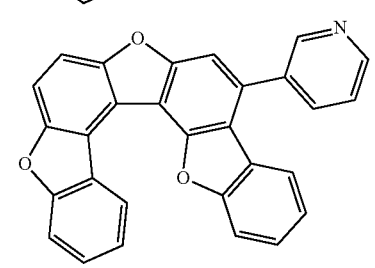
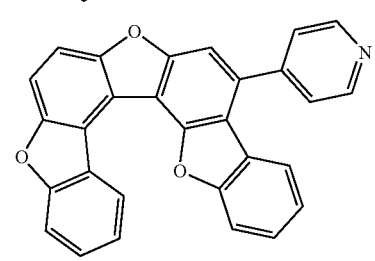

173
-continued
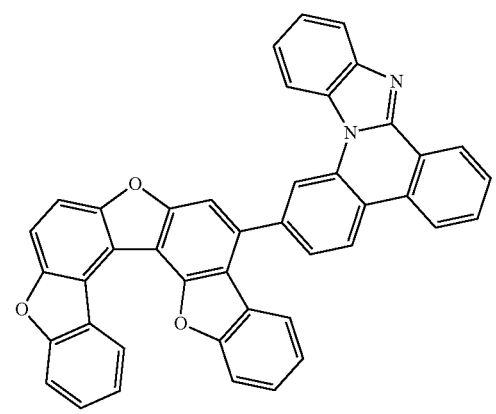
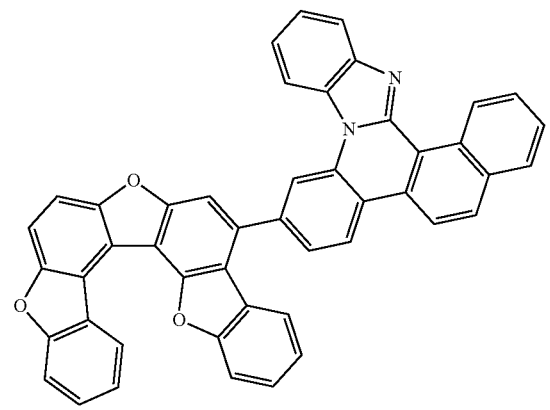
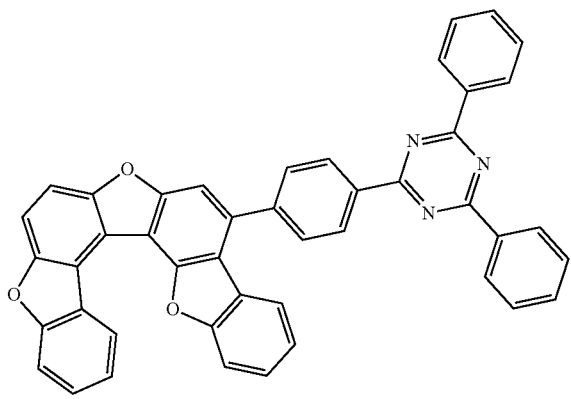
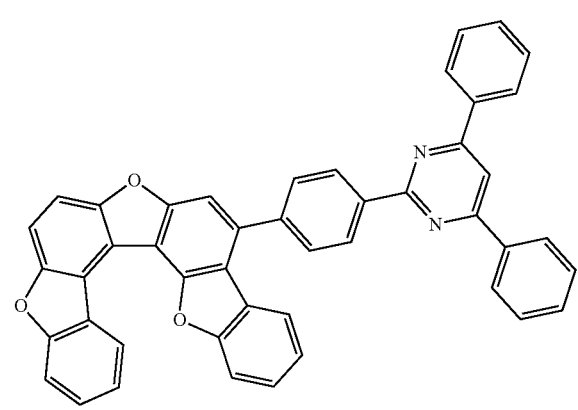
174
-continued
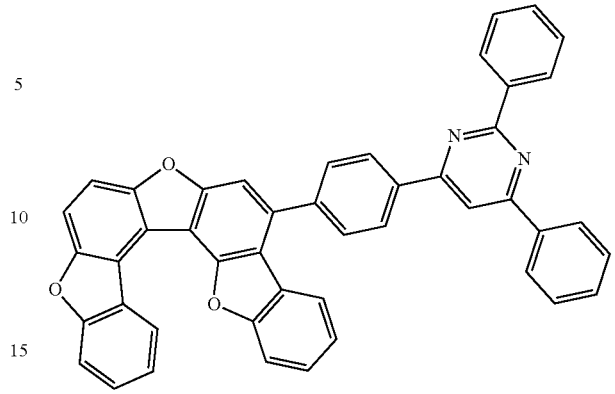
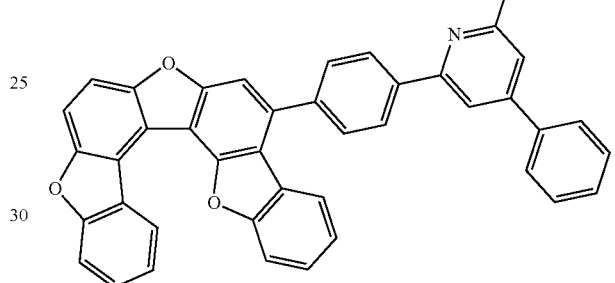
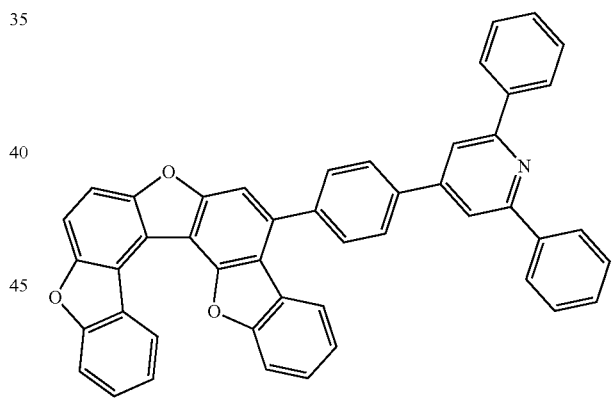
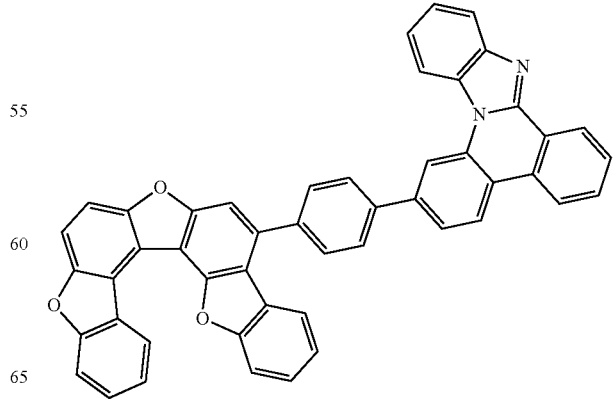

175
-continued
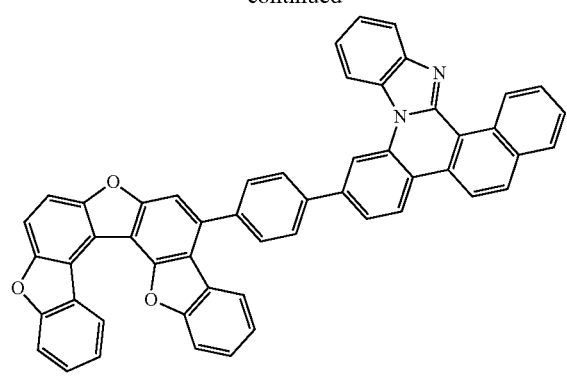
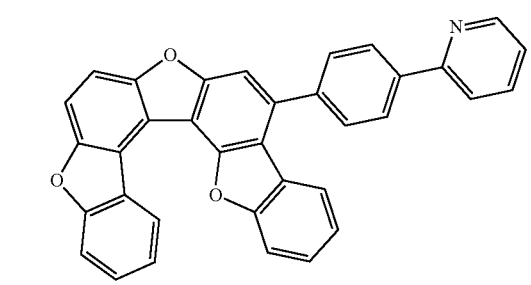
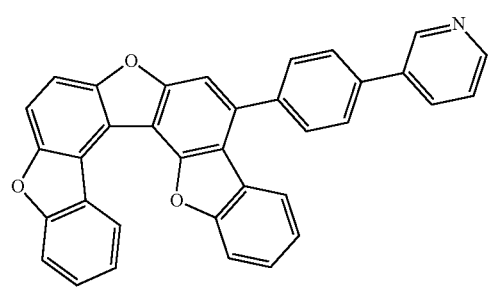
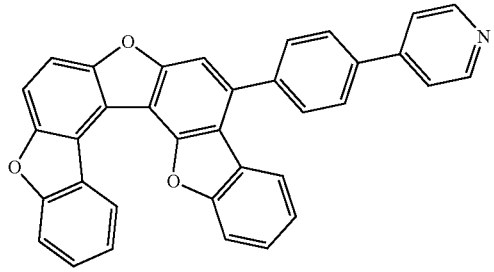
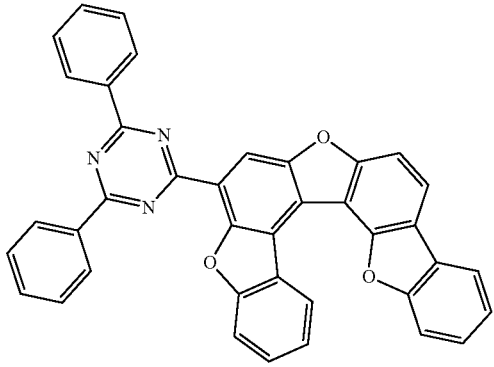
176
-continued
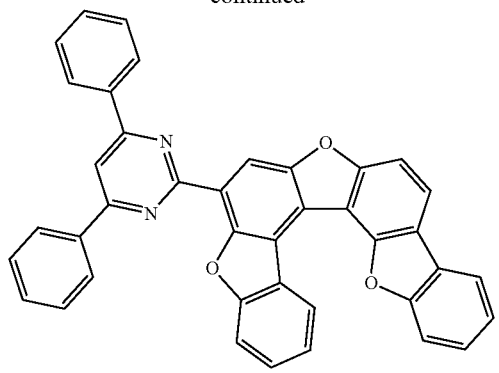
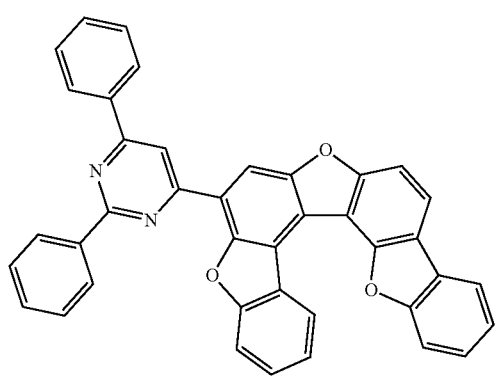
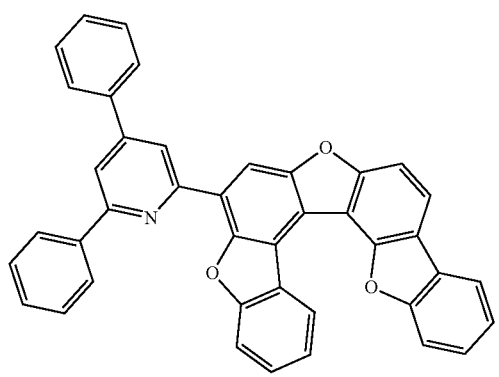
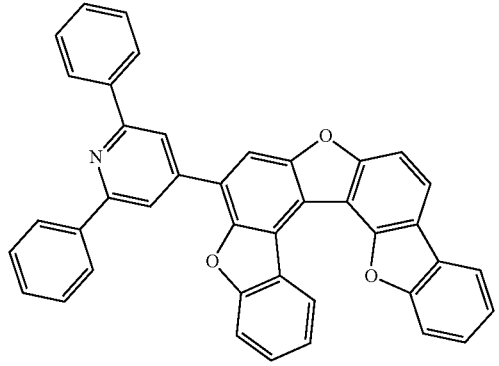

177
-continued
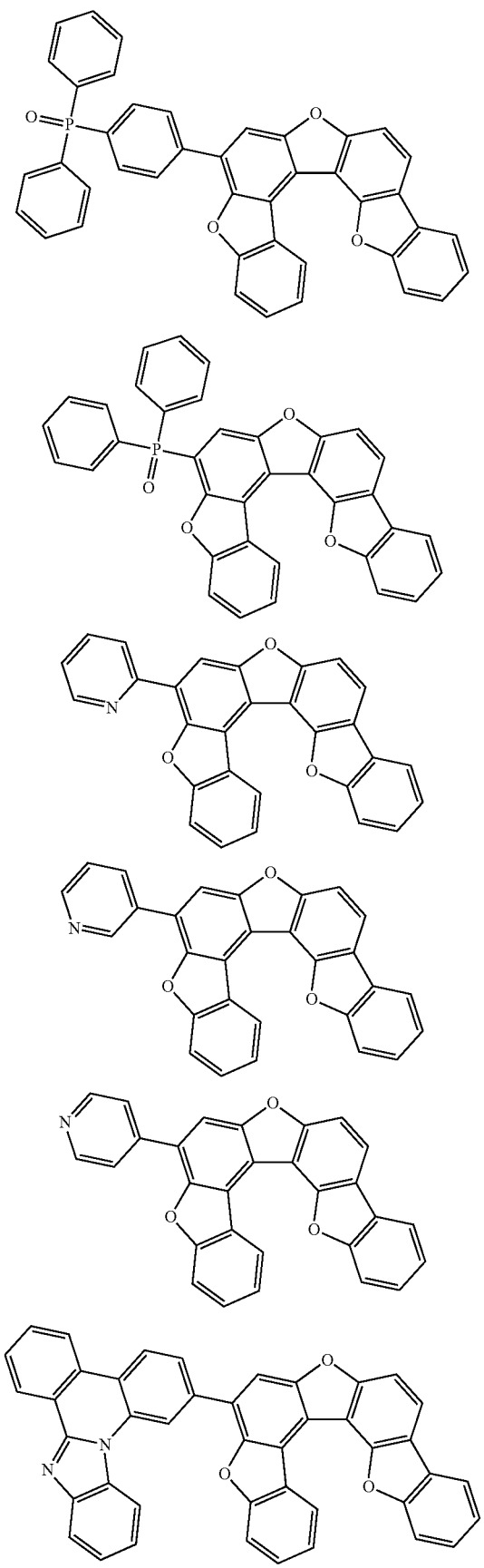
178
-continued
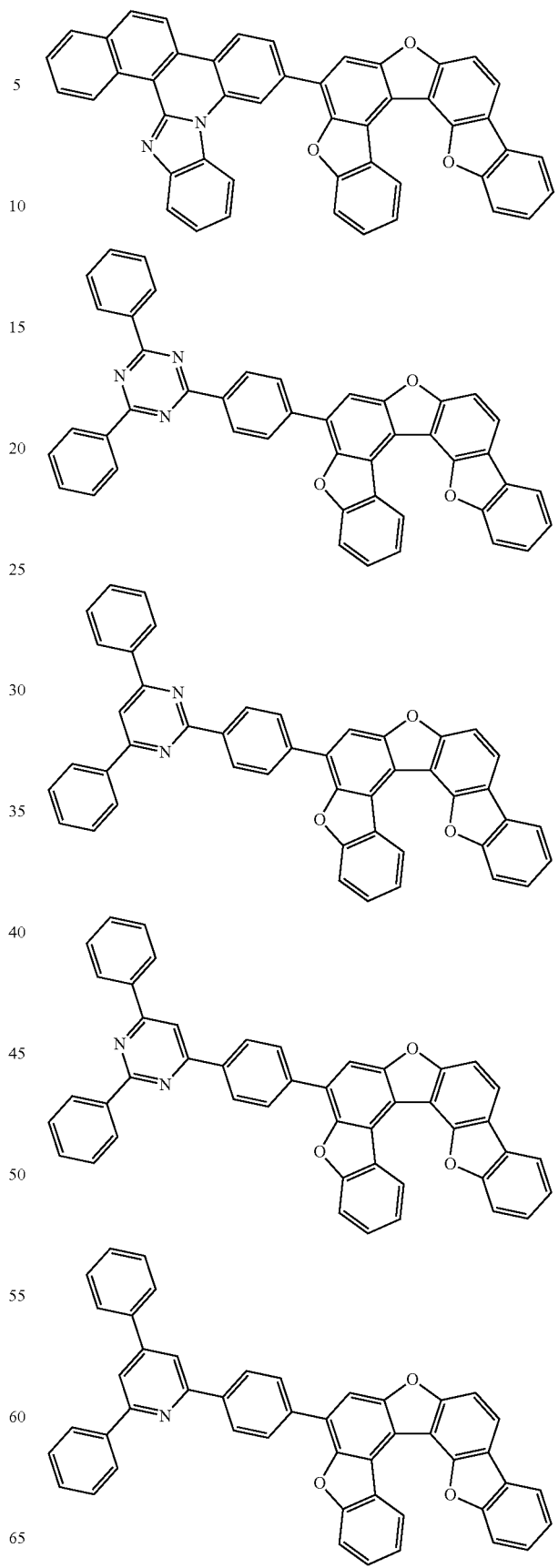

179
-continued
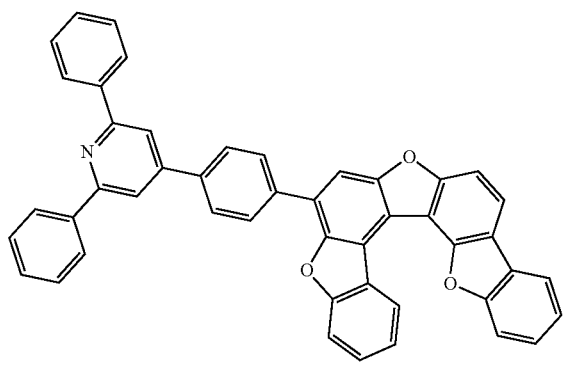
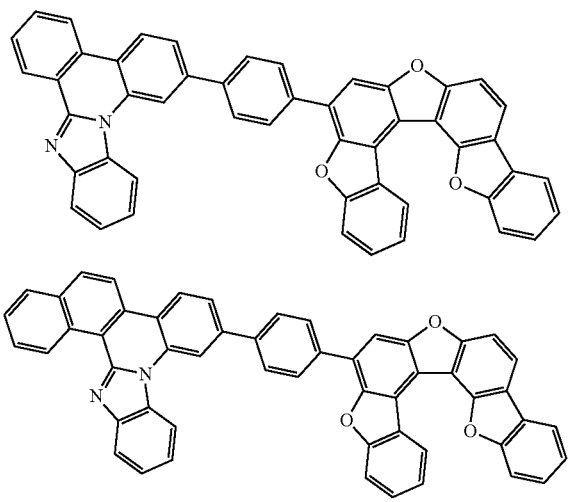
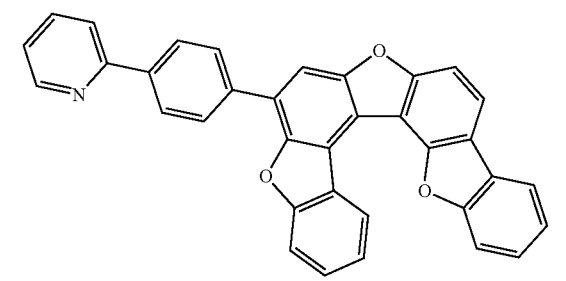
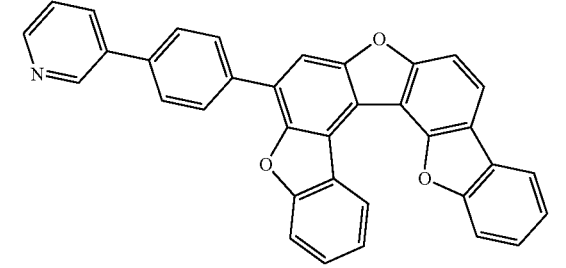
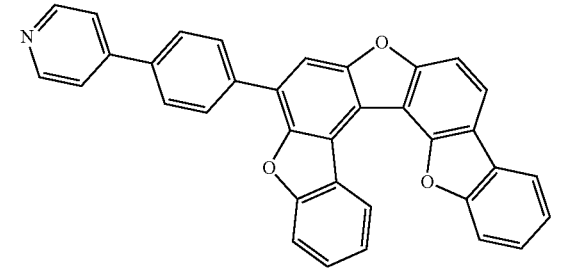
180
-continued
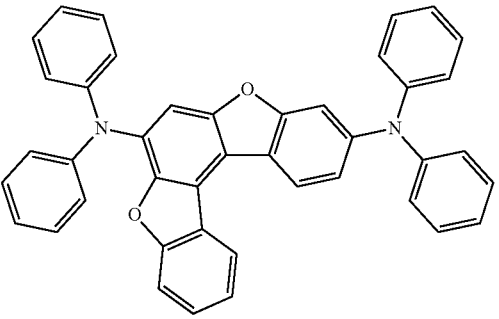
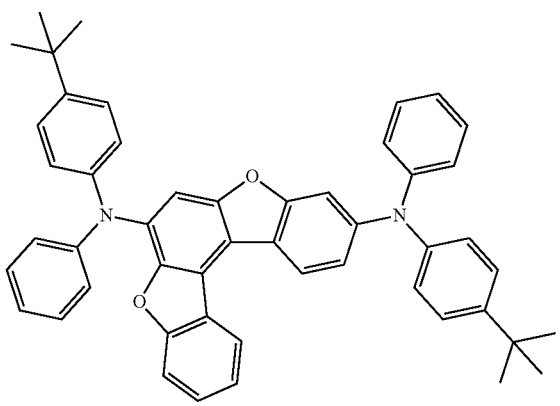
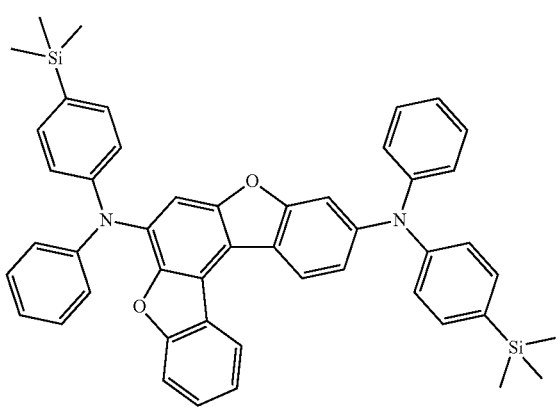
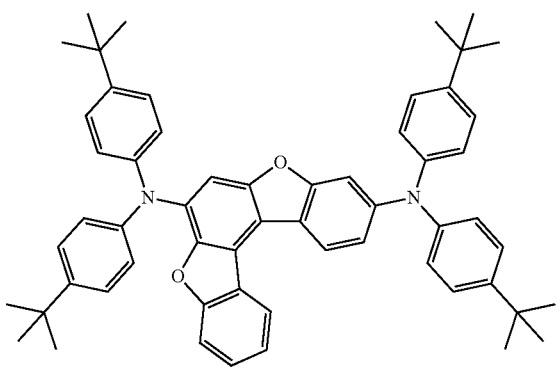

181
-continued
182
-continued
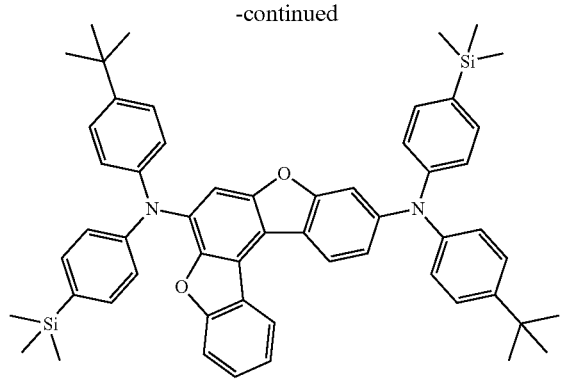
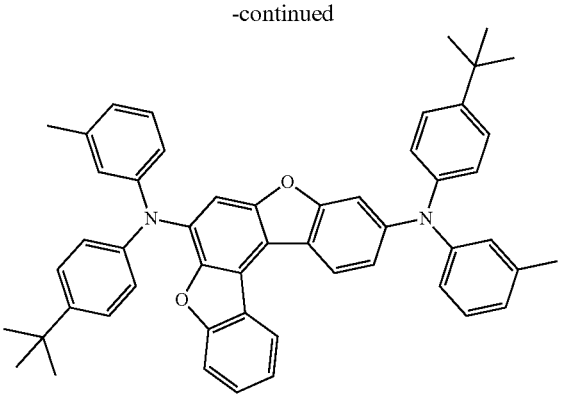
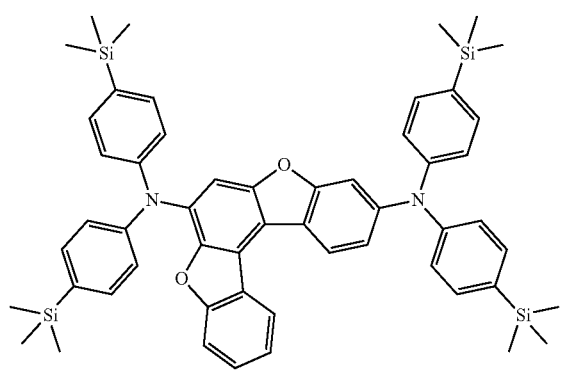
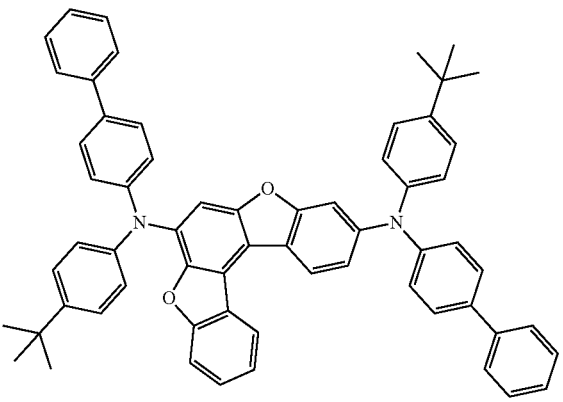
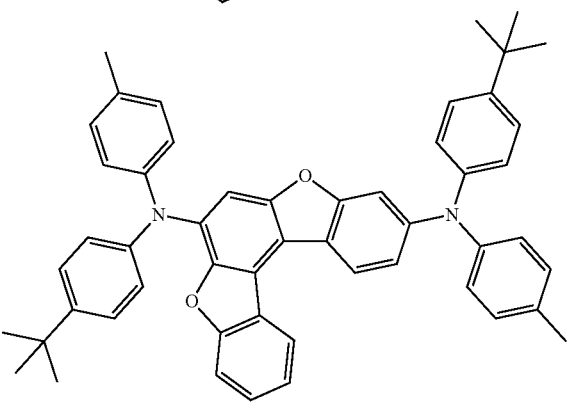
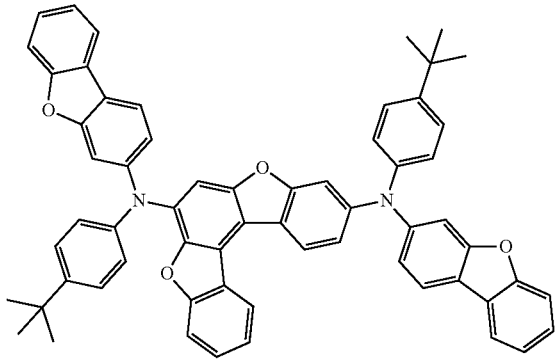

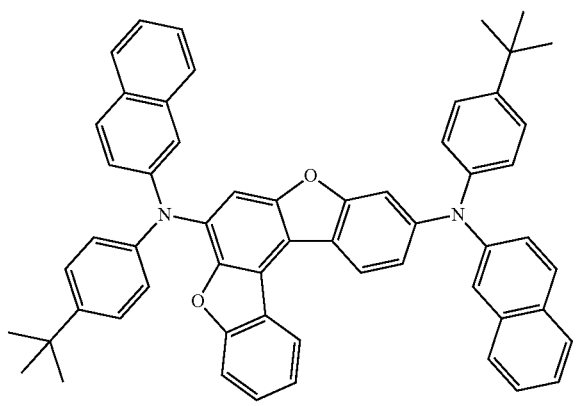
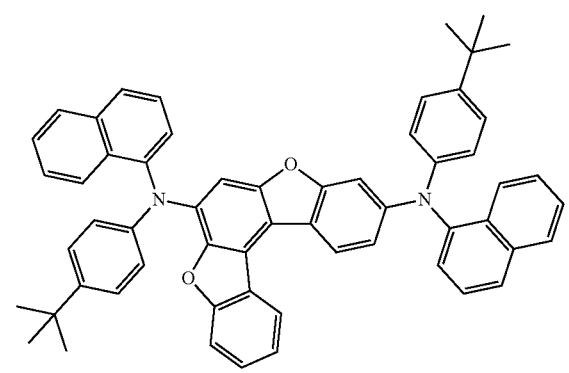
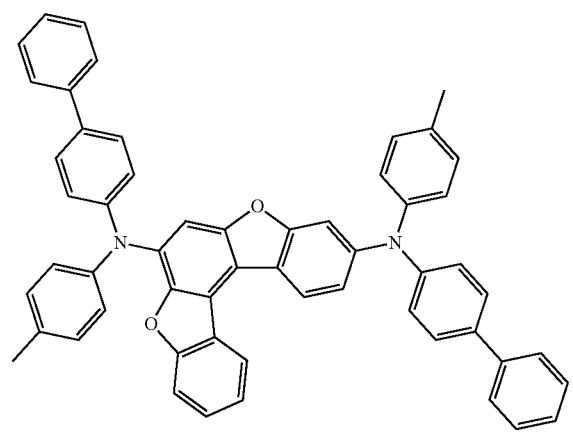
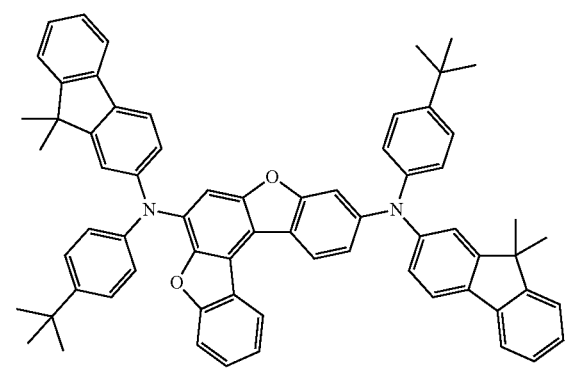
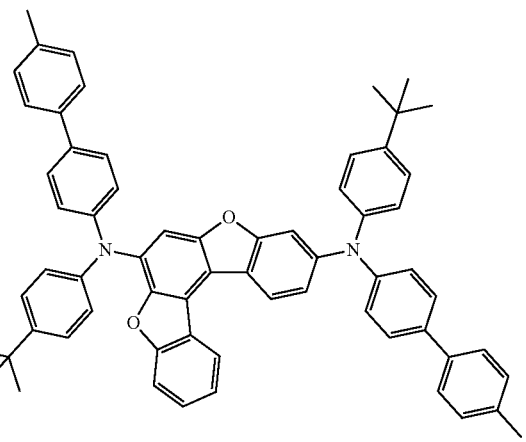
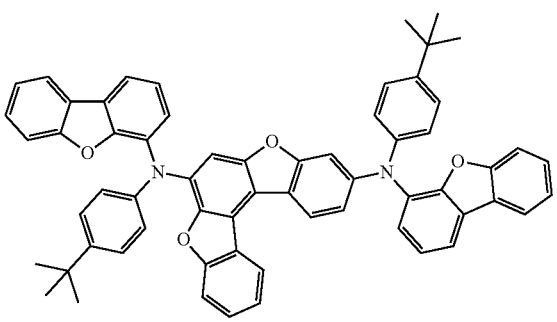
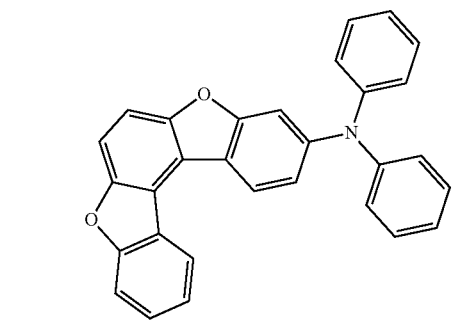
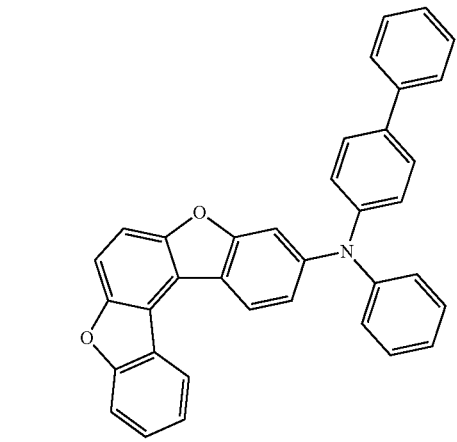

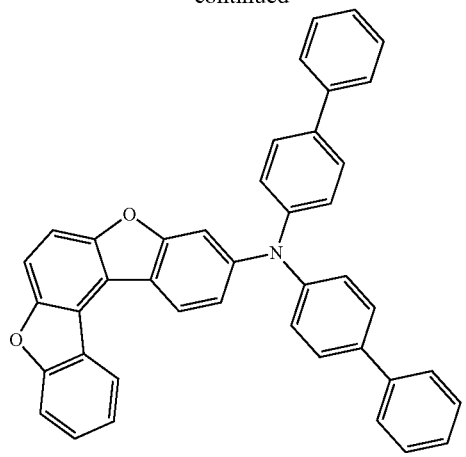
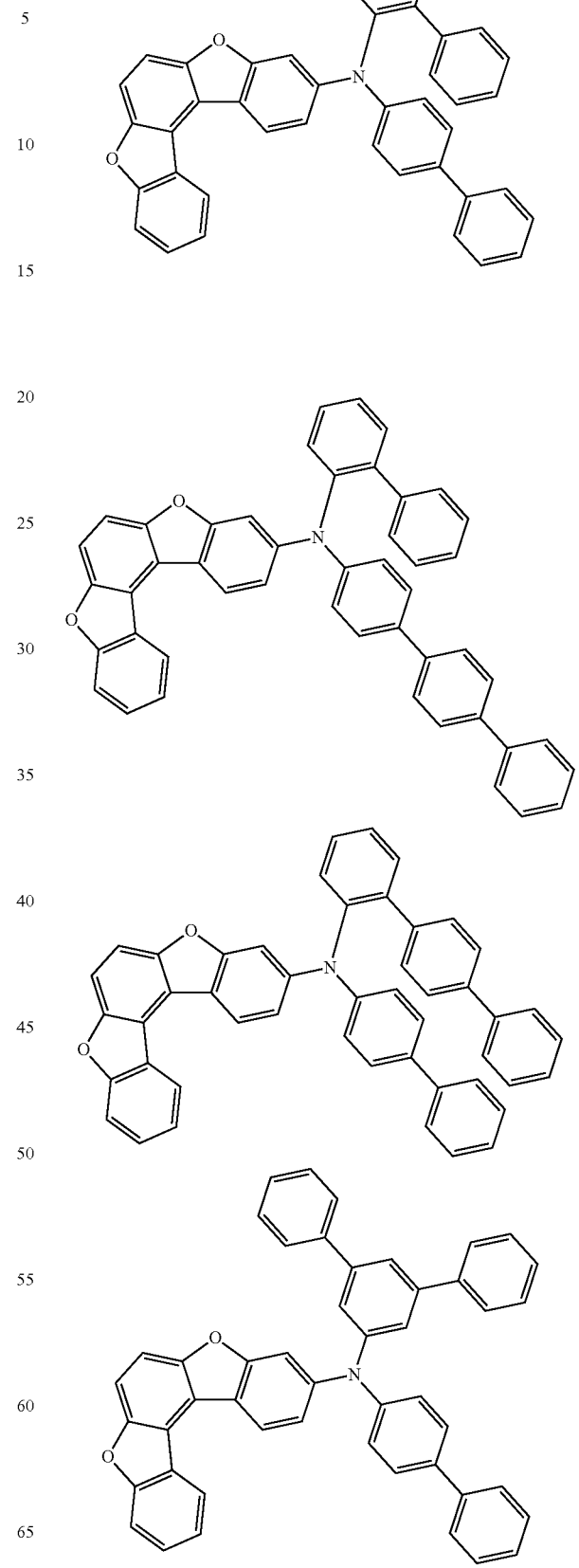

187
-continued
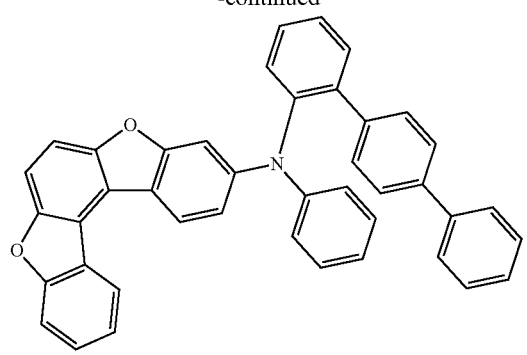
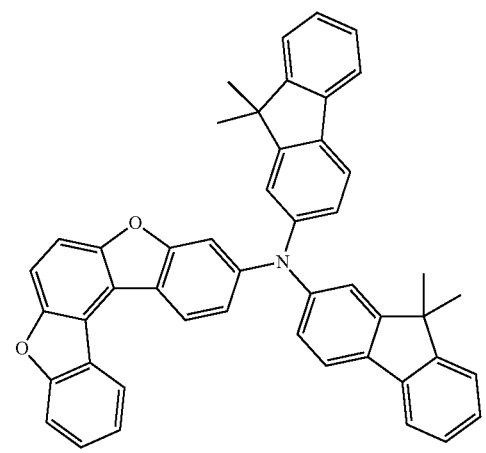
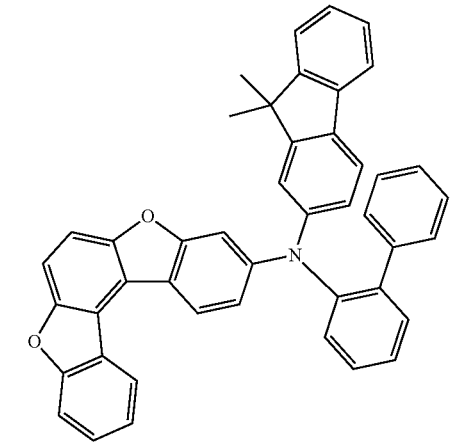
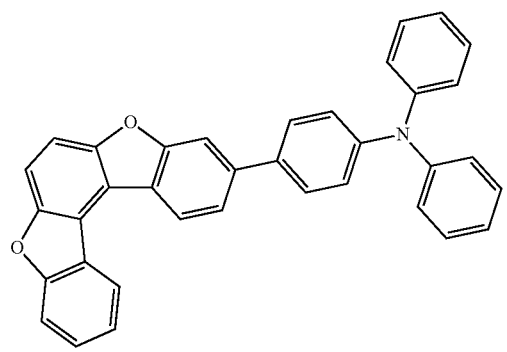
188
-continued
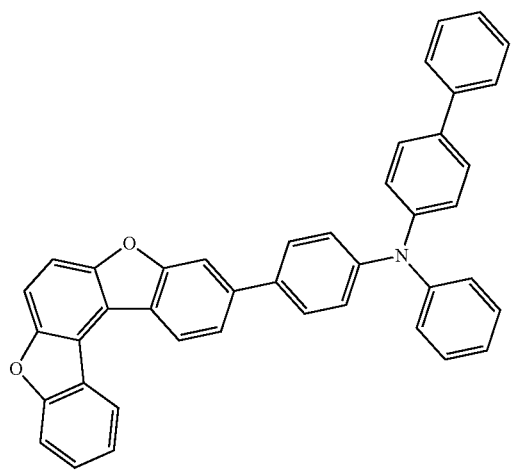
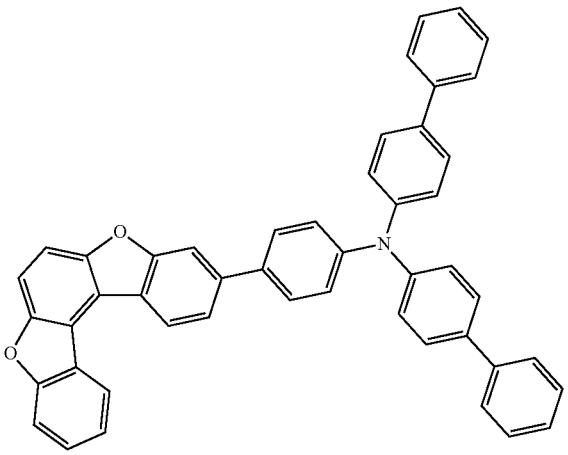
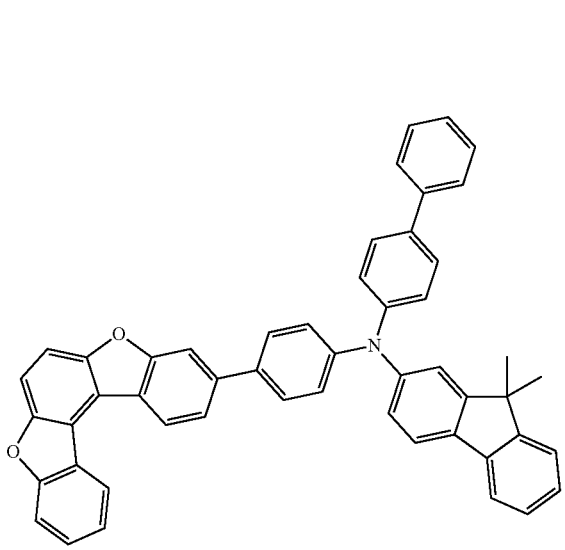

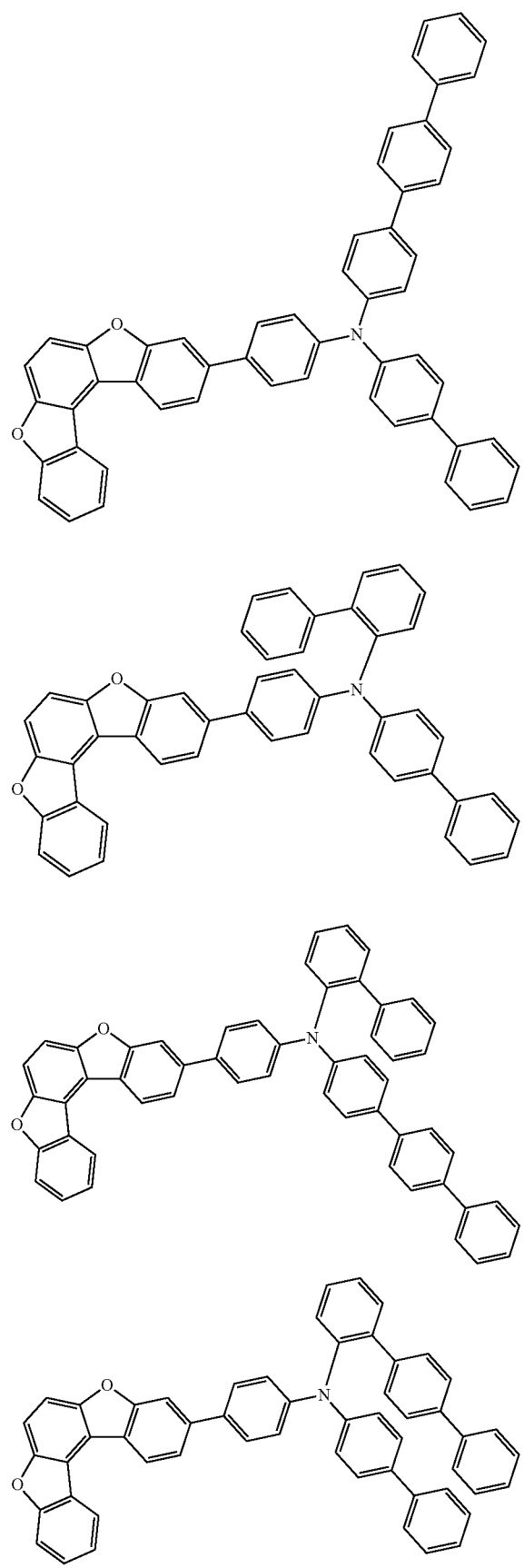
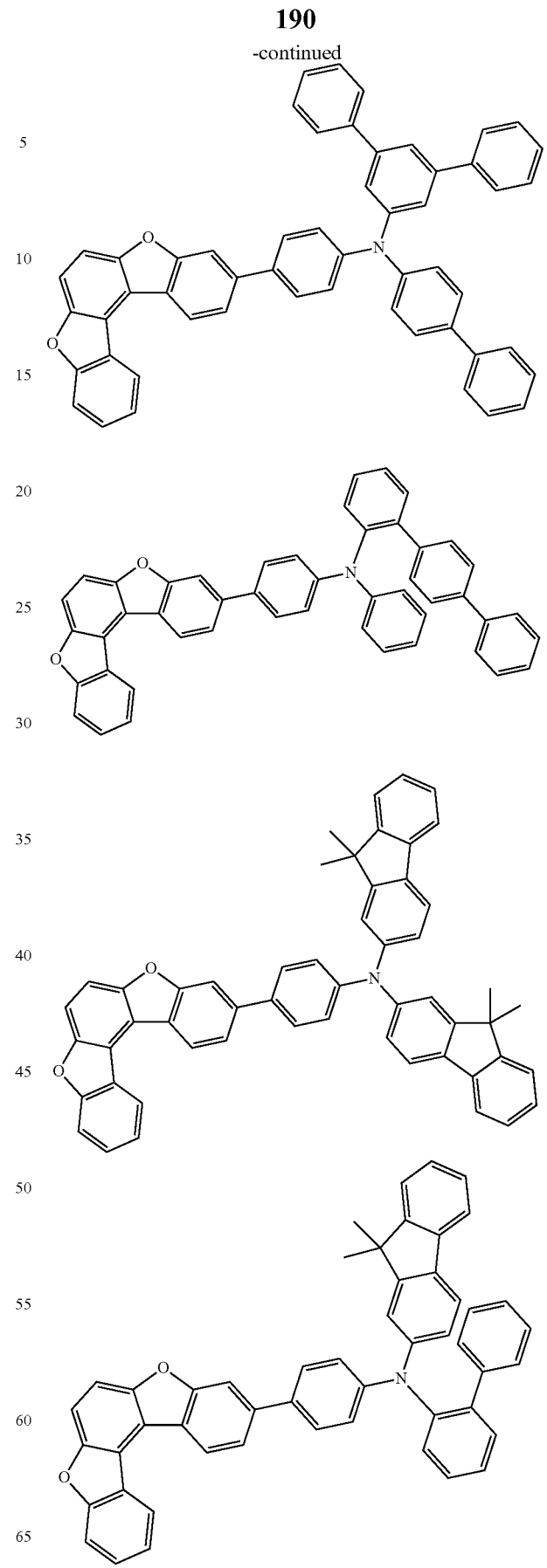

191
-continued
192
-continued
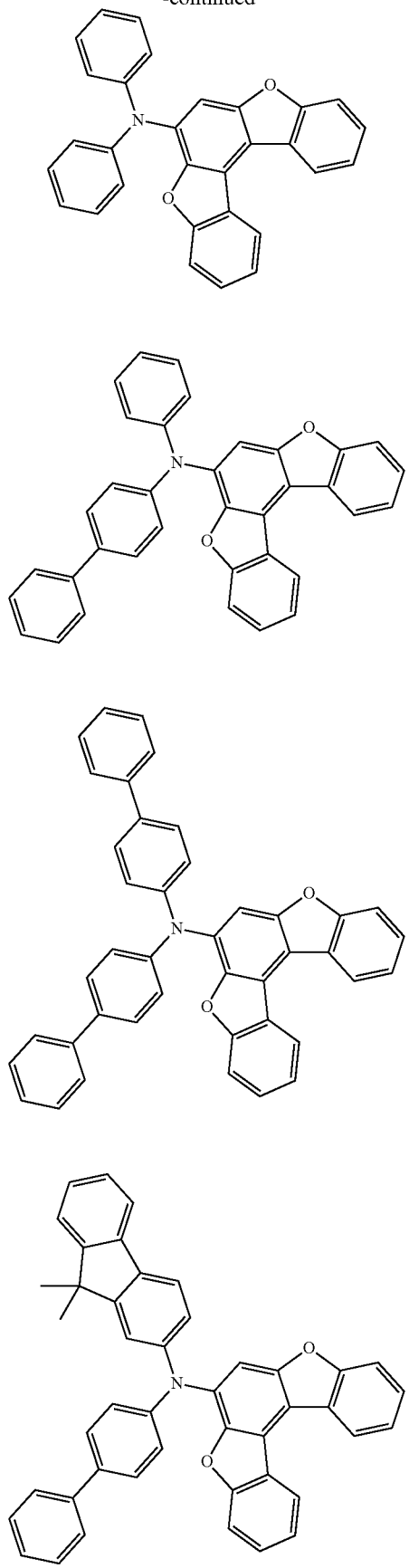
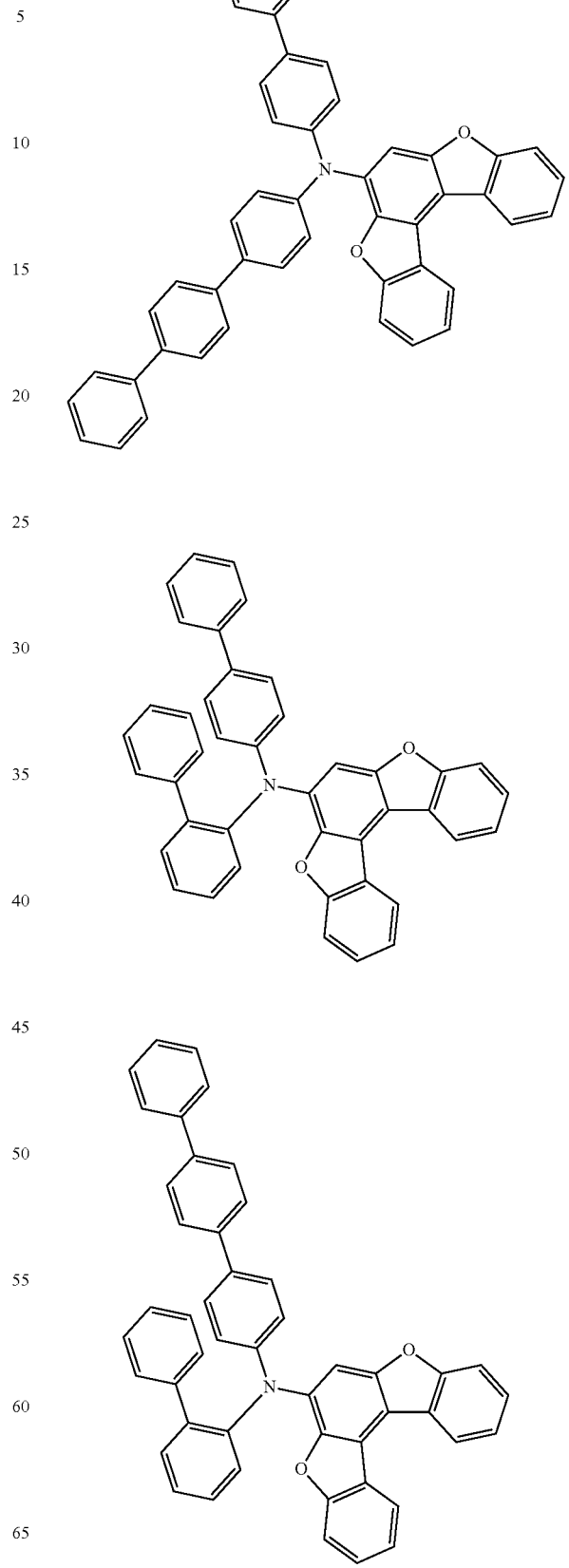

193
-continued
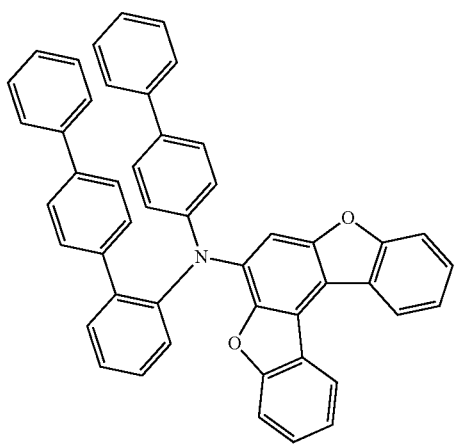
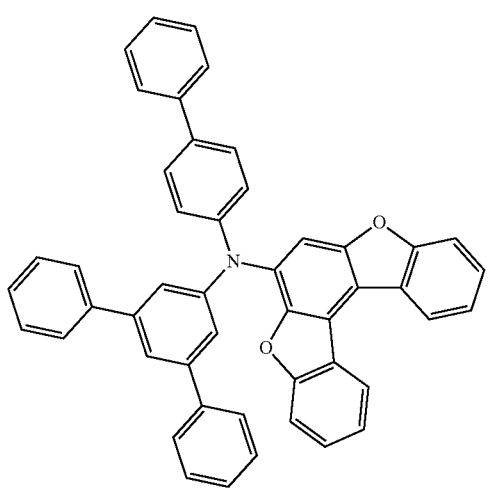
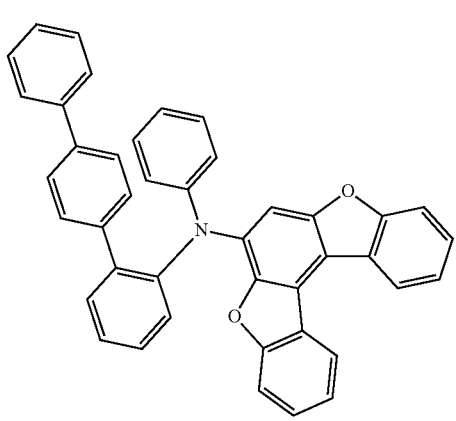
194
-continued
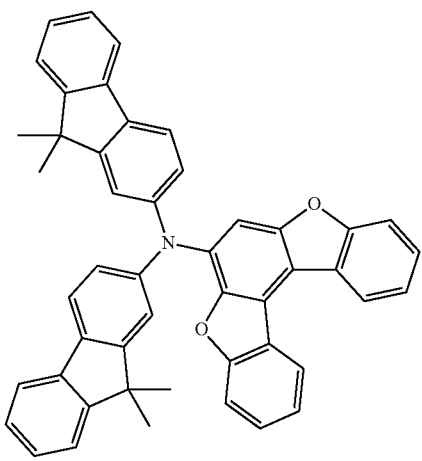
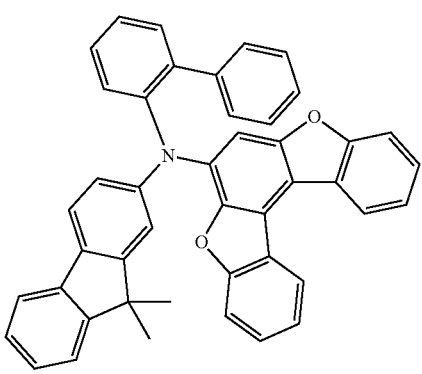
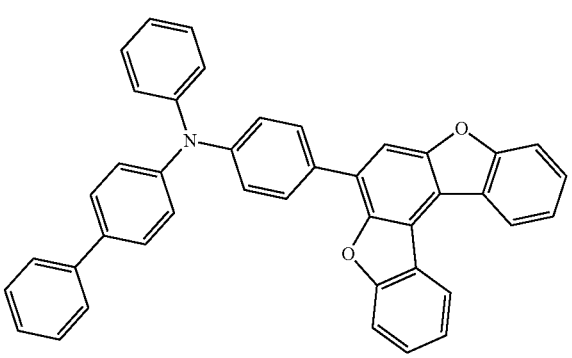

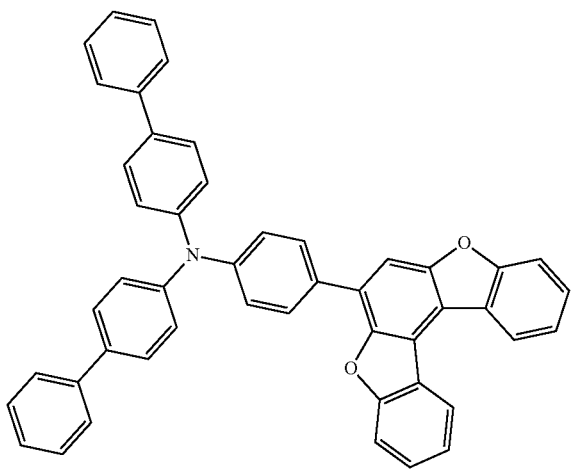
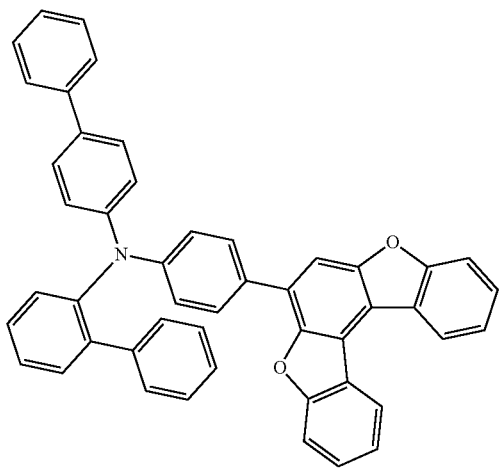
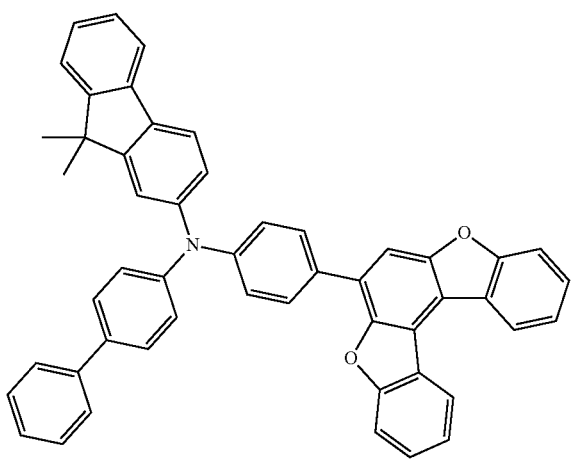
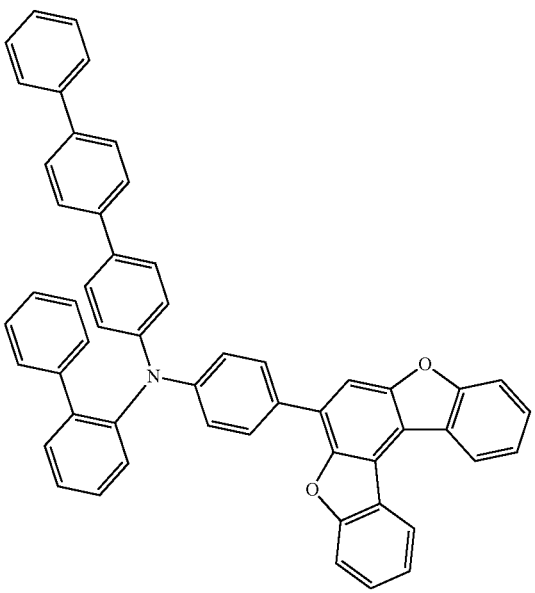
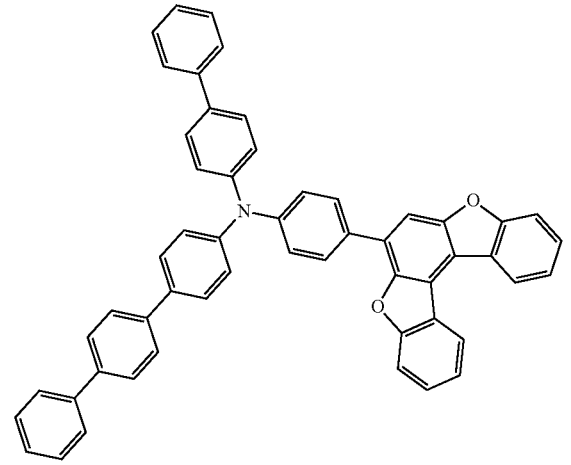
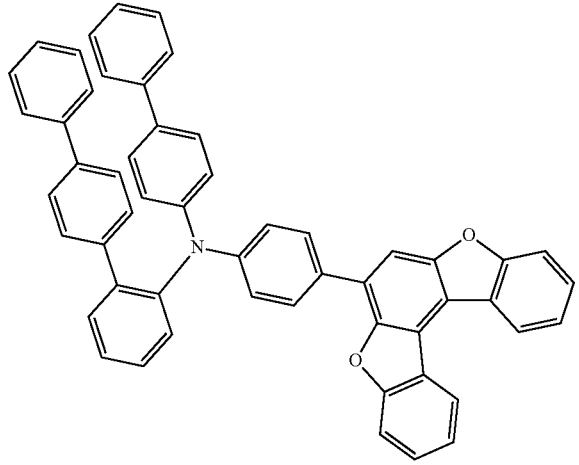

197
-continued
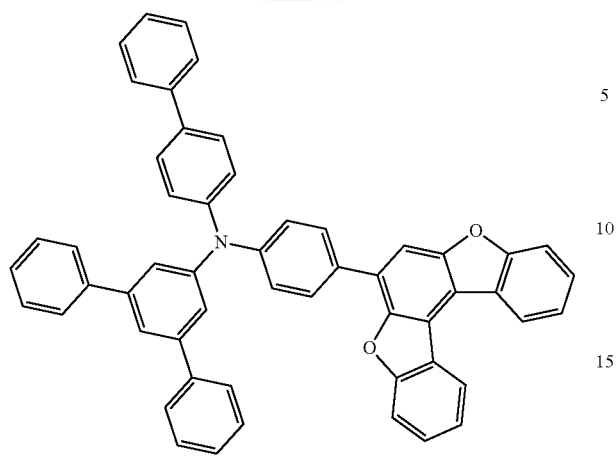
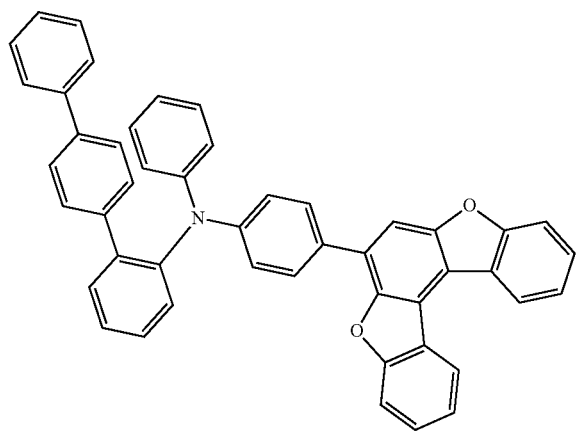
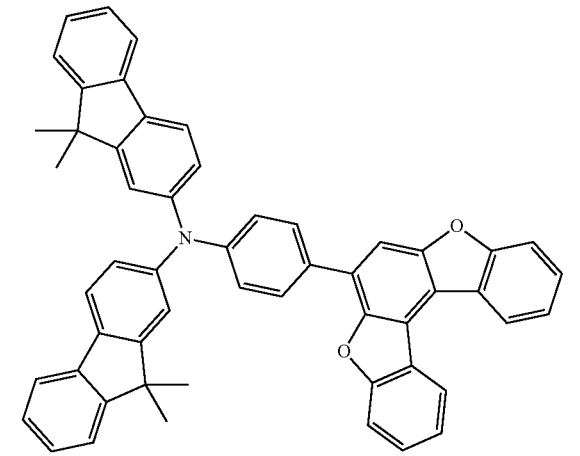
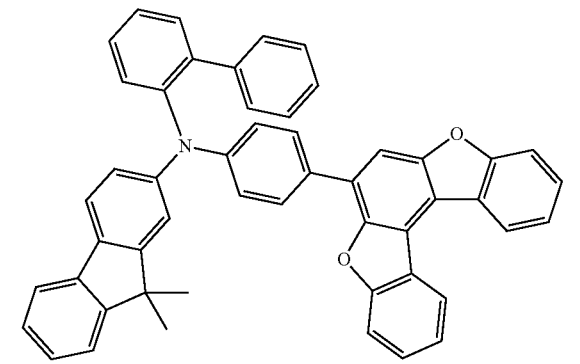
198
-continued
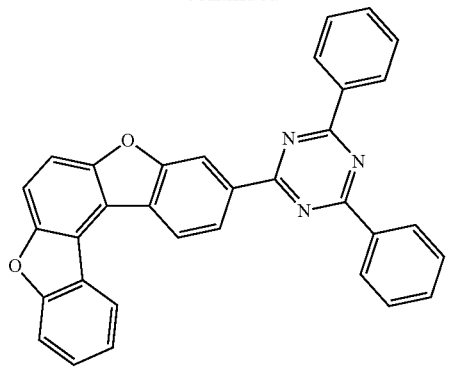
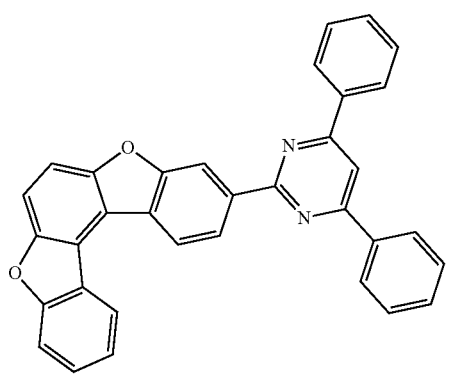
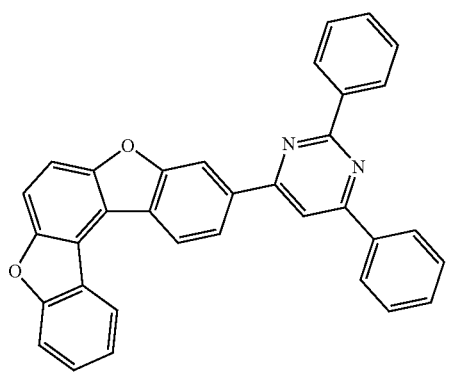
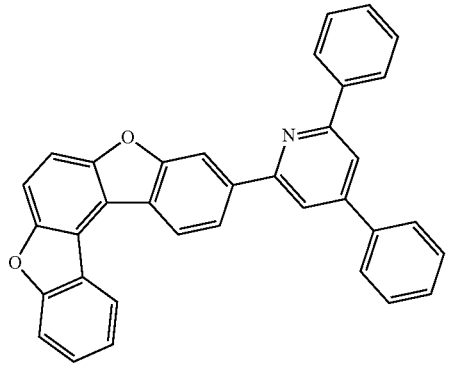

199
-continued
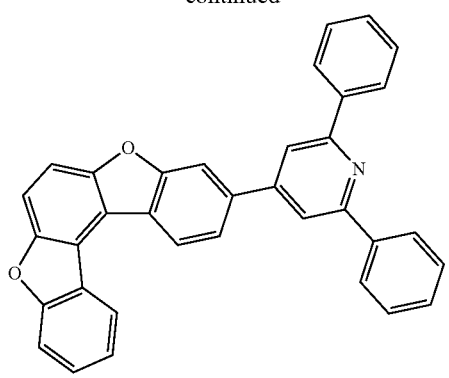
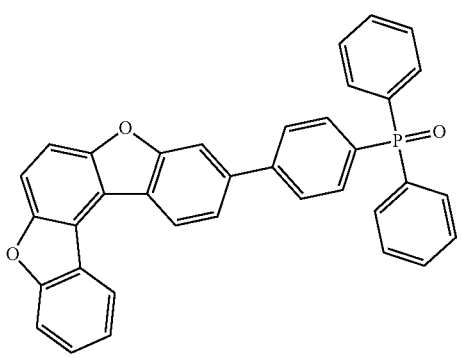
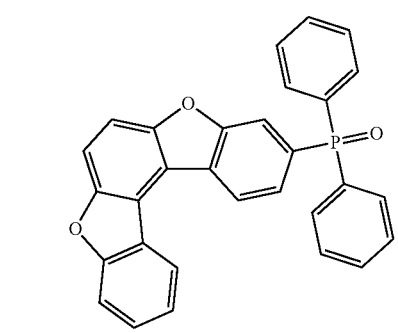
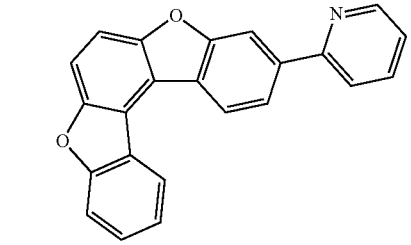
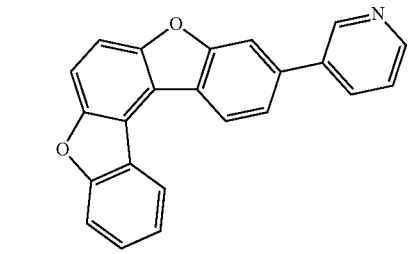
200
-continued
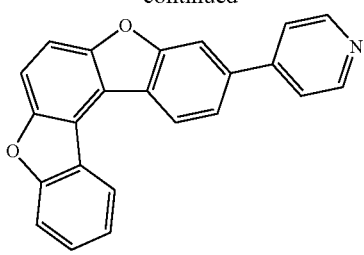
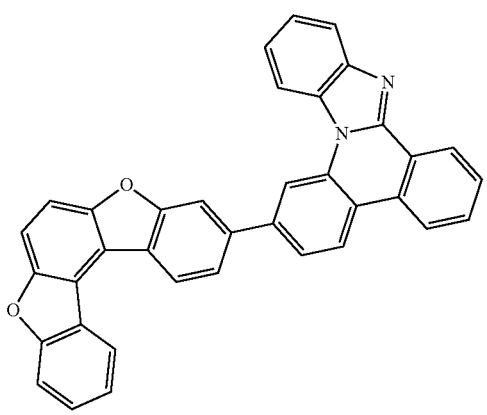
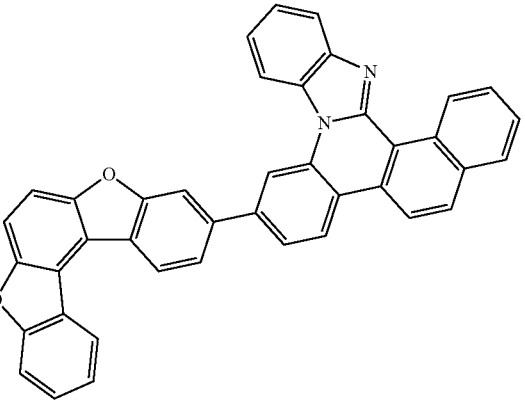
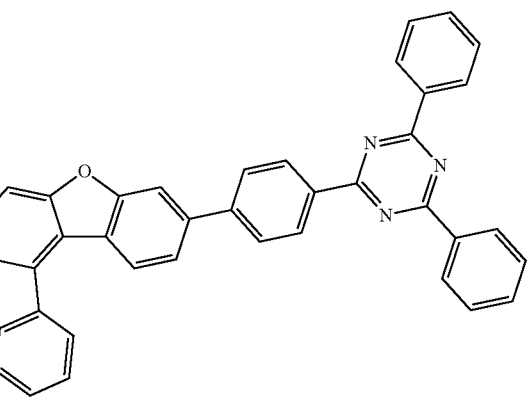

201
-continued
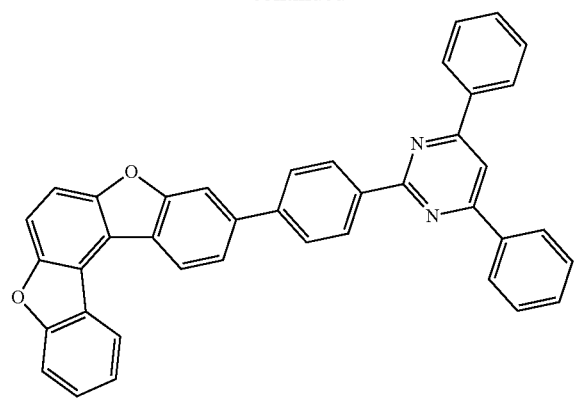
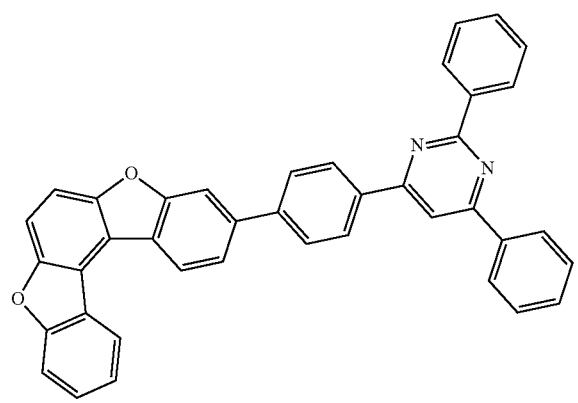
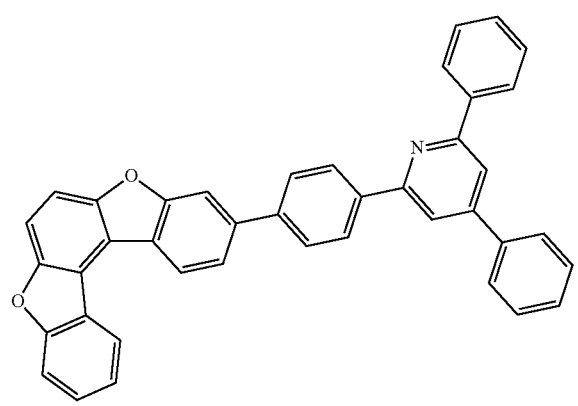
202
-continued
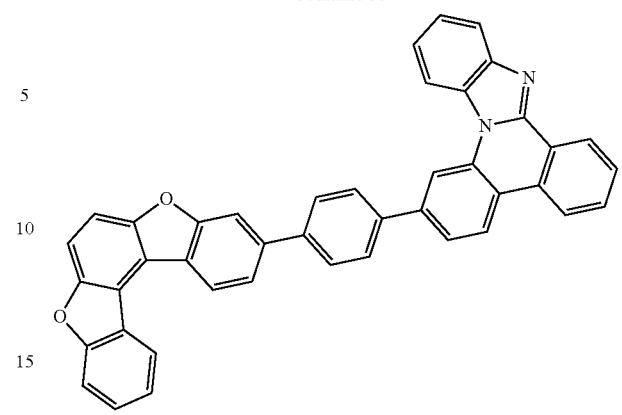
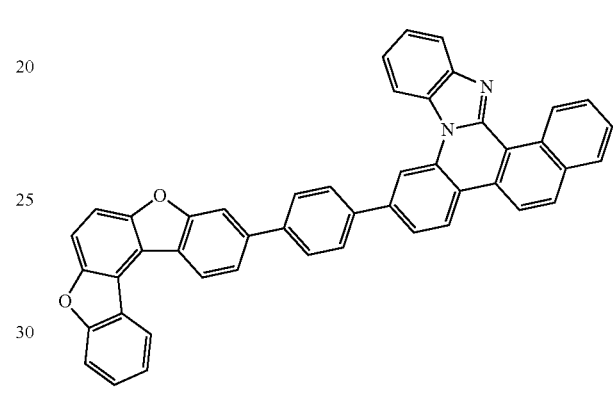
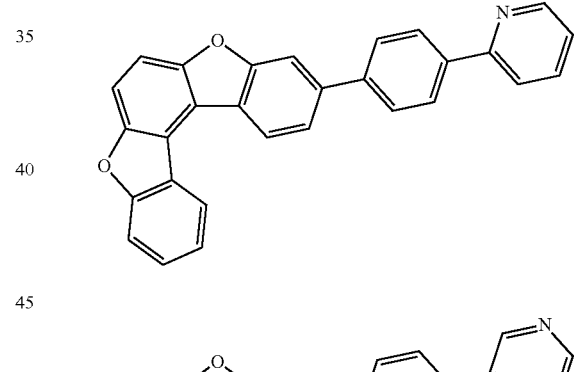

-continued
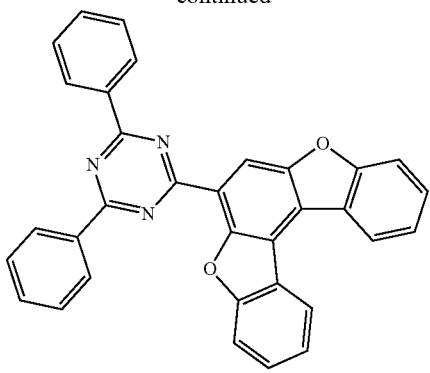
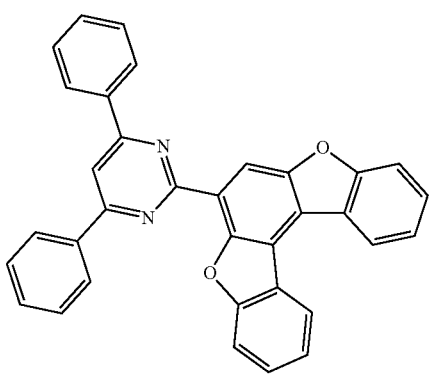
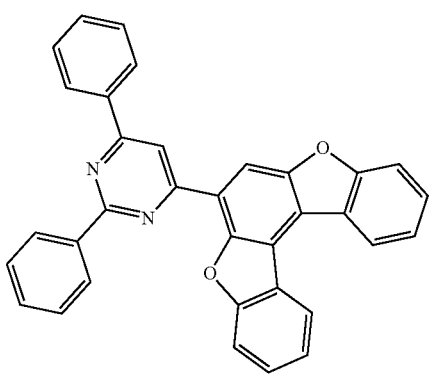
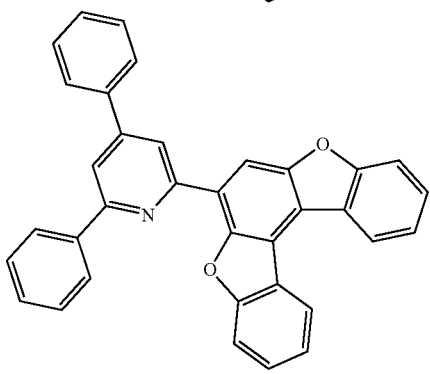
-continued
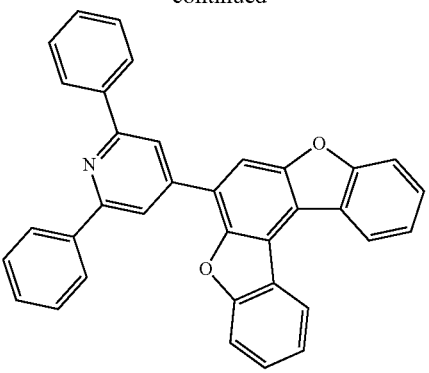
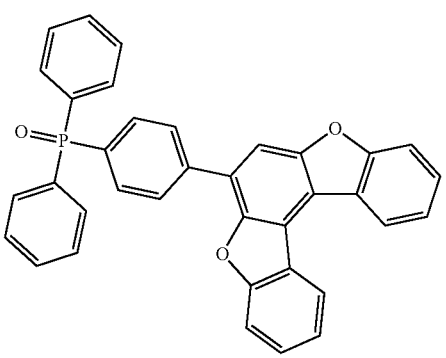
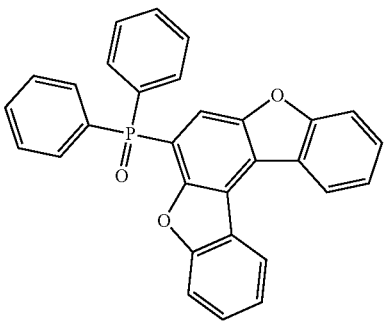
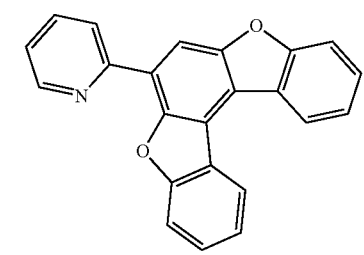
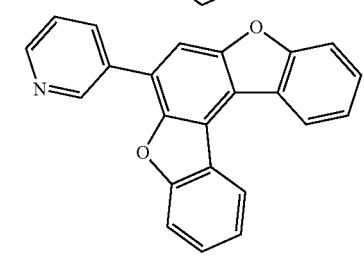

205
-continued
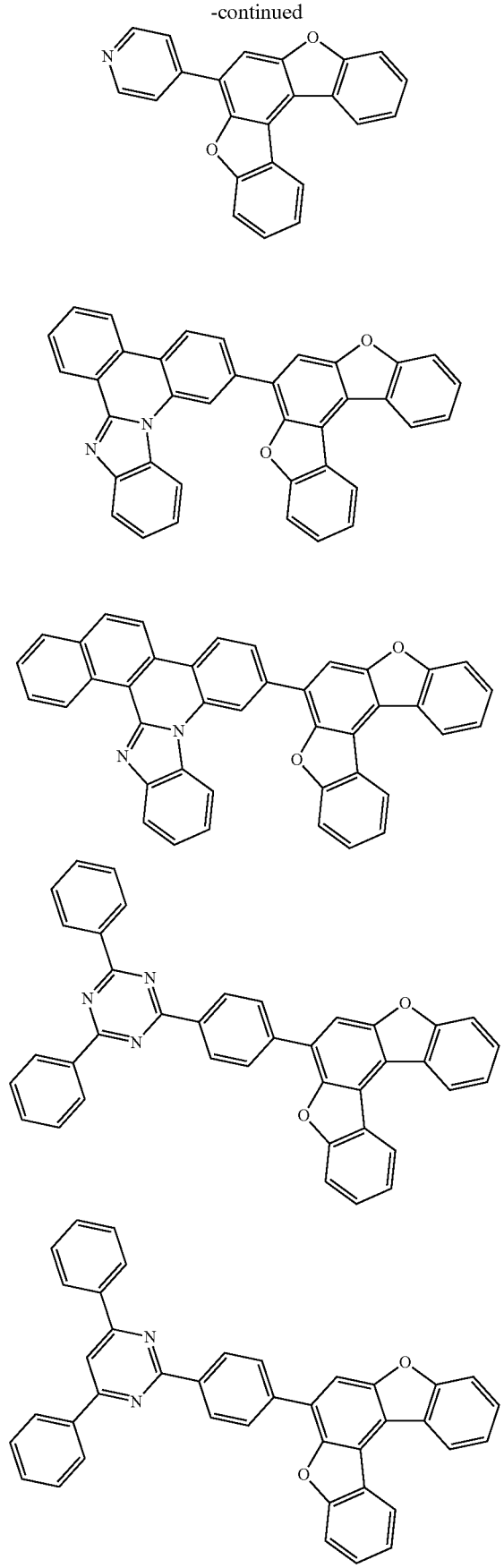
206
-continued
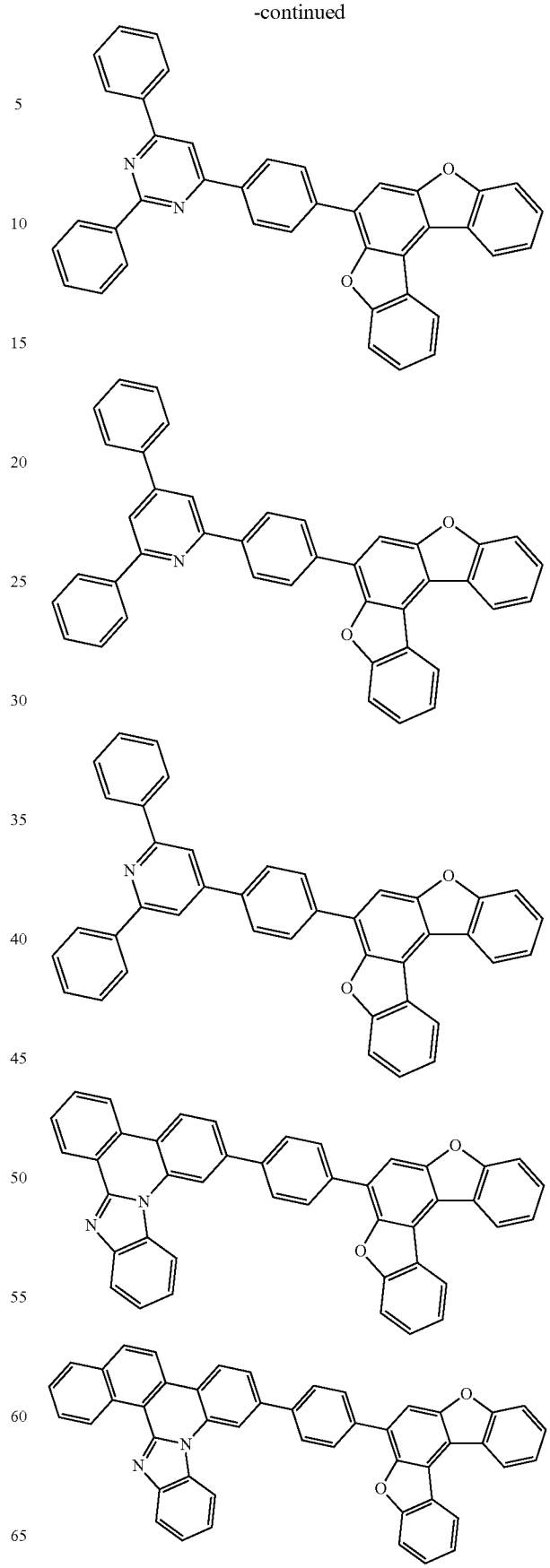

207
-continued
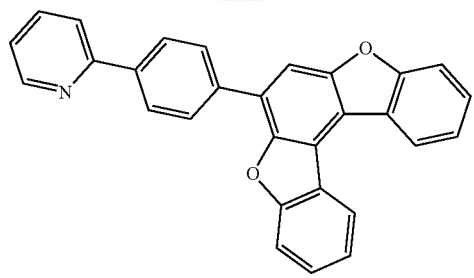
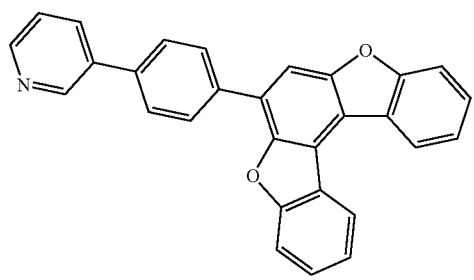
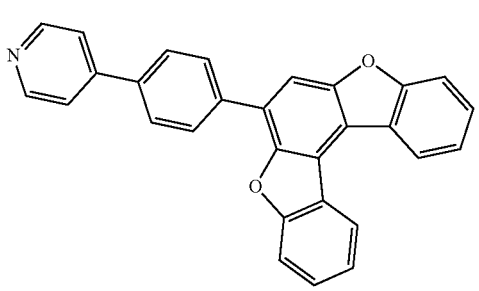
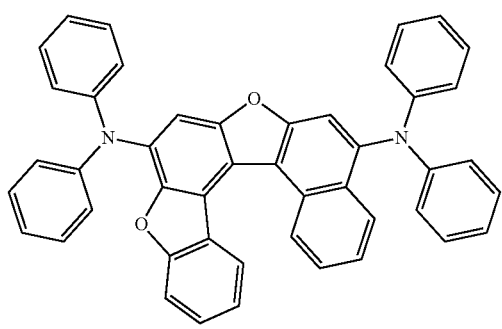
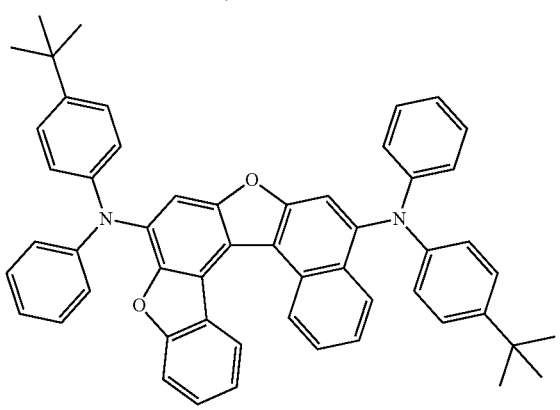
208
-continued
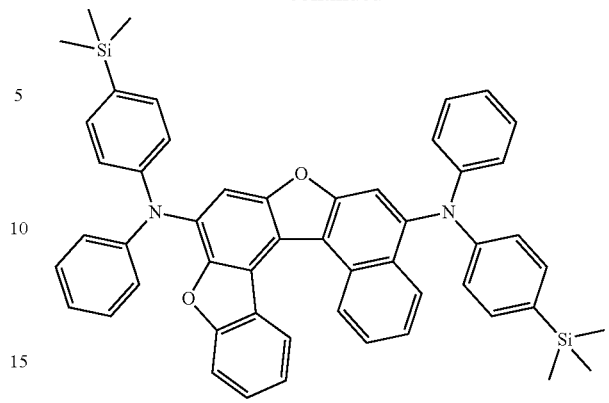
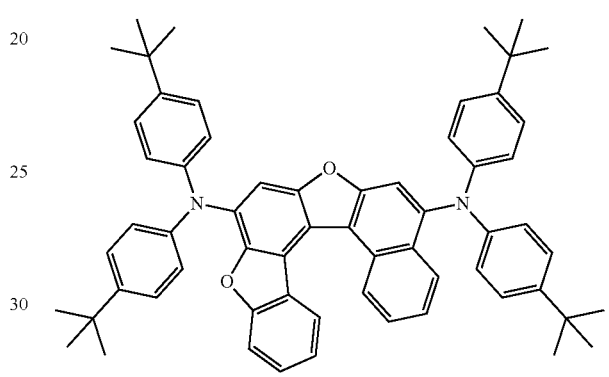
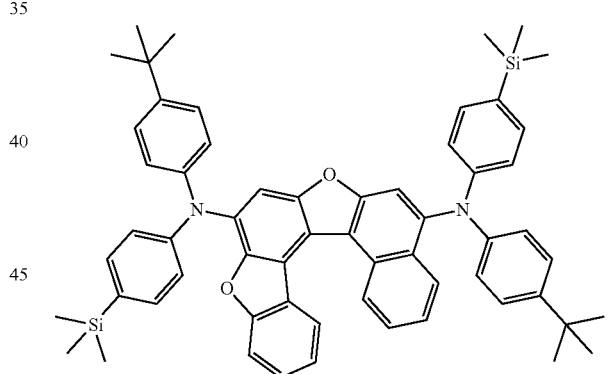
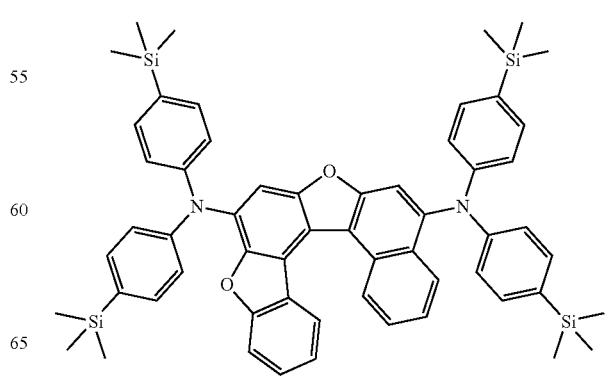

209
-continued
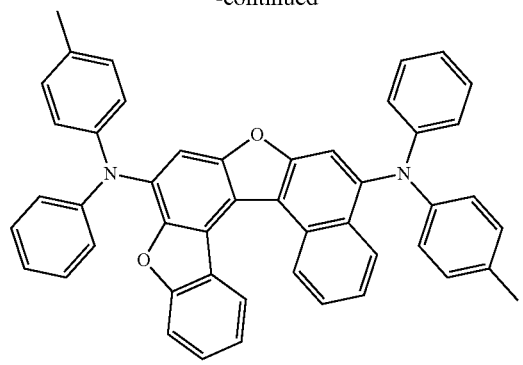
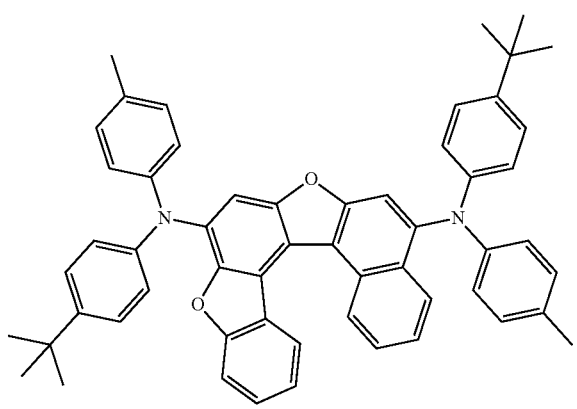
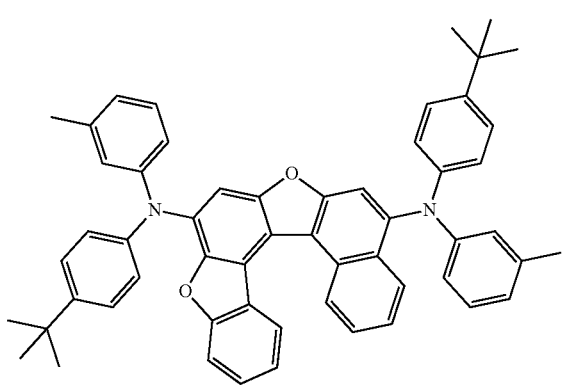
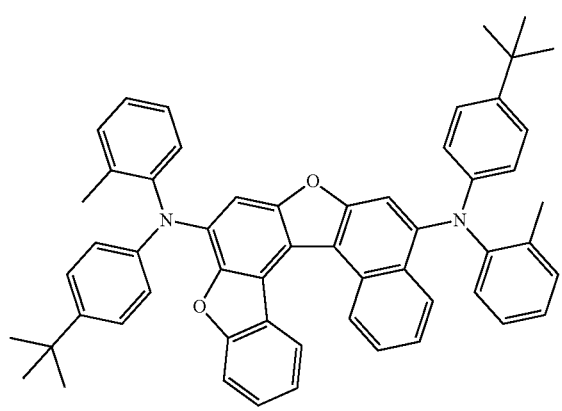
210
-continued
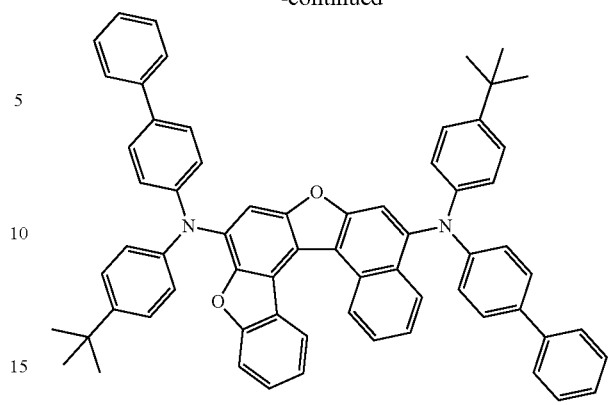
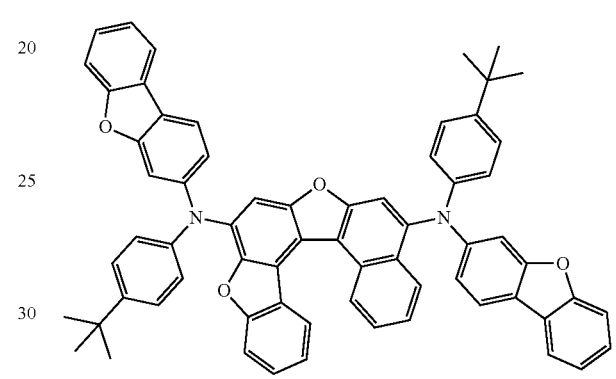
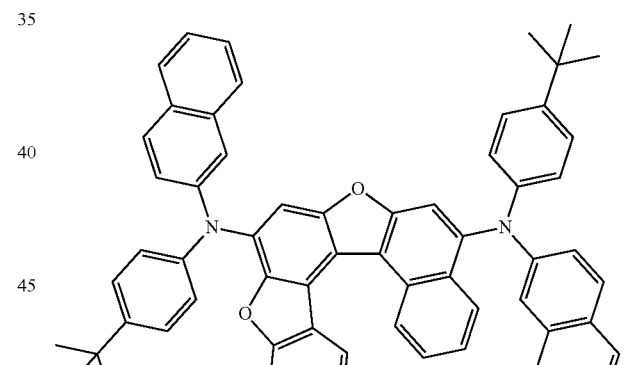
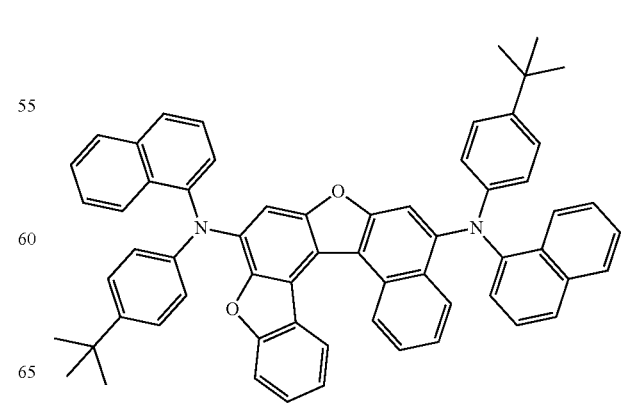

211
-continued
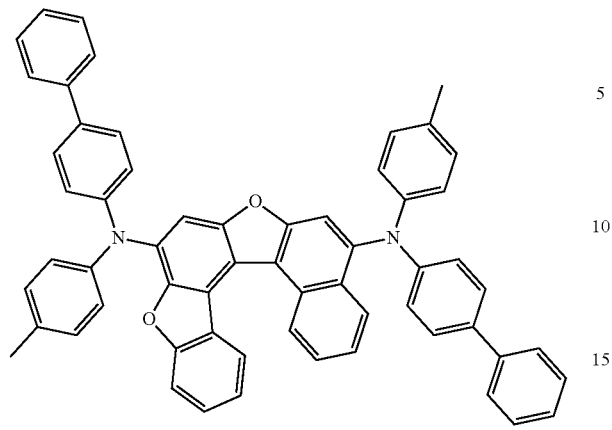
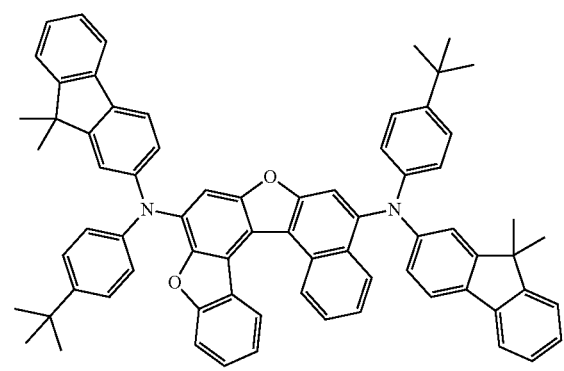
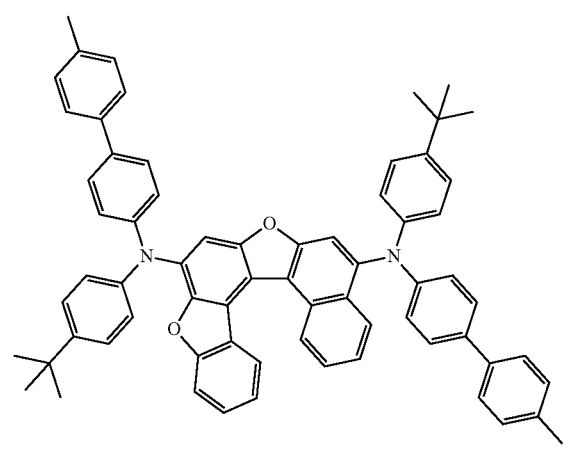
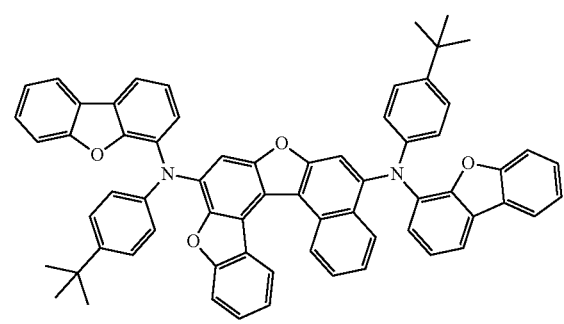
212
-continued
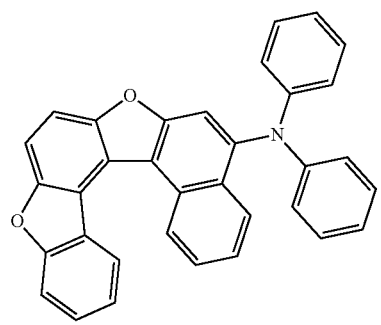
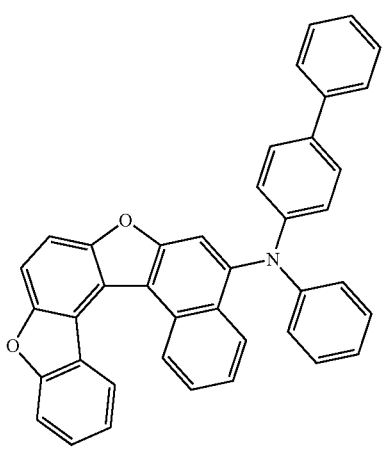
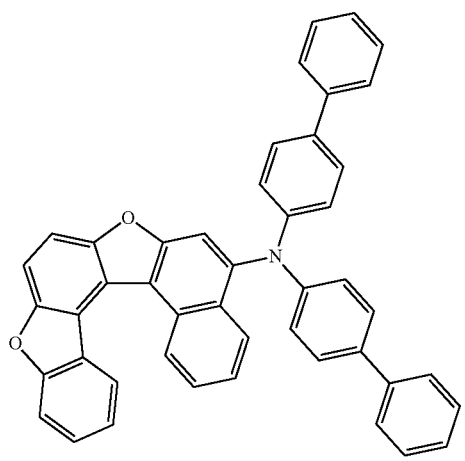
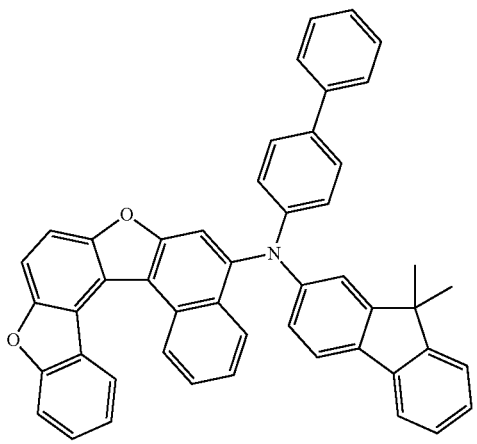

213
-continued
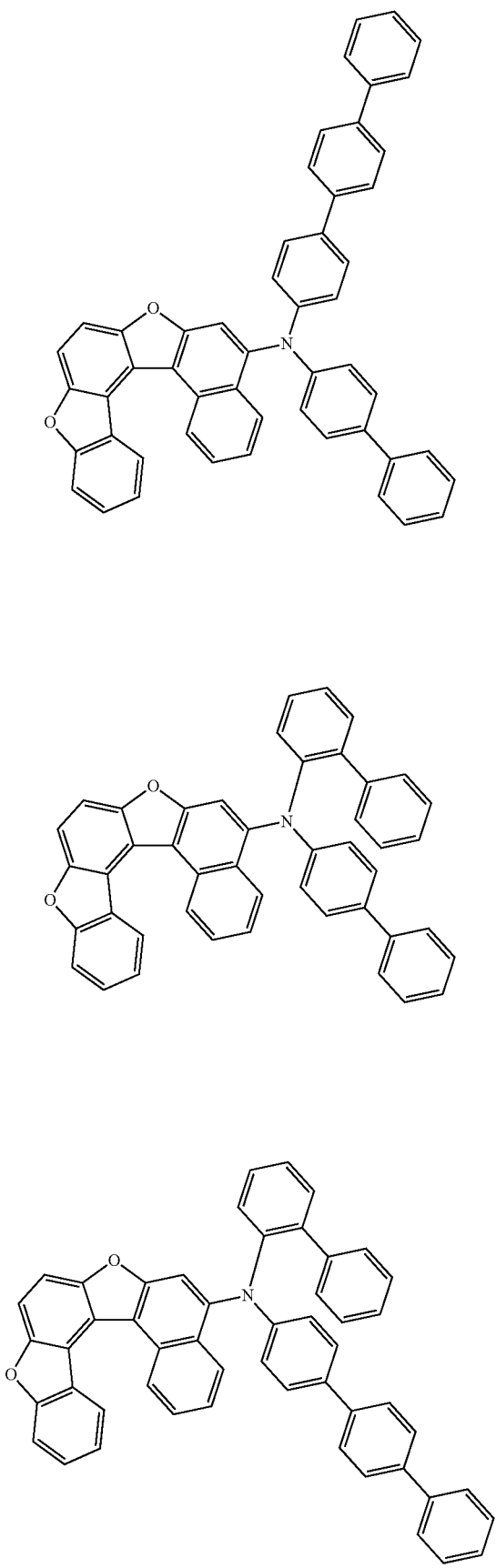
214
-continued
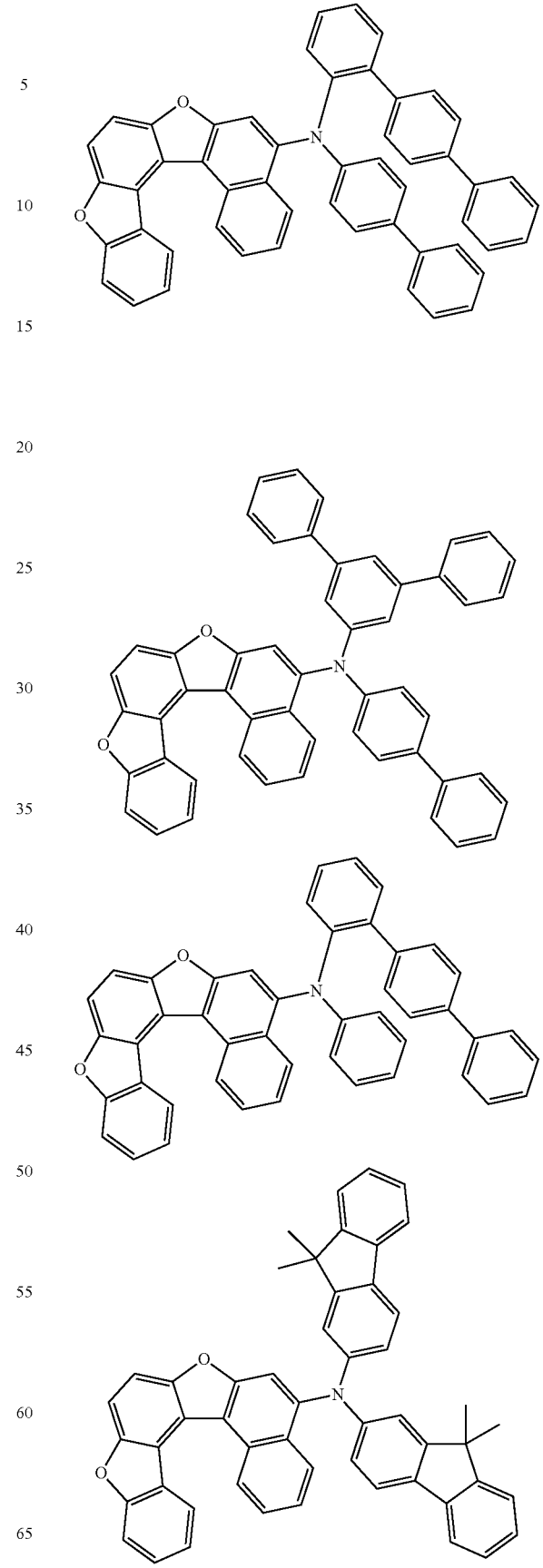

215
-continued
216
-continued
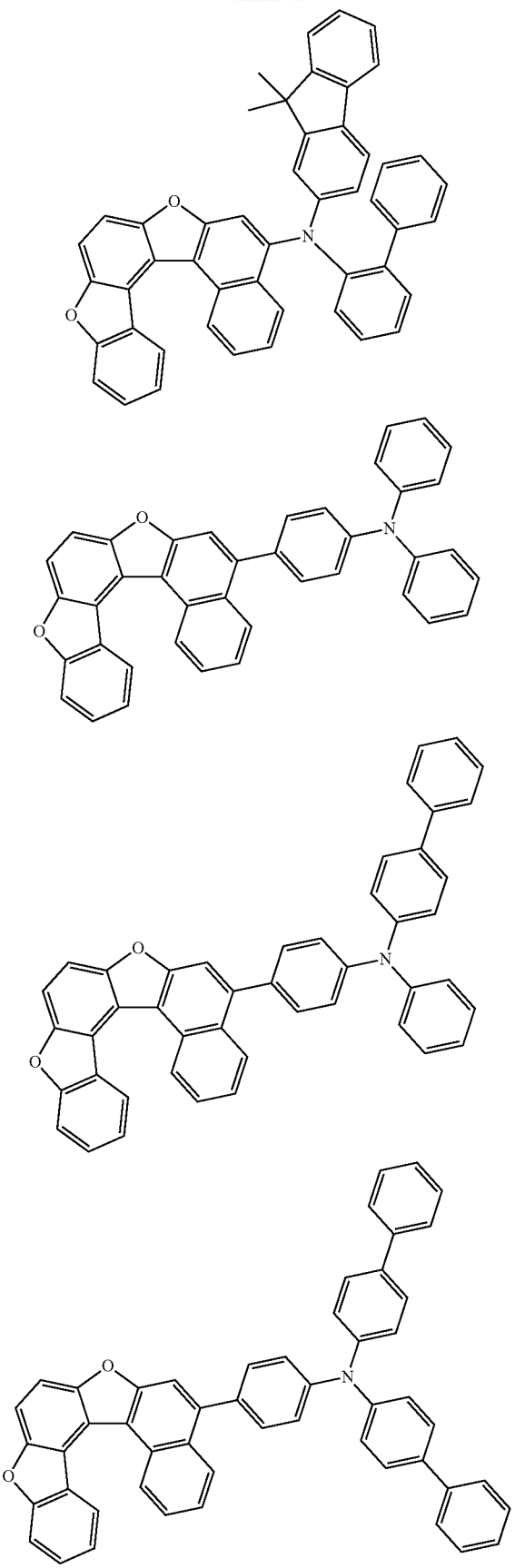
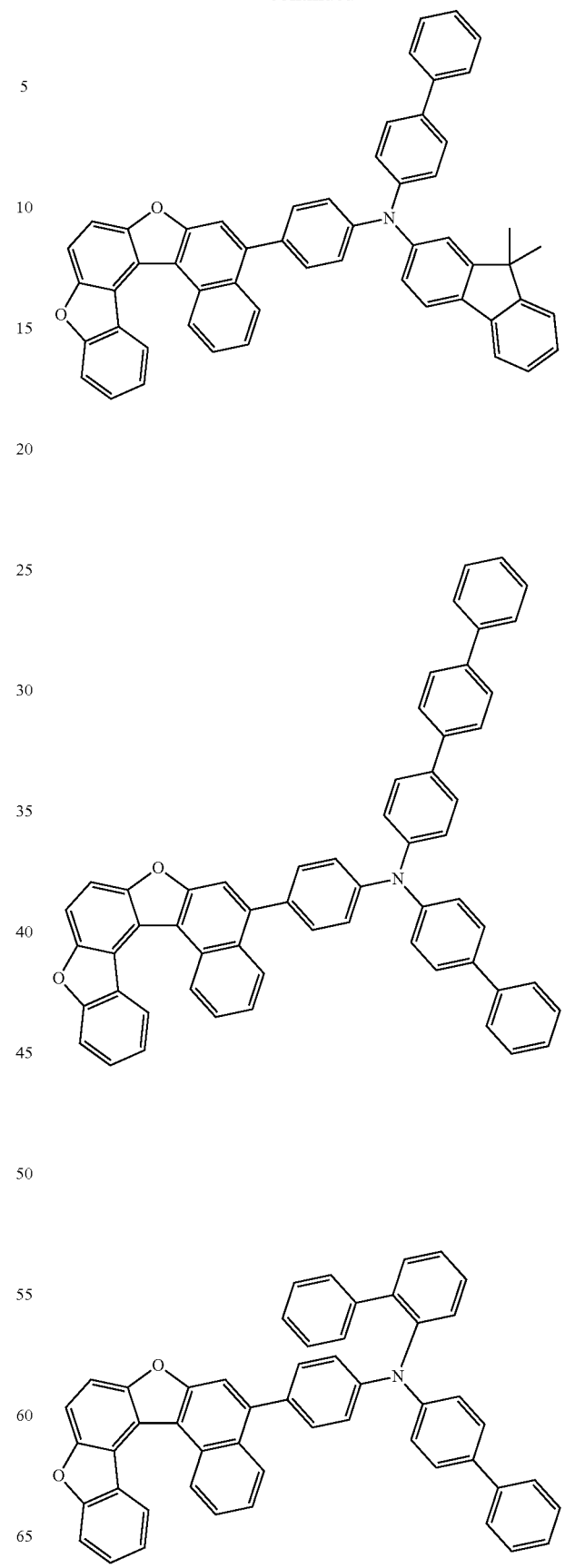

217
-continued
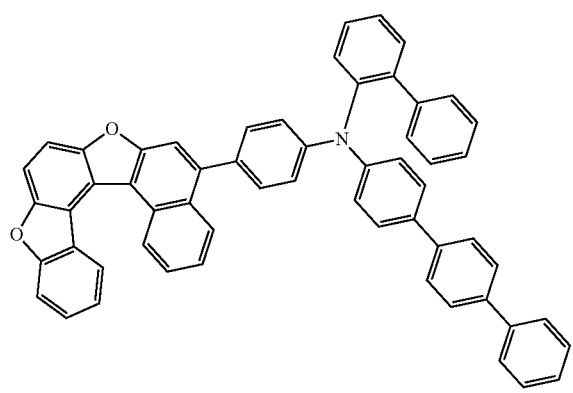
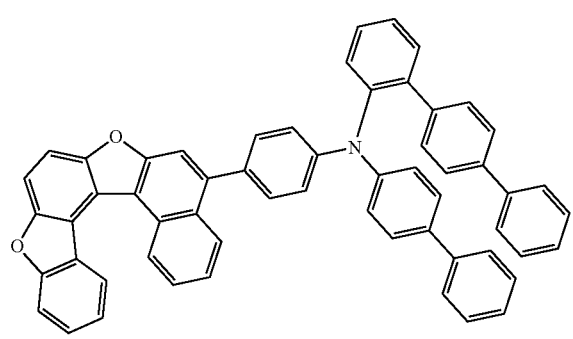
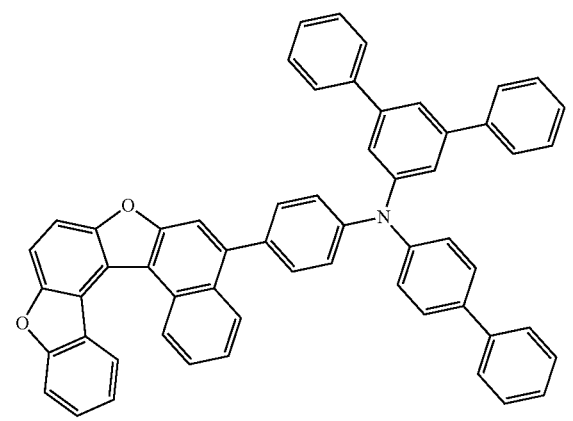
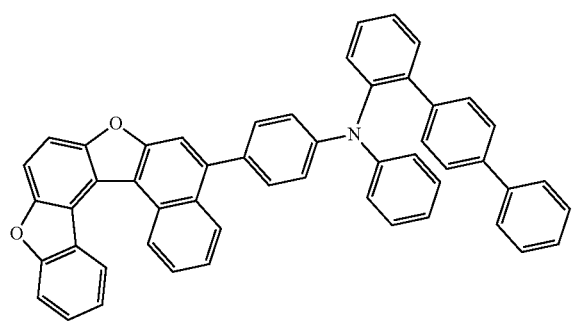
218
-continued
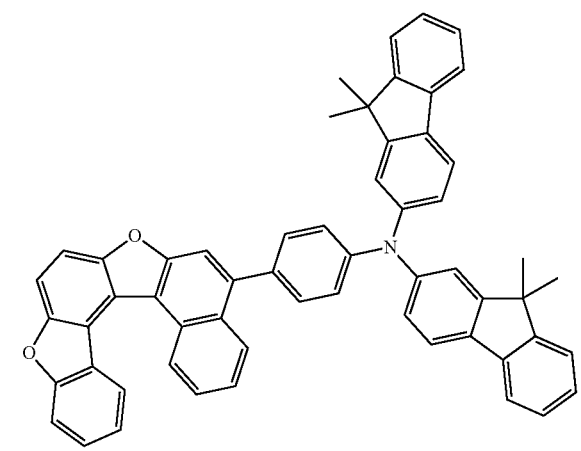
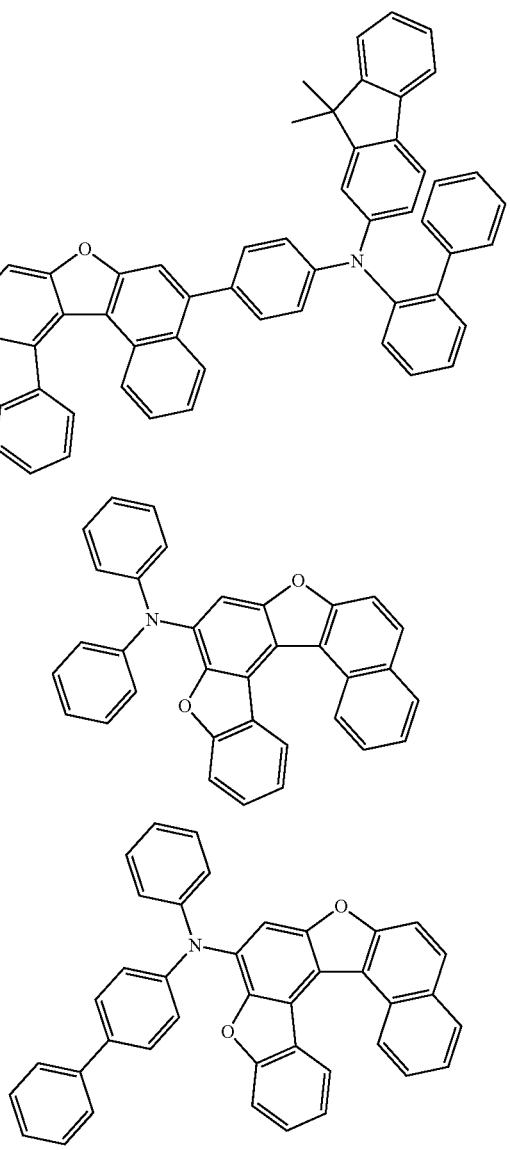

219
-continued
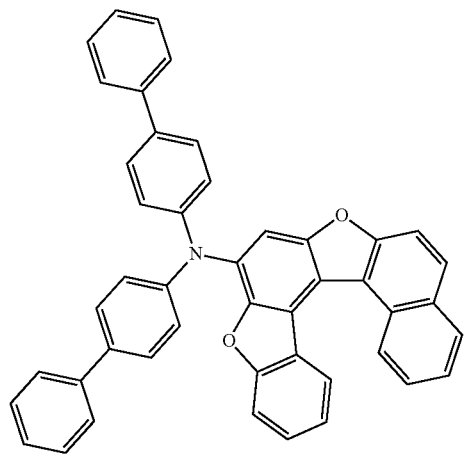
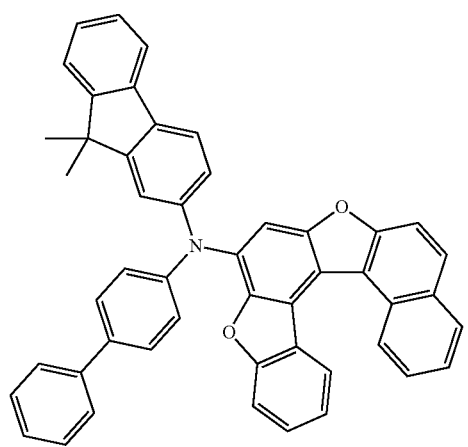
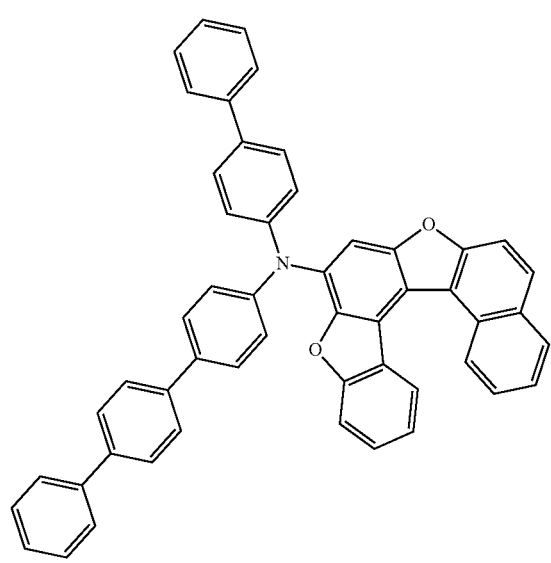
220
-continued
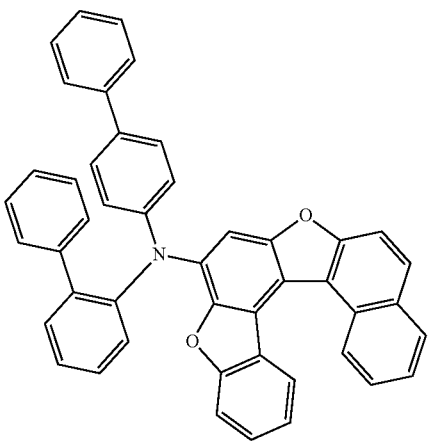
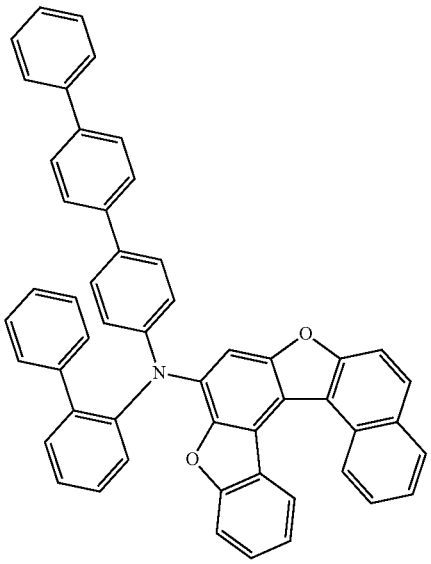
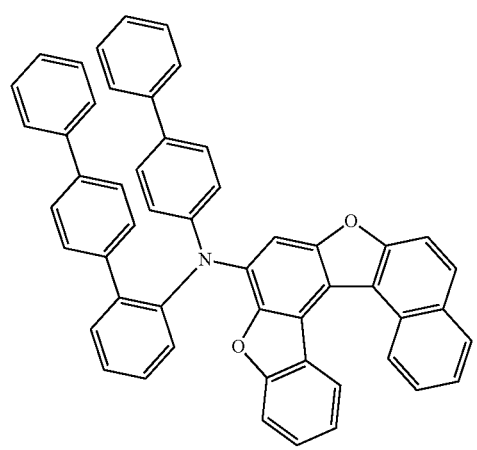

221
-continued
222
-continued
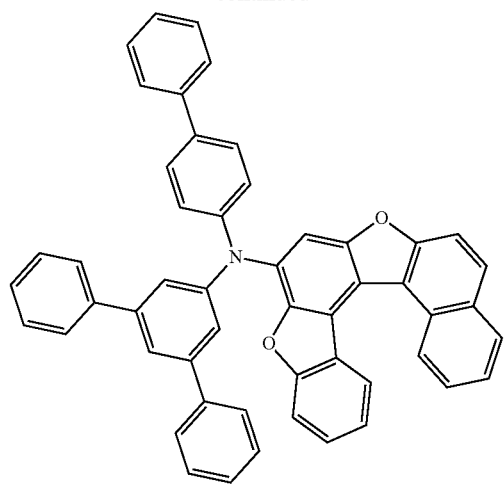
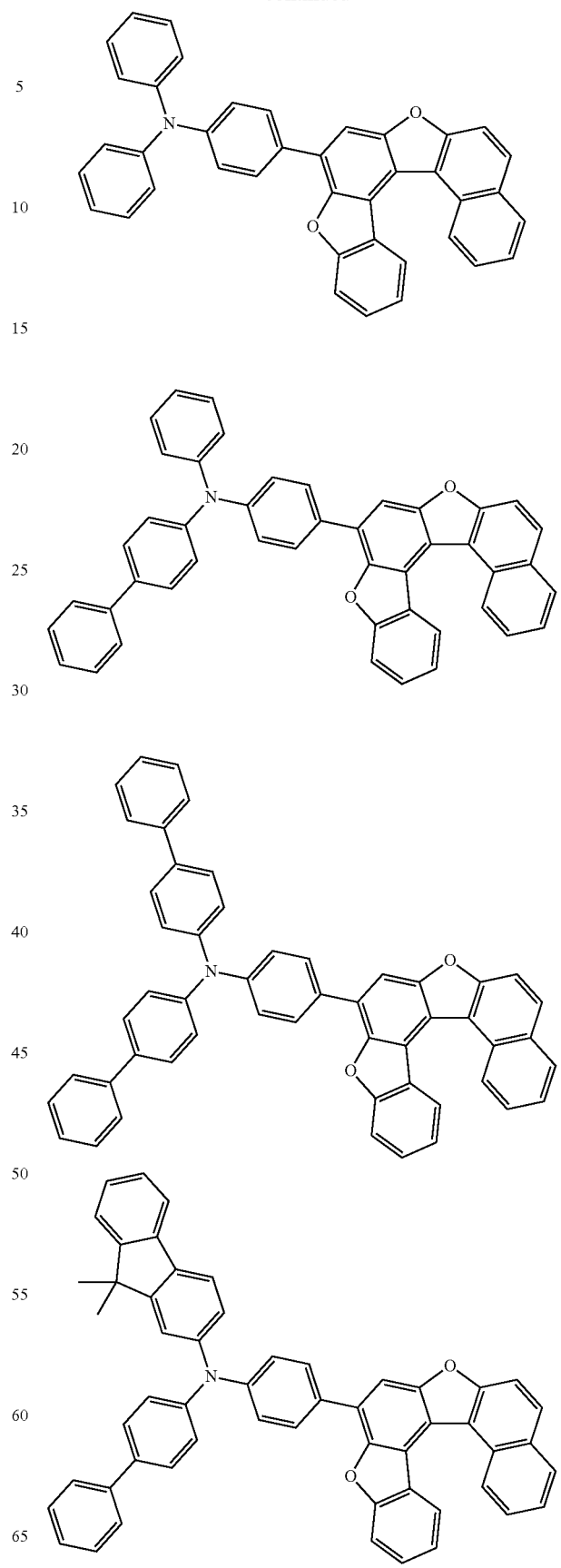

223
-continued
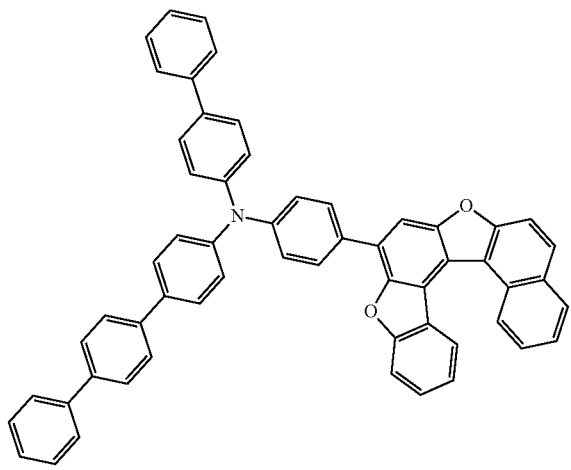
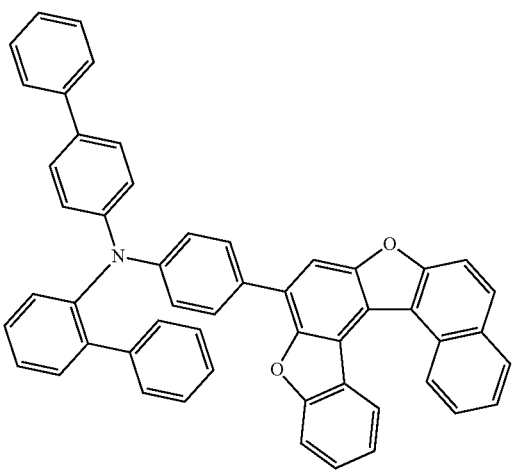
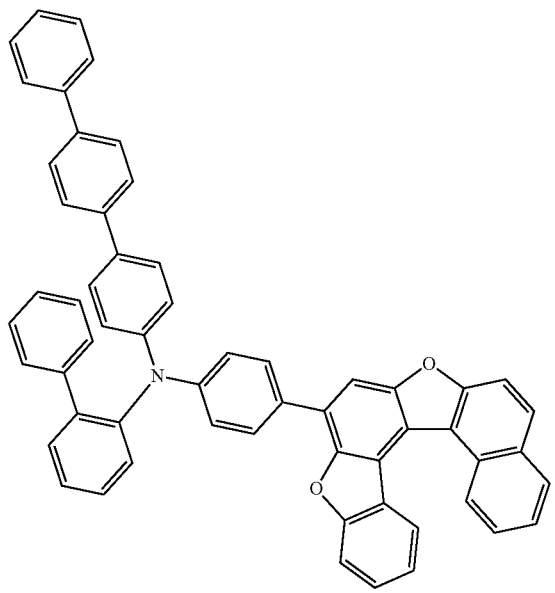
224
-continued
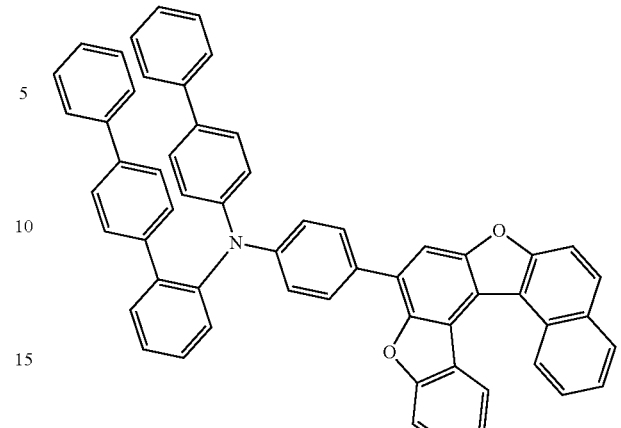
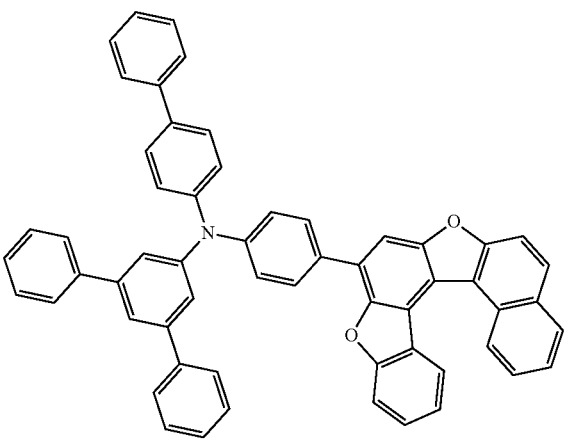

225
-continued
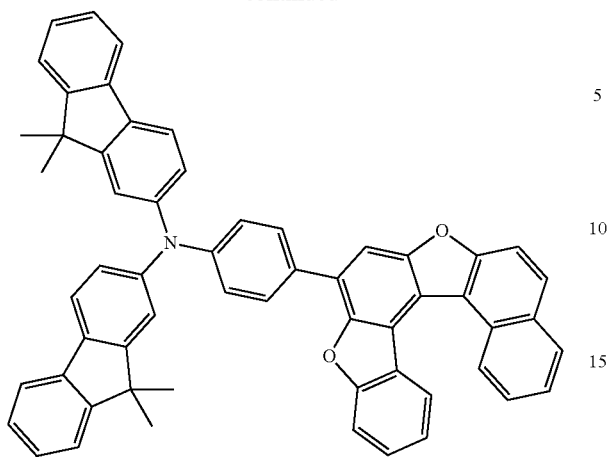
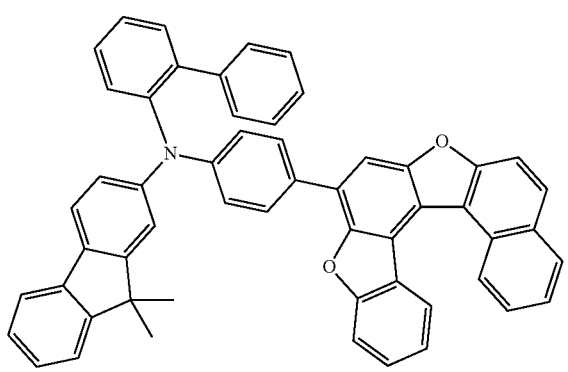
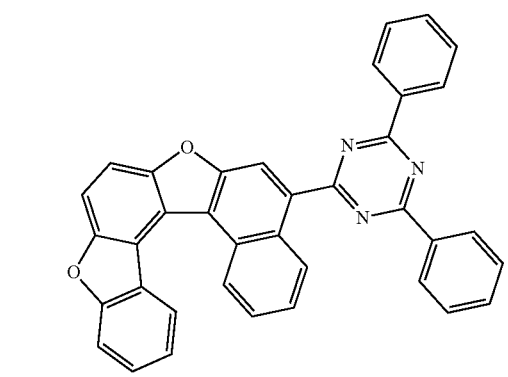
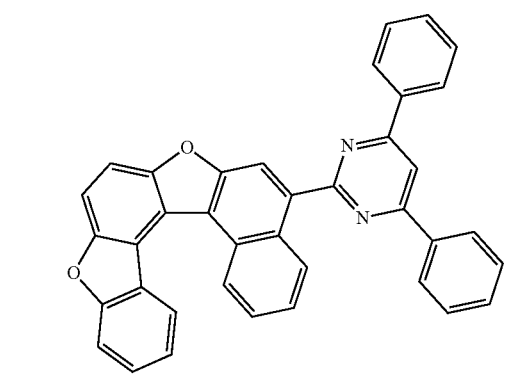
226
-continued
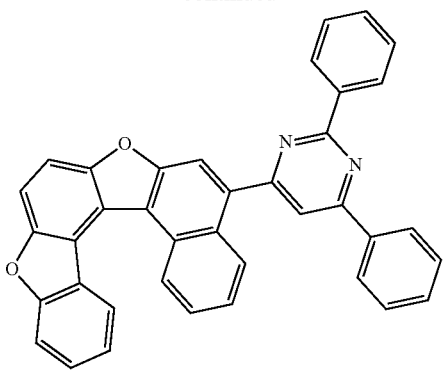
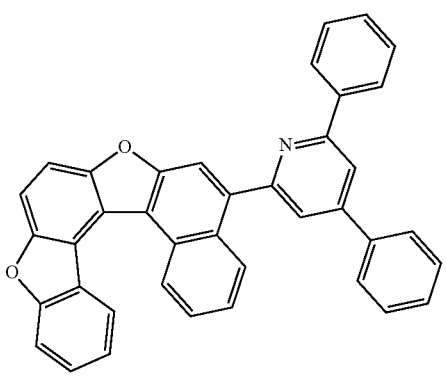
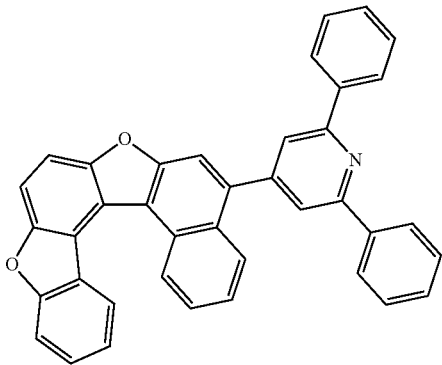
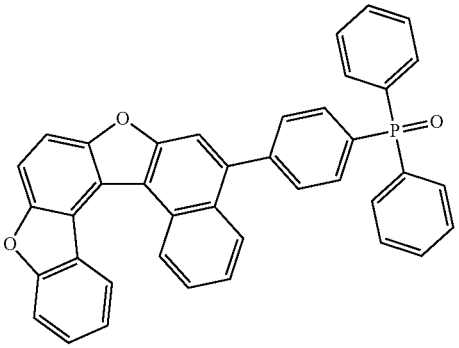

227
-continued
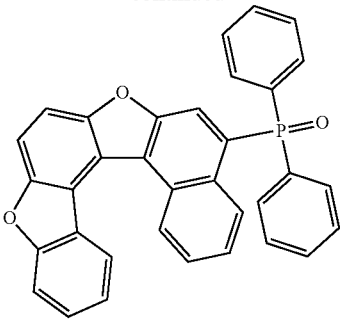
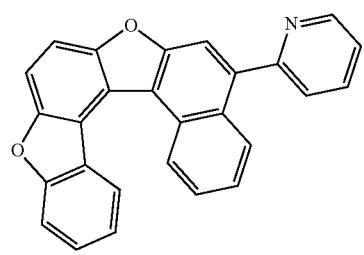
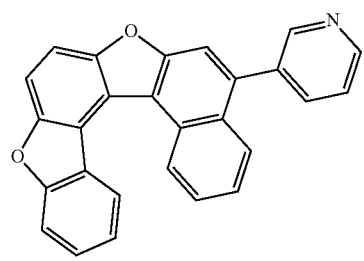
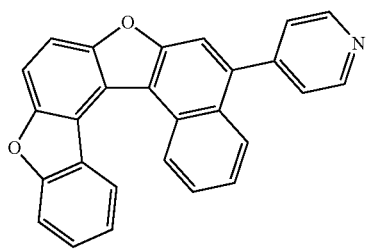
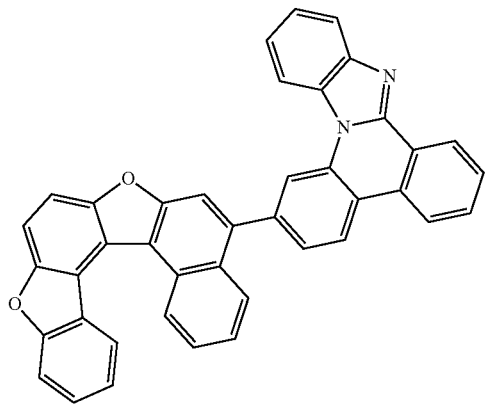
228
-continued
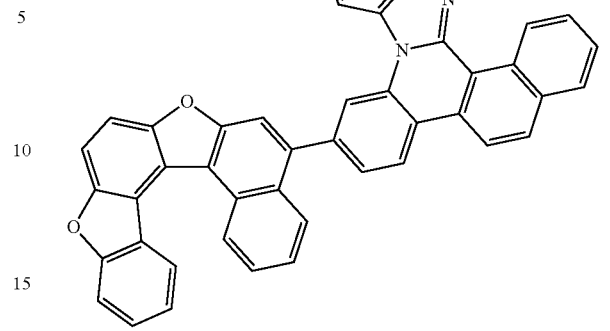
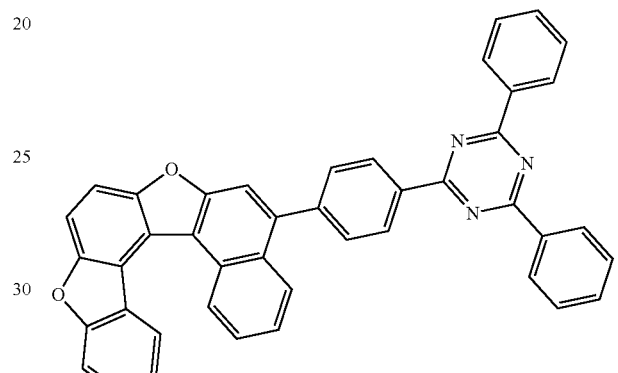
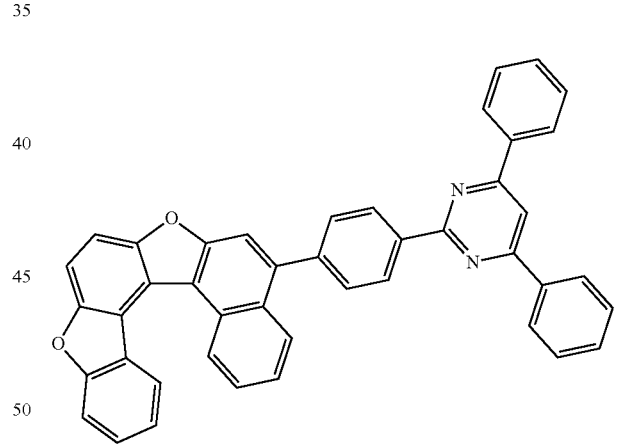
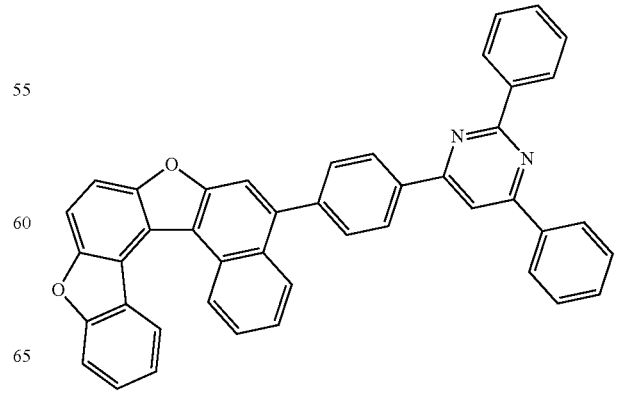

229
-continued
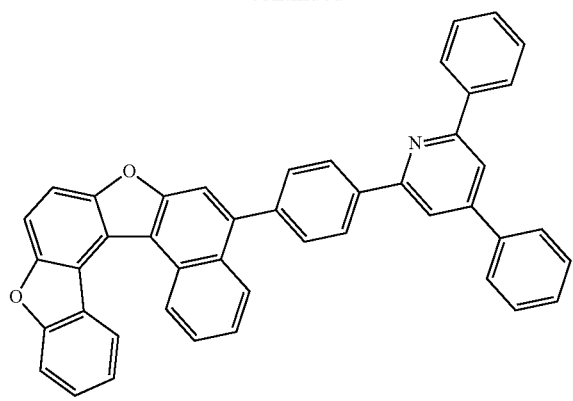
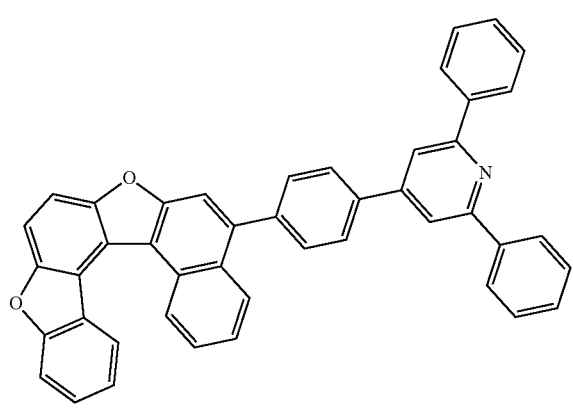
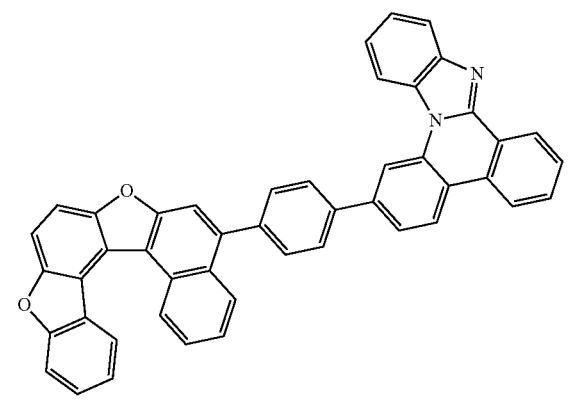
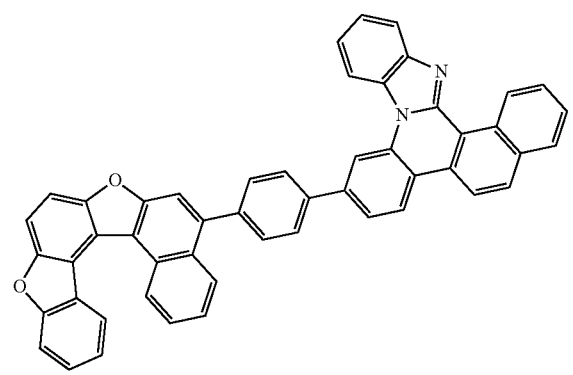
230
-continued
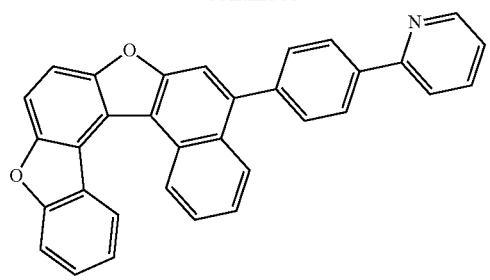
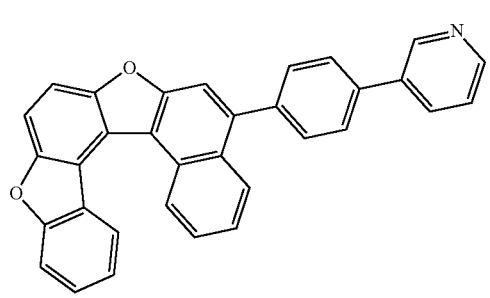
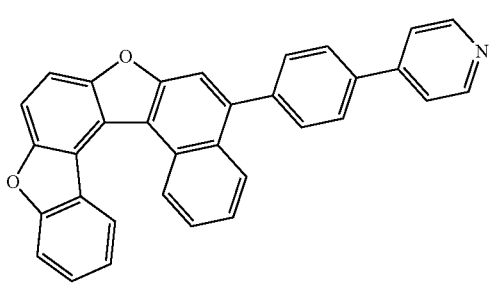
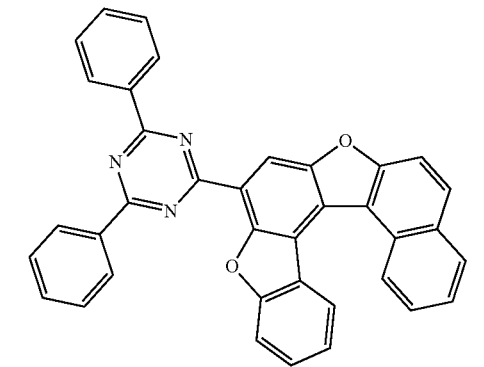
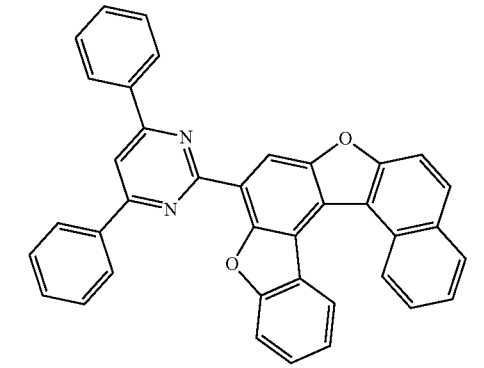

231
-continued
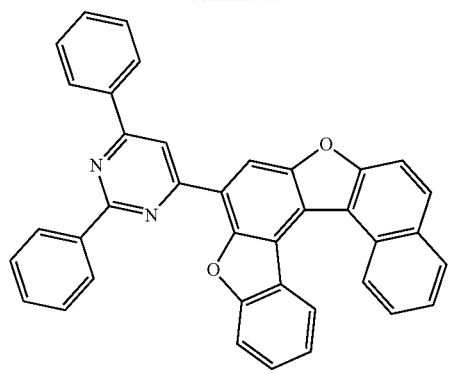
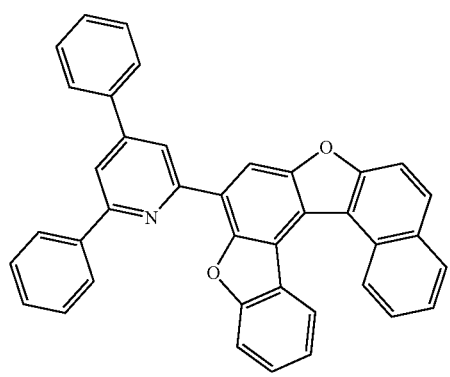
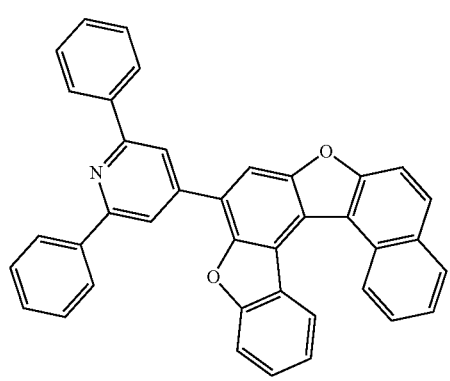
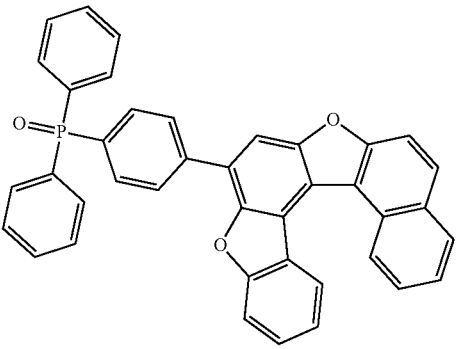
232
-continued
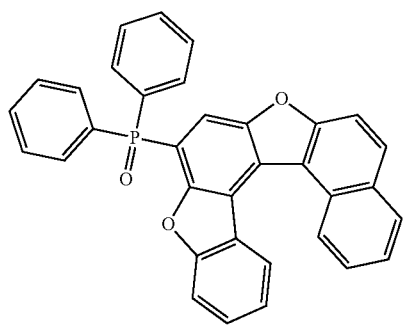
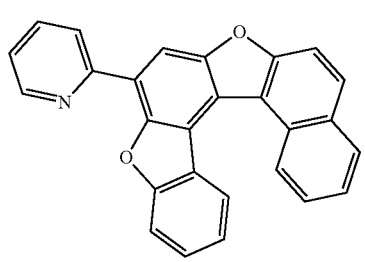
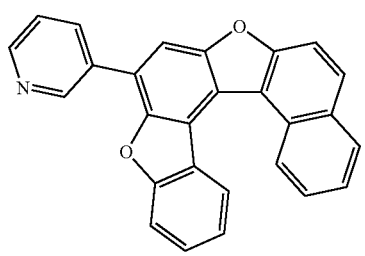
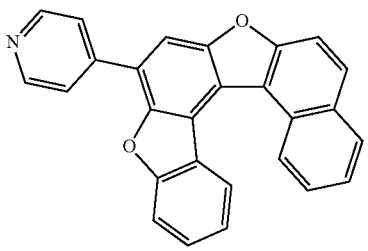
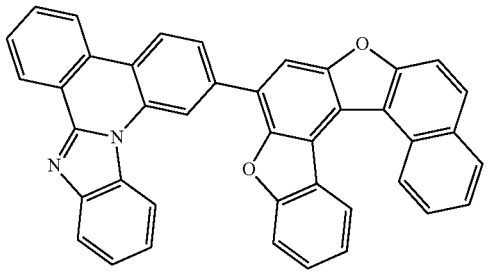
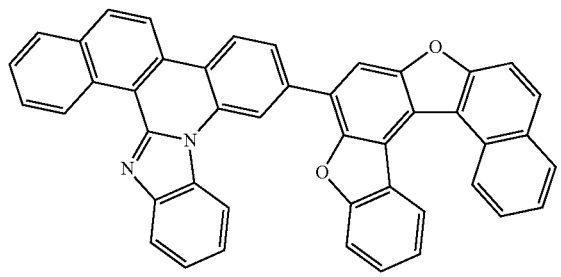

233
-continued
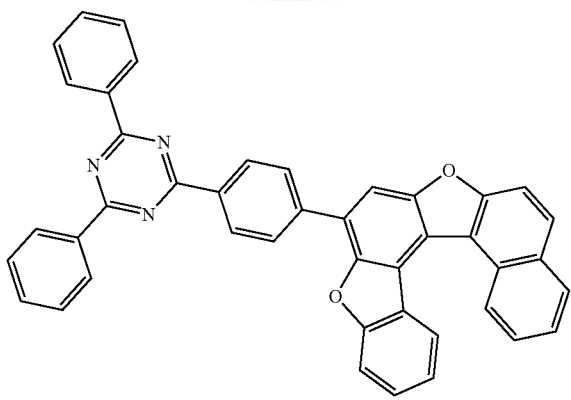
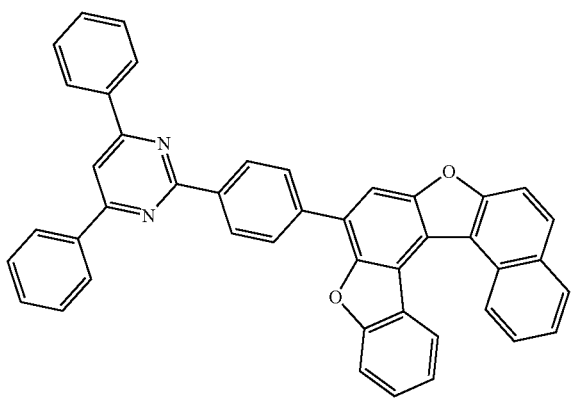
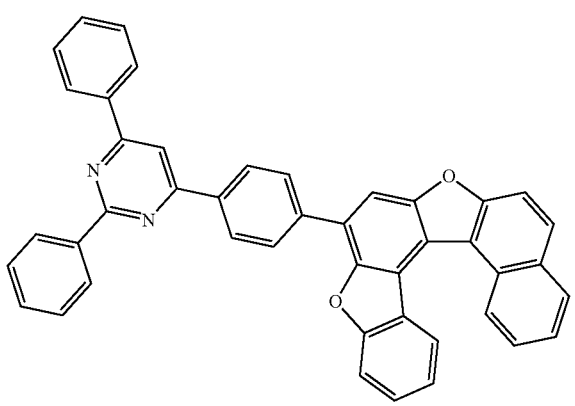
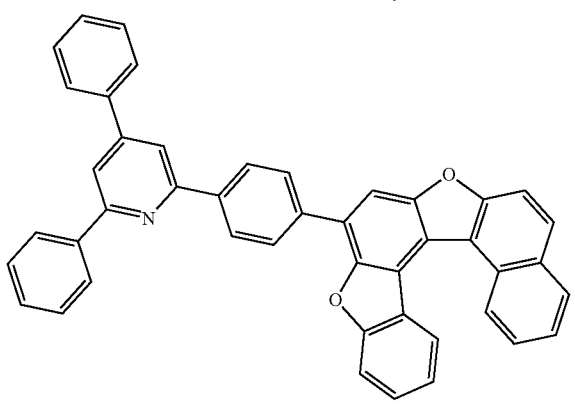
234
-continued
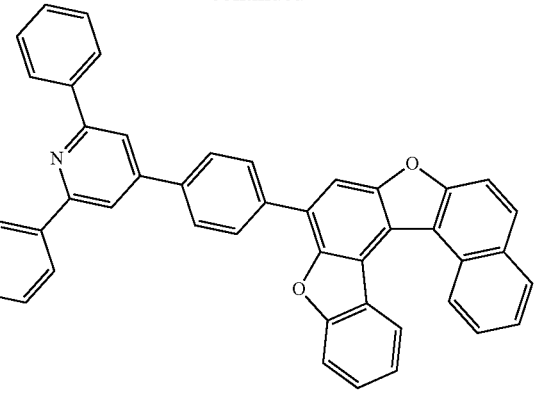
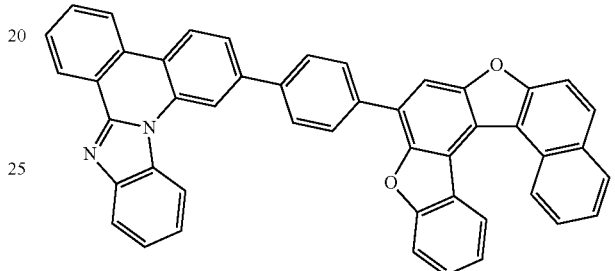
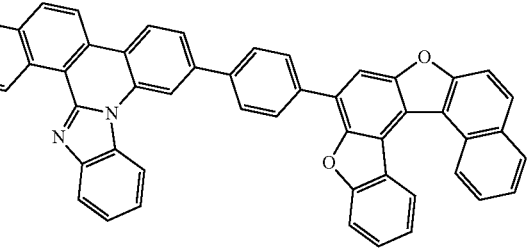
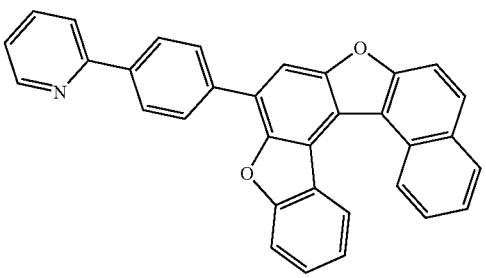
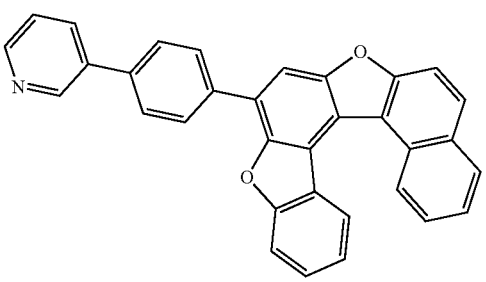

235
-continued
236
-continued
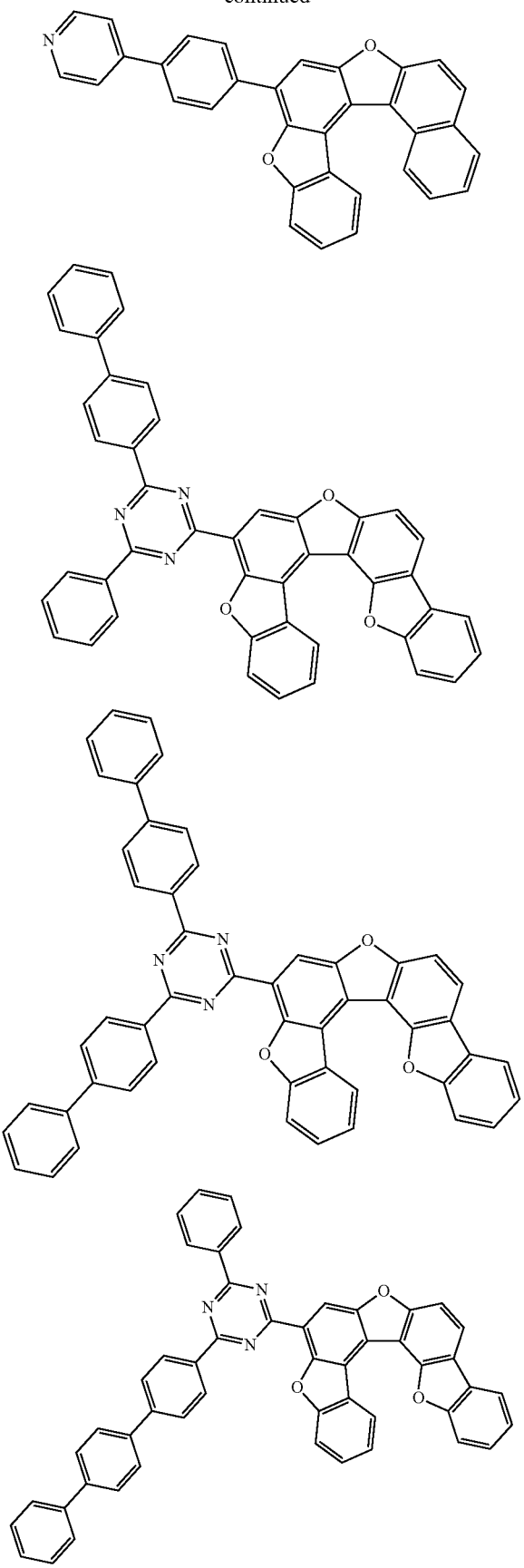
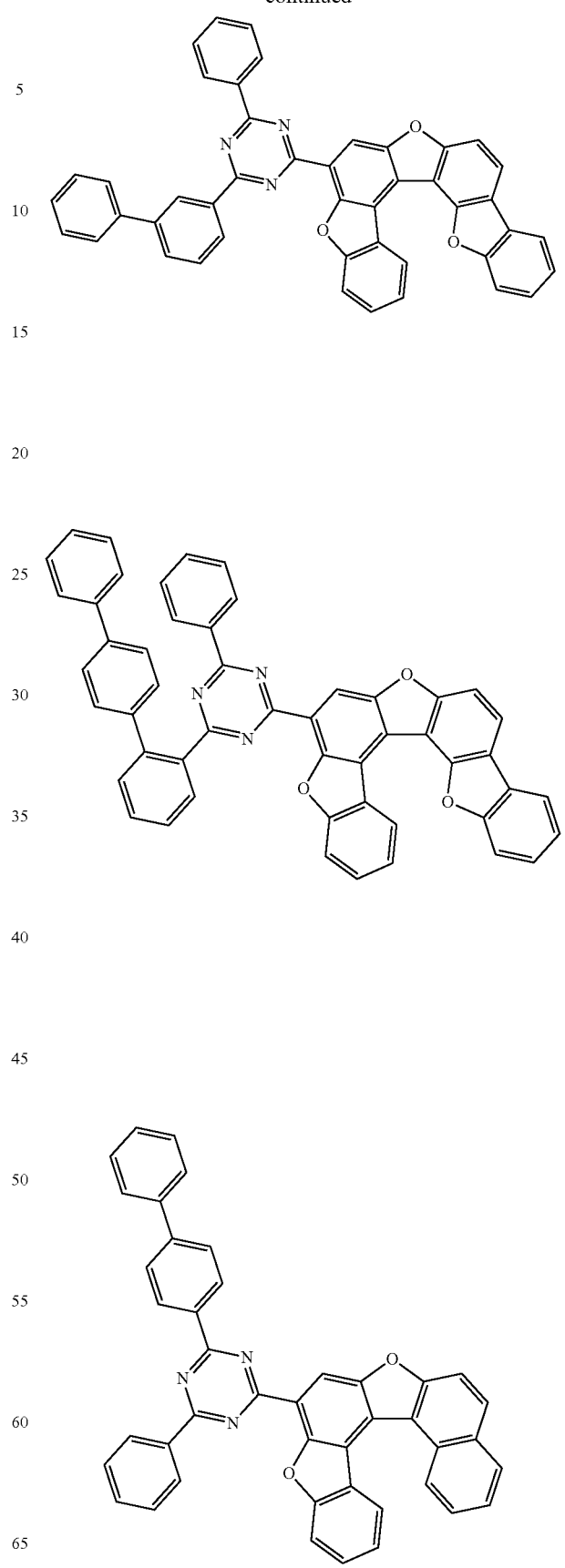

237
-continued
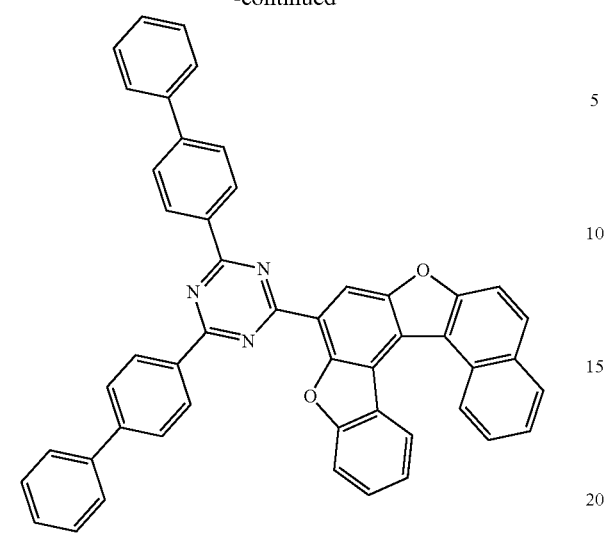
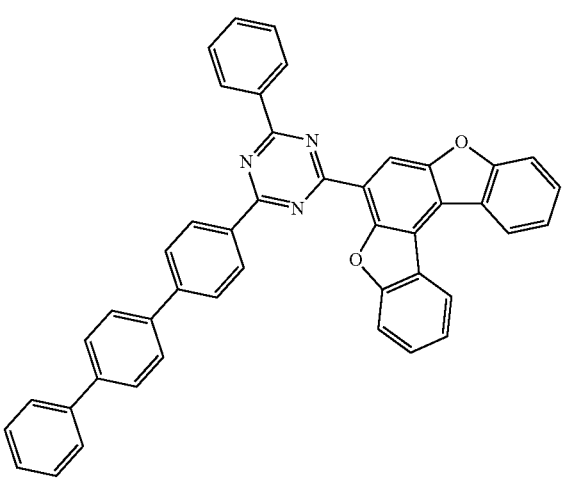
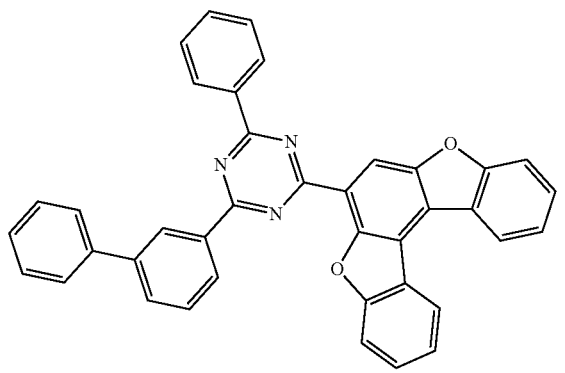
238
-continued
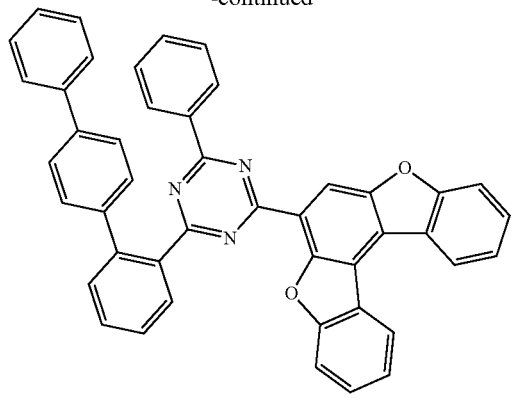
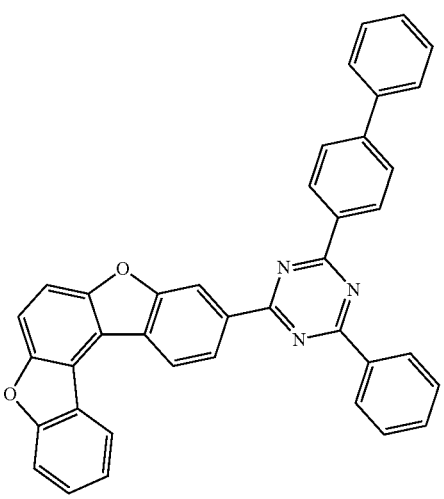
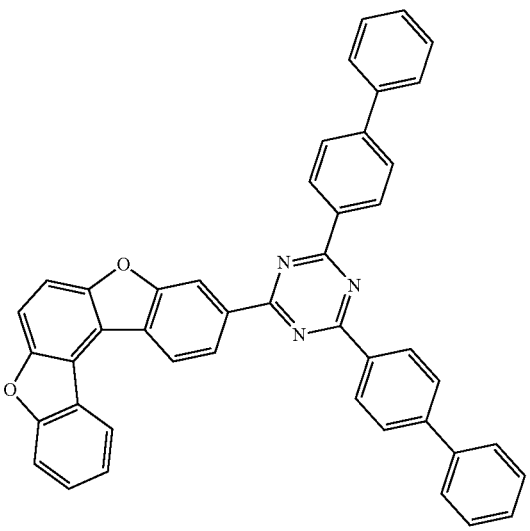

239
-continued
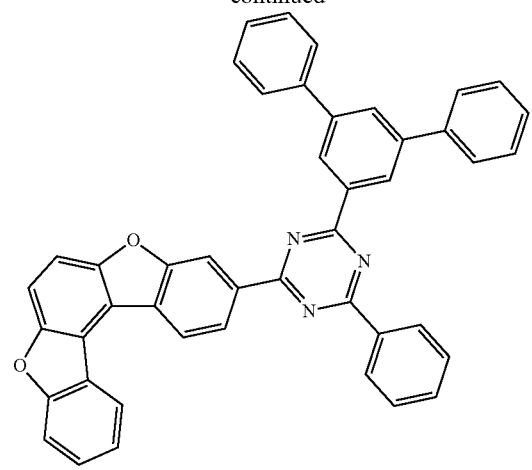
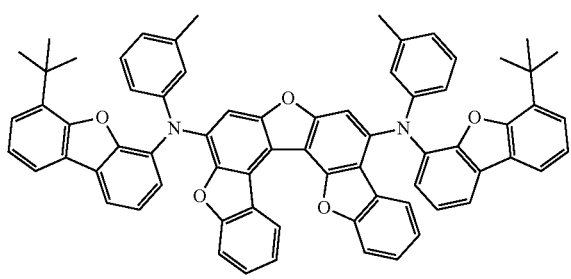
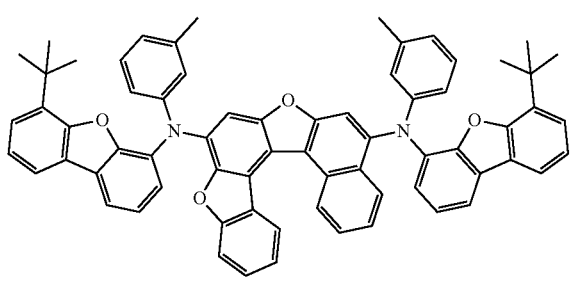
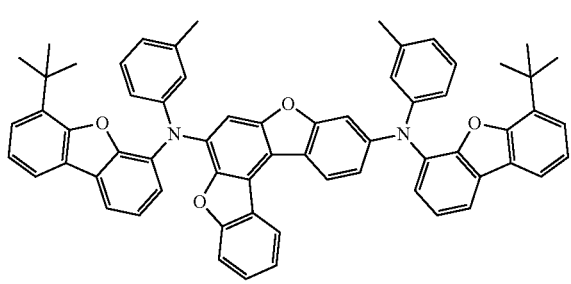
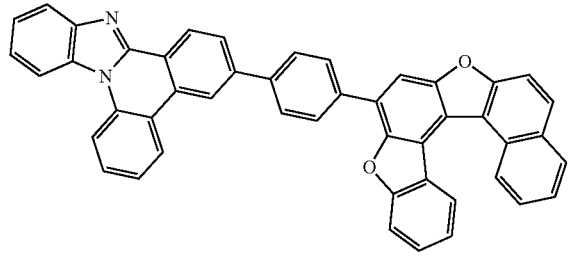
240
-continued
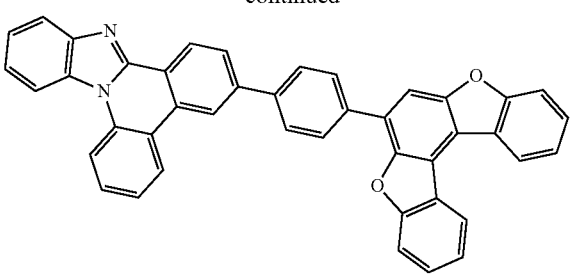
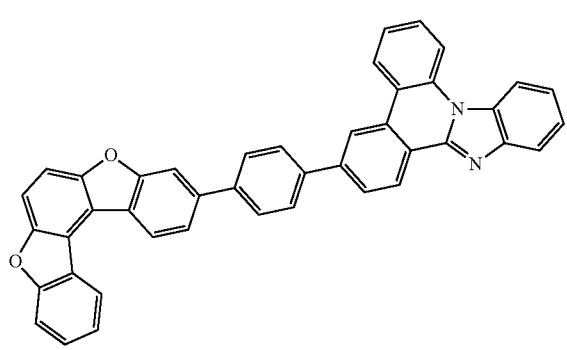
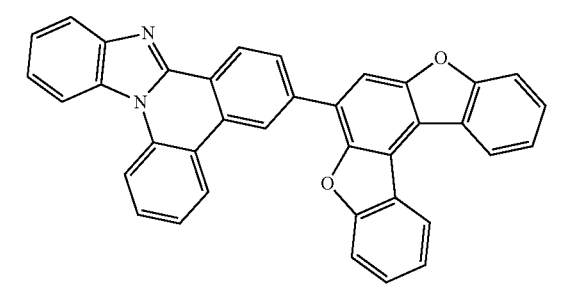
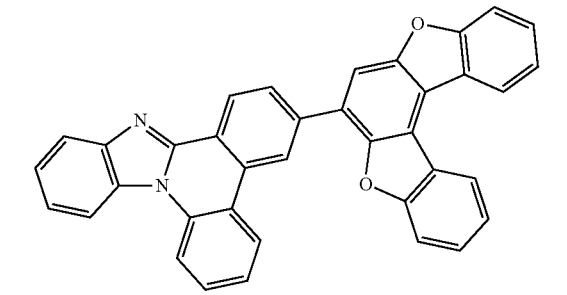
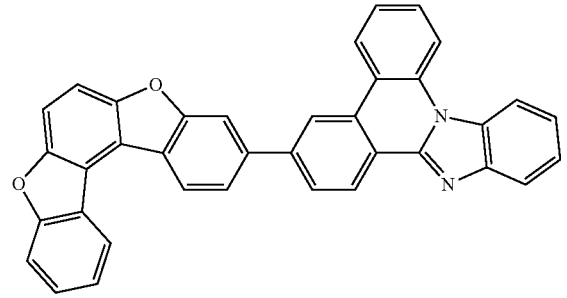

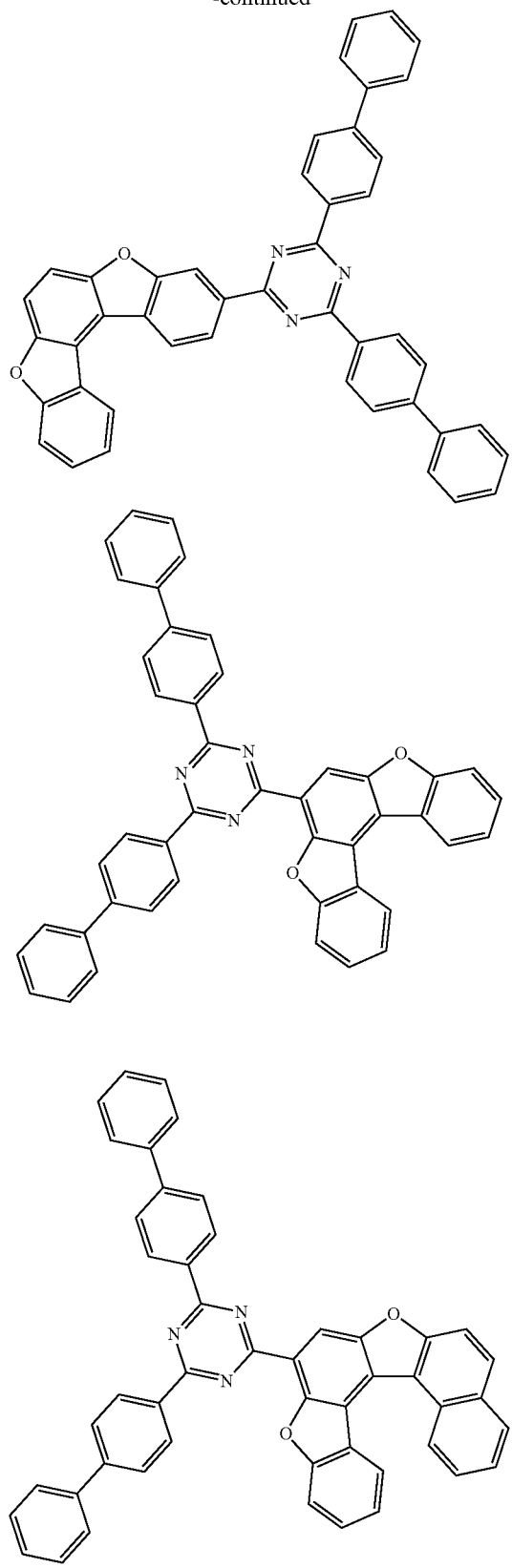
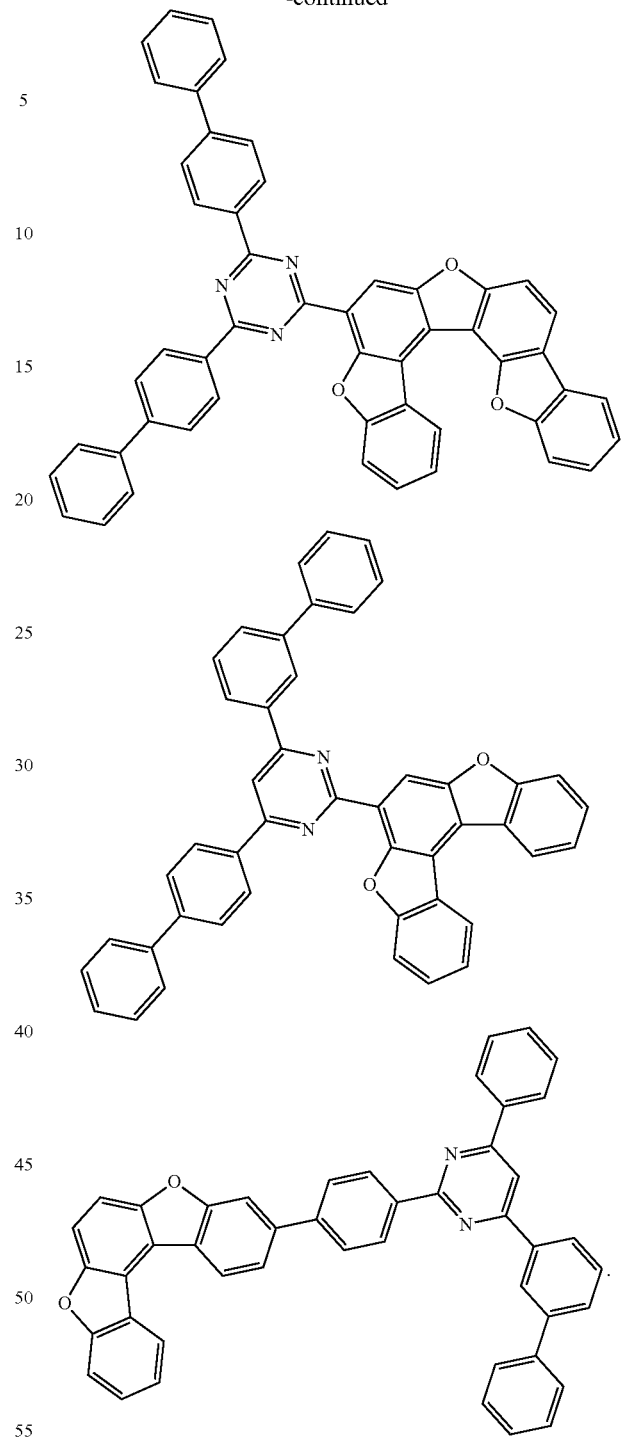
10. An organic light emitting device comprising a first electrode; a second electrode facing the first electrode; and at least one layer of the organic material layers provided between the first electrode and the second electrode, wherein the at least one layer of the organic material layers includes a compound according to claim 1.
* * * * *